United States Patent [19]

Murata et al.

[11] Patent Number: 5,608,056

[45] Date of Patent: Mar. 4, 1997

[54] SUBSTITUTED 3-PYRROLIDINYLTHIO-CARBAPENEMS AS ANTIMICROBIAL AGENTS

[75] Inventors: Masayoshi Murata, Osaka; Hideo Tsutsumi, Toyonaka; Keiji Matsuda, Takatsuki; Kohji Hattori, Takarazuka; Takashi Nakajima, Toyonaka, all of Japan

[73] Assignee: Fujisawa Pharmaceutical Co., Ltd., Osaka, Japan

[21] Appl. No.: 302,780

[22] PCT Filed: Apr. 9, 1993

[86] PCT No.: PCT/JP93/00469

§ 371 Date: Sep. 21, 1994

§ 102(e) Date: Sep. 21, 1994

[87] PCT Pub. No.: WO93/21186

PCT Pub. Date: Oct. 28, 1993

[30] Foreign Application Priority Data

| Apr. 13, 1992 | [GB] | United Kingdom | 9208133 |
| Oct. 5, 1992 | [GB] | United Kingdom | 9220893 |
| Feb. 24, 1993 | [GB] | United Kingdom | 9303720 |

[51] Int. Cl.$^6$ ............................ C07D 487/04

[52] U.S. Cl. ............................ 540/350; 514/210

[58] Field of Search ............................ 514/210; 540/350

[56] References Cited

U.S. PATENT DOCUMENTS

| 4,640,915 | 2/1987 | Hashimoto et al. . |
| 4,822,787 | 4/1989 | Murata et al. . |
| 4,921,852 | 5/1990 | Murata et al. . |
| 4,925,838 | 5/1990 | Murata et al. . |
| 4,963,543 | 10/1990 | Murata et al. . |
| 4,963,544 | 10/1990 | Murata et al. . |
| 4,983,596 | 1/1991 | Murata et al. . |
| 5,061,804 | 10/1991 | Murata et al. . |
| 5,138,064 | 8/1992 | Murata et al. . |
| 5,194,624 | 3/1993 | Murata et al. . |
| 5,202,437 | 4/1993 | Murata et al. . |

FOREIGN PATENT DOCUMENTS

| 333175 | 9/1989 | European Pat. Off. . |
| 343499 | 11/1989 | European Pat. Off. . |

*Primary Examiner*—Rebecca Cook
*Attorney, Agent, or Firm*—Oblon, Spivak, McClelland, Maier & Neustadt, P.C.

[57] ABSTRACT

A compound of the formula:

in which $R^1$ is carboxy or protected carboxy, $R^2$ is 1-hydroxyethyl, $R^3$ is methyl, $R^4$ is optionally substituted pyridyl(lower)alkyl, optionally N-substituted 2-oxopiperazin-1-yl-(lower)alkyl, optionally substituted imidazol-1-yl($C_2$-$C_3$)alkyl, optionally substituted imidazol-5-yl-(lower)alkyl, optionally substituted imidazol-2-yl-(lower)alkyl, optionally substituted pyrazol-4-(or 5-)yl(lower)alkyl, optionally substituted pyrazol-1-ylethyl, optionally substituted triazolyl(lower)alkyl, optionally substituted pyrimidinyl(lower)alkyl, optionally substituted dihydropyrimidinyl(lower)alkyl, or optionally substituted (2,3-dihydroimidazo-[1,2-b]pyrazol-1-yl)ethyl, and $R^5$ is hydrogen or imino-protective group, and pharmaceutically acceptable salts thereof, which have antimicrobial activity.

11 Claims, No Drawings

SUBSTITUTED 3-PYRROLIDINYLTHIO-CARBAPENEMS AS ANTIMICROBIAL AGENTS

TECHNICAL FIELD

This application is a 370 of PCT/JP93/00469 filed Apr. 9, 1993.

The present invention relates to novel azabicyclo compounds and pharmaceutically acceptable salts thereof.

More particularly, it relates to novel 3-pyrrolidinylthio-1-azabicyclo[3.2.0]hept-2-ene-2-carboxylic acid compounds and pharmaceutically acceptable salts thereof, which have antimicrobial activity, to processes for the preparation thereof, to a pharmaceutical composition comprising the same, and to a use of the same as a medicament and in the treatment of infectious diseases in a human being or animal.

INDUSTRIAL APPLICABILITY

Accordingly, one object of the present invention is to provide novel 3-pyrrolidinylthio-1-azabicyclo-[3.2.0]hept-2-ene-2-carboxylic acid compounds and pharmaceutically acceptable salts thereof, which are highly active against a number of pathogenic microorganisms and are useful as antimicrobial agents.

Another object of the present invention is to provide processes for the preparation of novel 3-pyrrolidinylthio-1-azabicyclo[3.2.0]hept-2-ene-2-carboxylic acid compounds and salts thereof.

A further object of the present invention is to provide a pharmaceutical composition comprising, as an active ingredient, said 3-pyrrolidinylthio-1-azabicyclo-[3.2.0]hept-2-ene-2-carboxylic acid compounds and pharmaceutically acceptable salts thereof.

Still further object of the present invention is to provide a use of said 3-pyrrolidinylthio-1-azabicyclo-[3.2.0]hept-2-ene-2-carboxylic acid compounds and pharmaceutically acceptable salts thereof as a medicament and in the treatment of infectious diseases by pathogenic microorganisms in a human being or animal.

DISCLOSURE OF INVENTION

The object 3-pyrrolidinylthio-1-azabicyclo[3.2.0]-hept-2-ene-2-carboxylic acid compounds are novel and can be represented by the following general formula:

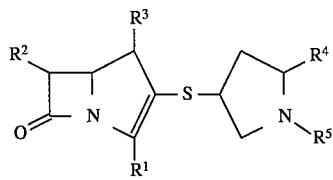

(I)

in which
$R^1$ is carboxy or protected carboxy,
$R^2$ is 1-hydroxyethyl,
$R^3$ is methyl,
$R^4$ is
  optionally substituted pyridyl(lower)alkyl,
  optionally N-substituted 2-oxopiperazin-1-yl(lower)alkyl,
  optionally substituted imidazol-1-yl($C_2$-$C_3$)alkyl,
  optionally substituted imidazol-5-yl(lower)alkyl,
  optionally substituted imidazol-2-yl(lower)alkyl,
  optionally substituted pyrazol-4-(or 5-)yl(lower)alkyl,
  optionally substituted pyrazol-1-ylethyl,
  optionally substituted triazolyl(lower)alkyl,
  optionally substituted pyrimidinyl(lower)alkyl,
  optionally substituted dihydropyrimidinyl(lower)alkyl,
  or optionally substituted 2,3-dihydro-imidazo[1,2-b]pyrazol-1-ylethyl, and
$R^5$ is hydrogen or imino-protective group, and pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, fluorosulfate, phosphate, etc.), an organic acid addition salt (e.g. formate, acetate, trifluoroacetate, maleate, tartrate, methanesulfonate, benzenesulfonate, trifluoromethanesulfonate etc.); a salt with a basic or acidic amino acid (e.g. arginine, aspartic acid, glutamic acid, etc.); an intermolecular or intramolecular quaternary salt; and the like.

The said intermolecular quaternary salt can be formed, for example, between the tertiary nitrogen atom of the pyridyl, 2-oxopiperazin-1-yl, dihydropyrimidinyl, pyrazolyl, triazolyl, pyrimidinyl, 2,3-dihydroimidazo-[1,2-b]pyrazol-1-yl, or the imidazolyl group in $R^4$ and lower alkyl (e.g. methyl, etc.), carbamoyl(lower)alkyl (e.g. carbamoylmethyl, etc.), N,N-di(lower)alkylcarbamoyl(lower)alkyl (e.g. dimethylcarbamoylmethyl, etc.), N-[hydroxy(lower)alkyl]carbamoyl(lower)alkyl [e.g. N-(2-hydroxyethyl)carbamoylmethyl, etc.], amino(lower)alkyl (e.g. 3-aminopropyl, etc.) or protected amino(lower)alkyl [e.g. 3-(allyloxycarbonylamino)propyl, etc.], and such a suitable intermolecular quaternary salt may include 3-(lower)alkyl-1-(or 2- or 5-)imidazolio (or trifluoromethanesulfonate), 3-carbamoyl(lower)alkyl-1-(or 2- or 5-)imidazolio (or trifluoromethanesulfonate), 3-amino(or protected amino)(lower)alkyl-1-imidazolio halide, 1-(lower)alkylpyridinio halide, 1-carbamoyl(lower)alkylpyridinio halide, 1-[N,N-di(lower)alkylcarbamoyl(lower)alkyl]pyridinio halide, 1-[N-{hydroxy(lower)alkyl}carbamoyl(lower)alkyl]pyridinio halide, N,N-di(lower)alkyl-2-oxo-1-piperazino halide, 2-(lower)alkyl-1-(or 4- or 5-)pyrazolio halide, 4-(lower)alkyl-1-(or 5-)[1,2,4-triazolio]halide, 2-(or 3-)(lower)alkyl-1-(1,2,3-triazolio]halide, 5-(lower)alkyl-2,3-dihydroimidazo[1,2-b]-1-pyrazolio halide, and the like, or can be formed when $R^4$ is, for example, 1-pyridinio(lower)alkyl, and such a suitable intermolecular quaternary salt may include 1-pyridinio(lower)alkyl halide (or trifluoromethanesulfonate), and the like.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:
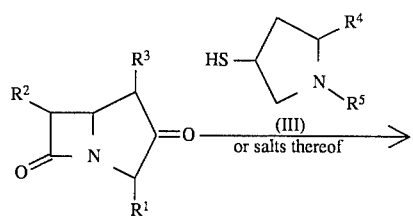
(II)
or a reactive derivative
at the oxo group thereof
or salts thereof
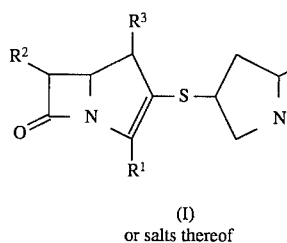
(I)
or salts thereof
Process 2:
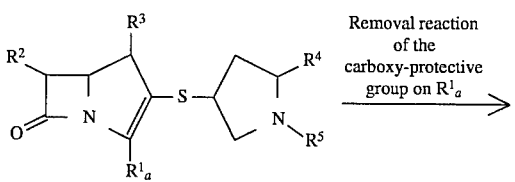
(I-a)
or salts thereof
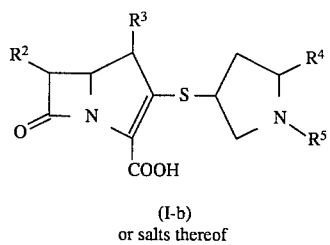
(I-b)
or salts thereof
Process 3:
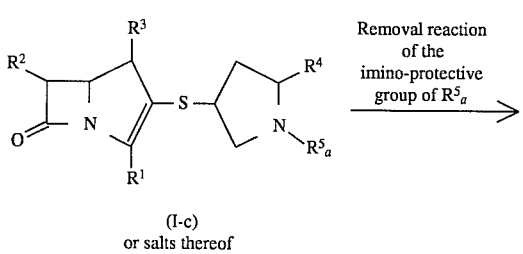
(I-c)
or salts thereof
Process 3:
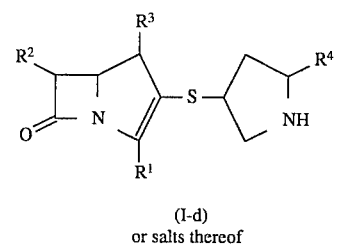
(I-d)
or salts thereof
Process 4:
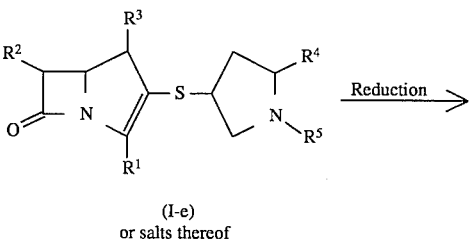
(I-e)
or salts thereof
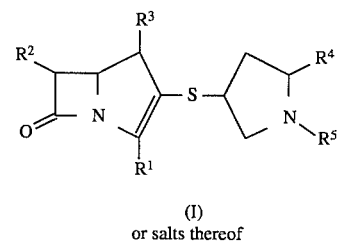
(I)
or salts thereof
Process 5:
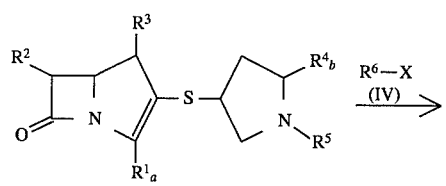
(I-f)
or salts thereof
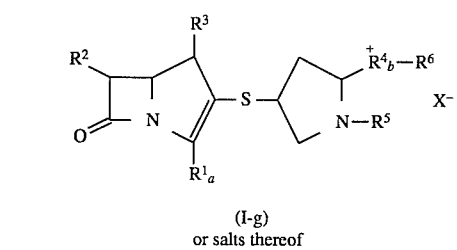
(I-g)
or salts thereof Process 6:

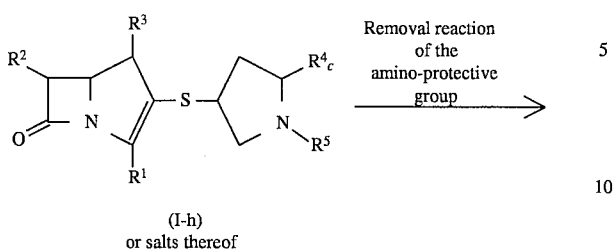

(I-h) or salts thereof

↓ Removal reaction of the amino-protective group (I-i) or salts thereof

Process 7:

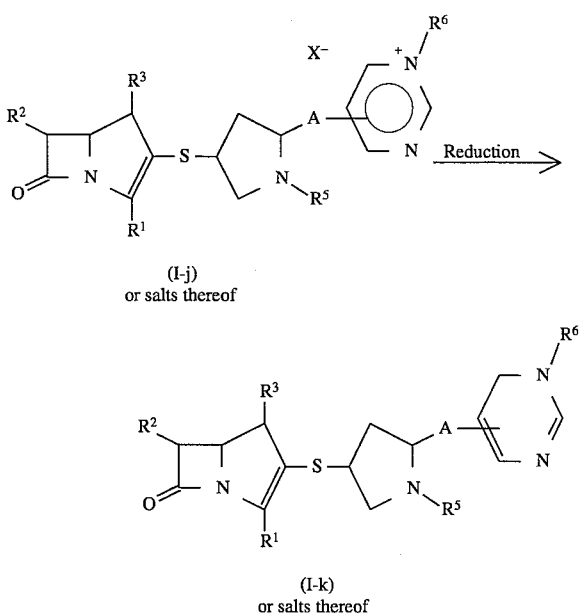

(I-j) or salts thereof

↓ Reduction (I-k) or salts thereof in which $R^1$, $R^2$, $R^3$, $R^4$ and $R^5$ are each as defined above, $R_a^1$ is protected carboxy,
$R_a^4$ is
  optionally substituted pyridyl(lower)alkenyl,
  optionally N-substituted 2-oxopiperazin-1-yl(lower)alkenyl,
  optionally substituted imidazol-1-yl($C_2$-$C_3$)alkenyl,
  optionally substituted imidazol-5-yl(lower)alkenyl,
  optionally substituted imidazol-2-yl(lower)alkenyl,
  optionally substituted pyrazol-4-(or 5-)yl(lower)alkenyl,
  optionally substituted pyrazol-1-ylethenyl,
  optionally substituted triazolyl(lower)alkenyl,
  optionally substituted pyrimidinyl(lower)alkenyl,
  optionally substituted dihydropyrimidinyl(lower)alkenyl,
  or optionally substituted 2,3-dihydroimidazo[1,2-b]pyrazol-1-ylethenyl, $R_b^4$ is pyridin-2-(or 3- or 4-)yl(lower)alkyl, N-(lower)alkyl-2-oxopiperazin-1-yl(lower)alkyl, imidazol-1-yl($C_2$-$C_3$)alkyl, imidazol-2-(or 5-)yl(lower)alkyl, pyrazol-1-ylethyl, pyrazol-4-(or 5-)yl(lower)alkyl, pyrimidinyl(lower)alkyl, 1,2,4-triazol-1-(or 5-)yl(lower)alkyl, 1,2,3-triazol-1-yl(lower)alkyl, or 2,3-dihydroimidazo[1,2-b]pyrazol-1-ylethyl, each of which is optionally substituted by suitable substituent(s), $R_b^{+4}$ is 2-(or 3- or 4-)pyridinio(lower)alkyl, N-(lower)alkyl-2-oxo-1-piperazinio(lower)alkyl, 1-imidazolio($C_2$-$C_3$)alkyl, 2-(or 5-)imidazolio(lower)alkyl, (1-pyrazolio)ethyl, 4-(or 5-)pyrazolio(lower)alkyl, pyrimidinio(lower)alkyl, 1-(or 5-)(1,2,4-triazolio)(lower)alkyl, 1-(1,2,3-triazolio)(lower)alkyl, or 2,3-dihydro-1-imidazo[1,2-b]pyrazolioethyl, each of which is optionally substituted by suitable substituent(s), $R_c^4$ is
  protected amino(lower)alkyl-substituted pyridyl(lower)alkyl,
  N-[protected amino(lower)alkyl]substituted 2-oxopiperazin-1-yl(lower)alkyl,
  protected amino(lower)alkyl-substituted imidazol-1-yl($C_2$-$C_3$)alkyl,
  protected amino(lower)alkyl-substituted imidazol-5-yl(lower)alkyl,
  protected amino(lower)alkyl-substituted imidazol-2-yl(lower)alkyl,
  protected amino(lower)alkyl-substituted pyrazol-4-(or 5-)yl(lower)alkyl,
  protected amino(lower)alkyl-substituted pyrazol-1-ylethyl,
  protected amino(lower)alkyl-substituted triazolyl(lower)alkyl,
  protected amino(lower)alkyl-substituted pyrimidinyl(lower)alkyl,
  protected amino(lower)alkyl-substituted dihydropyrimidinyl(lower)alkyl,
  or protected amino(lower)alkyl-substituted 2,3-dihydroimidazo[1,2-b]-pyrazol-1-ylethyl, each of which is further optionally, substituted by suitable substituent(s), $R_d^4$ is
  amino(lower)alkyl-substituted pyridyl(lower)alkyl,
  N-[amino(lower)alkyl]-substituted-2-oxopiperazin-1-yl(lower)alkyl,
  amino(lower)alkyl-substituted imidazol-1-yl($C_2$-$C_3$)alkyl,
  amino(lower)alkyl-substituted imidazol-5-yl(lower)alkyl,
  amino(lower)alkyl-substituted imidazol-2-yl(lower)alkyl,
  amino(lower)alkyl-substituted pyrazol-4-(or 5-)yl(lower)alkyl,
  amino(lower)alkyl-substituted pyrazol-1-ylethyl,
  amino(lower)alkyl-substituted triazolyl(lower)alkyl,
  amino(lower)alkyl-substituted pyrimidinyl(lower)alkyl,
  amino(lower)alkyl-substituted dihydropyrimidinyl(lower)alkyl,
  or amino(lower)alkyl-substituted 2,3-dihydroimidazo[1,2-b]pyrazol-1-ylethyl, each of which is further optionally substituted by suitable substituent(s), $R_a^5$ is imino-protective group,
$R^6$ is lower alkyl, carbamoyl(lower)alkyl, N,N-di(lower)alkylcarbamoyl(lower)alkyl, N-[hydroxy(lower)alkyl]carbamoyl(lower)alkyl or protected amino(lower)alkyl, A is lower alkylene,
X is an acid residue.

The compound (III) used in the Process 1 is new and can be prepared, for example, by the following methods or a conventional manner.

Method A:

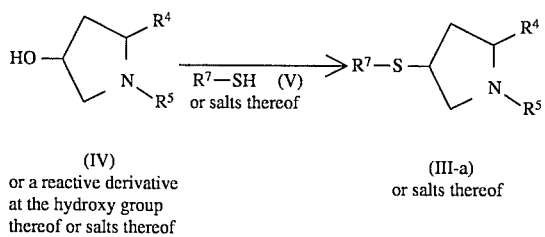

(IV)
or a reactive derivative
at the hydroxy group
thereof or salts thereof (III-a)
or salts thereof Method B:

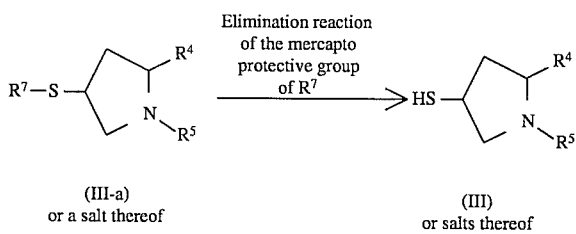

(III-a)
or a salt thereof (III)
or salts thereof in which $R^4$, $R^5$ and A are each as defined above, and $R^7$ is mercapto-protective group.

In the above and subsequent descriptions of the present specification, suitable examples and illustrations of the various definitions which the present invention includes within the scope thereof are explained in detail as follows.

The term "lower" is intended to mean 1 to 6, preferably 1 to 4 carbon atom(s), unless otherwise indicated.

Suitable "hydroxy(lower)alkyl" and hydroxy(lower)alkyl moiety in the term "N-[hydroxy(lower)alkyl]carbamoyl-(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy($C_1$-$C_4$)alkyl and the most preferable one may be 2-hydroxyethyl and hydroxymethyl.

Suitable "lower alkyl", and "lower alkyl" moiety may include straight or branched one such as methyl, ethyl, propyl, isopropyl, butyl, t-butyl, pentyl, hexyl, and the like, in which more preferable example may be $C_1$-$C_4$ alkyl and the most preferable one may be methyl, ethyl and propyl.

Preferable example of carbamoyl(lower)alkyl may be carbamoyl($C_1$-$C_4$)alkyl and the most preferable one may be carbamoylmethyl.

Preferable example of mono- or di(lower)alkylcarbamoyl(lower)alkyl may be N,N-di($C_1$-$C_4$)alkylcarbamoyl-($C_1$-$C_4$)alkyl and the most preferable example may be N,N-dimethylcarbamoylmethyl.

Preferable example of N-[hydroxy(lower)alkyl]-carbamoyl(lower)alkyl may be N-[hydroxy($C_1$-$C_4$)alkyl]carbamoyl($C_1$-$C_4$)alkyl and the most preferable one may be N-(2-hydroxyethyl)carbamoylmethyl.

Suitable "mercapto-protective group" may include acyl such as aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl, isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aromatic acyl may include $C_6$-$C_{10}$ aroyl (e.g. benzoyl, toluoyl, xyloyl, etc.), N-($C_6$-$C_{10}$)arylcarbamoyl (e.g. N-phenylcarbamoyl, N-tolylcarbamoyl, N-naphthylcarbamoyl, etc.), $C_6$-$C_{10}$ arenesulfonyl (e.g. benzenesulfonyl, tosyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl (e.g. nitrobenzyloxycarbonyl, etc.), and the like.

More preferable example of "mercapto-protective group" thus defined may be $C_1$-$C_4$ alkanoyl and $C_6$-$C_{10}$ aroyl and the most preferable one may be acetyl and benzoyl.

Suitable "acid residue" may include an inorganic acid residue such as azido, halogen (e.g. chlorine, bromine, fluorine or iodine), and the like, an organic acid residue such as acyloxy (e.g. benzenesulfonyloxy, tosyloxy, methanesulfonyloxy, etc.), and the like, in which more preferable example may be halogen and the most preferable one may be iodine.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, t-butyl ester, pentyl ester, hexyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1-(or 2-)acetoxyethyl ester, 1-(or 2- or 3-)acetoxypropyl ester, 1-(or 2- or 3- or 4-)acetoxybutyl ester, 1-(or 2-)propionyloxyethyl ester, 1-(or 2- or 3-)propionyloxypropyl ester, 1-(or 2-)butyryloxyethyl ester, 1-(or 2-)isobutyryloxyethyl ester, 1-(or 2-)pyvaloyloxyethyl ester, 1-(or 2-)hexanoyloxyethyl ester, isobutyryloxymethyl ester, 2-ethylbutyryloxymethyl ester, 3,3-dimethylbutyryloxymethyl ester, 1-(or 2-)pentanoyloxyethyl ester, etc.], lower alkanesulfonyl(lower)alkyl ester (e.g. 2-mesylethyl ester, etc.), mono(or di or tri)halo(lower)alkyl ester (e.g. 2-iodoethyl ester, 2,2,2-trichloroethyl ester, etc.); lower alkoxycarbonyloxy(lower)alkyl ester [e.g. methoxycarbonyloxymethyl ester, ethoxycarbonyloxymethyl ester, propoxycarbonyloxymethyl ester, t-butoxycarbonyloxymethyl ester, 1-(or 2-)methoxycarbonyloxyethyl ester, 1-(or 2-)ethoxycarbonyloxyethyl ester, 1-(or 2-) isopropoxycarbonyloxyethyl ester, etc.], phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); aryl ester which may have at least one suitable substituent(s) (e.g. phenyl ester, 4-chlorophenyl ester, tolyl ester, t-butylphenyl ester, xylyl ester, mesityl ester, cumenyl ester, etc.); phthalidyl ester; and the like.

More preferable example of the protected carboxy thus defined may be $C_2$-$C_4$ alkenyloxycarbonyl and phenyl(or nitrophenyl)($C_1$-$C_4$)alkoxycarbonyl, and the most preferable one may be allyloxycarbonyl.

Suitable "imino-protective group" may include acyl as mentioned in the explanation of mercapto-protective group, in which more preferable example may be $C_2$-$C_4$ alkenyloxycarbonyl and the most preferable one may be allyloxycarbonyl.

Suitable "lower alkenyloxycarbonyl" may be the same as those explained in "protected carboxy" and the preferable example may be $C_2$-$C_6$ alkenyloxycarbonyl and the most preferable one may be allyloxycarbonyl.

Suitable "lower alkoxy(lower)alkyl" may be aforementioned hydroxy($C_1$-$C_4$)alkyl, wherein the hydroxy group is substituted by aforementioned $C_1$-$C_4$ alkyl, and the most preferable example may be methoxymethyl.

Preferable example of amino(lower)alkyl may be amino($C_1$-$C_4$)alkyl and the most preferable example may be 3-aminopropyl.

Suitable "protected amino(lower)alkyl" may be aforementioned amino(lower)alkyl, wherein the amino group is protected by a suitable amino-protective group such as acyl as explained in marcapto-protective group, in which more preferable example may be lower alkenyloxycarbonylamino(lower)alkyl and the most preferable one may be 3-(allyloxycarbonylamino)propyl.

Suitable lower alkenyl moiety of "carbamoyl(lower)alkenyl" may be straight or branched one such as vinyl, allyl, isopropenyl, 1-propenyl, butenyl, pentenyl, hexenyl, and the like.

Preferable example of "carbamoyl(lower)alkenyl" may be carbamoyl($C_2$-$C_4$)alkenyl, and the most preferable one may be 2-carbamoylethenyl.

Preferable substituent(s) of optionally substituted pyridyl(lower)alkyl, optionally N-substituted 2-oxopiperazin-1-yl(lower)alkyl, optionally substituted imidazol-1-yl($C_2$-$C_3$)alkyl, optionally substituted imidazol-5-yl(lower)alkyl, optionally substituted imidazol-2-yl(lower)alkyl, optionally substituted pyrazol-4(or 5)-yl(lower)alkyl, optionally substituted pyrazol-1-ylethyl, optionally substituted triazolyl(lower)alkyl, optionally substituted pyrimidinyl(lower)alkyl, optionally substituted dihydropyrimidinyl(lower)alkyl, or optionally substituted 2,3-dihydroimidazo[1,2-b]pyrazol-1-ylethyl may be lower alkyl as mentioned above, carbamoyl(lower)alkyl as mentioned above, mono- or di(lower)alkylcarbamoyl(lower)alkyl as mentioned above, N-[hydroxy(lower)alkyl]carbamoyl(lower)alkyl as mentioned above, lower alkenyloxycarbonyl as mentioned above, carbamoyl, hydroxy(lower)alkyl as mentioned above, lower alkoxy(lower)alkyl as mentioned above, cyano, amino(lower)alkyl as mentioned above, protected amino(lower)alkyl as mentioned above, and carbamoyl(lower)alkenyl as mentioned above.

Suitable example of optionally substituted pyridyl(lower)alkyl may be pyridyl(lower)alkyl optionally substituted by the group consisting of lower alkyl, carbamoyl(lower)alkyl, mono- or di(lower)alkylcarbamoyl(lower)alkyl and N-[hydroxy(lower)alkyl]carbamoyl(lower)alkyl, and more preferable one may be pyridyl($C_1$-$C_2$)alkyl optionally substituted by the group consisting of methyl, carbamoylmethyl, N,N-dimethylcarbamoylmethyl and N-(2-hydroxyethyl)carbamoylmethyl.

Suitable example of optionally N-substituted 2-oxopiperazin-1-yl(lower)alkyl may be 2-oxopiperazin-1-yl(lower)alkyl optionally N-substituted by the group consisting of lower alkenyloxycarbonyl and lower alkyl, and more preferable one may be 2-oxopiperazin-1-ylmethyl optionally N-substituted by the group consisting of methyl and allyloxycarbonyl.

Suitable example of optionally substituted imidazol-1-yl($C_2$-$C_3$)alkyl may be imidazol-1-yl($C_2$-$C_3$)alkyl optionally substituted by the group consisting of lower alkyl, carbamoyl, carbamoyl(lower)alkyl, hydroxy(lower)alkyl, lower alkoxy(lower)alkyl, cyano, amino(lower)alkyl, protected amino(lower)alkyl and carbamoyl(lower)alkenyl, and more preferable example may be imidazol-1-yl($C_2$-$C_3$)alkyl optionally substituted by the group consisting of methyl, carbamoyl, carbamoylmethyl and hydroxymethyl.

Suitable example of optionally substituted imidazol-5-yl(lower)alkyl may be imidazol-5-yl(lower)alkyl optionally substituted by lower alkyl, and more preferable example may be imidazol-5-ylmethyl optionally substituted by lower alkyl.

Suitable example of optionally substituted imidazol-2-yl(lower)alkyl may be imidazol-2-yl(lower)alkyl optionally substituted by the group consisting of lower alkyl and carbamoyl(lower)alkyl, and more preferable example may be imidazol-2-yl($C_1$-$C_3$)alkyl optionally substituted by the group consisting of methyl and carbamoylmethyl.

Suitable example of optionally substituted pyrazol-4-(or 5-)yl(lower)alkyl may be pyrazol-4-(or 5-)yl(lower)alkyl optionally substituted by lower alkyl, and more preferable example may be pyrazol-4-(or 5-)ylmethyl optionally substituted by methyl.

Suitable example of optionally substituted pyrazol-1-ylethyl may be pyrazol-1-ylethyl optionally substituted by lower alkyl, and more preferable example may be 2-(pyrazol-1-yl)ethyl optionally substituted by methyl.

Suitable example of optionally substituted triazolyl(lower) alkyl may be 1,2,4-(or 1,2,3-)triazolyl(lower)alkyl optionally substituted by lower alkyl, and more preferable example may be 1,2,4-triazol-1-(or 5-)yl($C_1$-$C_2$)alkyl or 1,2,3-triazol-1-ylmethyl, each of which is optionally substituted by methyl.

Suitable example of optionally substituted pyrimidinyl(lower)alkyl may be pyrimidinyl(lower)alkyl optionally substituted by lower alkyl, and more preferable example may be pyrimidin-2- (or 5- )ylmethyl optionally substituted by methyl.

Suitable example of optionally substituted dihydropyrimidinyl(lower)alkyl may be dihydropyrimidinyl(lower)alkyl optionally substituted by lower alkyl, and more preferable example may be 1,6-(dihydropyrimidin-5-yl)methyl) optionally substituted by methyl.

Suitable example of optionally substituted (2,3-dihydroimidazo[1,2-b]pyrazol-1-yl)ethyl may be (2,3-dihydroimidazo[1,2-b]pyrazol-1-yl)ethyl optionally substituted by lower alkyl, and more preferable example may be 2-(2,3-dihydroimidazo[1,2-b]pyrazol-1-yl)ethyl optionally substituted by methyl.

Suitable "lower alkylene" means straight or branched one such as methylene, ethylene, trimethylene, methylethylene, and the like, in which more preferable example may be $C_1$-$C_4$ alkylene and the most preferable one may be methylene.

Preferable examples of $R^1$, $R^2$, $R^3$, $R^4$ and $R^5$ are as follows.

$R^1$ is carboxy or esterified carboxy,
$R^2$ is 1-hydroxyethyl,
$R^3$ is methyl,
$R^4$ is pyridyl(lower)alkyl optionally substituted by the group consisting of lower alkyl, carbamoyl(lower)alkyl, mono- or di(lower)alkylcarbamoyl(lower)alkyl and N-[hydroxy(lower)alkyl]carbamoyl(lower)alkyl; 2-oxopiperazin-1-yl(lower)alkyl optionally N-substituted by the group consisting of lower alkenyloxycarbonyl and lower alkyl; imidazol-1-yl($C_2$-$C_3$)alkyl optionally substituted by the group consisting of lower alkyl, carbamoyl, carbamoyl(lower)alkyl and hydroxy(lower)alkyl; imidazol-2-yl(lower)alkyl optionally substituted by the group consisting of lower alkyl and carbamoyl(lower)alkyl; or pyrazol-4-yl(lower)alkyl optionally substituted by lower alkyl; and $R^5$ is hydrogen or esterified carboxy, or
$R^1$ is carboxy or esterified carboxy,
$R^2$ is hydroxy(lower)alkyl,
$R^3$ is lower alkyl,
$R^4$ is pyridyl(lower)alkyl optionally substituted by the group consisting of lower alkyl, carbamoyl(lower)alkyl, mono- or di(lower)alkylcarbamoyl(lower)alkyl and N-[hydroxy(lower)alkyl]carbamoyl(lower)alkyl;

2-oxopiperazin-1-yl(lower)alkyl optionally N-substituted by the group consisting of lower alkenyloxycarbonyl and lower alkyl;

imidazol-1-yl(C2-C3)alkyl optionally substituted by the group consisting of lower alkyl, carbamoyl, carbamoyl(lower)alkyl, hydroxy(lower)alkyl, lower alkoxy(lower)alkyl, cyano, amino(lower)alkyl, protected amino(lower)alkyl and carbamoyl(lower)alkenyl;

imidazol-5-yl(lower)alkyl optionally substituted by lower alkyl;

imidazol-2-yl(lower)alkyl optionally substituted by the group consisting of lower alkyl and carbamoyl(lower)alkyl;

pyrazol-4-(or 5-)yl(lower)alkyl optionally substituted by lower alkyl;

pyrazol-1-ylethyl optionally substituted by lower alkyl;

1,2,4-(or 1,2,3-)triazolyl(lower)alkyl optionally substituted by lower alkyl;

pyrimidinyl(lower)alkyl optionally substituted by lower alkyl;

dihydropyrimidinyl(lower)alkyl optionally substituted by lower alkyl;

or (2,3-dihydroimidazo[1,2-b]pyrazol-1-yl)ethyl optionally substituted by lower alkyl; and $R^5$ is hydrogen or esterified carboxy.

More preferable examples of $R^1$, $R^2$, $R^3$, $R^4$ and $R^5$ are as follows.

$R^1$ is carboxy,
$R^2$ is 2-hydroxyethyl,
$R^3$ is methyl,
$R^4$ is pyridyl($C_1$-$C_2$)alkyl optionally substituted by the group consisting of methyl, carbamoylmethyl, N,N-dimethylcarbamoylmethyl and N-(2-hydroxyethyl)carbamoylmethyl;

2-oxopiperazin-1-ylmethyl optionally N-substituted by the group consisting of allyloxycarbonyl and methyl;

imidazol-1-yl($C_2$-$C_3$)alkyl optionally substituted by the group consisting of methyl, carbamoyl, carbamoylmethyl, hydroxymethyl, methoxymethyl, cyano, aminopropyl, (allyloxycarbonylamino)propyl and carbamoylethenyl;

imidazol-5-ylmethyl optionally substituted by methyl;

imidazol-2-yl($C_2$-$C_3$)alkyl optionally substituted by the group consisting of methyl and carbamoylmethyl;

pyrazol-4-(or 5-)ylmethyl optionally substituted by methyl;

2-(pyrazol-1-yl)ethyl optionally substituted by methyl;

1,2,4-triazolyl($C_1$-$C_2$)alkyl optionally substituted by methyl;

1,2,3-triazol-1-ylethyl optionally substituted by methyl;

pyrimidin-2-(or 5-)ylmethyl optionally substituted by methyl;

(1,6-dihydropyrimidinyl)(lower)alkyl optionally substituted by methyl;

or 2-(2,3-dihydroimidazo[1,2-b]pyrazol-1-yl)ethyl optionally substituted by methyl; and $R^5$ is hydrogen.

The processes for the preparation of the object compound (I) of the present invention are explained in detail in the following.

Examples of the object compound (I) of the present invention are:

(4R,5S,6S)-6-[(1R)-1-hydroxyethyl]-4-methyl-3-[(2R,4S)-2-{2-(1-methyl-3-pyridinio)ethyl}pyrrolidin-4-yl]thio-7-oxo-1-azabicyclo[3.2.0]hept-2-ene-2-carboxylic acid chloride, (4R,5S,6S)-3-[(2R,4S)-2-[2-{1-(N,N-dimethylcarbamoylmethyl)-3-pyridinio}ethyl]pyrrolidin-4-yl]thio-6-[(1R)-1-hydroxyethyl]-4-methyl-7-oxo-1-azabicyclo-[3.2.0]hept-2-ene-2-carboxylic acid chloride, (4R,5S,6S)-6-[(1R)-1-hydroxyethyl]-4-methyl-3-[(2R,4S)-2-{2-(1-carbamoylmethyl-3-pyridinio)ethyl}-pyrrolidin-4-yl]thio-7-oxo-1-azabicyclo[3.2.0]hept-2-ene-2-carboxylic acid chloride, (4R,5S,6S)-6-[(1R)-1-hydroxyethyl]-4-methyl-3-[(2R,4S)-2-{2-(1-carbamoylmethyl-4-pyridinio)ethyl}-pyrrolidin-4-yl]thio-7-(1-azabicyclo[3.2.0]hept-2-ene-2-carboxylic acid chloride, (4R,5S,6S)-6-[(1R)-1-hydroxyethyl]-3-[(2R,4S)-2-[2-[1-{N-(2-hydroxyethyl)carbamoylmethyl}-3-pyridinio]ethyl]pyrrolidin-4-yl]thio-4-methyl-7-oxo-1-azabicyclo[3.2.0]hept-2-ene-2-carboxylic acid chloride, (4R,5S,6S)-6-[(1R)-1-hydroxyethyl]-4-methyl-3-[(2R,4S)-2-{2-(1-methyl-2-pyridinio)ethyl}pyrrolidin-4-yl]thio-7-oxo-1-azabicyclo[3.2.0]hept-2-ene-2-carboxylic acid chloride, (4R,5S,6S)-6-[(1R)-1-hydroxyethyl]-3-[2R,4S)-2-{2-(1-carbamoylmethyl-2-pyridinio)ethyl}pyrrolidin-4-yl]thio-4-methyl-7-oxo-1-azabicyclo[3.2.0]hept-2-ene-2-carboxylic acid chloride, (4R,5S,6)-3-[(2R,4S)-2-(1-methyl-2-pyridinio)methylpyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-3-[(2R,4S)-2-(1-methyl-3-pyridiniomethyl)pyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-6-[(1R)-1-hydroxyethyl]-3-[(2R,4S)-2-(1-methyl-4-pyridiniomethyl)pyrrolidin-4-yl]thio-4-methyl-7-oxo-1-azabicyclo[3.2.0]hept-2-ene-2-carboxylic acid chloride, (4R,5S,6S)-3-[(2R,4S)-2-(1-methyl-2-pyridinio)methylpyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-3-[(2R,4S)-2-{2-(1-pyridinio)ethyl}pyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-3-[(2R,4S)-2-(1,2-dimethyl-4-pyrazoliomethyl)pyrrolidin-4-yl]thio-6-[(1R)-1-hydroxyethyl]-4-methyl-7-oxo-1-azabicyclo[3.2.0]-hept-2-ene-2-carboxylic acid chloride, and (4R,5S,6S)-3-[(2R,4S)-2-(1,2-dimethyl-5-pyrazoliomethyl)pyrrolidin-4-yl]thio-6-[(1R)-1-hydroxyethyl]-4-methyl-7-oxo-1-azabicyclo[3.2.0]-hept-2ene-2-carboxylic acid chloride.

(1) Process 1:

The compound (I) or salts thereof can be prepared by reacting the compound (II) or a reactive derivative at the oxo group thereof or salts thereof with the compound (III) or salts thereof.

Suitable salts of the compound (II) may be salts with bases such as those given for the compound (I).

The reactive derivative at the oxo group of the compound (II) can be represented by the following formula (II'), which is preferably used in this reaction and can be prepared by reacting the compound (II) or salts thereof with an acylating agent.

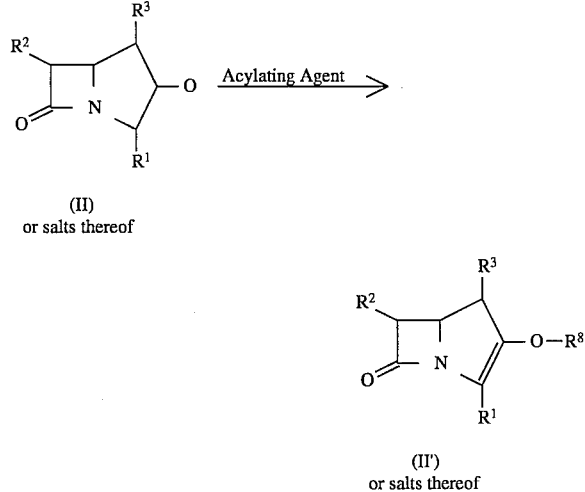

in which $R^1$, $R^2$ and $R^3$ are each as defined above, and $R^8$ is acyl as exemplified for the imino-protective group and further O,O-substituted phosphono derived from, for example, organic phosphoric acid mentioned hereinbelow.

Suitable acylating agents may include conventional ones which can introduce the acyl group as mentioned above into the compound (II), and preferable acylating agents may be organic sulfonic or phosphoric acid or its reactive derivative such as acid halide, acid anhydride, and the like, for example, arenesulfonyl halide (e.g. benzenesulfonyl chloride, p-toluenesulfonyl chloride, p-nitrobenzenesulfonyl chloride, p-bromobenzenesulfonyl chloride, etc.), arenesulfonic anhydride (e.g. benzenesulfonic anhydride, p-toluenesulfonic anhydride, p-nitrobenzenesulfonic anhydride, etc.), lower alkanesulfonyl halide which may have additional halogen (e.g. methanesulfonyl chloride, ethanesulfonyl chloride, trifluoromethanesulfonyl chloride, etc.), lower alkanesulfonic anhydride which may have halogen (e.g. methanesulfonic anhydride, ethanesulfonic anhydride, trifluoromethanesulfonic anhydride, etc.), di(lower)alkyl phosphorohaloridate (e.g. diethyl phosphorochloridate, etc.), diaryl phosphorohaloridate (e.g. diphenyl phosphorochloridate, etc.), and the like.

This acylation reaction is usually carried out in a conventional solvent which does not adversely influence the reaction such as acetone, dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

When the acylating agent is used in a free acid form or its salt form in this reaction, the reaction is preferably carried out in the presence of a conventional condensing agent such as carbodiimide compound [e.g. N,N'-diethylcarbodiimide, N,N'-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)carbodiimide, N-ethyl-N'-(3-dimethylaminopropyl)carbodiimide, etc.]; N,N'-carbonyldiimidazole, N,N'-carbonylbis(2-methylimidazole); keteneimine compound (e.g. pentamethyleneketene-N-cyclohexylimine, diphenylketene-N-cyclohexylimine, etc.); ethoxyacetylene; 1-alkoxy-1-chloroethylene; ethyl polyphosphate; isopropylpolyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; and the like.

This acylation reaction may be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compound [e.g. pyridine, picoline, lutidine, N,N-di(lower)alkylaminopyridine such as N,N-dimethylaminopyridine, etc.], quinoline, N-lower alkylmorpholine (e.g. N-methylmorpholine, etc.), N,N-di(lower)alkylbenzylamine (e.g. N,N-dimethylbenzylamine, etc.), alkali metal alkoxide (e.g. sodium methoxide, sodium ethoxide, potassium butoxide, etc.), and the like.

The reaction temperature of this acylation reaction is not critical and the reaction is usually carried out under from cooling to warming.

With regard to the compound (II), it is to be noted that the 3,7-dioxo-1-azabicyclo[3.2.0]heptane ring system of the following formula (IIA) is well known to lie to tautomeric relation with the 3-hydroxy-7-oxo-1-azabicyclo[3.2.0]hept-2-ene ring system of the following formula (IIB), and accordingly, it is to be understood that both of these ring systems are substantially the same.

(IIA)          (IIB)

The compound (II') or salts thereof can be used with or without isolation for the subsequent reaction with the compound (III) or salts thereof.

Suitable salts of the compound (III) may be the same as those for the compound (I) and silver salt.

The reaction of the compound (II) or its reactive derivative or salts thereof with the compound (III) or salts thereof can be carried out in the presence of an organic or inorganic base such as those given in the explanation of the acylation reaction as stated above.

This reaction can be carried out in a conventional solvent which does not adversely influence the reaction such as those given in the explanation of the acylation reaction.

The reaction temperature is not critical and the reaction is usually carried out under from cooling to warming.

(2) Process 2:

The compound (I-b) or salts thereof can be prepared by subjecting the compound (I-a) or salts thereof to removal reaction of the carboxy-protective group on $R_a^1$.

Suitable salts of the compounds (I-a) and (I-b) may be the same as those for the compound (I).

The present reaction is usually carried out by a conventional method such as hydrolysis, reduction, and the like.

(i) Hydrolysis:

Hydrolysis is preferably carried out in the presence of a base or an acid. Suitable base may include an alkalimetal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

In case that the hydroxy-protective group is tri(lower)alkylsilyl, the hydrolysis can be carried out in the presence of tri(lower)alkylammonium halide (e.g. tributylammonium fluoride, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction:

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenyl phosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoylacetate, 2-methyl-3-oxovaleric acid, etc.), a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

This reaction can also be carried out in the presence of a conventional reducing agent such as sodium borohydride, tributyltin hydride, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, acetic acid, etc., or a mixture thereof.

The removal reaction can be selected according to the kind of carboxy-protective group to be removed.

The present process includes within the scope thereof a case that the imino-protective group of $R^5$ is removed at the same time during the reaction.

(3) Process 3:

The compound (I-d) or salts thereof can be prepared by subjecting the compound (I-c) or salts thereof to removal reaction of the imino-protective group on $R_a^5$.

Suitable salts of the compounds (I-c) and (I-d) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy-protective group on $R^1$ is removed at the same time during the reaction.

(4) Process 4:

The compound (I) or salts thereof can be prepared by reducing the compound (I-e) or salts thereof.

Suitable salts of the compound (I-e) may be the same as those for the compound (I).

The method of reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the starting compound (I-e) constitutes intermolecular quaternary salt(s), the counter anion may be changed in the resulting compound (I-f).

(5) Process 5:

The compound (I-g) or salts thereof can be prepared by reacting the compound (I-f) or salts thereof with the compound (IV).

Suitable salts of the compounds (I-f) and (I-g) may be the same as those for the compound (I).

This reaction is usually carried out in a conventional solvent which does not adversely influence the reaction such as water, dioxane, tetrahydrofuran, acetone, acetonitrile, etc., or a mixture thereof.

The reaction temperature is not critical, and the reaction is usually carried out under from cooling to warming.

(6) Process 6:

The compound (I-i) or salts thereof can be prepared by subjecting the compound (I-h) or salts thereof to removal reaction of the amino-protective group on $R_c^4$.

Suitable salts of the compounds (I-h) and (I-i) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy-protective group on $R^1$ and/or imino-protective group of $R^5$ are removed at the same time during the reaction.

(7) Process 7:

The compound (I-k) or salts thereof can be prepared by reducing the compound (I-j) or salts thereof.

Suitable salts of the compounds (I-j) and (I-k) may be the same as those for the compound (I).

The method of reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the starting compound (I-e) constitutes intermolecular quaternary salt(s), the counter anion may be changed in the resulting compound (I-f).

Method A and B for preparing the new starting compound (III) or salts thereof are explained in detail in the following.

Method A

The compound (III-a) or salts thereof can be prepared by reacting the compound (IV) or a reactive derivative at the hydroxy group thereof or salts thereof with the compound (V) or salts thereof.

Suitable salts of the compounds (III-a) and (IV) may be the same as those for the compound (I).

Suitable salts of the compound (V) may be salts with bases such as those given for the compound (I).

Suitable reactive derivative at the hydroxy group of the compound (IV) may include a conventional one such as halide (e.g. chloride, bromide, iodide, etc.), sulfonate (e.g. methanesulfonate, benzenesulfonate, toluenesulfonate, etc.), and the like, in which more preferable example may be sulfonate.

The starting compound (IV) of this method is new and can be prepared by the methods described in the Preparations mentioned below.

Preferable example of the compound (V) may be ar(lower)alkanethiol such as mono- or di- or triphenyl(lower)alkanethiol (e.g. phenylmethanethiol, diphenylmethanethiol, triphenylmethanethiol, etc.), thio(lower)alkanoic S-acid (e.g. thioacetic S-acid, etc.) or salts thereof, thioarenoic S-acid or salts thereof (e.g. thiobenzoic S-acid, etc.), and the like, in which more preferable example may be triphenyl($C_1$-$C_4$)alkanethiol, thio($C_1$-$C_4$)alkanoic S-acid or alkali metal salts thereof and thio($C_6$-$C_{10}$)arenoic S-acid or alkali metal salts thereof, and the most preferable one may be triphenylmethanethiol, thioacetic S-acid and potassium thioacetate.

In case that the compound (V) may be ar(lower)alkanethiol, the starting compound (IV) of the present reaction is preferably used in the form of its reactive derivative at the hydroxy group, and in such a case, this reaction is usually carried out in the presence of an organic or inorganic base such as those exemplified in the explanation of Process 2.

In case that suitable example of compound (V) may be thio(lower)alkanoic S-acid or thioarenoic S-acid, this reaction is preferably carried out in the presence of a conventional condensing agent such as combination of triarylphosphine (e.g. triphenylphosphine, etc.) and di(lower)alkyl azodicarboxylate (e.g. diethyl azodicarboxylate, etc.).

This reaction is usually carried out in a conventional solvent which does not adversely influence the reaction such as dichloromethane, methanol, ethanol, propanol, pyridine, N,N-dimethylformamide, 4-methyl-2-pentanone, tetrahydrofuran, etc., or a mixture thereof.

The reaction temperature is not critical and the reaction is usually carried out under from cooling to warming.

In this method, the configuration on the carbon atom substituted with the hydroxy group of the compound (IV) is inverted in the compound (III-a).

(B) Method B

The compound (III) or salts thereof can be prepared by subjecting the compound (III-a) or salts thereof to elimination reaction of the mercapto-protective group.

This elimination reaction can be carried out by a conventional method as described below, which can be selected according to the kind of mercapto-protective group to be eliminated.

In case that the protective groups may be ar(lower)alkyl group, it can generally be eliminated by treating, for example, with a silver compound (e.g. silver nitrate, silver carbonate, etc.).

The reaction with the silver compound as stated above is preferably carried out in the presence of an organic base (e.g. pyridine, etc.).

The resultant silver salt of compound (III) can be transformed into its alkali metal salt, if necessary, by reacting with alkali metal halide (e.g. sodium iodide, potassium iodide, etc.).

Further, in case that the protective groups may be acyl group, it can generally be eliminated by solvolysis such as hydrolysis using an acid or base, alcoholysis using a base, and the like.

Suitable acid or base used in these reactions may be the same such as those given in the explanation of hydrolysis of the Process 2.

The hydrolysis is usually carried out in a conventional solvent which does not adversely influence the reaction such as water, alcohol (e.g. methanol, ethanol, etc.), pyridine, N,N-dimethylformamide, etc., or a mixture thereof, and further in case that the base or acid to be used is in liquid, it can also be used as a solvent.

The alcoholysis is usually carried out in a conventional alcohol such as methanol, ethanol, and the like.

The reaction temperature is not critical and the reaction is usually carried out under from cooling to warming.

The object compounds obtained according to the above Processes can be isolated and purified in a conventional manner, for example, extraction, precipitation, fractional crystallization, recrystallization, chromatography, and the like.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

In the present invention, the object compound (I) possessing more potent antimicrobial activity can be represented by the following formula:

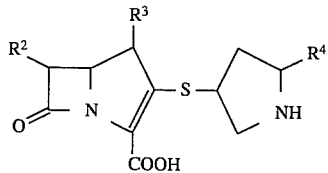

which $R^2$, $R^3$, $R^4$ and A are each as defined above, and pharmaceutically acceptable salts thereof.

Particularly, the compound (I) possessing the most potent antimicrobial activity can be represented by the following formula:

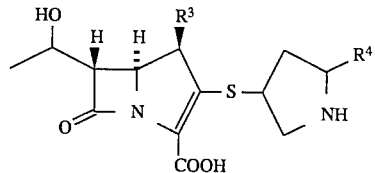

in which $R^3$, $R^4$ and A are each as defined above, and pharmaceutically acceptable salts thereof.

Now in order to show the utility of the object compound (I), the test data on antimicrobial activity of the representative compound of the compound (I) of this invention is shown in the following.

in vitro Antimicrobial Activity

Test Method:

in vitro Antimicrobial Activity was determined by the two-fold agar-plate dilution method as described below.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of µg/ml after incubation at 37° C. for 20 hours.

Test Compound:

The compound of Example 4-4).

Test Result:

| Test Strain | MIC (µg/ml) |
|---|---|
| *P. aeruginosa* IAM1095 | 0.78 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 2000 mg, of the object compound (I) of the present invention may be used in treating diseases infected by pathogenic microorganisms.

The following Preparations and Examples are given for the purpose of illustrating this invention in more detail.

Preparation 1-1)

To a solution of oxalyl chloride (2.53 ml) and dichloromethane (90 ml) was dropwise added dimethyl sulfoxide (4.31 ml) at –40° C.—50° C. with stirring and the mixture was stirred at the same temperature for 5 minutes. To the solution was added dropwise a solution of (2S,4R)-1-allyloxycarbonyl-4-t-butyldimethylsiloxy-2-(hydroxymethyl)pyrrolidine (8.70 g) in dichloromethane (45 ml) at –40° C.—50° C. After 10 minutes with stirring, triethylamine (19.2 ml) was dropwise added to the solution and the mixture was stirred at 0°–10° C. for 30 minutes. The insoluble material was filtered off and the filtrate was washed successively with 1N hydrochloric acid, water, saturated aqueous sodium bicarbonate and saturated aqueous sodium chloride, dried over anhydrous magnesium sulfate and evaporated in vacuo to give a residue of (2S, 4R)-1-allyloxycarbonyl-4-t-butyldimethylsiloxy-2-formylpyrrolidine.

On the other hand, to a solution of 3-picolyltriphenylphosphonium chloride (11.8 g) in a mixture of tetrahydrofuran (60 ml) and dimethyl sulfoxide (60 ml) was added portionwise potassium t-butoxide (3.40 g) at 0°~5° C. with stirring and then stirred at the same temperature for 30 minutes. The reaction mixture was dropwise added to a solution of the residue obtained above in tetrahydrofuran (100 ml) at 0° C. and the mixture was stirred at the same temperature for 2 hours. To the reaction mixture was added ethyl acetate and the mixture was washed successively with 1N hydrochloric acid, saturated aqueous sodium bicarbonate, saturated aqueous sodium chloride, dried over anhydrous magnesium sulfate and evaporated in vacuo. The resulting residue was chromatographed on silica gel (250 g) eluting with a mixture of n-hexane and ethyl acetate (2:1, V/V). The first fractions were collected and evaporated in vacuo to give (2S,4R) -1-allyloxycarbonyl-4-t-butyldimethylsiloxy-2-[(Z)-2-(pyridin-3-yl)vinyl]pyrrolidine (4.60 g).

NMR (CDCl$_3$, δ): 0.06 (6H, s), 0.80 (9H, s), 1.65–1.90 (1H, m), 1.98–2.10 (1H, m), 3.34–3.56 (2H, m), 4.30–4.39 (1H, m), 4.40–4.56 (2H, m), 4.70–4.90 (1H, m), 4.95–5.55 (2H, m), 5.64 (1H, dd, J=9.4 Hz, J=11.6 Hz), 5.70–6.00 (1H, m), 6.25–6.43 (1H, m), 7.17–7.25 (1H, m), 7.40–7.80 (1H, m), 8.40–8.50 (2H, m)

The second fractions were collected and evaporated in vacuo to give (2S,4R)-1-allyloxycarbonyl-4-t-butyldimethylsiloxy-2-[(E)-2-(pyridin-3-yl)vinyl]pyrrolidine (3.73 g).

NMR (CDCl$_3$, δ): 0.06 (6H, s), 0.82 (9H, s), 1.76–1.90 (1H, m), 1.96–2.10 (1H, m), 3.35–3.50 (2H, m), 4.25–4.60 (4H, m), 4.90–5.25 (2H, m), 5.60–5.92 (1H, m), 6.08 (1H, broad d), 6.25–6.50 (1H, m), 7.08–7.20 (1H, m), 7.79 (1H, broad d, J=7.9 Hz), 8.36 (1H, broad d, J=3.97 Hz), 8.49 (1H, broad s)

Preparation 1-2)

(2S,4R)-1-Allyloxycarbonyl-4-hydroxy-2-[(E)-2-(pyridin-3-yl)vinyl]pyrrolidine was obtained in substantially the same manner as that of Preparation 2-2).

NMR (CDCl$_3$, δ): 1.90–2.05 (1H, m), 2.15–2.35 (1H, m), 3.58–3.80 (2H, m), 4.45–4.80 (4H, m), 5.05–5.40 (2H, m), 5.75–6.05 (1H, m), 6.10–6.30 (1H, broad dd), 6.35–6.60 (1H, m), 7.20–7.30 (1H, m), 7.68 (1H, d, J=7.87 Hz), 8.43 (1H, d, J=3.99 Hz), 8.56 (1H, d, J=1.84 Hz)

Preparation 1-3)

(2S,4R)-1-Allyloxycarbonyl-4-methylsulfonyloxy-2-[(E)-2-(pyridin-3-yl)vinyl]pyrrolidine was obtained in substantially the same manner as that of Preparation 2-3).

NMR (CDCl$_3$, δ): 2.00 –2.21 (1H, m), 2.52–2.68 (1H, m), 3.07 (3H, s), 3.72 (1H, dd, J=4.18 Hz, J=12.9 Hz), 3.90–4.10 (1H, m), 4.50–4.80 (3H, m), 5.10–5.35 (3H, m), 5.75–6.00 (1H, m), 6.19 (1H, dd, J=8.2 Hz, J=17.1 Hz), 6.50 (1H, broad d, J=17.1 Hz), 7.23–7.30 (1H, m), 7.69 (1H, d, J=7.90 Hz), 8.49 (1H, d), 8.59 (1H, s)

Preparation 1-4)

(2S,4S)-1-Allyloxycarbonyl-4-acetylthio-2-[(E)-2-(pyridin-3-yl)vinyl]pyrrolidine was obtained in substantially the same manner as that of Preparation 2-5).

NMR (CDCl$_3$, δ): 1.80–1.95 (1H, m), 2.34 (3H, s), 2.60–2.81 (1H, m) 3.34–3.43 (1H, m), 3.94–4.17 (2H, m), 4.50–4.70 (3H, m), 5.10–5.38 (2H, m), 5.75–6.05 (1H, m), 6.24 (1H, dd, J=6.76 Hz, J=15.9 Hz), 6.47 (1H, broad d, J=15.9 Hz), 7.21–7.28 (1H, m), 7.60–7.71 (1H, m), 8.40–8.60 (2H, m)

Preparation 1-5)

Allyl (4R,5S,6S)-3-[(2S,4S)-1-allyloxycarbonyl-2-{(E)-2-(Pyridin-3-yl)vinyl}pyrrolidin-4-yl]thio-6-[(1R)-1-hydroxyethyl]-4-methyl-7-oxo-1-azabicyclo[3.2.0]hept-2-ene-2-carboxylate was obtained in substantially the same manner as that of Example 2-1).

IR (Neat) : 1760, 1690, 1625, 1540, 1400, 1330 cm$^{-1}$

NMR (CDCl$_3$, δ): 1.38 (3H, d, J=7.23 Hz), 1.36 (3H, d, J=6.25 Hz), 1.82–1.97 (1H, m), 2.50–2.80 (1H, m), 3.20–3.80 (4H, m), 3.90–6.10 (14H, m), 6.27 (1H, dd, J=7.17 Hz, J=15.8 Hz), 6.52 (1H, broad d, J=15.8 Hz), 7.20–7.40 (1H, m), 7.65–7.78 (1H, m), 8.47 (1H, d, J=3.48 Hz), 8.57 (1H, s)

Preparation 1-6)

Allyl (4R,5S,6S)-3-[(2S,4S)-1-allyloxycarbonyl-2-{(E)-2-(1-methyl-3-pyridinio)vinyl}pyrrolidin-4-yl]thio-6-[(1R)-1-hydroxyethyl]-4-methyl-7-oxo-1-azabicyclo-[3.2.0]hept-2-ene-2-carboxylate was obtained in substantially the same manner as that of Example 3-2).

This product was immediately used as the starting compound for the next step.

Preparation 1-7)

(4R,5S,6S) -6-[(1R)-1-Hydroxyethyl]-4-methyl-3-[(2S,4S)-2-{(E)-2-(1-methyl-3-pyridinio)vinyl}-pyrrolidin-4-yl]thio-7-oxo-1-azabicyclo[3.2.0]hept-2-ene-2-carboxylic acid chloride was obtained in substantially the same manner as that of Example 4-2).

IR (Nujol) : 1740–1720, 1570–1530, 1130 cm$^{-1}$

NMR (D$_2$O, δ): 1.24 (3H, d, J=7.16), 1.30 (3H, d, J=6.34 Hz), 1.90–2.15 (1H, m), 2.80–3.05 (1H, m), 3.35–3.55 (3H, m), 3.81 (1H, dd, J=7.00 Hz, J=12.4 Hz), 4.00–4.30 (3H, m), 4.41 (3H, s), 6.75 (1H, dd, J=7.83 Hz, J=16.0 Hz), 6.98 (1H, d, J=16.0 Hz), 8.03 (1H, dd, J=6.1 Hz, J=8.1 Hz), 8.62 (1H, d, J=8.2 Hz), 8.71 (1H, d, J=6.1 Hz), 8.93 (1H, s)

FAB Mass: 430.2 (M$^+$)

Preparation 2-1)

To a solution of oxalyl chloride (2.51 ml) and dichloromethane (100 ml) was dropwise added dimethyl sulfoxide (4.27 ml) at –40°~–50° C. with stirring and the mixture was stirred at the same temperature for 5 minutes. To the solution was added dropwise a solution of (2S,4R)-1-benzyloxycarbonyl-4-(t-butyldimethylsilyloxy)-2-(hydroxymethyl)pyrrolidine (10 g) in dichloromethane (50 ml) at –40°~–50° C. After 10 minutes with stirring, triethylamine (19.0 ml) was dropwise added to the solution and the mixture was stirred at 0°~10° C. for 30 minutes. The insoluble material was filtered off and the filtrate was washed successively with 1N hydrochloric acid, water, saturated aqueous sodium bicarbonate and saturated aqueous sodium chloride, dried over anhydrous magnesium sulfate and evaporated in vacuo to give a residue.

On the other hand, to a solution of 3-picolyltriphenyl phosphonium chloride (11.7 g) in a mixture of tetrahydrofuran (50 ml) and dimethyl sulfoxide (50 ml) was added portionwise potassium t-butoxide (3.38 g) at 0°~5° C. with stirring and the mixture was stirred at the same temperature for 30 minutes. The reaction mixture was dropwise added to a solution of the residue obtained above in tetrahydrofuran (100 ml) at 0° C. and the mixture was stirred at the same temperature for 2 hours. To the reaction mixture was added ethyl acetate (200 ml) and the mixture was washed successively with water (100 ml) and saturated aqueous sodium chloride, dried over anhydrous magnesium sulfate and evaporated in vacuo. The resulting residue was chromatographed on silica gel (300 g) eluting with a mixture of n-hexane and ethyl acetate (2:1, V/V). The early fractions were collected and evaporated in vacuo to give (2S,4R)-1-benzyloxycarbonyl-4-(t-butyldimethylsilyloxy)-2-[(Z)-2-(pyridin-3-yl)vinyl]pyrrolidine (4.71 g).

NMR (CDCl$_3$, δ): 0.05 (6H, s), 0.84 (9H, s), 1.75–2.00 (1H, m), 2.11–2.35 (2H, m), 3.40–3.65 (2H, m), 4.35–4.45 (1H, m), 4.70–5.20 (3H, m), 5.71 (1H, dd), 6.40 (1H, dd), 7.00–7.40 (5H, m), 7.89 (1H, broad s), 8.30–8.60 (3H, m)

The next fractions were collected and evaporated in vacuo to give (2S,4R)-1-benzyloxycarbonyl-4-(t-butyldimethylsilyloxy)- 2-[(E)-2-(pyridin-3-yl)vinyl]pyrrolidine (3.85 g).

NMR (CDCl$_3$, δ): 0.67 (6H, s), 0.88 (9H, s), 1.85–1.96 (1H, m), 2.08–2.30 (2H, m), 3.50–3.65 (2H, m), 4.38–4.43 (1H, m), 4.51–4.75 (1H, m), 4.95–5.30 (2H, m), 6.00–6.60 (2H, m), 7.10–7.45 (6H, m), 7.50–7.80 (1H, m), 8.40–8.60 (2H, m)

Preparation 2-2)

To a solution of (2S,4R)-1-benzyloxycarbonyl-4-(t-butyldimethylsilyloxy)-2-[(Z)-2-(pyridin-3-yl)vinyl]-pyrrolidine (4.70 g) in methanol (50 ml) was added conc. hydrochloric acid (2.68 ml) at ambient temperature with stirring and the mixture was allowed to stand at the same temperature for 3 hours. To the reaction mixture was added 28% sodium methoxide-methanol solution (6.20 ml) under ice-cooling with stirring and the resulting insoluble material was filtered off. The filtrate was evaporated in vacuo to give a residue. The residue was chromatographed on silica gel (150 g) eluting with a mixture of chloroform and methanol (9:1, V/V). The fractions containing the desired compound were collected and evaporated in vacuo to give (2S,4R)-1-benzyloxycarbonyl-4-hydroxy-2-[(Z)-2-(pyridin-3-yl)vinyl]-pyrrolidine (5.20 g).

Preparation 2-3)

To a solution of (2S,4R)-1-benzyloxycarbonyl-4-hydroxy-2-[(Z)-2-(pyridin-3-yl)vinyl]pyrrolidine (5.2 g) in a mixture of ethyl acetate (50 ml) and triethylamine (2.90 ml) was added dropwise methanesulfonyl chloride (1.24 ml) under ice-cooling with stirring and the mixture was stirred at the same temperature for 1 hour. To the reaction mixture were added ethyl acetate (50 ml) and water (30 ml). The organic layer was washed successively with saturated aqueous sodium bicarbonate and saturated aqueous sodium chloride, dried over anhydrous magnesium sulfate and evaporated in vacuo. The resulting residue was chromatographed on silica gel (150 g) eluting with a mixture of n-hexane and ethyl acetate (1:2, V/V). The fractions containing the desired compound were collected and evaporated in vacuo to give (2S,4R)-1-benzyloxycarbonyl-4-methanesulfonyloxy-2-[(Z)-2-(pyridin-3-yl)vinyl]pyrrolidine (4.14 g).

NMR (CDCl$_3$, δ): 2.00–2.10 (1H, m), 2.40–2.70 (1H, m), 3.01 (3H, s), 3.70 (1H, dd, J=3.82 Hz, J=13.2 Hz), 3.90–4.10 (1H, m), 4.80–5.30 (4H, m), 5.67 (1H, t, J=11.3 Hz), 6.35–6.70 (1H, m), 7.10–7.45 (6H, m), 8.30–8.70 (2H, m)

Preparation 2-4)

A solution of (2S,4R)-1-benzyloxycarbonyl-4-methanesulfonyloxy-2-[(Z)-2-(pyridin-3-yl)vinyl]pyrrolidine (4.13 g), conc. hydrochloric acid (1.71 ml), 10% palladium on carbon (50% wet) (2.0 g) in methanol (80 ml) was stirred for 4 hours under atmospheric pressure of hydrogen at ambient temperature. After the catalyst was filtered off, the filtrate was evaporated in vacuo. The resulting residue was dissolved in a mixture of tetrahydrofuran (40 ml) and water (40 ml). To the solution was added dropwise a solution of allyl chloroformate (1.52 ml) in tetrahydrofuran (5 ml) with stirring, while keeping the pH to 8–10 with 4N aqueous sodium hydroxide under ice-cooling. The mixture was stirred at the same condition for 1 hour. The reaction mixture was evaporated in vacuo. The resulting residue was dissolved in ethyl acetate (200 ml). The organic layer was washed with saturated sodium chloride, dried over anhydrous magnesium sulfate and evaporated in vacuo. The resulting residue was chromatographed on silica gel (150 g) eluting with a mixture of chloroform and methanol (19:1, V/V). The fractions containing the desired compound were collected and evaporated in vacuo to give (2R,4R)-1-allyloxycarbonyl-4-methanesulfonyloxy-2-[2-(pyridin-3-yl)ethyl]pyrrolidine (3.40 g).

NMR (CDCl$_3$, δ): 1.65–1.80 (1H, m), 1.90–2.15 (1H, m), 2.20–2.70 (4H, m), 3.04 (3H, s), 3.50–3.65 (1H, m), 3.90–4.20 (2H, m), 4.59 (2H, m), 5.15–5.35 (3H, m), 5.83–6.04 (1H, m), 7.18–7.27 (1H, m), 7.40–7.60 (1H, m), 8.44–8.50 (2H, m)

Preparation 2-5)

To a solution of potassium t-butoxide (1.50 g) in N,N-dimethylformamide (20 ml) was added dropwise thioacetic acid (0.96 ml) with stirring at −10°—5° C. The mixture was stirred at the same temperature for 10 minutes. A solution of (2R,4R)-1-allyloxycarbonyl-4-methanesulfonyloxy-2-[2-(pyridin-3-yl)ethyl]pyrrolidine (3.39 g) in N,N-dimethylformamide (20 ml) was added to the mixture obtained above with stirring at the same temperature. The mixture was stirred at 80°–90° C. for 3 hours. The reaction mixture was poured into ice-water (120 ml) and extracted three times with ethyl acetate (80 ml). The extract was washed with saturated aqueous sodium chloride, dried over anhydrous magnesium sulfate and evaporated in vacuo. The resulting residue was chromatographed on silica gel (150 g) eluting with a mixture of chloroform and methanol (19:1, V/V). The fractions containing the desired compound were collected and evaporated in vacuo to give (2R,4S)-4-acetylthio-1-allyloxycarbonyl-2-[2-(pyridin-3-yl)ethyl]pyrrolidine (3.12 g).

NMR (CDCl$_3$, δ): 1.60–1.90 (2H, m), 2.35 (3H, s), 2.40–2.70 (4H, m), 3.18 (1H, dd, J=11.28 Hz, J=7.67 Hz), 3.80–4.15 (3H, m), 4.57 (2H, broad d, J=5.57 Hz), 5.18–5.34 (2H, m), 5.75–6.05 (1H, m), 7.19–7.28 (1H, m), 7.54 (1H, broad s), 8.47 (2H, broad s)

Preparation 3-1)

To a solution of (2S,4R)-1-allyloxycarbonyl-4-t-butyldimethylsilyloxy-2-formylpyrrolidine (30.0 g) in tetrahydrofuran (300 ml) was added methyl (triphenylphosphoranylidene)acetate (35.2 g) and the mixture was stirred at room temperature overnight. The solvent was evaporated and the residue was chromatographed on a 300 g of silica gel to give (2S,4R)-1-allyloxycarbonyl-4-t-butyldimethylsilyloxy-2-(3-methoxy-3-oxo-1-propenyl)pyrrolidine (29.8 g) as a colorless oil.

NMR (CDCl$_3$, 200 MHz, δ): 0.06 (6H, s), 0.87 (9H, s), 1.74–1.95 (1H, m), 2.01–2.22 (1H, m), 3.40–3.60 (2H, m), 3.73 (3H, s), 4.30–4.43 (1H, m), 4.49–4.68 (3H, m), 5.10–5.39 (2H, m), 5.75–6.00 (2H, m), 6.79–6.90 (1H, m)

Preparation 3-2)

To a solution of (2S,4R)-1-allyloxycarbonyl-4-t-butyldimethylsilyloxy-2-(3-methoxy-3-oxo-1-propenyl)pyrrolidine (18.7 g) in tetrahydrofuran (190 ml) were added successively sodium borohydride (3.83 g) and lithium iodide (13.5 g) at room temperature and the mixture was refluxed for 4 hours. After cooling to room temperature, the mixture was diluted with water (200 ml) and extracted with ethyl acetate (200 ml×3). The combined extracts were washed with brine (400 ml), dried over magnesium sulfate and concentrated to give (2R,4R)-1-allyloxycarbonyl-4-t-butyldimethylsilyloxy-2-(3-hydroxypropyl)pyrrolidine (17.2 g) as a pale yellow paste.

NMR (CDCl$_3$, 200 MHz, δ): 0.06 (6H, s), 0.86 (9H, s), 1.2–1.3 (6H, m), 3.36–3.37 (2H, m), 3.57–3.61 (2H, m), 3.95–4.11 (1H, m), 4.52–4.54 (2H, m), 5.10–5.29 (2H, m), 5.79–5.98 (1H, m)

Preparation 3-3)

To a solution of (2R,4R)-1-allyloxycarbonyl-4-t-butyldimethylsilyloxy-2-(3-hydroxypropyl)pyrrolidine (17.1 g) in dichloromethane (170 ml) were added successively triethylamine (10.4 ml) and methanesulfonyl chloride (4.63 ml) under an ice-bath. The mixture was stirred at 0° C. for 1.5 hours and quenched by the addition of water (85 ml). The aqueous layer was separated and extracted with dichloromethane (50 ml×2). The organic layers were combined and washed with 1N hydrochloric acid (85 ml), brine (85 ml) and dried over magnesium sulfate. Evaporation of the solvent gave (2R,4R)-1-allyloxycarbonyl-4-t-butyldimethylsilyloxy-2-(3-methanesulfonyloxypropyl)pyrrolidine (21.2 g) as a yellow paste.

NMR (CDCl$_3$, 200 MHz, δ): 0.06 (6H, s), 0.86 (9H, s), 1.43–2.04 (6H, m), 3.01 (3H, s), 3.35–3.67 (2H, m), 3.91–4.11 (1H, m), 4.21–4.27 (2H, m), 4.33–4.38 (1H, m), 4.49–4.69 (2H, m), 5.17–5.35 (2H, m), 5.84–6.03 (1H, m)

Preparation 3-4)

To a solution of imidazole (3.57 g) in dimethylformamide (100 ml) was added potassium t-butoxide (5.89 g) portionwise at room temperature and the mixture was stirred at the same temperature for 10 minutes. Then a solution of (2R,4R)-1-allyloxycarbonyl-4-t-butyldimethylsilyloxy-2-(3-methanesulfonyloxypropyl)pyrrolidine (20.1 g), in dimethylformamide (20 ml) was added and the mixture was heated at 60° C. After stirring for 1 hour, water (200 ml) was added and the mixture was extracted with hexane-ethyl acetate (2:1) (200 ml×5). The combined extract was washed with water (1 l), brine (1 l), and dried over magnesium sulfate. Evaporation of the solvent gave (2R,4R)-1-allyloxycarbonyl-4-t-butyldimethylsilyloxy-2-[3-(imidazol-1-yl)propyl]pyrrolidine (18.1 g) as a yellow paste.

NMR (CDCl$_3$, 200 MHz, δ): 0.05 (6H, s), 0.85 (9H, s), 1.17–2.05 (6H, m), 3.32–3.67 (2H, m), 3.82–4.09 (3H, m), 4.29–4.33 (1H, m), 4.58–4.61 (2H, m), 5.17–5.33 (2H, m), 5.80–6.06 (1H, m), 6.91 (1H, s), 7.05 (1H, s), 7.46 (1H, s)

Prepration 3-5)

To a solution of (2R,4R)-1-allyloxycarbonyl-4-t-butyldimethylsilyloxy-2-[3-(imidazol-1-yl)propyl]pyrrolidine (19.0 g) in acetonitrile (94 ml) was added conc. hydrochloric acid (9.4 ml) dropwise at 0° C. The solution was stirred at the same temperature for 30 minutes and quenched by the addition of triethylamine (16.7 ml). To the mixture was added ethyl acetate (200 ml) and the insoluble solid was removed by filtration. The filtrate was concentrated and the residue was dissolved in ethyl acetate (100 ml). The insoluble solid was filtered off and the filtrate was concentrated to give a light brown paste. The paste was chromatographed on a 90 g of silica gel to give (2R,4R)-1-allyloxycarbonyl-4-hydroxy-2-[3-(imidazol-1-yl)propyl]pyrrolidine (12.5 g) as a pale yellow paste.

NMR (CDCl$_3$, 200 MHz, δ): 1.3–3.0 (7H, m), 3.27–3.74 (2H, m), 3.85–4.12 (3H, m), 4.33–4.46 (1H, m), 4.53–4.66 (2H, m), 5.18–5.33 (2H, m), 5.78–6.06 (1H, m), 6.90 (1H, s), 7.04 (1H, s), 7.46 (1H, s)

Preparation 3-6)

To a solution of (2R,4R)-1-allyloxycarbonyl-4-hydroxy-2-[3-(imidazol-1-yl)propyl]pyrrolidine (12.5 g) in tetrahydrofuran (125 ml) were added successively triphenylphosphine (17.6 g) and diethyl azodicarboxylate (10.6 ml) at −10° C. and the solution was stirred at the same temperature for 30 minutes. Then thiobenzoic acid (9.5 ml) was added at the same temperature and the solution was stirred for 3 hours. To the solution was added ethyl acetate (125 ml) and washed with saturated aqueous sodium hydrogen carbonate (125 ml×2) and brine (250 ml). The solution was dried over magnesium sulfate and the solvent was evaporated to give a yellow oil. The oil was chromatographed on a 500 g of silica gel to give (2R,4S)-1-allyloxycarbonyl-4-benzoylthio-2-[3-(imidazol-1-yl)propyl]pyrrolidine (15.3 g) as a yellow paste.

NMR (CDCl$_3$, 200 MHz, δ): 1.4–2.8 (6H, m), 3.21–3.31 (1H, m), 3.95–4.25 (5H, m), 4.57–4.61 (2H, m), 5.20–5.35 (2H, m), 5.84–6.03 (1H, m), 6.93–8.10 (8H, m)

Preparation 4-1)

Acetyl chloride (380 ml) was dropwise added to methanol (3.5 l) at 10°–25° C. with stirring, followed by (2S,4R)-4-hydroxy-2-pyrrolidinecarboxylic acid (500 g). The mixture was refluxed for 3 hours. The mixture was cooled to the ambient temperature and poured into diethyl ether to give precipitates. The precipitates were collected by filtration and dried up in vacuo to give methyl (2S,4R)-4-hydroxy-2-pyrrolidinecarboxylate hydrochloride (676 g).

NMR (DMSO, δ): 2.01–2.26 (2H, m), 3.07 (1H, d, J=12.1 Hz), 3.37 (1H, dd, J=12.1 Hz, 4.4 Hz), 3.76 (3H, s), 4.12–4.51 (2H, m), 5.64 (1H, br), 9.92 (2H, br)

Preparation 4-2)

To a solution of methyl (2S,4R)-4-hydroxy-2-pyrrolidinecarboxylate hydrochloride (674 g) in dichloromethane (3.5 l) were added dropwise triethylamine (1.19 l) and benzyl chloride (552 ml) at 10°–20° C. under stirring and the mixture was refluxed for 6 hours. The mixture was cooled to ambient temperature, and the precipitates were removed by filtration. The filtrate was poured into 1N sodium hydroxide and extracted with dichloromethane. The organic layer was washed with brine, dried over anhydrous magnesium sulfate and evaporated in vacuo to give methyl (2S,4R)-1-benzyl-4-hydroxy-2-pyrrolidinecarboxylate (663 g).

NMR (CDCl$_3$, δ): 2.01–2.31 (2H, m), 2.42–2.49 (2H, m), 3.28–3.45 (2H, m), 3.53–3.75 (4H, m), 3.89 (1H, d, J=12.8 Hz), 4.44 (1H, br), 7.21–7.40 (5H, m)

Preparation 4-3)

To a solution of (2S,4R)-1-benzyl-2-methoxycarbonyl-4-hydroxypyrrolidine (661 g) in N,N-dimethylformamide (3.3 l) were added successively imidazole (383 g) and t-butyldimethylsilyl chloride (508 g) at 10°–20° C. with stirring and the solution was stirred at ambient temperature for 3 hours. The mixture was poured into 0.1N hydrochloric acid and extracted with ethyl acetate. The organic layer was washed with 5% aqueous sodium bicarbonate, water and 10% sodium chloride, dried with anhydrous magnesium sulfate and evaporated in vacuo to give (2S,4R)-1-benzyl-2-methoxycarbonyl-4-(t-butyldimethylsilyloxy)pyrrolidine (964 g).

NMR (CDCl$_3$, δ): 0.00 (3H, s), 0.01 (3H, s), 0.87 (9H, s), 1.93–2.23 (2H, m), 2.34 (1H, dd, J=5.2 Hz, 9.7 Hz), 3.23 (1H, dd, J=5.8 Hz, 9.7 Hz), 3.46–3.59 (2H, m), 3.61 (3H, s), 3.87 (1H, d, J=12.8 Hz), 4.33–4.44 (1H, m), 7.19–7.36 (5H, m)

Preparation 4-4)

To a suspension of sodium borohydride (16.2 g) and lithium chloride (18.1 g) in tetrahydrofuran (190 ml) were dropwise added (2S,4R)-1-benzyl-2-methoxycarbonyl-4-(t-butyldimethylsilyloxy)pyrrolidine (74.8 g) in tetrahydrofuran (190 ml), and ethanol (750 ml) under ice-cooling. The mixture was stirred at ambient temperature for 2 hours. The reaction mixture was cooled with dry ice-acetone bath and poured into ice-water. The mixture was adjusted to pH 6 with 1N hydrochloric acid and stirred for 10 minutes. The mixture was adjusted to pH 9~10 with 1N sodium hydroxide, and saturated with sodium chloride. After being extracted with ethyl acetate and tetrahydrofuran (1:1) three times, the organic layer was dried over anhydrous magnesium sulfate and evaporated in vacuo. To the residue was added chloroform. The chloroform layer was again dried over anhydrous magnesium sulfate, and evaporated in vacuo to give (2S,4R)-1-benzyl-2-hydroxymethyl-4-(t-butyldimethylsilyloxy)pyrrolidine (70.10 g).

Preparation 4-5)

To a solution of oxalyl chloride (20.0 ml) in dichloromethane (700 ml) was dropwise added dimethyl sulfoxide (34.0 ml) at −40° C.~−50° C. with stirring and the mixture was stirred at the same temperature for 5 minutes. To the solution was dropwise added a solution of (2S,4R)-1-benzyl-2-hydroxymethyl-4-(t-butyldimethylsilyloxy)pyrrolidine (70.10 g) in dichloromethane (300 ml) at −40° C.~−50° C. After 10 minutes with stirring, triethylamine (151.9 ml) was dropwise added to the solution and the mixture was stirred at ambient temperature for 1 hour. The reaction mixture was poured into 1N hydrochloric acid and extracted with ethyl acetate. The organic layer was washed with saturated aqueous sodium bicarbonate, water and brine. The layer was dried over anhydrous magnesium sulfate and evaporated in vacuo to give a residue.

On the other hand, to a suspension of methyl triphenyl phosphonium chloride (62.67 g) in tetrahydrofuran (300 ml) was portionwise added potassium t-butoxide (24.20 g) at 0°~5° C. with stirring and then stirred at ambient temperature for 2 hours. The reaction mixture was dropwise added to a solution of the residue obtained above in tetrahydrofuran (200 ml) at 0°~5° C. and the mixture was stirred at the same temperature for 1 hour. The mixture was poured into water and extracted with ethyl acetate. The organic layer was washed with brine, dried over anhydrous magnesium sulfate and evaporated in vacuo. The residue was purified by silica gel chromatography eluting with a mixture of n-hexane and ethyl acetate (15:1, V/V) to give (2S,4R)-1-benzyl-2-vinyl-4-(t-butyldimethylsilyloxy)pyrrolidine (35.10 g).

NMR (CDCl$_3$, δ): 0.02 (3H, s), 0.03 (3H, s), 0.86 (9H, s), 1.84–1.92 (2H, m), 2.09–2.16 (1H, dd, J=9.7 Hz, 5.5 Hz), 3.11–3.24 (3H, m), 4.01 (1H, d, J=13.0 Hz), 4.26–4.37 (1H, m), 5.16 (1H, dd, J=15.7 Hz, 1.9 Hz), 5.23 (1H, dd, J=22.8 Hz, 1.9 Hz), 5.64–5.82 (1H, m), 7.18–7.32 (5H, m)

Preparation 4-6)

To a solution of (2S,4R)-1-benzyl-2-vinyl-4-(t-butyldimethylsilyloxy)pyrrolidine (24.03 g) in tetrahydrofuran (120 ml) was added 0.5M solution of 9-borabicyclo[3.3.1]nonane in tetrahydrofuran (318 ml) at 0°~5° C. with stirring and then ambient temperature for 4 hours. To the reaction mixture were added water (200 ml) and sodium perborate tetrahydrate (87 g) at ambient temperature with stirring vigorously and then the mixture was stirred at the same temperature for 12 hours. The insoluble material was filtered off, and the filtrate was separated. The organic layer was dried over anhydrous magnesium sulfate and evaporated in vacuo. The residue was purified by silica gel chromatography eluting with a mixture of n-hexane and ethyl acetate (1:1, V/V) to give (2R,4R)-1-benzyl-2-(2-hydroxyethyl)-4-(t-butyldimethylsilyloxy)pyrrolidine (20.89 g).

NMR (CDCl$_3$, δ): 0.01 (3H, s), 0.03 (3H, s), 0.89 (9H, s), 1.45–1.57 (1H, m), 1.78–1.91 (1H, m), 1.98–2.27 (3H, m), 3.03 (1H, dd, J=10.3 Hz, 5.4 Hz), 3.20–3.30 (1H, m), 3.30 (1H, d, J=12.6 Hz), 3.68–3.78 (1H, m), 3.68–3.77 (1H, m), 3.94–4.06 (1H, m), 4.20 (1H, d, J=12.5 Hz), 4.27–4.38 (1H, m), 7.22–7.36 (5H, m)

Preparation 4-7)

A mixture of (2R,4R)-1-benzyl-2-(2-hydroxyethyl)-4-(t-butyldimethylsilyloxy)pyrrolidine (20.89 g) and 10% palladium on carbon (50% wet, 8.0 g) in methanol (200 ml) was stirred for 3 hours under atmospheric pressure of hydrogen at ambient temperature. After the catalyst was filtered off, the filtrate was evaporated in vacuo. The resulting residue was dissolved in a mixture of tetrahydrofuran (80 ml) and water (80 ml). To the solution was dropwise added a solution of allyl chloroformate (7.27 ml) in tetrahydrofuran (20 ml) with stirring while keeping the pH 8–10 with 6N sodium hydroxide under ice-cooling. The reaction mixture was stirred at the same condition for a half hour. To the resulting mixture was added ethyl acetate and the solution was separated. The organic layer was washed with brine, dried over anhydrous magnesium sulfate and evaporated in vacuo. The residue was purified by silica gel chromatography eluting with a mixture of hexane and ethyl acetate (2:1, V/V) to give (2R,4R)-1-allyloxycarbonyl-2-(2-hydroxyethyl)-4-(t-butyldimethylsilyloxy)pyrrolidine (18.52 g).

NMR (CDCl$_3$, δ): 0.00 (6H, s), 0.81 (9H, s), 1.49 (1H, br), 1.66–1.77 (2H, m), 1.95–2.08 (1H, m), 3.18 (1H, br), 3.33–3.39 (2H, m), 3.52–3.58 (2H, m), 4.12 (1H, br), 4.29–4.40 (1H, m), 4.54 (2H, d, J=5.5 Hz), 5.13–5.30 (2H, m), 5.79–5.98 (1H, m)

Preparation 4-8)

To a solution of (2R,4R)-1-allyloxycarbonyl-2-(2-hydroxyethyl)-4-(t-butyldimethylsilyloxy)pyrrolidine (18.52 g) in a mixture of ethyl acetate (180 ml) and triethylamine (8.62 ml) was dropwise added methanesulfonyl chloride (4.79 ml) under ice-cooling with stirring and the mixture was stirred at the same temperature for 1 hour. The reaction mixture was poured into water and extracted with ethyl acetate. The organic layer was washed with brine, dried over anhydrous magnesium sulfate and evaporated in vacuo. The resulting residue was purified by silica gel chromatography eluting with a mixture of hexane and ethyl acetate (3:1, V/V) to give (2R,4R)-1-allyloxycarbonyl-2-(2-methanesulfonyloxy)ethyl-4-(t-butyldimethylsilyloxy)pyrrolidine (17.31 g).

NMR (CDCl$_3$, δ): 0.00 (6H, s), 0.80 (9H, s), 1.66–1.88 (2H, m), 1.98–2.08 (1H, m), 2.18–2.28 (1H, m), 2.96 (3H, s), 3.29–3.46 (2H, m), 4.00–4.11 (1H, m), 4.21–4.34 (3H, m), 4.53 (2H, br), 5.12–5.28 (2H, m), 5.78–5.94 (1H, m)

Preparation 4-9)

To a solution of imidazole (1.52 in N,N-dimethylformamide (70 ml) were added potassium t-butoxide (2.51 g) and a solution of (2R,4R)-1-allyloxycarbonyl-2-(2-methanesulfonyloxyethyl)-4-(t-butyldimethylsilyloxy)pyrrolidine (8.3 g) in N,N-dimethylformamide (13 ml) at ambient temperature with stirring, and the mixture was stirred at about 60° C. for 1 hour. The reaction mixture was cooled with ice-cooling, and water and ethyl acetate were added thereto. After separation, the organic layer was washed with brine, dried over anhydrous magnesium sulfate and evaporated in vacuo. The resulting residue was purified by silica gel chromatography eluting with a mixture of chloroform and methanol (10:0.3, V/V) to give (2R,4R)-1-allyloxycarbonyl-2-[2-(imidazol-1-yl)ethyl]-4-(t-butyldimethylsilyloxy)pyrrolidine (11.11 g).

NMR (CDCl$_3$, δ): 0.05 (6H, s), 0.85 (9H, s), 1.62 (1H, br), 1.82–1.97 (2H, m), 2.32 (1H, br), 3.34–3.47 (2H, m), 4.02 (3H, br), 4.31–4.35 (1H, m), 4.59–4.62 (2H, m), 5.20–5.35 (2H, m), 5.84–6.04 (1H, m), 6.97 (1H, br), 7.06 (1H, s), 7.52 (1H, br)

Preparation 4-10)

To a solution of (2R,4R)-1-allyloxycarbonyl-2-[2-(imidazol-1-yl)ethyl]-4-(t-butyldimethylsilyloxy)pyrrolidine (11.11 g) in methanol (110 ml) was added conc. hydrochloric acid (7.32 ml) at ambient temperature with stirring and the solution was stirred at the same temperature for 2 hours. To a reaction solution was added 28% sodium methoxide-methanol solution (16.89 ml) under ice-cooling with stirring and the resulting insoluble material was filtered off. The filtrate was evaporated in vacuo to give a residue. To the residue was added chloroform. The organic layer was dried over anhydrous magnesium sulfate and evaporated in vacuo to give crude (2R,4R)-1-allyloxycarbonyl-2-[2-(imidazol-1-yl)ethyl]-4-hydroxypyrrolidine (9.19 g).

NMR (CDCl$_3$, δ): 1.74–1.95 (2H, m), 2.22 (1H, br), 2.48 (1H, br), 3.43 (1H, dd, J=4.0 Hz, 11.8 Hz), 3.70–3.74 (1H, m), 3.96–4.18 (3H, m), 4.43 (1H, br), 4.57 (2H, d, J=5.4 Hz), 4.79 (2H, br), 5.19–5.34 (2H, m), 5.83–6.02 (1H, m), 7.17 (2H, br), 8.01 (1H, s)

Preparation 4-11)

To a solution of (2R,4R)-1-allyloxycarbonyl-2-[2-(imidazol-1-yl)ethyl]-4-hydroxypyrrolidine (9.19 g) in dichloromethane (92 ml) were dropwise added triethylamine (5.79 ml) and methanesulfonyl chloride (3.22 ml) under ice cooling with stirring, and the solution was stirred at the same temperature for 1 hour. The reaction mixture was poured into water and extracted with dichloromethane. The organic layer was washed with brine, dried over anhydrous magnesium sulfate and evaporated in vacuo. The residue was purified by silica gel chromatography eluting with a mixture of chloroform and methanol (9:1, V/V) to give (2R,4R)-1-allyloxycarbonyl-2-[2-(imidazol-1-yl)ethyl]-4-(methanesulfonyloxy)pyrrolidine (4.24 g).

NMR (CDCl$_3$, δ): 1.82–2.00 (2H, m); 2.43 (2H, br), 3.05 (3H, s), 3.51–3.57 (1H, m), 4.03 (4H, br), 4.62 (2H, d, J=4.4 Hz), 5.18–5.37 (3H, m), 5.85–6.04 (1H, m), 6.97 (1H, br), 7.06 (1H, s), 7.51 (1H, s)

Preparation 4-12)

To a solution of potassium t-butoxide (1.80 g) in N,N-dimethylformamide (21 ml) was dropwise added thioacetic acid (1.24 ml) under ice-cooling with stirring. The solution was stirred at the same temperature for 30 minutes. To a solution of (2R,4R)-1-allyloxycarbonyl-2-[2-(imidazol-1-yl)ethyl]-4-methanesulfonyloxypyrrolidine (4.24 g) in N,N-dimethylformamide (21 ml) was added the mixture obtained above with stirring at ambient temperature. The mixture was stirred at 80°–90° C. for 1.5 hours.

The mixture was cooled with ice-water, and water and ethyl acetate were added to it. After being separated, the organic layer was washed with brine, dried over anhydrous magnesium sulfate and evaporated in vacuo. The residue was purified by silica gel chromatography eluting with a mixture of chloroform and methanol (10:0.3, V/V) to give (2R,4S)-4-acetylthio-1-allyloxycarbonyl-2-[2-(imidazol-1-yl)ethyl]pyrrolidine (4.54 g).

NMR (CDCl$_3$, δ): 1.58 (1H, br), 1.85–2.03 (1H, m), 2.26–2.62 (5H, m), 3.22 (1H, dd, J=4.3 Hz, 8.0 Hz), 3.80–4.14 (5H, m), 4.59 (2H, d, J=5.7 Hz), 5.21–5.36 (2H, m), 5.84–6.03 (1H, m), 6.96 (1H, s), 7.06 (1H, s), 7.50 (1H, s)

Preparation 5-1)

(2S,4R)-1-Benzyloxycarbonyl-4-(t-butyldimethylsilyloxy)-2-[(Z)-2-(pyridin-4-yl)vinyl]pyrrolidine (2.41 g) and (2S,4R)-1-benzyloxycarbonyl-4-(t-butyldimethylsilyloxy)-2-[(E)-2-(pyridin-4-yl)vinyl]pyrrolidin (9.54 g) were obtained by reacting (2S,4R)-1-benzyloxycarbonyl-4-(t-butyldimethylsilyloxy)-2-(hydroxymethyl)pyrrolidine (20 g) with dimethyl sulfoxide (8.88 ml), oxalyl chloride (5.21 ml) and triethylamine (39.7 ml) in dichloromethane (300 ml), and then (pyridin-4-yl)methyltriphenylphosphonium chloride hydrochloride (26.7 g) and potassium t-butoxide (14.0 g) in a mixture of tetrahydrofuran (300 ml) and dimethyl sulfoxide (100 ml) in substantially the same manner as that of Preparation 2-1).

(E)-form: NMR (CDCl$_3$, δ): 0.11 (6H, s), 0.89 (9H, s), 1.83–1.95 (1H, m), 2.09–2.21 (1H, m), 3.45–3.70 (2H, m), 4.36–4.62 (2H, m), 5.01–5.26 (2H, m), 6.30–6.43 (1H, m), 7.09–7.36 (8H, m), 8.44–8.55 (2H, m)

(Z)-form: NMR (CDCl$_3$, δ): 0.05 (6H, s), 0.85 (9H, s), 1.86 (1H, br), 2.40 (1H, br), 3.54–3.56 (2H, m), 4.38–4.41 (1H, m), 4.93–5.11 (3H, m), 6.27–6.41 (1H, m), 6.95–7.33 (8H, m), 8.46–8.55 (2H, m)

Preparation 5-2)

(2S,4R)-1-Benzyloxycarbonyl-4-hydroxy-2-[(E)-2-(pyridin-4-yl)vinyl]pyrrolidine (7.05 g) was obtained by reacting (2S,4R)-1-benzyloxycarbonyl-4-(t-butyldimethylsilyloxy)-2-[(E)-2-(pyridin-4-yl)vinyl]pyrrolidine (9.54 g) with conc. hydrochloric acid (5.44 ml) in methanol (95 ml) in substantially the same manner as that of Preparation 2-2).

This compound was immediately used as the starting compound for the next step.

Preparation 5-3)

(2S,4R)-1-Benzyloxycarbonyl-4-methanesulfonyloxy-2-[(E)-2-(pyridin-4-yl)vinyl]pyrrolidine (6.35 g) was obtained by reacting (2S,4R)-1-benzyloxycarbonyl-4-hydroxy-2-[(E)-2-(pyridin-4-yl)vinyl]pyrrolidine (7.05 g) with triethylamine (3.64 ml) and methanesulfonyl chloride (2.02 ml) in a mixture of ethyl acetate (40 ml) and dichloromethane (40 ml) in substantially the same manner as that of Preparation 2-3).

NMR (CDCl$_3$, δ): 0.08 (6H, s), 0.92 (9H, s), 2.04–2.19 (1H, m), 2.38 (1H, br), 3.04 (3H, s), 3.68–3.76 (1H, m), 4.00 (1H, br), 4.70 (1H, br), 5.18–5.27 (3H, m), 6.32 (1H, br), 7.15–7.37 (8H, m), 8.51–8.55 (2H, m)

Preparation 5-4)

(2R,4R)-1-Allyloxycarbonyl-4-methanesulfonyloxy-2-[2-(pyridin-4-yl)ethyl]pyrrolidine (5.35 g) was obtained by reacting (2S,4R)-1-benzyloxycarbonyl-4-methanesulfonyloxy-2-[(E)-2-(pyridin-4-yl)vinyl]pyrrolidine (6.35 g) with 10% palladium on carbon (50% wet) (2.5 g) and conc. hydrochloric acid (2.63 ml) under hydrogen in a mixture of tetrahydrofuran (60 ml) and methanol (120 ml), and then allyl chloroformate (1.86 ml) in a mixture of tetrahydrofuran (30 ml) and water (15 ml) in substantially the same manner as that of Preparation 2-4).

NMR (CDCl$_3$, d): 1.75–2.69 (6H, m), 3.05 (3H, s), 3.53–3.59 (1H, m), 3.94–4.06 (2H, m), 4.59–4.62 (2H, m), 5.21–5.36 (3H, m), 5.84–6.03 (1H, m), 7.14 (2H, br), 8.50 (2H, d, J=5.9 Hz)

Preparation 5-5)

(2R,4S)-4-Acetylthio-1-allyloxycarbonyl-2-[2-(pyridin-4-yl)ethyl]pyrrolidine (4.35 g) was obtained by reacting (2R,4R)-1-allyloxycarbonyl-4-methanesulfonyloxy-2-[2-(pyridin-4-yl)ethyl]pyrrolidine (5.27 g) with thioacetic acid (1.49 ml) and potassium t-butoxide (2.17 g) in N,N-dimethylformamide (52 ml) in substantially the same manner as that of Preparation 2-5).

NMR (CDCl$_3$, δ): 1.62–1.76 (2H, m), 2.35 (3H, s), 2.45–2.63 (4H, m), 3.19 (1H, dd, J=7.7 Hz, 11.3 Hz), 3.80–4.03 (3H, m), 4.58 (2H, d, J=5.5 Hz), 5.20–5.34 (2H, m), 5.83–6.02 (1H, m), 7.15 (2H, br), 8.50 (2H, d, J=5.8 Hz)

Preparation 6-1)

Allyl (4R,5S,6S)-3-[(2S,4S)-1-allyloxycarbonyl-2-[(Z)-2-{1-(N,N-dimethylcarbamoylmethyl)-3-pyridinio}vinyl]-pyrrolidin-4-yl]thio-6-[(1R)-1-hydroxyethyl]-4-methyl-7-oxo-1-azabicyclo[3.2.0]hept-2-ene-2-carboxylate iodide (2.51 g) was obtained by reacting allyl (4R,5S,6S)-3-[(2S,4S)-1-allyloxycarbonyl-2-{(Z)-2-(pyridin-3-yl)vinyl}pyrrolidin-4-yl]thio-6-[(1R)-1-hydroxyethyl]-4-methyl-7-oxo-1-azabicyclo[3.2.0]hept-2-ene-2-carboxylate (1.80 g) with N,N-dimethyliodoacetoamide (2.13 g) in substantially the same manner as that of Example 3-1).

This compound was immediately used as the starting compound for the next step.

Preparation 6-2)

(4R,5S,6S)-3-[(2S,4S)-2-[(Z)-2-{1-(N,N-Dimethyl carbamoylmethyl)-3-pyridinio}vinyl]pyrrolidin-4-yl]thio-6-[(1R)-1-hydroxyethyl]-4-methyl-7-oxo-1-azabicyclo[3.2.0]-hept-2-ene-2-carboxylic acid chloride (575 mg) was obtained by reacting allyl (4R,5S,6S)-3-[(2S,4S)-1-allyloxycarbonyl-2-{(Z)-2-{1-(N,N-dimethylcarbamoylmethyl)-3-pyridinio}vinyl]pyrrolidin-4-yl]thio-6-[(1R)-1-hydroxyethyl]-4-methyl-7-oxo-1-azabicyclo[3.2.0]hept-2-ene-2-carboxylate iodide (2.51 g) with triphenylphosphine (87 mg), acetic acid (0.76 ml), tetrakis(triphenylphosphine)palladium(0) (116 mg) and tri-n-butylthin hydride (3.59 ml) in a mixture of tetrahydrofuran (25 ml) and ethanol (25 ml) in substantially the same manner as that of Example 4-1).

IR (Nujol) : 1730, 1650–1630, 1570 $cm^{-1}$

NMR ($D_2O$, δ): 1.22 (3H, d, J=7.31 Hz), 1.29 (3H, d, J=6.34 Hz), 1.89–2.05 (1H, m), 2.78–2.95 (1H, m), 3.03 (3H, s), 3.17 (3H, s), 3.28–3.55 (3H, m), 3.71 (1H, dd, J=6.76 Hz, J=12.3 Hz), 4.00–4.35 (3H, m), 4.45–4.60 (1H, m), 5.77 (2H, s), 6.33 (1H, t, J=10.8 HZ), 6.99 (1H, d, J=11.5 Hz), 8.05–8.20 (1H, m), 8.54 (1H, d, J=8.07 Hz), 8.60–8.85 (2H, m)

FAB Mass: 501.1 ($M^+$)

Preparation 7-1)

(2S,4R)-1-Benzyloxycarbonyl-4-(t-butyldimethylsilyloxy)-2-[(E)-2-(pyridin-2-yl)vinyl]pyrrolidine (8.02 g) was obtained by reacting (2S,4R)-1-benzyloxycarbonyl-4-(t-butyldimethylsilyloxy)-2-(hydroxymethyl)pyrrolidine (6.47 g) with oxalyl chloride (1.62 ml), dimethyl sulfoxide (2.76 ml), triethylamine (12.3 ml) and then successively with 2-picolyl triphenyl phosphonium chloride (8.30 g) in substantially the same manner as that of Preparation 2-1).

NMR ($CDCl_3$, δ): 0.64 (6H, s), 0.87 (9H, s), 1.91–2.15 (2H, m), 3.35–3.65 (2H, m), 4.35–5.25 (4H, m), 6.35–6.80 (2H, m), 7.05–7.35 (7H, m), 7.63 (1H, dt, J=1.79 Hz, J=7.68 Hz), 8.55 (1H, broad d, J=4.00 Hz)

Preparation 7-2)

(2S,4R)-1-Benzyloxycarbonyl-4-hydroxy-2-[(E)-2-(pyridin-2-yl)vinyl]pyrrolidine (7.36 g) was obtained by reacting (2S,4R)-1-benzyloxycarbonyl-4-(t-butyldimethylsilyloxy)-2-[(E)-2-(pyridin-2-yl)vinyl]pyrrolidine (8.01 g) with conc. hydrochloric acid (4.56 ml) in methanol (80 ml) in substantially the same manner as that of Preparation 2-2).

NMR ($CDCl_3$, δ): 1.90–2.35 (2H, m), 3.55–3.75 (2H, m), 4.40–5.25 (4H, m), 6.35–6.75 (2H, m), 7.00–7.45 (7H, m), 7.61 (1H, dt, J=1.82 Hz, J=7.69 Hz), 8.52 (1H, broad d, J=3.72 Hz)

Preparation 7-3)

(2S,4R)-1-Benzyloxycarbonyl-4-methanesulfonyloxy-2-[(E)-2-(pyridin-2-yl)vinyl]pyrrolidine (6.32 g) was obtained by reacting (2S,4R)-1-benzyloxycarbonyl-4-hydroxy-2-[(E)-2-(pyridin-2-yl)vinyl]pyrrolidine (7.36 g) with triethylamine (4.11 ml) and methanesulfonyl chloride (1.93 ml) in ethyl acetate (70 ml) in substantially the same manner as that of Preparation 2-3).

NMR ($CDCl_3$, δ): 2.10–2.26 (1H, m), 2.45–2.70 (1H, m), 3.02 (3H, s), 3.73 (1H, dd, J=4.32 Hz, J=12.9 Hz), 3.90–4.15 (1H, m), 4.65–5.35 (4H, m), 6.40–6.75 (2H, m), 7.00–7.45 (7H, m), 7.62 (1H, dt, J=1.81 Hz, J=7.68 Hz), 8.55 (1H, d, J=4.09 Hz)

Preparation 7-4)

(2R,4R)-1-Allyloxycarbonyl-4-methanesulfonyloxy-2-[2-(pyridin-2-yl)ethyl]pyrrolidine (5.43 g) was obtained by reacting (2S,4R)-1-benzyloxycarbonyl-4-methanesulfonyloxy-2-[(E)-2-(pyridin-2-yl)vinyl]pyrrolidine (6.31 g) with 10% palladium on carbon (50% wet) (3.0 g) in methanol (120 ml) and then allyloxycarbonyl chloride (2.16 ml) in a mixture of tetrahydrofuran (60 ml) and water (60 ml) in substantially the same manner as that of Preparation 2-4).

NMR ($CDCl_3$, δ): 1.80–2.15 (2H, m), 2.20–2.90 (4H, m), 3.03 (3H, s), 3.45–4.20 (3H, m), 4.59 (2H, broad d, J=5.43 Hz), 5.15–5.40 (3H, m), 5.80–6.05 (1H, m), 7.05–7.27 (2H, m), 7.60 (1H, dt, J=1.83 Hz, J=7.65 Hz), 8.50 (1H, broad d, J=4.20 Hz)

Preparation 7-5)

(2R,4S)-1-Allyloxycarbonyl-4-acetylthio-2-[2-(pyridin-2-yl)ethyl]pyrrolidine (4.41 g) was obtained by reacting (2R,4R)-1-allyloxycarbonyl-4-methanesulfonyloxy-2-[2-(pyridin-2-yl)ethyl]pyrrolidine (5.42 g) with potassium t-butoxide (2.23 g) and thioacetic acid (1.42 ml) in N,N-dimethylformamide (100 ml) in substantially the same manner as that of Preparation 2-5).

NMR ($CDCl_3$, δ): 1.60–2.05 (2H, m), 2.33 (3H, s), 2.30–2.90 (4H, m), 3.16 (1H, dd, J=8.18 Hz, J=11.3 Hz), 3.70–4.20 (3H, m), 4.50–4.60 (2H, m), 5.10–5.35 (2H, m), 5.70–6.00 (1H, m), 7.00–7.25 (2H, m), 7.60 (1H, dt, J=1.82 Hz, J=7.66 Hz), 8.51 (1H, d, J=4.13 Hz)

Preparation 8-1)

To a solution of oxalyl chloride (1.75 ml) in dichloromethane (70 ml) was dropwise added dimethyl sulfoxide (2.99 ml) at –40°—50° C. with stirring and the mixture was stirred at the same temperature for 5 minutes. To the solution was added dropwise a solution of (2S,4R)-1-benzyloxycarbonyl-4-(t-butyldimethylsilyloxy)-2-(hydroxymethyl)pyrrolidine (7 g) in dichloromethane (35 ml) at –40°—50° C. After 10 minutes with stirring, triethylamine (13.3 ml) was added dropwise to the solution and then the mixture was stirred at ambient temperature for 30 minutes. The insoluble material was filtered off and the filtrate was washed successively with 1N hydrochloric acid, water, saturated aqueous sodium bicarbonate and saturated aqueous sodium chloride, dried over anhydrous magnesium sulfate and evaporated in vacuo to give a residue.

On the other hand, to a solution of (1-methylimidazol-2-yl)methyl triphenyl phosphonium chloride hydrochloride (8.28 g) in a mixture of tetrahydrofuran (40 ml) and dimethyl sulfoxide (40 ml) was added portionwise potassium t-butoxide (4.30 g) at 0°–5° C. with stirring and then the mixture was stirred at the same temperature for 30 minutes. The reaction mixture was dropwise added to a solution of the residue obtained above in tetrahydrofuran (70 ml) at 0° C. and the mixture was stirred at the same temperature for 2 hours. To the reaction mixture was added ethyl acetate. The organic layer was separated and then washed with successively with 1N hydrochloric acid, saturated aqueous sodium bicarbonate and saturated aqueous sodium chloride, dried over anhydrous magnesium sulfate and evaporated in vacuo. The resulting residue was chromatographed on silica gel (250 g) eluting with a mixture of n-hexane and ethyl acetate (1:2, V/V). The fractions containing the desired compound were collected and evaporated in vacuo to give (2S,4R)-1-benzyloxycarbonyl-4-(t-butyldimethylsilyloxy)-2-[2-(1-methylimidazol-2-yl)vinyl]pyrrolidine (11.98 g).

NMR (CDCl$_3$, δ): 0.06 (6H, s), 0.87 (9H, s), 1.88–2.04 (1H, m), 2.45–2.65 (1H, m), 3.25–3.70 (4H, m), 4.40–4.50 (1H, m), 4.55–4.73 (1H, m), 5.0–5.20 (2H, m), 6.40–6.65 (2H, m), 6.79 (1H, s), 7.00 (1H, s), 7.10–7.35 (5H, m)

Preparation 8-2)

To a solution of (2S,4R)-1-benzyloxycarbonyl-4-(t-butyldimethylsilyloxy)-2-[2-(1-methylimidazol-2-yl)vinyl]pyrrolidine (11.97 g) in methanol (80 ml) was added conc. hydrochloric acid (4.79 ml) at ambient temperature with stirring and the mixture was allowed to stand overnight at the same temperature. To the reaction mixture was added 28% sodium methoxide-methanol solution (11.4 ml) under ice-cooling with stirring and the resulting insoluble material was filtered off. The filtrate was evaporated in vacuo to give a residue. The residue was chromatographed on silica gel (200 g) eluting with a mixture of chloroform and methanol (9:1, V/V). The fractions containing the desired compound were collected and evaporated in vacuo to give (2S,4R)-1-benzyloxycarbonyl-4-hydroxy-2-[2-(1-methylimidazol-2-yl)vinyl]pyrrolidine (5.47 g).

NMR (CDCl$_3$, δ): 1.93–2.05 (1H, m), 2.06–2.30 (1H, m), 3.25 (1H, s), 3.59 (3H, s), 4.46 (1H, broad s), 4.50–4.70 (1H, m), 4.90–5.10 (2H, m), 5.95–6.55 (2H, m), 6.77 (1H, s), 6.95 (1H, s), 7.10–7.35 (5H, m)

Preparation 8-3)

To a solution of (2S,4R)-1-benzyloxycarbonyl-4-hydroxy-2-[2-(1-methylimidazol-2-yl)vinyl]pyrrolidine (5.45 g) in a mixture of ethyl acetate (60 ml) and trimethylamine (3.01 ml) was added dropwise methanesulfonyl chloride (1.42 ml) under ice-cooling with stirring and the mixture was stirred at the same temperature for 1 hour. To the reaction mixture were added ethyl acetate (100 ml) and water (50 ml). The organic layer was washed successively with saturated aqueous sodium bicarbonate and saturated aqueous sodium chloride, dried over anhydrous magnesium sulfate and evaporated in vacuo. The resulting residue was chromatographed on silica gel (150 g) eluting with a mixture of dichloromethane and methanol (19:1, V/V). The fractions containing the desired compound were collected and evaporated in vacuo to give (2S,4R)-1-benzyloxycarbonyl-4-methanesulfonyloxy-2-[2-(1-methylimidazol-2-yl)vinyl]pyrrolidine (5.70 g).

NMR (CDCl$_3$, δ): 2.09–2.23 (1H, m), 2.45–2.70 (1H, m), 3.02 (3H, s), 3.31–3.65 (3H, m), 3.65–4.15 (2H, m), 4.60–4.80 (1H, m), 4.95–5.30 (3H, m), 6.10–6.60 (2H, m), 6.81 (1H, s), 7.00 (1H, s), 7.10–7.40 (5H, m)

Preparation 8-4)

A solution of (2S,4R)-1-benzyloxycarbonyl-4-methanesulfonyloxy-2-[2-(1-methylimidazol-2-yl)vinyl]pyrrolidine (5.70 g), conc. hydrochloric acid (2.34 ml) and 10% palladium on carbon (50% wet) (3.0 g) in methanol (120 ml) was stirred under atmospheric pressure of hydrogen at ambient temperature for 4 hours. The catalyst was filtered off and the filtrate was concentrated in vacuo. The resulting residue was dissolved in a mixture of tetrahydrofuran (60 ml) and water (60 ml). To solution was added dropwise a solution of allyloxycarbonyl chloride (1.94 ml) in tetrahydrofuran (5 ml) keeping the pH 8–10 with 4N sodium hydroxide under ice-cooling and then the mixture was stirred at the same temperature for 1 hour. The reaction mixture was concentrated in vacuo to give a residue. The residue was dissolved in ethyl acetate (100 ml) and then the solution was washed twice with saturated aqueous sodium chloride, dried over anhydrous magnesium sulfate and evaporated in vacuo. The resulting residue was chromatographed on silica gel (150 g) eluting with chloroform and methanol (19:1, V/V). The fractions containing the desired compound were collected and evaporated in vacuo to give (2R,4R)-1-allyloxycarbonyl-2-[2-(1-methylimidazol-2-yl)ethyl]-4-methanesulfonyloxypyrrolidine (5.69 g).

NMR (CDCl$_3$, δ): 1.80–2.10 (2H, m), 2.20–2.75 (4H, m), 3.03 (3H, s), 3.48 (4H, broad s), 3.85–4.20 (2H, m), 4.55–4.65 (2H, m), 5.17–5.35 (3H, m), 5.82–6.89 (1H, m), 6.79 (1H, s), 6.89 (1H, s)

Preparation 8-5)

To a solution of potassium t-butoxide (2.32 g) in N,N-dimethylformamide (25 ml) was added dropwise thioacetic acid (1.48 ml) with stirring at −10°–−5° C. and the mixture was stirred at −5°–0° C. for 10 minutes. To a solution of (2R,4R)-1-allyloxycarbonyl-2-[2-(1-methylimidazol-2-yl)ethyl]-4-methanesulfonyloxypyrrolidine (5.69 g) in N,N-dimethylformamide (55 ml) was added the mixture obtained above with stirring at ambient temperature. The mixture was stirred at 80°–90° C. for 3 hours. The reaction mixture was poured into ice-water (100 ml) and extracted three times with ethyl acetate (100 ml). The extract was washed with saturated aqueous sodium chloride, dried over anhydrous magnesium sulfate and evaporated in vacuo, the resulting residue was chromatographed on silica gel (150 g) eluting with a mixture of chloroform and methanol (19:1, V/V). The fractions containing the desired compound were collected and evaporated in vacuo to give (2R,4S)-4-acetylthio-1-allyloxycarbonyl-2-[2-(1-methylimidazol-2-yl)ethyl]pyrrolidine (3.20 g).

NMR (CDCl$_3$, δ): 1.64–1.80 (1H, m), 1.86–2.05 (1H, m), 2.33 (3H, s), 2.45–2.80 (4H, m), 3.70 (3H, s), 3.80–4.20 (3H, m), 4.56 (2H, d, J=5.51 Hz), 5.15–5.33 (2H, m), 5.80–6.01 (1H, m), 6.79 (1H, d, J=1.23 Hz), 6.90 (1H, d, J=1.23 Hz)

Preparation 9-1)

To a solution of (2S,4R)-1-benzyl-4-(t-butyldimethylsilyloxy)-2-methoxycarbonylpyrrolidine (20 g) in toluene (100 ml) was added dropwise diisobutyl aluminum hydride (1.02M solution in toluene) (112 ml) with stirring at a temperature kept below −60° C. and the mixture was stirred at the same temperature for 1 hour. To the reaction mixture was added dropwise ethanol (20.1 ml) with stirring at a temperature kept below −60° C. After stirring for 30 minutes at the same temperature, 5N aqueous sodium hydroxide solution was carefully added. This solution was stirred without further cooling until the temperature reached 20° C. (ca. 1.5 hours). The reaction mixture was allowed to stand for 10 minutes. The organic layer was separated, washed with water (100 ml), dried over anhydrous magnesium sulfate and evaporated in vacuo to give a solution of (2R,4S)-1-benzyl-2-formyl-4-(t-butyldimethylsilyloxy)pyrrolidine (ca. 40 ml) in toluene.

This compound was immediately used as the starting compound for the next step.

Preparation 9-2)

To a suspension of methyltriphenylphosphonium bromide (1.07 g) was portionwise added potassium t-butoxide (337 mg) with stirring under ice-cooling. The mixture was stirred at ambient temperature for 2 hours. To the solution cooled on ice-bath was added dropwise (2S,4R)-1-benzyl-2-formyl-4-(t-butyldimethylsilyloxy)pyrrolidine (0.92 g) in toluene (2 ml) and the mixture was stirred at the same temperature for 1 hour. The reaction mixture was poured into a mixture of water (10 ml) and ethyl acetate (20 ml). The organic layer was separated, washed with saturated aqueous sodium chloride, dried over anhydrous magnesium sulfate and evaporated in vacuo to give a residue. To the residue was added n-hexane (30 ml). The resulting precipitates were filtered off and the filtrate was evaporated in vacuo. The resulting residue was chromatographed on silica gel (1 g) eluting with a mixture of n-hexane and ethyl acetate (5:1 v/v). The fractions containing the desired compound were collected and evaporated in vacuo to give (2S,4R)-1-benzyl-2-vinyl-4-(t-butyldimethylsilyloxy)pyrrolidine (765 mg).

NMR (CDCl$_3$, δ): 0.02 (3H, s), 0.03 (3H, s), 0.86 (9H, s), 1.84–1.92 (2H, m), 2.09–2.16 (1H, dd, J=9.7 Hz, 5.5 Hz), 3.11–3.24 (3H, m), 4.01 (1H, d, J=13.0 Hz), 4.26–4.37 (1H, m), 5.16 (1H, dd, J=15.7 Hz, 1.9 Hz), 5.23 (1H, m), 5.64–5.82 (1H, m), 7.18–7.32 (5H, m)

Preparation 10-1)

A solution of (2R,4R)-1-allyloxycarbonyl-4-(t-butyldimethylsilyloxy)-2-(2-hydroxyethyl)pyrrolidine (5.0 g) and conc. hydrochloric acid (2.53 ml) in methanol (25 ml) was stirred under ice-cooling for 10 minutes and then stirred at ambient temperature for 1 hour. To the reaction mixture cooled at 0° C. was added 28% sodium methoxide in methanol solution (5.84 ml). The resulting precipitates were filtered off and the filtrate was evaporated in vacuo to give a residue. The residue was dissolved in dichloromethane (15 ml) and the solution was dried over anhydrous magnesium sulfate and evaporated in vacuo to give a residue. The residue was washed with n-hexane and dried in vacuo to give (2R,4R)-1-allyloxycarbonyl-4-hydroxy-2-(2-hydroxyethyl)pyrrolidine (3.10 g).

NMR (CDCl$_3$, δ): 1.60–1.75 (2H, m), 1.77–1.95 (1H, m), 2.05–2.30 (1H, m), 2.65–2.95 (1H, m), 3.35–3.75 (4H, m), 3.85–4.10 (1H, m), 4.15–4.50 (2H, m), 4.60 (2H, m), 5.15–5.40 (2H, m), 5.84–6.04 (1H, m)

Preparation 10-2)

To a solution of (2R,4R)-1-allyloxycarbonyl-4-hydroxy-2-(2-hydroxyethyl)pyrrolidine (8.28 g) and triethylamine (11.3 ml) in dichloromethane (46 ml) was dropwise added methanesulfonyl chloride (6.26 ml) with stirring under ice-cooling and the mixture was stirred at the same temperature for 1 hour. To the reaction mixture was added water (40 ml). The organic layer was separated, washed in turn with 1N hydrochloric acid, saturated aqueous sodium bicarbonate and 10% aqueous sodium chloride, dried over anhydrous magnesium sulfate and evaporated in vacuo to give (2R,4R)-1-allyloxycarbonyl-4-methanesulfonyloxy-2-(2-methanesulfonyloxyethyl)pyrrolidine (10.32 g).

NMR (CDCl$_3$, δ): 1.80–2.70 (4H, m), 3.04 (3H, s), 3.05 (3H, s), 3.45–3.70 (1H, m), 3.90–4.45 (4H, m), 4.55–4.70 (2H, m), 5.15–5.40 (3H, m), 5.80–6.05 (1H, m)

Preparation 10-3 )

To a solution of (2R,4R)-1-allyloxycarbonyl-4-methanesulfonyloxy-2-(2-methanesulfonyloxyethyl)pyrrolidine (5.35 g) in N,N-dimethylformamide (54 ml) were added imidazole (1.18 g) and potassium t-butoxide (1.78 g) with stirring under ice-cooling. The mixture was stirred at 40°–45° C. for 40 minutes. The reaction mixture was poured into water (100 ml) and extracted with dichloromethane (80 ml). The extract was washed in turn with water (50 ml) and 10% aqueous sodium chloride (50 ml), dried over anhydrous magnesium sulfate and evaporated in vacuo to give (2R,4R)-1-allyloxycarbonyl-2-[2-(imidazol-1-yl)ethyl]-4-methanesulfonyloxypyrrolidine.

This compound was immediately used as the starting compound for the next step.

Preparation 11-1)

To a suspension of sodium hydride (60% in oil, 1.11 g) in N,N-dimethylformamide (100 ml) was added 4-formylpiperazin-2-one (3.56 g) under ice cooling with stirring, and the mixture was ambient temperature for 1 hour. To the mixture was added (2S,4R)-1-allyloxycarbonyl-2-methanesulfonyloxymethyl-4-(t-butyldimethylsilyloxy pyrrolidine (9.94 g) in N,N-dimethylformamide (20 ml) under ice cooling with stirring, and the mixture was stirred at 60° C. for 2 hours.

The reaction mixture was cooled with ice-cooling, and water and ethyl acetate were added to it. The organic layer was separated washed with brine, dried over anhydrous magnesium sulfate and evaporated in vacuo. The resulting residue was purified by silica gel chromatography eluting with a mixture of chloroform and methanol (30:1 v/v) to give (2S,4R)-1-allyloxycarbonyl-4-(t-butyldimethylsilyloxy)-2-(4-formyl-2-oxopiperazin-1-yl)methylpyrrolidine (11.74 g).

NMR (CDCl$_3$, δ): 0.00 (6H, s), 0.80 (9H, s), 1.82–1.91 (2H, m), 3.37–3.74 (8H, m), 3.98–4.38 (4H, m), 4.50–4.52 (2H, m), 5.12–5.28 (2H, m), 5.77–5.93 (1H, m), 8.03 (1H, s)

Preparation 11-2)

To a solution of (2S,4R)-1-allyloxycarbonyl-4-(t-butyldimethylsilyloxy)-2-(4-formyl-2-oxopiperazin-1-yl) methylpyrrolidine (11.74 g) in tetrahydrofuran (100 ml) was added n-tetrabutylammonium fluoride under ice cooing with stirring, and the mixture was stirred at the same temperature for 1 hour. Water was added to the mixture, and the mixture was evaporated in vacuo. Ethanol was added to the residue, and the mixture was stirred at 60° C. for 20 minutes. The mixture was filtered, and the filtrate was evaporated in vacuo. The residue was purified by silica gel chromatography eluting with a mixture of chloroform and methanol (9:1 v/v) to give (2S,4R)-1-allyloxycarbonyl-2-(4-formyl-2-oxopiperazin-1-yl) methyl-4-hydroxypyrrolidine (11.38 g).

NMR (CDCl$_3$, δ): 1.99–2.04 (2H, m), 3.32–3.77 (7H, m), 4.03–4.28 (3H, m), 4.56 (4H, m), 5.19–5.34 (3H, m), 5.86–6.00 (1H, m), 8.09 (1H, s)

Preparation 11-3)

To a solution of (2S,4R)-1-allyloxycarbonyl-2-(4-formyl-2-oxopiperazin-1-yl) methyl-4-hydroxypyrrolidine (11.38 g) in ethyl acetate (110 ml) were added triethylamine (5.6 ml) and methanesulfonyl chloride (3.11 ml) under ice-cooling with stirring, and the mixture was stirred at the same temperature for 1 hour. To the mixture was added water and the mixture was evaporated in vacuo. To the residue was added tetrahydrofuran, and the mixture was stirred at 50° C. for 20 minutes. The mixture was filtered and the filtrate was dried over anhydrous magnesium sulfate, and evaporated in vacuo to give (2S,4R)-1-allyloxycarbonyl-2-(4-formyl-2-oxopiperazin-1-yl) methyl-4-(methanesulfonyloxy)pyrrolidine (14.2 g).

NMR (CDCl$_3$, δ): 1.58–1.66 (2H, m), 2.19 (1H, m), 2.40 (1H, m), 3.07 (3H, s), 3.09–3.97 (7H, m), 4.05–4.49 (2H, m), 4.90–4.95 (2H, m), 5.22–5.83 (3H, m), 5.83–5.94 (1H, m), 8.10 (1H, d, J=2.3 Hz)

Preparation 11-4)

To a solution of (2S,4R)-1-allyloxycarbonyl-2-(4-formyl-2-oxopiperazin-1-yl) methyl-4-(methanesulfonyloxy)pyrrolidine (14.2 g) in methanol (60 ml) was added conc. hydrochloric acid (12.2 ml) under ice cooling with stirring, and the mixture was stirred at the same temperature for 10 hours. The mixture was cooled to 5° C. and 28% sodium methoxidemethanol solution (28.2 ml) was added to it. The mixture was filtered, and the filtrate was evaporated in vacuo. To the residue was added chloroform. The mixture was dried over anhydrous magnesium sulfate and evaporated in vacuo to give (2S,4R)-1-allyloxycarbonyl-2-(2- oxopiperazin-1-yl) methyl-4-(methanesulfonyloxy)pyrrolidine (6.54 g).

NMR (CDCl$_3$, δ): 1.61–1.69 (2H, m), 2.30–2.32 (2H, m), 3.04 (3H, s), 3.08–3.69 (7H, m), 3.89–3.95 (1H, m), 4.24–4.30 (1H, m), 4.59–4.61 (2H, m), 5.22–5.35 (3H, m), 5.89–5.95 (1H, m)

Preparation 11-5)

To a solution of (2S,4R)-1-allyloxycarbonyl-2-(2-oxopiperazin-1-yl) methyl-4-(methanesulfonyloxy)pyrrolidine (6.37 g) in dichloromethane (60 ml) were added N,N-diisopropyl-N-ethylamine (3.38 ml) and methyl iodide (1.64 ml) under ice cooling with stirring, and the mixture was allowed to stay in a refrigeration for 12 hours. The mixture was evaporated in vacuo. The residue was purified by silica gel column chromatography eluting with a mixture of ethyl acetate, methanol and isopropylamine (10:1:0.3 v/v/v) to give (2S,4R)-1-allyloxycarbonyl-2-(2-oxo-4-methylpiperazin-1-yl) methyl-4-(methanesulfonyloxy)pyrrolidine (3.19 g).

NMR (CDCl$_3$, δ): 2.19–2.34 (5H, m), 2.66 (2H, m), 3.03 (3H, s), 3.12 (2H, s), 3.37–3.95 (6H, m), 4.24 (1H, m), 4.59–4.62 (2H, m), 5.21–5.35 (3H, m), 5.87–6.00 (1H, m)

Preparation 11-6)

To a solution of pottasium t-butoxide (1.24 g) in N,N-dimethylformamide (15 ml) was dropwise added thioacetic acid (0.85 ml) under ice cooling with stirring. The mixture was stirred at the same temperature for 30 minutes. To the solution of (2S,4R)-1-allyloxycarbonyl-2-(2-oxo-4-methylpiperazin-1-yl) methyl-4-(methanesulfonyloxy)pyrrolidine (3.19 g) in N,N-dimethylformamide (15 ml) was added the mixture obtained above at ambient temperature with stirring. The mixture was stirred at 80°–90° C. for 1.5 hours. The mixture was poured into water and extracted with ethyl acetate. The organic layer was washed with brine, dried over anhydrous magnesium sulfate and evaporated in vacuo. The residue was purified by silica gel column chromatography eluting with a mixture of chloroform and methanol (20:1 v/v) to give (2S,4S)-4-acetylthio-1-allyloxycarbonyl-2-(2-oxo-4-methylpiperazin-1-yl) methylpyrrolidine (3.24 g).

NMR (CDCl$_3$, δ): 1.85–2.01 (1H, m), 2.33 (3H, s), 2.43 (3H, s), 2.43–2.54 (1H, m), 2.65 (2H, m), 3.13–3.48 (6H, m), 3.84 (2H, m), 4.12 (2H, m), 4.60 (2H, m), 5.20–5.35 (2H, m), 5.84–6.00 (1H, m)

Preparation 12-1)

(2S,4R)-1-Allyloxycarbonyl-2-(4-allyloxycarbonyl-2-oxopiperazin-1-yl) methyl-4-(t-butyldimethylsilyloxy)pyrrolidine (0.77 g) was obtained by reacting (2S,4R)-1-allyloxycarbonyl-4-(t-butyldimethylsilyloxy)-2-methanesulfonyloxy) methylpyrrolidine (1.0 g) with 4-allyloxycarbonyl-2-oxopiperazine (515 mg) and sodium hydride (60% in oil, 112 mg) in N,N-dimethylformamide (12 ml) in substantially the same manner as that of Preparation 11-1).

NMR (CDCl$_3$, δ): 0.01 (6H, s), 0.80 (9H, s), 1.88 (2H, t, J=5.6 Hz), 3.36–3.40 (4H, m), 3.54–3.67 (4H, m), 4.04–4.16 (3H, m), 4.34–4.37 (1H, m), 4.51–4.58 (4H, m), 5.13–5.31 (4H, m), 5.78–5.95 (2H, m)

Preparation 12-2)

(2S,4R)-1-Allyloxycarbonyl-2-(4-allyloxycarbonyl-2-oxopiperazin-1-yl) methyl-4-hydroxypyrrolidine (3.01 g) was obtained by reacting (2S,4R)-1-allyloxycarbonyl-2-(4-allyloxycarbonyl-2-oxopiperazin-1-yl) methyl-4-(t-butyldimethylsilyloxypyrrolidine (3.95 g) and conc. hydrochloric acid (0.82 ml) in methanol (40 ml) in substantially the same manner as that of Preparation 11-2).

This compound was immediately used as the starting compound for the next step.

Preparation 12-3)

(2S,4R)-1-Allyloxycarbonyl-2-(4-allyloxycarbonyl-2-oxopiperazin-1-yl) methyl-4-(methanesulfonyloxy)pyrrolidine (3.63 g) was obtained by reacing (2S,4R)-1-allyloxy-carbonyl-2-(4-allyloxycarbonyl-2-oxo-piperazin-1-yl)-methyl-4-hydroxypyrrolidine (3.01 g) with methanesulfonyl chloride (0.76 ml) and triethylamine (1.49 ml) in ethyl acetate (40 ml) in substantially the same manner as that of Preparation 11-3).

This compound was immediately used as the starting compound for the next step.

Preparation 12-4)

(2S, 4S)-4-Acetylthio-1-allyloxycarbonyl-2-(4-allyloxycarbonyl-2-oxopiperazin-1-yl) methylpyrrolidine (2.41 g) was obtained by reacting (2S,4R)-1-allyloxycarbonyl-2-(4-allyloxycarbonyl-2-oxopiperazin-1-yl) methyl-4-(methanesulfonyloxy)pyrrolidine (3.63 g) with thioacetic acid (0.82 ml) and sodium hydride (60% in oil, 0.42 g) in N,N-dimethylformamide (36 ml) in substantially the same manner as that of Preparation 11-6).

NMR (CDCl$_3$, δ): 1.84–1.95 (1H, m), 2.34 (3H, s), 2.47–2.54 (1H, m), 3.24 (1H, dd, J=6.9 Hz, 11.4 Hz), 3.47–4.17 (11H, m), 4.56–4.64 (4H, m), 5.21–5.37 (4H, m), 5.86–6.01 (4H, m)

Preparation 13-1)

To a solution of 2-bromopyridine (21.9 g) in tetrahydrofuran (310 ml) was added dropwise n-butyl lithium (1.65N) in hexane (78 ml) under −60° C. After stirring for 15 minutes, (2S,4R)-1-allyloxycarbonyl-4-(t-butyldimethylsilyloxy)-2-formylpyrrolidine (31 g) was added dropwise under −60° C. After stirring for 30 minutes, the reaction mixture was quenched with water and extracted three times with ethyl acetate. The combined organic layer was washed with water and brine, dried over magnesium sulfate and evaporated under reduced pressure. The residue was column chromatographed on silica gel to give 1-{(2S,4R)-1-allyloxycarbonyl-4-(t-butyldimethyl-silyloxy) pyrrolidin-2-yl}-1-(pyridin-2-yl)methanol (13.3 g).

IR (Neat): 3400, 1690, 1590, 1400 cm$^{-1}$

NMR (CDCl$_3$, δ): 0.05 (6H, s), 0.85 (9H, s), 1.50–2.20 (2H, m), 3.40–3.60 (2H, m), 4.32–4.45 (1H, m), 4.50–4.70 (3H, m), 5.20–5.45 (3H, m), 5.86–6.03 (1H, m), 7.18–7.42 (2H, m), 7.66–7.74 (1H, m), 8.50–8.60 (1H, m)

Preparation 13-2)

To a solution of 1-{(2S,4R)-1-allyloxycarbonyl-4-(t-butyldimethylsilyloxy) pyrrolidin-2-yl}-1-(pyridin-2yl)methanol (19.82 g) and triphenylphosphine (21.2 g) in tetrahydrofuran (400 ml) at room temperature was added portionwise tetrabromomethane (25.1 g). The reaction mixture was stirred for two hours and stood for overnight. After filtration, the filtrate was evaporated under reduced pressure. To a solution of the residue in dimethylformamide (200 ml) and acetic acid (60 ml) was added portionwise zinc dust (16.5 g) under 30° C. After the addition, the mixture was stirred for one hour at room temperature, then neutralized with sodium bicarbonate (84 g) in water and extracted three times with ethyl acetate. The combined organic layer was washed with brine, dried over magnesium sulfate and evaporated under reduced pressure to give (2R,4R)-1-allyloxycarbonyl-1-4-t-butyldimethylsilyloxy-2-(2-pyridylmethyl)pyrrolidine (17.7

IR (Neat): 1745, 1680, 1580, 1400 cm$^{-1}$

NMR (CDCl$_3$, δ): 0.00 (6H, s), 0.83 (9H, s), 1.60–2.20 (3H, m), 2.83–3.10 (1H, m), 3.10–3.60 (2H, m), 4.00–4.10 (1H, m), 4.10–4.48 (1H, m), 4.48–4.78 (2H, m), 5.10–5.40 (2H, m), 5.80–6.08 (1H, m), 7.00–7.40 (2H, m), 7.50–7.90 (1H, m), 8.48–8.72 (1H, m)

Preparation 13-3)

To a solution of (2R,4R)-1-allyloxycarbonyl-4-t-butyldimethylsilyloxy-2-(2-pyridylmethyl)pyrrolidine (4.88 g) in acetonitrile (50 ml) was added dropwise conc. hydrochloric acid (3.3 ml) at room temperature. The reaction mixture was stirred for 5 hours, then neutralized with saturated aqueous sodium bicarbonate and diluted with ethyl acetate. The organic layer was separated, washed with brine, dried over magnesium sulfate and evaporated under reduced pressure to give (2R,4R)-1-allyloxycarbonyl-4-hydroxy-2-(2-pyridylmethyl) pyrrolidine (2.46 g). On the other hand the aqueous layer was extracted five times with chloroform. The combined chloroform layer was washed with brine, dried over magnesium sulfate and evaporated under reduced pressure to give (2R,4R)-1-allyloxycarbonyl-4-hydroxy-2-(2-pyridylmethyl) pyrrolidine (0.23 g).

IR (Neat): 3350, 1670, 1590, 1400 cm$^{-1}$

NMR (CDCl$_3$, δ): 1.80–2.20 (2H, m), 2.91 (1H, dd, J=8.7 and 12.9 Hz), 3.35 (1H, dd, J=4.6 and 11.7 Hz), 3.20–3.70 (2H, m), 4.20–4.53 (2H, m), 4.53–4.70 (2H, m), 5.10–5.40 (2H, m), 5.80–6.10 (1H, m), 7.00–7.33 (2H, m), 7.50–7.80 (1H, m), 8.40–8.60 (1H, m)

Preparation 13-4)

To a solution of (2R,4R)-1-allyloxycarbonyl-4-hydroxy-2-(2-pyridylmethyl) pyrrolidine (1.0 g), thiobenzoic acid (973 µl) and triphenylphosphine (1.30 g) in tetrahydrofuran (20 ml) was added dropwise diethyl azodicarboxylate (1.2 ml) at 0° C. The reaction mixture was stirred for 30 minutes, and then diluted with water and ethyl acetate. The aqueous layer was separated and extracted twice with ethyl acetate. The combined organic layer was washed with water (twice) and brine, dried over magnesium sulfate and evaporated under reduced pressure. The residue was column chromatographed on silica gel to give (2R,4S)-1-allyloxycarbonyl-4-benzoylthio-2-(2-pyridylmethyl)pyrrolidine (1.34 g).

IR (Neat): 1680, 1660, 1580, 1400 cm$^{-1}$

Preparation 14-1)

1-{(2S,4R)-1-Allyloxycarbonyl-4-(t-butyldimethyl-silyloxy) pyrrolidin-2-yl}-1-(pyridin-3-yl)methanol was obtained in substantially the same manner as that of Preparation 13-1).

NMR (CDCl$_3$, δ): 0.05 (6H, s), 0.83 (9H, s), 1.5–2.1 (3H, m), 3.3–3.7 (2H, m), 4.0–4.5 (2H, m), 4.5–4.8 (2H, m), 5.2–5.4 (2H, m), 5.8–6.2 (1H, m), 7.2–7.4 (1H, m), 7.6–7.9 (1H, m), 8.5–8.7 (2H, m)

Preparation 14-2)

(2R,4R)-1-Allyloxycarbonyl-4-t-butyldimethylsilyloxy-2-(3-pyridylmethyl) pyrrolidine was obtained in substantially the same manner as that of Preparation 13-2).

NMR (CDCl$_3$, δ): 0.00 (6H, s), 0.84 (9H, s), 1.7–2.2 (2H, m), 2.7–3.6 (4H, m), 4.0–4.4 (2H, m), 4.6–4.8 (2H, m), 5.2–5.4 (2H, m), 5.9–6.1 (1H, m), 7.2–7.4 (1H, m), 7.4–7.6 (1H, m), 8.4–8.7 (2H, m)

Preparation 14-3)

(2R,4R)-1-Allyloxycarbonyl-4-hydroxy-2-(3-pyridylmethyl pyrrolidine was obtained in substantially the same manner as that of Preparation 13-3).

NMR (CDCl$_3$, δ): 1.7–2.1 (2H, m), 2.7–2.9 (1H, m), 3.1–3.4 (3H, m), 4.2–4.3 (2H, m), 4.5–4.7 (2H, m), 5.2–5.4 (2H, m), 5.8–6.1 (1H, m), 7.2–7.4 (1H, m), 7.4–7.6 (1H, m), 8.3–8.6 (2H, m)

Preparation 14-4)

(2R,4S)-1-Allyloxycarbonyl-4-benzoylthio-2-(3-pyridylmethyl)pyrrolidine was obtained in substantially the same manner as that of Preparation 13-4).

NMR (CDCl$_3$, δ): 1.7.1.9 (2H, m), 2.2–3.0 (2H, m), 3.2–3.4 (2H, m), 4.0–4.2 (2H, m), 4.6–4.7 (2H, m), 5.2–5.4 (2H, m), 5.9–6.1 (1H, m), 7.2–7.8 (6H, m), 7.9–8.0 (2H, m), 8.4–8.5 (2H, m)

Preparation 15-1)

A solution of 4-bromopyridine hydrochloride (18.57 g) in ethyl ether (50 ml) and water (50 ml) was neutralized with sodium hydrogen carbonate in water (50 ml). After stirring for 10 minutes, the mixture was extracted three times with ethyl ether. The combined organic layer was washed with brine, dried over magnesium sulfate and evaporated under reduced pressure to give a residue. To a solution of the residue in ethyl ether (300 ml) was added n-butyllithium (1.68N solution in n-hexane) (63 ml) under –60° C. After the addition, the mixture was stirred for 30 minutes at –78° C. Then (2S,4R)-1-benzyl-4-(t-butyldimethylsilyloxy)-2-formylpyrrolidine (30.52 g) was added dropwise to the mixture under –60° C. After the addition, the mixture was stirred at –70° C. for 30 minutes and then warmed to room temperature. The raction mixture was quenched with water and extracted three times with ethyl acetate. The combined organic layer was washed with brine, dried over magnesium sulfate and evaporated under reduced pressure. The residue was column chromatographed on silica gel eluting with ethyl acetate:n-hexane=3:7 to 1:1) to give 1-{(2S,4R)-1-benzyl-4-(t-butyl-dimethylsilyloxy)pyrrolidin-2-yl}-1-(4-pyridyl)methanol (14.68 g).

NMR (CDCl$_3$, δ): 0.00–0.07 (6H, m), 0.85 (4.5H, s), 0.91 (4.5H, s), 1.2–1.9 (1H, m), 2.0–2.1 (1H, m), 2.4–2.6 (1H, m), 3.0–4.8 (6H, m), 7.1–7.4 (7H, m), 8.5–8.6 (2H, m)

Preparation 15-2)

To a solution of 1-{(2S,4R)-1-benzyl-4-(t-butyldimethyl-silyloxy) pyrrolidin-2-yl}-1-(4-pyridyl)methanol (32.73 g) in ethanol (300 ml) was added acetic acid (9.4 ml) and palladium hydroxide on carbon (10 g). The mixture was stirred vigorously under an atmosphere of hydrogen at room temperature for 6 hours. The palladium catalyst was removed by filtration and washed with ethanol. The combined organic layer was evaporated under reduced pressure to give a residue. To a solution of the residue in water (300 ml) and tetrahydrofuran (THF) (300 ml) was added dropwise allyl chloroformate (9.6 ml) under pH 9~10 at 0° C. After stirring the mixture at 0° C. for 1 hour, the reaction mixture was extracted three times with ethyl acetate. The combined organic layer was washed with brine, dried over magnesium sulfate and evaporated under reduced pressure. The residue was column chromatographed on silica gel (eluting with ethyl acetate:n-hexane=7:3) to give 1-{(2S, 4R)-1-allyloxycarbonyl-4-(t-butyldimethylsilyloxy) pyrrolidin-2-yl}-1-(4-pyridyl)methanol (21.74 g).

NMR (CDCl$_3$, δ): 0.00 (6H, m), 0.82 (9H, s), 1.4–2.0 (3H, m), 3.0–3.7 (2H, m), 4.0–4.4 (2H, m), 4.5–4.8 (2H, m), 5.1–5.4 (2H, m), 5.8–6.1 (1H, m), 7.2–7.4 (2H, m), 8.5–8.6 (2H, m)

Preparation 15-3)

(2R,4R)-1-Allyloxycarbonyl-4-(t-butyldimethyl-silyloxy)-2-(4-pyridylmethyl) pyrrolidine was obtained in 89% yield in substantially the same manner as that of Preparation 13-2).

NMR (CDCl$_3$, δ): 0.00 (6H, s), 0.83 (9H, s), 1.6–2.0 (2H, m), 2.7–2.9 (1H, m), 3.0–3.5 (3H, m), 4.1–4.4 (2H, m), 4.6–4.7 (2H, m), 5.1–5.4 (2H, m), 5.8–6.1 (1H, m), 7.0–7.2 (2H, m), 8.5–8.6 (2H, m)

Preparation 15-4)

(2R,4R)-1-Allyloxycarbonyl-4-hydroxy-2-(4-pyridylmethyl)pyrrolidine was obtained in 68% yield in substantially the same manner as that of Preparation 13-3).

NMR (CDCl$_3$, δ): 1.6–1.9 (2H, m), 2.3–2.6 (1H, m), 2.77 (1H, dd, J=12.7 Hz, 8.8 Hz), 3.0–3.3 (1H, m), 3.33 (1H, dd, J=11.9 Hz, 4.3 Hz), 3.4–3.7 (1H, m), 4.1–4.4 (2H, m), 4.5–4.7 (2H, m), 5.1–5.4 (2H, m), 5.8–6.1 (1H, m), 7.0–7.1 (2H, m), 8.48 (2H, d, J=6.0 Hz)

Preparation 15-5)

(2R,4S)-1-Allyloxycarbonyl-4-benzoylthio-2-(4-pyridylmethyl)pyrrolidine was obtained quantitatively in substantially the same manner as that of Preparation 13-4).

NMR (CDCl$_3$, δ): 1.6–1.9 (1H, m), 2.2–2.6 (1H, m), 2.80 (1H, dd, J=13.0 Hz, 9.6 Hz), 3.2–3.6 (2H, m), 4.0–4.3 (3H, m), 4.6–4.7 (2H, m), 5.2–5.4 (2H, m), 5.8–6.1 (1H, m), 7.0–7.1 (2H, m), 7.5–8.0 (5H, m), 8.4–8.6 (2H, m)

Preparation 16-1)

To a solution of N-methylimidazole (84.0 ml) in tetrahydrofuran (1.25 l) was added dropwise n-butyllithium (1.56N, 500 ml and 1.60N, 120 ml) in hexane keeping the temperature below −65° C. After stirring for 30 minutes, to the mixture was added dropwise a solution of (2S,4R)-1-benzyl-4-(t-butyldimethylsilyloxy)-2-formylpyrrolidine (259 g) in THF (1.25 l) at −65°~−60° C. for 30 minutes. The mixture was stirred at −60°~0° C. for 1.5 hours and at 0°~5° C. for 30 minutes. The reaction mixture was poured into a mixture of cold water (5 l) and ethyl acetate (5 l). The organic layer was separated, washed with water and brine, dried over magnesium sulfate and evaporated under reduced pressure. To the residue was added ethyl acetate (180 ml) and n-hexane (620 ml). The precipitate was collected by filtration to give isomer A of 1-{(4R)-1-benzyl-4-(t-butyldimethylsilyloxy) pyrrolidin-2-yl}-1-[1-methylimidazol-2-yl]methanol (480 g). The filtrate was evaporated in vacuo. The residue was chromatographed on silica gel (2.6 kg, eluent; AcOEt:n-hexan=3:2 to 10:0), and the eluate was evaporated to give isomer B of the same (147.4 g) containing 17% of isomer A, as a solid.

Isomer B:

NMR (CDCl$_3$, δ): 0.01, 0.02 (total 6H, each s), 0.86 (9H, s), 1.84–2.04 (2H, m), 2.57 (1H, dd, J=3.3 Hz, 7.8 Hz), 2.97 (1H, dd, J=4.7 Hz, 6.4 Hz), 3.66 (3H, s), 3.80 and 4.10 (2H, ABq, J=13.0 Hz), 3.81–3.91 (1H, m), 4.18–4.25 (1H, m), 4.41 (1H, d, J=5.6 Hz), 6.79 (1H, d, J=1.2 Hz), 6.93 (1H, d, J=1.2 Hz), 7.20–7.30 (5H, m)

APCI-Mass (m/z): 402 (MH$^+$)

Isomer A:

NMR (CDCl$_3$, δ): 0.02, 0.03 (6H, s), 0.85 (9H, s), 2.17–2.31 (1H, m), 1.89–2.03 (1H, m), 2.42 (1H, dd, J=6.3 Hz, 9.6 Hz), 3.13 (1H, dd, J=5.4 Hz, 9.6 Hz), 3.44–3.51 (2H, m), 3.57 and 3.88 (2H, ABq, J=13.1 Hz), 3.67 (3H, s), 4.22–4.34 (1H, m), 4.70 (1H, d, J=3.6 Hz), 6.79 (1H, d, J=1.2 Hz), 6.96 (1H, d, J=1.2 Hz), 7.22–7.37 (5H, m)

APCI-Mass (m/z) : 402 (MH$^+$)

Preparation 16-2)

To a solution of isomer B obtained in Preparation 16-1) (55.0 g) in dichloromethane (1.1 l) was added dropwise thionyl chloride (11.0 ml) at −10°~−7° C. for 20 minutes with stirring. The mixture was stirred at the same temperature for 20 minutes and at −7°~5° C. for 1 hour. To the reaction mixture was added dropwise thiophenol (15.4 ml) at 3°~6° C. for 5 minutes, and the mixture was stirred at the same temperature for 1 hour. To the reaction mixture was added triethylamine (9.53 ml×2) at 3°~6° C. After stirring for 30 minutes, water (500 ml) was added to the reaction mixture. The separated organic layer was washed with brine, dried over magnesium sulfate and evaporated. The residue was chromatographed on silica gel column (2 kg, eluent; CHCl$_3$:MeOH=50:1 to 30:1), and evaporated to give as an amorphous solid, isomer B of (2S,4R)-1-benzyl-4-t-butyldimethylsilyloxy-2-{1-(1-methylimidazol-2-yl)-1-(phenylthio)methyl}pyrrolidine (48.6 g).

NMR (CDCl$_3$, δ): 0.02, 0.05 (total 6H, each s), 0.87 (9H, s), 2.15–2.44 (3H, m), 3.03 (1H, dd, J=4.8 Hz, 10.1 Hz), 3.25 (3H, s), 3.55 and 3.71 (2H, ABq, J=13.1 Hz), 4.23 (1H, d, J=6.5 Hz), 4.29–4.40 (1H, m), 6.61 (1H, d, J=1.2 Hz), 6.96 (1H, J=1.2 Hz), 7.06–7.32 (10H, m)

APCI-Mass (m/z) : 494 (MH$^+$)

Preparation 16-3)

To a suspension of Raney nickel (NDT-90, 710 ml) and acetone (300 ml) was added isomer B obtained in Preparation 16-2) (47.8 g) in acetone (500 ml) under an atmosphere of nitrogen. The mixture was stirred and heated under reflux for 1.5 hours. After cooling, the Raney nickel was removed by filtration, and washed with acetone (500 ml×5). The filtrate and the washings were combined and evaporated in vacuo. The residue was chromatographed on silica gel (1.2 kg, eluent; CHCl$_3$:MeOH =30:1), and evaporated to give (2R,4R)-1-benzyl-4-(t-butyldimethylsilyloxy)-2-{(1-methylimidazol-2-yl) methyl}pyrrolidine (23.8 g) as an oil.

NMR (CDCl$_3$, δ) : 0.00, 0.09 (total 9H, each s), 0.86 (9H, s), 1.88–1.95 (2H, m), 2.28 (1H, dd, J=5.7 Hz, 9.8 Hz), 2.68 (1H, dd, J=8.4 Hz, 14.6 Hz), 2.94 (1H, dd, J=4.8 Hz, 14.6 Hz), 3.13 (1H, dd, J=5.7 Hz, 9.8 Hz), 3.21–3.36 (1H, m), 3.44 and 3.92 (2H, ABq, J=13.1 Hz), 3.55 (3H, s), 4.25–4.34 (1H, m), 6.77 (1H, d, J=1.2 Hz), 6.94 (1H, d, J=1.2 Hz), 7.21–7.33 (5H, m)

APCI-Mass (m/z): 386 (MH$^+$)

Preparation 16-4)

To a solution of (2R,4R)-1-benzyl-4-(t-butyldimethylsilyloxy)-2-{(1-methylimidazol-2-yl)methyl}pyrrolidine (23.7 g) in methanol (240 ml) was added ammonium formate (15.5 g) and 10% palladium on carbon (Pd-C) (wet, 7.1 g). The mixture was refluxed for 1.5 hours. After cooling, the 10% Pd-C was removed by filtration. The filtrate was evaporated. To the residue was added dichloromethane (300 ml) and precipitated excess ammonium formate was filtered off. The filtrate was evaporated in vacuo to give (2R,4R)-4-(t-butyldimethylsilyloxy)-2-{(1-methylimidazol-2-yl)methyl}pyrrolidin formate (20.1 g) as an oil.

NMR (CDCl$_3$, δ): 0.01 (6H, s), 0.81 (9H, s), 1.96–2.03 (2H, m), 2.99–3.11 (2H, m), 3.32 (1H, dd, J=8.0 Hz, 16.2 Hz), 3.50–3.63 (1H, m), 3.57 (3H, s), 4.18–4.29 (1H, m), 4.50–4.51 (1H, m), 6.76 (1H, d, J=1.3 Hz), 6.82 (1H, d, J=1.3 Hz), 8.40 (1H, s), 8.90 (2H, br s)

APCI-Mass (m/z): 296 (MH$^+$-HCOOH)

Preparation 16-5)

To a solution of (2R,4R)-4-(t-butyldimethylsilyloxy)-2-{(1-methylimidazol-2-yl)methyl}pyrrolidineformate (20.0 g) in tetrahydrofuran (300 ml) and water (200 ml) was added dropwise a solution of allyl chloroformate (7.45 ml) in THF (20 ml), adjusting pH to 9.0–9.5 with 5N-aqueous sodium hydroxide solution, at −3°~1° C. over 10 minutes. The mixture was stirred at the same temperature for 50 minutes. To the reaction mixture was added ethyl acetate (600 ml) and ice water (400 ml). The organic layer was separated and the aqueous layer was extracted with ethyl acetate (100 ml). The combined organic layer was washed with water and brine, dried over magnesium sulfate and evaporated in vacuo to give (2R,4R)-1-allyloxycarbonyl-4-(t-butyldimethylsilyloxy)-2-{(1-methylimidazol-2-yl) methyl}pyrrolidine (20.5 g) as an oil.

NMR (CDCl$_3$, δ): 0.02 (6H, s), 0.83 (9H, 1.84–1.97 (1H, m), 2.18–2.30 (1H, m), 2.84 (1H, dd, J=8.8 Hz, 14.3 Hz), 3.30–3.36 (2H, m), 3.65 (3H, s), 4.10–4.23 (2H, m), 4.62 (2H, m), 5.19–5.35 (2H, m), 5.85–6.10 (1H, m), 6.80 (1H, s), 6.91 (1H, s)

APCI-Mass (m/z) : 380 (MH$^+$)

Preparation 16-6)

(2R,4R)-1-Allyloxycarbonyl-4-hydroxy-2-{(1-methylimidazol-2-yl) methyl}pyrrolidine (12.0 g) was obtained in 84.2% yield by the similar procedure as Preparation 13-3).

NMR (CDCl$_3$, δ): 2.00–2.06 (1H, m), 2.23–2.32 (1H, m), 2.70–2.82 (1H, m), 3.15–3.58 (3H, m), 3.68 (3H, s), 4.18 (1H, m), 4.43–4.48 (1H, m), 4.60–4.63 (2H, m), 5.20–5.36 (2H, m), 5.86–6.05 (1H, m), 6.80 (1H, d, J=1.2 Hz), 6.87 (1H, d, J=1.2 Hz)

APCI-Mass (m/z): 266 (MH$^+$)

Preparation 16-7)

(2R,4S)-1-Allyloxycarbonyl-4-benzoylthio-2-{(1-methylimidazol-2-yl) methyl}pyrrolidine (2.0 g) was obtained in 68.8% yield by the similar procedure as Preparation 13-4).

NMR (CDCl$_3$, δ): 2.10–2.39 (1H, m), 2.42–2.73 (1H, m), 2.92 (1H, dd, J=10.1 Hz, 15.6 Hz), 3.32 (1H, dd, J=6.3 Hz, 10.8 Hz), 3.36–3.70 (2H, m), 3.68 (3H, s), 4.03–4.38 (3H, m), 4.57–4.71 (2H, m), 5.21–5.37 (2H, m), 5.86–5.97 (1H, m), 6.81 (1H, d, J=1.2 Hz), 6.93 (1H, d, J=1.2 Hz), 7.40–7.69 (5H, m)

APCI-Mass (m/z) : 386 (MH$^+$)

Preparation 17-1)

To a stirred mixture of bromine (50.2 ml) in dichloromethane (14) and anhydrous sodium carbonate (206.8 g) was added a solution of N-methylpyrazole (80 g) in dichloromethane (100 ml) at 0°~5° C. After stirring for 1 hour at the same temperature, the mixture was stirred for a further one hour at room temperature and then ice cooled. To the reaction mixture, water (1 l) was added. The dichloromethane layer was separated and the aqueous layer was extracted twice with dichloromethane. The combined organic layer was washed with water and brine, dried over magnesium sulfate and evaporated under reduced pressure. The resulting residue was distilled in vacuo to afford 4-bromo-1-methylpyrazole (150.6 g).

bp: 82° C. (20 mmHg)

IR (Neat): 3100, 2930 cm$^{-1}$

NMR (CDCl$_3$, δ): 3.89 (3H, s), 7.38 (1H, s), 7.44 (1H, s)

APCI-Mass (m/z) : 161, 163 (MH$^+$)

Preparation 17-2)

To a solution of 4-bromo-1-methylpyrazole (170.7 g) in diethyl ether (2 l) was added dropwise n-butyllithium (1.6N) in hexane (713 ml) keeping the temperature below −60° C. After stirring for 45 minutes, a solution of (2S,4R)-1-benzyl-4-(t-butyldimethylsilyloxy)-2-formylpyrrolidine (260 g) in diethyl ether (200 ml) was added dropwise. After stirring for 30 minutes, the mixture was warmed to 0°~5° C. over 2.5 hours and stirred for 45 minutes. The reaction mixture was quenched with ice water (1 l) and the organic layer was separated. The aqueous layer was extracted with ethyl acetate (×2), and the combined organic layer was washed with water and brine, dried over magnesium sulfate and evaporated under reduced pressure. The residue was column chromatographed on silica gel (3.5 kg, eluting with n-hexane:AcOEt=3:2 to 1:1 to 0:1) to give (2S,4R)-1-{1-benzyl-4-(t-butyldimethyl-silyloxy) pyrrolidin-2-yl}-1-(1-methyl-4-pyrazolyl)methanol (211.2 g) as a 1:1 mixture of diastereomers.

IR (CHCl$_3$): 2400–3500 (br) cm$^{-1}$

NMR (CDCl$_3$, δ): 0.01, 0.02, 0.04 (total 6H, each s), 0.85, 0.89 (total 9H, each s), 1.46–1.62, 1.80–2.13 (total 2H, m), 2.41 (dd, J=9.7 Hz, 5.6 Hz) 2.52 (dd, J=10.2 Hz, 3.5 Hz)} total 1H, 3.00 (dd, J=11.0 Hz, 4.7 Hz) 3.12–3.25 (m) 3.27–3.38 (m)}total 2H, 3.54 (d, J=13.0 Hz) 3.72 (d, J=13.1 Hz)}total 2H, 3.91 (d, J=13.1 Hz) 4.11 (d, J=13.0 Hz) 3.88, 3.95 (total 3H, each s), 4.15–4.35 (total 1H, m), 4.41 (d, J=5.4 Hz) 4.85 (d, J=2.7 Hz)}total 1H, 7.23–7.40 (total 6H, m), 7.41, 7.45 (total 1H, each s)

APCI-Mass (m/z) : 402 (MH$^+$)

Preparation 17-3)

To a solution of (2S,4R)-1-{1-benzyl-4-(t-butyl-dimethylsilyloxy) pyrrolidin-2-yl}-1-(1-methyl-4-pyrazolyl) methanol (70 g) in methanol (700 ml) was added ammonium formate (44 g) and 10% Pd-C (wet, 20 g). The mixture was refluxed for 40 minutes, then cooled. After filtration of Pd-C, the solvent was evaporated. To the residue was added chloroform (500 ml) and precipitated excess ammonium formate was filtered off with celite. The filtrate was concentrated under reduced pressure. The residue was dissolved in tetrahydrofuran-water (1:1, 1 l) and a solution of allyl chloroformate (22.3 ml) in tetrahydrofuran (60 ml) was added thereto, while adjusting pH to 8.5~10 with 4N-sodium hydroxide solution at 0°~5° C. The mixture was stirred for 30 minutes at the same temperature. The organic layer was separated and the aqueous layer was extracted with ethyl acetate (×2). The combined organic layer was washed with water and brine, dried over magnesium sulfate and evaporated under reduced pressure to give 1-{(2S,4R)-1-allyloxycarbonyl-4-(t-butyldimethylsilyloxy) pyrrolidin-2-yl}-1-(1-methylpyrazol-4-yl) methanol (66.2 g).

IR (Neat): 3300, 1670, 1400, 1100 cm$^{-1}$

NMR (CDCl$_3$, δ): 0.01, 0.02 (total 6H, each s), 0.83 0.84 (total 9H, each s), 1.50–2.00 (3H, m), 3.08–3.70 (2H, m), 3.87, 3.88 (total 3H, each s), 4.10–4.50 (2H, m), 4.58–4.70 (2H, m), 4.72–5.00 (1H, m), 5.19–5.45 (2H, m), 5.86–6.05 (1H, m), 7.26, 7.37, 7.41 (total 2H, each s)

APCI-Mass (m/z): 396 (MH$^+$), 378 (MH$^+$-H$_2$O)

Preparation 17-4)

To an ice-cooled solution of 1-{(2S,4R)-1-allyloxy-carbonyl-4-(t-butyldimethylsilyloxy) pyrrolidin-2-yl}-1-(1-methylpyrazol-4-yl) methanol (71.2 g) in dichloromethane (700 ml) were added pyridine (54 ml) and phenyl chlorothioformate (34.3 g). The mixture was stirred for 30 minutes at the same temperature, then stirred for 3 hours at room temperature. Dichloromethane was evaporated and the residue was poured into saturated sodium bicarbonate solution, and then extracted with ethyl acetate. The organic layer was washed with water and brine, dried over magnesium sulfate and evaporated under reduced pressure. The residue was column chromatographed on silica gel (2 kg, eluting with n-hexane: ethyl acetate (AcOEt)=5:3 to 5:4)) to give (2S,4R)-1-allyloxycarbonyl-4-(t-butyldimethylsilyloxy)-2-{1-(1-methylpyrazol-4-yl)-1-(phenoxythiocarbonyloxy)methyl}pyrrolidine (46.2 g).

IR (Neat): 1685, 1400, 1090 cm$^{-1}$

NMR (CDCl$_3$, δ): 0.02, 0.04 (total 6H, each s), 0.84 (9H, s), 1.86–2.16 (2H, m), 2.95–3.18 and 3.35–3.80 (total 2H, m), 3.80–3.92 (3H, m), 3.92–4.10 and 4.32–4.42 (total 1H, m), 4.42–4.73 (3H, m), 5.08–5.43 (3H, m), 5.82–6.10 (1H, m), 7.05–7.51 (7H, m)

APCI-Mass (m/z): 532 (MH$^+$)

Preparation 17-5)

To a solution of (2S,4R)-1-allyloxycarbonyl-4-(t-butyldimethylsilyloxy)-2-{1-(1-methylpyrazol-4-yl)-1(phenoxythiocarbonyloxy)methyl}pyrrolidine (42.9 g) in toluene (600 ml) was added tri-n-butyltin hydride (43.5 ml) and AIBN (2.65 g). Under nitrogen atmosphere, the mixture was refluxed for 3.5 hours then cooled. To the mixture was added tri-n-butyltin hydride (10.9 ml) and 2,2'-azobisisobutyronitrile (AIBN) (1.33 g), then refluxed again for 3.5 hours. After cooling, the solvent was evaporated and the residue was column chromatographed on silica gel (2.4 kg, eluting with n-hexane:AcOEt=5:4) to give (2R,4R)-1-allyloxycarbonyl-4-(t-butyldimethylsilyl-oxy)-2-{(1-methylpyrazol-4-yl)methyl)pyrrolidine (22.3 g).

IR (Neat): 1680, 1395, 1090 cm$^{-1}$

NMR (CDCl$_3$, δ): 0.01 (6H, s), 0.83 (9H, s), 1.65–2.00 (2H, m), 2.70–2.95 (2H, m), 3.26 (1H, dd, J=11.2 Hz, 4.7 Hz), 3.28–3.45 (1H, m), 3.84 (3H, s), 4.03–4.22 (2H, m), 4.58–4.70 (2H, m), 5.17–5.40 (2H, m), 5.86–6.06 (1H, m), 7.12 (1H, s), 7.25 (1H, s)

APCI-Mass (m/z) : 380 (MH$^+$)

Preparation 17-6)

To an ice-cooled solution of (2R,4R)-1-allyloxy-carbonyl-4-(t-butyldimethylsilyloxy)-2-{(1-methyl-pyrazol-4-yl)methyl)pyrrolidine (22.3 g) in methanol (220 ml) was added 1N-hydrochloric acid (118 ml). The mixture was stirred for 15 minutes at the same temperature, then stirred for 1.5 hours at room temperature. After cooling with an ice bath, sodium bicarbonate (10.4 g) was added, and methanol was evaporated under reduced pressure. The resulting aqueous residue was extracted with chloroform (×3). The combined organic layer was washed with water and brine, dried over magnesium sulfate and evaporated under reduced pressure. The residue was column chromatographed on silica gel (600 g, eluting with chloroform (CHCl$_3$): methanol (MeOH)=10:1) to give (2R,4R)-1-allyloxycarbonyl-4-hydroxy-2-{(1-methylpyrazol-4-yl)methyl}pyrrolidine (15.3 g).

IR (Neat): 3350, 1670, 1410 cm$^{-1}$

NMR (CDCl$_3$, δ): 1.75–2.10 (3H, m), 2.70–3.00 (2H, m), 3.20–3.38 (1H, m), 3.45–3.70 (1H, m), 3.85 (3H, s), 4.10–4.33 (2H, m), 4.55–4.75 (2H, m), 5.20–5.40 (2H, m), 5.87–6.08 (1H, m), 7.13 (1H, s), 7.27 (1H, s)

APCI-Mass (m/z): 266 (MH$^+$)

Preparation 17-7)

To a solution of (2R,4R)-1-allyloxycarbonyl-4-hydroxy-2-{(1-methylpyrazol-4-yl)methyl)pyrrolidine (15.3 g) and triphenylphosphine (19.67 g) in tetrahydrofuran (180 ml) was added diethyl azodicarboxylate (13.06 g) at −30° C. After 15 minutes, thiobenzoic acid (9.5 ml) was added thereto. The mixture was warmed up to 0°~5° C. over 25 minutes and stirred for 2 hours. After evaporation of tetrahydrofuran, the resulting residue was dissolved in ethyl acetate (500 ml). The organic layer was washed with saturated sodium bicarbonate solution (×3), water and brine, dried over magnesium sulfate and evaporated under reduced pressure. After storing the residue overnight in an ice box, a precipitate had appeared. To the precipitate was added a solution of diisopropyl ether (IPE)—diethyl ether (1:1, 100 ml) and the solid was removed by filtration. The filtrate was evaporated and the residue was column chromatographed on silica gel (1.1 kg, eluting with AcOEt-IPE=2:3 to 1:1) to give (2R,4S)-1-allyloxycarbonyl-4-benzoylthio-2-{(1-methylpyrazol-4-yl)methyl}pyrrolidine (21.8 g).

IR (Neat): 1680, 1655, 1400, 1195 cm$^{-1}$

NMR (CDCl$_3$, δ): 1.81 (1H, qn, J=6.3 Hz), 2.40–2.60 (1H, m), 2.79 (1H, dd, J=14.2 Hz, 8.9 Hz), 2.90–3.15 (1H, m), 3.19 (1H, dd, J=10.8 Hz, 7.3 Hz), 3.86 (3H, s), 3.95–4.25 (3H, m), 4.58–4.74 (2H, m), 5.19–5.42 (2H, m), 5.87–6.08 (1H, m), 7.17 (1H, s), 7.31 (1H, s), 7.37–7.74 (5H, m)

APCI-Mass (m/z): 386 (MH$^+$)

Preparation 18-1)

(2R,4R)-1-Allyloxycarbonyl-4-methylsulfonyloxy-2-(2-methylsulfonyloxyethyl) pyrrolidine (28.8 g) and 2-(t-butyldimethylsilyloxymethyl)imidazole (18.1 g) were reacted in substantially the same manner as that of Preparation 10-3) to give (2R,4R)-1-allyloxycarbonyl-2-[2-(2-(t-butyldimethylsilyloxymethyl) imidazol-1-yl)ethyl]-4-methylsulfonyloxypyrrolidine (34.5 g) as a yellow paste.

NMR (CDCl$_3$, 200 MHz, δ): 0.08 (6H, s), 0.90 (9H, s), 1.8–2.1 (2H, m), 2.3–2.6 (2H, m), 3.04 (3H, s), 3.4–3.6 (1H, m), 3.9–4.2 (4H, m), 4.6–4.7 (2H, m), 4.77 (2H, s), 5.1–5.4 (3H, m), 5.7–5.9 (1H, m), 6.8–7.1 (2H, m)

Preparation 18-2)

To a solution of (2R,4R)-1-allyloxycarbonyl-2-[2-{2-(t-butyldimethylsilyloxymethyl)imidazol-1-yl}ethyl]-4-methylsulfonyloxypyrrolidine (34.5 g) in methanol (170 ml) was added concentrated hydrochloric acid (17 ml) dropwise under cooling in an ice bath. After stirring for 10 minutes, the mixture was warmed to room temperature and stirred for another 3 hours. The mixture was quenched by the addition of a solution of sodium methoxide in methanol (28% W/W, 39.4 g), then ethyl acetate (340 ml) was added. The precipitate was filtered off and the filtrate was concentrated to give a crude oil. The oil was chromatographed on a 300 g of silica gel eluting with a mixture of chloroform and methanol (100:0 to 95:5) to give (2R,4R)-1-allyloxycarbonyl-2-[2-(2-hydroxymethylimidazol-1-yl) ethyl]-4-methylsulfonyloxypyrrolidine (15.7 g) as a light brown paste.

NMR (CDCl$_3$, 200 MHz, δ): 1.8–2.1 (2H, m), 2.2–2.6 (2H, m), 3.02 (3H, s), 3.5–3.7 (2H, m), 3.9–4.2 (4H, m), 4.5–4.7 (4H, m), 5.1–5.4 (3H, m), 5.8–6.0 (1H, m), 6.8–7.0 (2H, m)

Preparation 18-3)

(2R,4R)-1-Allyloxycarbonyl-2-[2-(2-hydroxymethyl-imidazol-1-yl) ethyl]-4-methanesulfonyloxypyrrolidine (15.7 g) was reacted with thioacetic S-acid (6.30 ml) in substantially the same manner as that of Preparation 4-12) to give (2R,4S)-4-acetylthio-1-allyloxycarbonyl-2-[2-(2-hydroxymethylimidazol-1-yl) ethyl]pyrrolidine (5.93 g) as an orange paste.

NMR (CDCl$_3$, 200 MHz, δ): 1.9–2.1 (2H, m), 2.34 (3H, s), 2.4–2.7 (2H, m), 3.2–3.3 (1H, m), 3.8–4.2 (6H, m), 4.5–4.7 (4H, m), 5.1–5.4 (2H, m), 5.8–6.0 (1H, m), 6.8–7.1 (2H, m)

Preparation 19-1)

(2R,4R)-1-Allyloxycarbonyl-4-methylsulfonyloxy-2-(2-methylsulfonyloxyethyl) pyrrolidine (21.5 g) and 2-carbamoylimidazole (7.07 g) were reacted in substantially the same manner as that of Preparation 10-3) to give (2R,4R)-1-allyloxycarbonyl-2-{2-(2-carbamoylimidazol-1-yl) ethyl}-4-methylsulfonyloxypyrrolidine (15.2 g) as a yellow solid.

NMR (CDCl$_3$, 200 MHz, δ): 1.9–2.2 (2H, m), 2.4–2.6 (2H, m), 3.04 (3H, s), 3.5–3.7 (1H, m), 3.9–4.1 (2H, m), 4.5–4.6 (4H, m), 5.1–5.3 (3H, m), 5.63 (1H, br), 5.8–6.0 (1H, m), 7.0–7.3 (3H, m)

Preparation 19-2)

To a solution of potassium t-butoxide (8.42 g) in dimethylformamide (70 ml) was added thiobenzoic S-acid (9.27 ml) dropwise at –20° C. under dry ice—acetone bath. After the addition, the solution was warmed to room temperature, and then stirred for 75 minutes. To the solution was added a solution of (2R,4R)-1-allyloxycarbonyl-2-[2-(2-carbamoylimidazol-1-yl)ethyl]-4-methylsulfonyloxypyrrolidine (14.5 g) in dimethylformamide (70 ml) and the mixture was heated to 85° C. and stirred for 2 hours. After cooling to room temperature, the mixture was quenched by the addition of water (280 ml) and extracted with ethyl acetate (140 ml×3). The combined extract was washed with aqueous saturated sodium bicarbonate solution (140 ml×2), water (200 ml×2), and brine (200 ml×2), and then dried over magnesium sulfate. The solvent was evaporated and the residue was chromatographed on a 150 g of silica gel eluting with a mixture of chloroform and methanol (95:5, V/V) to give (2R,4S)-1-allyloxycarbonyl-4-benzoylthio-2-[2-(2-carbamoylimidazol-1-yl) ethyl]pyrrolidine (11.2 g) as a yellow paste.

NMR (CDCl$_3$, 200 MHZ, δ): 1.7–2.2 (2H, m), 2.4–2.6 (2H, m), 3.3–3.4 (1H, m), 4.0–4.3 (3H, m), 4.5–4.6 (4H, m), 5.2–5.4 (2H, m), 5.46 (1H, br), 5.8–6.0 (1H, m), 7.0–8.0 (8H, m)

Preparation 20-1)

To a solution of 1,2,4-triazole (100 g) in methanol (200 ml) was added 28% sodium methoxide in methanol solution (278.3 ml), followed by iodomethane (205.5 g) and the solution was warmed to 40° C. for 18 hours. The solution was concentrated in vacuo to remove methanol then treated with benzene (150 ml), warmed to 70° C. and decanted. This was repeated with 3×150 ml portions of chloroform. The combined organic layer was concentrated in vacuo to ca. 100 ml and the white precipitate was removed by filtration. After evaporation of the filtrate the resulting red liquid residue was distilled at atmospheric pressure to give 1-methyl-1,2,4-triazole (71.45 g) as a colorless liquid that solidified in the refrigerator.

bp: 175°–180° C.

IR (Neat): 3100, 2950 cm$^{-1}$

NMR (CDCl$_3$, δ): 3.95 (3H, s), 7.94 (1H, s), 8.05 (1H, s)

EI-Mass (m/z) : 83 (M$^+$)

Preparation 20-2)

To a solution of 1-methyl-1,2,4-triazole (3.12 g) in tetrahydrofuran (47 ml) at –70° C. was added dropwise n-butyllithium (1.6N) in hexane (25.5 ml) keeping the temperature below –60° C. After 15 minutes at –70° C., the mixture was warmed quickly to 0° C., stirred 5 minutes then recooled to –70° C. and stirred for 30 minutes. To the mixture was added a solution of (2S,4R)-1-benzyl-4-(t-butyldimethylsilyloxy)-2-formylpyrrolidine (10.0 g) in tetrahydrofuran (10 ml) keeping the temperature below –60° C. After 30 minutes the cooling bath was removed and the mixture was warmed to 0° C. over 30 minutes. After a further 2 hours the mixture was quenched with saturated sodium bicarbonate solution and extracted with ethyl acetate (×2). The combined organic layer was washed with brine and water, dried over magnesium sulfate and evaporated under reduced pressure. The residue was column chromatographed on silica gel (300 g, eluting with chloroform-methanol (30:1)) and then again on silica gel (300 g) eluting with ethyl acetate) to give 1-{(2S,4R)-1-benzyl-4-(t-butyldimethylsilyloxy) pyrrolidin-2-yl}-1-(1-methyl-1,2,4-triazol-5-yl) methanol (6.16 g) (as a 4.3:1 mixture of diastereoisomers).

NMR (CDCl$_3$, δ): 0.01, 0.00–0.01 (total 6H, each s), 0.86, 0.84, 0.83 (total 9H, each s), 1.75–2.12 (2H, m), 2.30–2.50 (M) 2.61 (dd, J=3.85 Hz, 11.2 Hz)}total 1H, 2.99 (dd, J=4.5 Hz, 11.2 Hz) 3.08–3.20 (M)}total 1H, 3.30–3.68 (1H, m), 3.94, 3.87 (total 3H, each s), 3.72–3.99 (2H, m), 4.21–4.28 (1H, m), 4.51 (d, J=4.7 Hz) 4.79 (d, J=3.5 Hz)}total 1H, 7.18–7.32 (5H, m), 7.75, 7.77 (total 1H, each s)

APCI-Mass (m/z): 403 (MH⁺)

Preparation 20-3)

1-{(2S,4R)-1-Allyloxycarbonyl-4-(t-butyldimethyl-silyloxy) pyrrolidin-2-yl}-1-(1-methyl-1,2,4-triazol-5-yl) methanol (5.96 g) was obtained by the same procedure as Preparation 17-3).

NMR (CDCl₃, δ): −0.02–0.06 (total 6H, m), 0.84–0.89 (9H, m), 1.60–2.00 (2H, m), 3.25–3.70 (2H, m), 3.98–4.05 (total 3H, m), 4.15–4.70 and 4.95–5.40 (total 7H, each m), 5.87–6.05 (total 2H, m), 7.79 (1H, s)

APCI-Mass (m/z): 397 (MH⁺)

Preparation 20-4)

(2S,4R)-1-Allyloxycarbonyl-4-t-butyldimethylsilyloxy-2-{1-(1-methyl-1,2,4-triazol-5-yl)-1-(phenoxythiocarbonyloxy) methyl}pyrrolidine (7.40 g) was obtained by the same procedure as Preparation 17-4).

NMR (CDCl₃, δ): 0.03, 0.05, 0.06, 0.064 (total 6H, each s), 0.85 (9H, s), 1.90–2.20 (1H, m), 2.60–3.03 (1.5H, m), 3.30–3.70 (1.5H, m), 3.91–4.36 (total 4H, m), 4.50–4.80 (3H, m), 5.15–5.44 (2H, m), 5.80–6.08 (1H, m), 6.60–6.90 (1H, m), 7.05–7.14 (2H, m), 7.22–7.44 (3H, m), 7.87 and 7.88 (total 1H, each s)

APCI-Mass (m/z): 533 (MH⁺)

Preparation 20-5)

(2R,4R)-1-Allyloxycarbonyl-4-t-butyldimethylsilyloxy-2-(1-methyl-1, 2,4-triazol-5-ylmethyl)pyrrolidine (2.69 g) was obtained by the same procedure as Preparation 17-5).

NMR (CDCl₃, δ): 0.03 (6H, s), 0.84 (9H, s), 1.89–2.28 (2H, m), 2.97–3.09 (1H, m), 3.55–3.23 (3H, m), 3.81–3.88 (3H, m), 4.15–4.30 (2H, m), 4.60–4.62 (2H, m), 5.195–5.34 (2H, m), 5.84–5.01 (1H, m), 7.78 (1H, s)

APCI-Mass (m/z): 381 (MH⁺)

Preparation 20-6)

(2R,4R)-1-Allyloxycarbonyl-4-hydroxy-2-(1-methyl-1, 2,4-triazol-5-ylmethyl)pyrrolidine (2.44 g) was obtained by the same procedure as Preparation 17-6).

NMR (CDCl₃, δ): 2.00–2.45 (3H, m), 2.95–3.07 (1H, m), 3.20–3.70 (3H, m), 3.80–3.95 (3H, m), 4.20–4.45 (2H, m), 4.55–4.70 (2H, m), 5.15–5.40 (2H, m), 5.85–6.02 (1H, m), 7.78 (1H, s)

APCI-Mass (m/z): 267 (MH⁺)

Preparation 20-7)

(2R,4S)-1-Allyloxycarbonyl-4-benzoylthio-2-(1-methyl-1, 2,4-triazol-5-ylmethyl)pyrrolidine (3.55 g) was obtained by the same procedure as those of Preparations 17-7) and 20-6).

NMR (CDCl₃, δ): 2.10–2.32 (1H, m), 2.52–2.75 (1H, m), 3.08 (1H, dd, J=9.5 Hz, 14.5 Hz), 3.25–3.60 (2H, m), 3.90 (3H, br s), 4.05–4.40 (3H, m), 4.62 (2H, d, J=5.6 Hz), 5.22–5.36 (2H, m), 5.85–6.05 (1H, m), 7.80 (1H, s), 7.40–8.30 (5H, m)

APCI-Mass (m/z): 387 (MH⁺)

Preparation 21-1)

To a solution of 1-methylpyrazole (30.5 g) in tetrahydrofuran (460 ml) was added dropwise n-butyllithium (1.6N) in hexane (250 ml) keeping the temperature below −60° C. The mixture was warmed to 0°–5° C. over 30 minutes, and stirred for 30 minutes, then cooled to −70°–60° C. To the mixture was added a solution of (2S,4R)-1-benzyl-4-(t-butyldimethylsilyloxy)-2-formylpyrrolidine (91.4 g) in tetrahydrofuran (90 ml) keeping the temperature below −60° C. The reaction mixture was warmed to 0°–5° C. over 40 minutes, and stirred for 2 hours. The mixture was quenched with ice water (300 ml) and the organic layer was separated. The aqueous layer was extracted with ethyl acetate (×2), and the combined organic layer was washed with water and brine, dried over magnesium sulfate and evaporated under reduced pressure. The residue was column chromatographed on silica gel (3 kg, eluting with ethyl acetate-n-hexane (1:1 to 5:1)) to give 1-{(2S,4 R)-1-benzyl-4-(t-butyldimethylsilyloxy)-pyrrolidin-2-yl }-1-(1-methylpyrazol-5-yl)methanol (101 g) (as a 2:1 mixture of diastereomer).

IR (Neat): 3200, 1240 cm⁻¹

IR (Neat): 3200, 1240 cm⁻¹

NMR (CDCl₃, δ): 0.01, 0.03, 0.05 (total 6H, each s), 0.86, 0.89 (total 9H, each s), 1.56–1.85 (1H, m), 1:93–2.20 (1H, m),

| 2.48 (dd, J=9.9Hz, 5.8Hz) | } total 1H, |
| 2.61 (dd, J=11.5Hz, 2.9Hz) | |

| 3.02 (dd, J=11.5Hz, 4.5Hz) | } total 1H, |
| 3.20 (dd, J=9.9Hz, 5.2Hz) | |

3.24–3.51 (1H, m), 3.82, 3.86 (total 3H, each s),

| 3.66 (d, J=12.9Hz) | } total 2H, |
| 3.79 (d, J=13.1Hz) | |
| 3.93 (d, J=13.1Hz) | |
| 4.02 (d, J=12.9Hz) | |

4.18–4.39 (1H, m),

| 4.41 (d, J=6.1Hz) | } total 1H, |
| 4.69 (d, J=2.7Hz) | |

| 6.14 (d, J=1.9Hz) | } total 1H, |
| 6.18 (d, J=1.9Hz) | |

7.20–7.38 (5H, m),

| 7.38 (d, J=1.9Hz) | } total 1H |
| 7.40 (d, J=1.9Hz) | |

APCI-Mass (m/z): 402 (MH⁺)

Preparation 21-2)

1-{(2S,4R)-1-Allyloxycarbonyl-4-(t-butyldimethylsilyloxy) pyrrolidin-2-yl}-1-(1-methylpyrazol-5-yl)methanol (103.6 g) was obtained in the same procedure as Preparation 17-3).

IR (Neat): 3220, 1665, 1395, 1100 cm⁻¹

NMR (CDCl₃, δ): 0.01, 0.02, 0.03 (total 6H, each s), 0.84, 0.85 (total 9H, each s), 1.42–2.08 (total 2H, m), 3.28–3.70 (total 2H, m), 3.85–4.00 (total 3H, m), 4.10–4.80 and 5.18–5.38 (total 7H, each m), 5.85–6.06 (total 1H, m), 6.12–6.18 (total 1H, m), 7.35–7.41 (total 1H, m)

APCI-Mass (m/z): 396 (MH⁺)

Preparation 21-3)

(2S,4R)-1-Allyloxycarbonyl-4-t-butyldimethylsilyloxy-2-{1-(1-methylpyrazol-5-yl)-1-(phenoxythiocarbonyloxy)methyl}pyrrolidine (109.7 g) was obtained in the same procedure as Preparation 17-4).

IR (Neat): 1685, 1390, 1095 cm⁻¹

NMR (CDCl₃, δ) 0.03, 0.06, 0.07 (total 6H, each s), 0.84, 0.86 (total 9H, each s), 1.82–2.50 (2H, m), 2.90–3.12 and 3.25–3.70 (total 2H, each m), 3.86, 3.96, 4.06 (total 3H, each s), 4.20–4.35 and 3.92–4.13 (total 1H, each m), 4.45–4.75 (3H, m), 5.18–5.43 (2H, m), 5.80–6.10 (1H, m), 6.23–6.35 (1H, m), 6.52–6.98 (1H, m), 7.00–7.13 (2H, m), 7.20–7.50 (4H, m)

APCI-MS (m/z): 532 (MH⁺)

Preparation 21-4)

(2R,4R)-1-Allyloxycarbonyl-4-(t-butyldimethylsilyloxy)-2-(1-methylpyrazol-5-ylmethyl) pyrrolidine (55.5 g) was obtained in the same procedure as Preparation 17-5).

IR (Neat): 1680, 1395, 1090 cm⁻¹

NMR (CDCl₃, δ): 0.03 (6H, s), 0.84 (9H, s), 1.73–2.00 (2H, m), 2.65–2.83 (1H, m), 3.03–3.50 (3H, m), 3.75–3.90 (3H, m), 4.08–4.28 (2H, m), 4.55–4.68 (2H, m), 5.18–5.38 (2H, m), 5.86–6.06 (1H, m), 6.01 (1H, d, J=1.8 Hz), 7.39 (1H, d, J=1.8 Hz)

APCI-Mass (m/z): 380 (MH⁺)

Preparation 21-5)

(2R,4R)-1-Allyloxycarbonyl-4-hydroxy-2-(1-methylpyrazol-5-ylmethyl) pyrrolidine (7.0 g) was obtained in the same procedure as Preparation 17-6).

IR (Neat): 3300, 1665, 1400 cm⁻¹

NMR (CDCl₃, δ): 1.80–2.15 (3H, m), 2.75 (1H, dd, J=14.5 Hz, 9.1 Hz), 3.10–3.70 (3H, m), 3.70–3.92 (3H, m), 4.10–4.40 (2H, m), 4.52–4.70 (2H, m), 5.15–5.40 (2H, m), 5.86–6.06 (1H, m), 6.01 (1H, d, J=1.8 Hz), 7.38 (1H, d, J=1.8 Hz)

APCI-Mass (m/z): 266 (MH⁺)

Preparation 21-6)

(2R,4S)-1-Allyloxycarbonyl-4-benzoylthio-2-(1-methylpyrazol-5-ylmethyl) pyrrolidine (10.0 g) was obtained in the same procedure as Preparation 17-7).

IR (Neat): 1680, 1650, 1390, 1195 cm⁻¹

NMR (CDCl₃, δ): 1.80–2.00 (1H, m), 2.42–2.68 (1H, m), 2.75–3.00 (1H, m), 3.20–3.55 (2H, m), 3.75–3.98 (3H, br s), 4.00–4.30 (3H, m), 4.52–4.70 (2H, m), 5.18–5.40 (2H, m), 5.86–6.06 (1H, m), 6.04 (1H, d, J=1.8 Hz), 7.40 (1H, d, J=1.8 Hz), 7.30–8.20 (5H, m)

APCI-Mass (m/z): 386 (MH⁺)

Preparation 22-1)

To a solution of 1-methyl-2-phenylthioimidazole (148 g) in tetrahydrofuran (1500 ml) and 1,2-dimethoxyethane (750 ml) was added dropwise lithium diisoprophylamide in tetrahydrofuran and n-hexane solution (1.55 mol/l) keeping the temperature below −65° C. After stirring for 50 minutes, to the mixture was added dropwise a solution of (2S,4R)-1-benzyl-4-(t-butyldimethylsilyloxy)-2-formylpyrrolidine (272 g) in tetrahydrofuran (500 ml) and 1,2-dimethoxyethane (250 ml) at −65°–−58° C. for 60 minutes. The mixture was stirred at −65°–−58° C. for 30 minutes and at −60°–−5° C. for 2 hours. The reaction mixture was poured into a mixture of cold water (4 l) and ethyl acetate (3 l). The organic extract was washed with water and brine, dried over magnesium sulfate and evaporated under reduced pressure. To the residue was added diisopropyl ether (1.5 l). The precipitate was collected by filtration and washed with diisopropyl ether and n-hexane to give 1-{(2S,4R)-1-benzyl-4-(t-butyldimethylsilyloxy) pyrrolidin-2-yl}-1-(1-methyl-2-thiophenylimidazol-5-yl) methanol (222.4 g).

NMR (CDCl₃, δ): −0.05–0.13 (6H, m), 0.83 and 0.86 (total 9H, each s), 1.66–1.85 (1H, m), 1.92–2.29 (1H, m), 2.35–2.68 (1H, m), 2.90–3.22 (1H, m), 3.23–3.57 (1H, m), 3.50–4.03 (2H, m), 3.55 (3H, s), 4.18–4.61 (2H, m), 7.00–7.35 (12H, m)

APCI-Mass (m/z): 50 (MH⁺)

Preparation 22-2)

To a Raney-Nickel (NDT-90, 1400 ml) was added 1-{(2S,4R)-1-benzyl-4-(t-butyldimethylsilyloxy) pyrrolidin-2-yl}-1-(1-methyl-2-thiophenylimidazol-5-yl)methanol (222 g) in ethanol (4.4 l) under an atmosphere of nitrogen. The mixture was stirred and heated under reflux for 2.5 hours. After cooling, the Raney-Nickel was removed by filtration and washed with ethanol (1 l×5). The filtrate and the washings were combined, dried over magnesium sulfate, evaporated in vacuo to give 1-{(2S,4R)-1-benzyl-4-(t-butyldimethylsilyloxy) pyrrolidin-2-yl}-1-(1-methylimidazol-5-yl)methanol (133.4 g) as an amorphous solid.

NMR (CDCl₃, δ): 0.06–0.18 (6H, m), 0.85 and 0.87 (total 9H, each s), 1.69–2.71 (3H, m), 2.97–3.27 (1H, m), 3.44–3.64 (5H, m), 3.92 and 4.11 (0.66H, ABq, J=13 Hz), 3.66 and 4.02 (1.34H, ABq, J=13 Hz), 4.23–4.41 (1H, m), 4.31 and 4.68 (total 1H, each d, J=7.6 Hz, 2.2 Hz), 6.90 and 6.94 (total 1H, each s), 7.19–7.42 (6H, m)

APCI-Mass (m/z): 402 (MH⁺)

Preparation 22-3)

(2S,4R)-1-Benzyl-4-t-butyldimethylsilyloxy-2-{1-(1-methylimidazol-5-yl)-1-(phenylthio) methyl}pyrrolidine (123 g) was obtained by the similar procedure as Preparation 16-2).

NMR (CDCl₃, δ): 0.03 (3H, s), 0.23 (3H, s), 0.88 (9H, s), 2.18–2.34 (1H, m), 1.93–2.10 (1H, m), 2.40 (1H, dd, J=5.4 Hz, 9.9 Hz), 3.10 (1H, dd, J=5.0 Hz, 9.9 Hz), 3.31 (3H, s), 3.42–3.52 (1H, m), 3.59 and 3.89 (2H, ABq, J=13.0 Hz), 4.22 (1H, d, J=4.5 Hz), 4.33–4.44 (1H, m), 7.01 (1H, s), 7.13–7.33 (11H, m)

APCI-Mass (m/z): 494 (MH⁺)

Preparation 22-4)

(2R,4R)-1-Benzyl-4-t-butyldimethylsilyloxy-2-(1-methylimidazol-5-ylmethyl) pyrrolidine (6.59 g) was obtained by the similar procedure as Preparation 16-3).

NMR (CDCl₃, δ): 0.06 (6H, s), 0.86 (9H, s), 1.74–1.92 (2H, m), 2.27 (1H, dd, J=5.70 Hz, 9.81 Hz), 2.52 (1H, dd, J=8.95 Hz, 15.2 Hz), 2.84 (1H, dd, J=3.91 Hz, 15.2 Hz), 2.99–3.20 (2H, m), 3.44 and 4.01 (2H, ABq, J=13.0 Hz), 3.51 (3H, s), 4.03–4.35 (1H, m), 6.83 (1H, d, J=0.8 Hz), 7.21–7.42 (6H, m)

APCI-Mass (m/z) : 386 (MH⁺)

Preparation 22-5)

(2R,4R)-1-Allyloxycarbonyl-4-t-butyldimethylsilyloxy-2-(1-methylimidazol-5-ylmethyl) pyrrolidine (6.40 g) was obtained by the similar procedure as Preparation 17-3).

NMR (CDCl₃, δ): 0.04 (6H, s), 0.85 (9H, s), 1.78–2.05 (2H, m), 2.54–2.74 (1H, m), 3.12–3.27 (1H, m), 3.36–3.52 (1H, m), 3.50–3.61 (1H, m), 3.80 (3H, s), 4.04–4.20 (1H, m), 4.20–4.35 (1H, m), 4.54–4.71 (2H, m), 5.12–5.37 (2H, m), 5.86–6.06 (1H, m), 6.79 (1H, s), 7.40 (1H, s) APCI-Mass (m/z): 380 (MH⁺)

Preparation 22-6)

(2R,4R)-1-Allyloxycarbonyl-4-hydroxy-2-(1-methyl-imidazol-5-ylmethyl) pyrrolidine (2.43 g) was obtained by the similar procedure as Preparation 17-6).

NMR (CDCl₃, δ): 1.80–2.15 (2H, m), 2.28–2.73 (1H, m), 2.98–3.70 (4H, m), 3.64 (3H, s), 4.00–4.24 (1H, m), 4.31–4.45 (1H, m), 4.52–4.70 (2H, m), 5.16–5.22 (2H, m), 5.80–6.10 (1H, m), 6.73 (1H, s), 7.37 (1H, s)

APCI-Mass (m/z): 266 (MH⁺)

Preparation 22-7)

(2R,4S)-1-Allyloxycarbonyl-4-benzoylthio-2-(1-methyl-imidazol-5-ylmethyl) pyrrolidine (3.53 g) was obtained by the similar procedure as Preparation 17-7).

NMR (CDCl₃, δ): 1.82–2.02 (1H, m), 2.41–2.72 (1H, m), 2.70–2.98 (1H, m), 3.20–3.74 (5H, m), 3.92–4.30 (3H, m), 4.49–4.73 (2H, m), 5.15–5.42 (2H, m), 5.82–6.16 (1H, m), 6.82 (1H, s), 7.30–7.70 (4H, m), 7.80–8.22 (2H, m)

APCI-Mass (m/z): 386 (MH⁺)

Preparation 23-1)

Under nitrogen atmosphere to a solution of 5-bromopyrimidine (18.3 g) in tetrahydrofuran (360 ml) and diethyl ether (360 ml) was slowly dropped 1.56 mol/l n-butyllithium in hexane solution (73.6 ml) at −90° C. to −95° C. The reaction mixture was stirred at the same temperature for an hour, and then the solution of (2S,4R)-1-allyloxycarbonyl-4-(t-butyldimethylsilyloxy)-2-formylpyrrolidine (30.0 g) in tetrahydrofuran (60 ml) and ether (60 ml) was dropped into the reaction mixture below −85° C. The reaction mixture was stirred at −50° C. for an hour, then water (150 ml) was dropped thereto below −10° C. The reaction mixture was poured into ethyl acetate (500 ml) and ice-water (300 ml) and adjusted to pH 7.0 with concentrated hydrochloric acid. Insoluble material was removed by filtration and washed with ethyl acetate (200 ml). The organic layer was separated, washed with water (300 ml) and brine (300 ml), and then dried over magnesium sulfate, and evaporated. The residue was subjected to column chromatography on silica gel (360 g) [solvent; hexane:ethyl acetate=4:1 to 2:1 to 1:3] to give 1-{(2S,4R)-1-allyloxycarbonyl-4-(t-butyldimethyl-silyloxy) pyrrolidin-2-yl}-1-(pyrimidin-5-yl)methanol (25.1 g) as an oil.

IR (Neat): 3350–3200, 2920, 1665, 1555, 1400, 1240, 1100, 825, 765 cm⁻¹

NMR (DMSO-d₆, δ): 0.00–0.08 (6H, m), 0.83 (5.4H, s), 0.86 (3.6H, s), 1.45–1.65 (0.4H, m), 1.85–2.25 (1.6H, m), 2.85–2.98 (0.6H, m), 3.25–3.53 (1.4H, m), 3.80–4.18 (1H, m), 4.25–4.65 (3H, m), 5.05–5.37 (3H, m), 5.88–6.02 (1H, m), 8.65 (1.2H, s), 8.76 (0.8H, s), 9.14 (1H, s)

LC-Mass: M⁺+1=394

Preparation 23-2)

To a solution of thionyl chloride (6.05 g) in dichloromethane (70 ml) was added 2,6-lutidine (6.53 g) at 5° C. to 10° C. After the solution was stirred for 30 minutes at the same temperature, the solution of 1-{(2S,4R)-1-allyloxycarbonyl-4-(t-butyldimethylsilyloxy)-pyrrolidin-2-yl}-1-(pyrimidin-5-yl)methanol (20.0 g) in dichloromethane (100 ml) was slowly dropped thereto below 10° C. After the reaction mixture was stirred for an hour below 10° C., it was stirred at room temperature for 2 hours, then thionyl chloride (6.05 g) and 2,6-lutidine (6.53 g) were added to the reaction mixture. After the reaction mixture was stirred another one hour, thionyl chloride (6.05 g) and 2,6-lutidine (6.53 g) were added to the reaction mixture. The reaction mixture was stirred at room temperature for 2 hours, then it was poured into ice-water (500 ml) and dichloromethane (400 ml) and adjusted to pH 5.1 with saturated aqueous sodium hydroxide below 15° C. The organic layer was separated and washed with water (400 ml) at pH 4.3 and brine (350 ml). The organic layer was dried over magnesiumsulfate and evaporated. The residue was subjected to column chromatography on silica gel (200 g) [solvent; hexane:ethyl acetate=5:1 to 2:1 to 1:1] to give 1-{(2S,4R)-1-allyloxycarbonyl-4-(t-butyldimethylsilyloxy)-pyrrolidin-2-yl }-1-(pyrimidin-5-yl)-1-chloromethane (9.9 g) as an oil.

NMR (CDCl₃, δ): −0.08–0.00 (6H, m), 0.79 (2.7H, s), 0.80 (6.3H, s), 1.61–1.93 (1H, m), 2.10–2.31 (1H, m), 2.67–2.75 (0.3H, m), 3.30–3.75 (1.7H, m), 4.29–4.47 (1.7H, m), 4.55–4.68 (2.3H, m), 5.15–5.36 (2H, m), 5.53–5.68 (0.3H, m), 5.82–6.01 (1.7H, m), 8.73 (0.6H, s), 8.79 (1.4H, s), 9.14 (1H, s)

LC-Mass: M⁺+1=412

Preparation 23-3)

Under nitrogen atmosphere to a solution of 1-{(2S,4R)-1-allyloxycarbonyl-4-(t-butyldimethylsilyloxy)-pyrrolidin-2-yl }-1-(pyrimidin-5-yl)-1-chloromethane (37.4 g) in toluene (750 ml) were added firstly tributyltin hydride (29.1 g) and secondly azoisobutyronitrile (0.45 g) at room temperature. After the reaction mixture was stirred at 80° C. for two hours, it was cooled and concentrated under reduced pressure. The residue was subjected to silica gel column chromatography (400 g) (solvent; hexane:ethyl acetate=4:1 to 2:1 to 1:2) to give (2R,4R)-1-allyloxycarbonyl-4-t-butyldimethylsilyloxy-2-(pyrimidin-5-ylmethyl) pyrrolidine (29.1 g) as an oil.

IR (Neat): 2920, 1680, 1545, 1395, 1100, 825, 760 cm⁻¹

NMR (CDCl₃, δ): −0.06 (6H, s), 0.82 (9H, s), 1.62–1.78 (1H, m), 1.80–1.98 (1H, m), 2.75–3.60 (4H, m), 4.09–4.28 (2H, m), 4.60–4.64 (2H, m), 5.20–5.36 (2H, m), 5.85–6.05 (1H, m), 8.55 (2H, s), 9.10 (1H, s)

LC-Mass: M⁺+1=378

Preparation 23-4)

To a solution of (2R,4R)-1-allyloxycarbonyl-4-t-butyldimethylsilyloxy-2-(pyrimidin-5-ylmethyl)pyrrolidine (29.1 g) in methanol (146 ml) was added concentrated hydrochloric acid (12.9 ml) at 5° to 7° C. After the reaction mixture was stirred for an hour at room temperature, 28% sodium methoxide in methanol (29.7 ml) was dropped thereto at 5° C. to 10° C., and then the solution was stirred for 30 minutes at 10° C. Insoluble material was removed by filtration, then the filtrate was concentrated. Acetonitrile (120 ml) was added to the residue, and the mixture was stirred with magnesium sulfate. Magnesium sulfate was removed by filtration and the filtrate was concentrated until the volume amounted to 60 ml. Heptane (80 ml) was added thereto, and the acetonitrile layer was washed with Heptane (80 ml) four times. The acetonitrile layer was evaporated under reduced pressure and then the residue was distilled off with toluene (20 ml) to give (2R,4R)-1-allyloxycarbonyl-4- hydroxy-2-(pyrimidin-5-ylmethyl) pyrrolidine (24.1 g) as an oil.

IR (Neat): 3500–3200, 1660, 1555, 1400, 1320, 1100 cm⁻¹

NMR (CDCl₃, δ): 1.65–1.82 (1H, m), 1.93–2.15 (1H, m), 2.80–3.75 (4H, m), 4.22–4.35 (2H, m), 4.61 (2H, d, J=5.5 Hz), 5.22–5.37 (2H, m), 5.85–6.04 (1H, m), 8.65 (2H, s), 9.13 (1H, s)

LC-Mass: M⁺+1=264

Preparation 23-5)

Under nitrogen atmosphere to a solution of (2R,4R)-1-allyloxycarbonyl-4-hydroxy-2-(pyrimidin-5-ylmethyl)pyrrolidine (21.0 g) in dichloromethane (105 ml) were added triethylamine (16.1 g) firstly and methanesulfonyl chloride (13.7 g) secondly at 5° to 10° C. After the reaction mixture was stirred for an hour at the same temperature, dichloromethane (50 ml) and ice-water (150 ml) were added thereto, and then the solution was stirred vigorously for twenty minutes. The organic layer was separated and washed with 1N-hydrochloric acid (100 ml), 1N-sodium hydroxide (200 ml), and brine (200 ml). The organic layer was dried over magnesium sulfate and evaporated under reduced pressure to give (2R,4R)-1-allyloxycarbonyl-4-methanesulfonyloxy-2-(pyrimidin-5-ylmethyl) pyrrolidine (25.2 g) as an oil.

IR (Neat): 2930, 1675, 1550, 1400, 1330, 1160, 1110, 950, 890 cm⁻¹

NMR (CDCl₃, δ): 1.85–1.95 (1H, m), 2.30–2.45 (1H, m), 2.90–3.25 (2H, m), 3.02 (3H, s), 3.32–3.40 (1H, m), 3.90–4.10 (1H, m), 4.25–4.39 (1H, m), 4.63–4.67 (2H, m), 5.10 (1H, s), 5.24–5.39 (2H, m), 5.86–6.06 (1H, m), 8.57 (2H, s), 9.13 (1H, s)

LC-MASS: M⁺+1=342

Preparation 23-6)

Under nitrogen atmosphere to a solution of potassium tert-butoxide (17.0 g) in N,N-dimethylformamide (77 ml) was slowly dropped thioacetic acid (12.1 g) at 0° to 10° C., and then the solution was stirred for 30 minutes at the same temperature. This solution was added to a solution of (2R,4R)-1-allyloxycarbonyl-4-methanesulfonyloxy-2-(pyrimidin-5-ylmethyl) pyrrolidine (25.8 g) in N,N-dimethylformamide (154 ml) at 15° to 25° C. under nitrogen atmosphere, and the reaction mixture was stirred for 2 hours at 80° to 90° C. After the reaction mixture was cooled and poured into ice-water (500 ml) and ethyl acetate (300 ml), the aqueous layer was adjusted to pH 8.2 with 1N-sodium hydroxide. The organic layer was separated and washed with water containing 10% sodium chloride (300 ml). This fraction and the fraction reextracted from the aqueous layer were combined, dried over magnesium sulfate, and evaporated under reduced pressure to give an oil. The oil was dissolved in toluene (300 ml) and it was washed with water (150 ml), dried over magnesium sulfate and then evaporated. The residue was subjected to column chromatography on silica gel (250 g) (solvent; hexane:ethyl acetate=3:1 to 1:6) to give (2R,4S)-4-acetylthio-1-allyloxycarbonyl-2-(pyrimidin-5-ylmethyl) pyrrolidine (17.7 g) as an oil.

IR (Neat): 1670, 1550, 1400, 1320, 1190, 1100 cm⁻¹

NMR (CDCl₃, δ): 1.55–1.70 (1H, m), 2.34 (3H, s), 2.34–2.50 (1H, m), 2.75–2.95 (1H, m), 3.05–3.35 (2H, m), 3.83–3.92 (1H, m), 4.02–4.21 (2H, m), 4.60–4.64 (2H, m), 5.23–5.38 (2H, m), 5.85–6.05 (1H, m), 8.58 (2H, s), 9.11 (1H, s)

LC-Mass: M⁺+1=322

Preparation 24-1)

To a solution of (2R, 4R) -1-allyloxycarbonyl-2-cyanomethyl-4-t-butyldimethylsilyloxypyrrolidine (4.65 g) in methanol (23.3 ml) was added conc. hydrochloric acid (2.38 ml) at ice-cooling. After stirring at 15°–25° C. for 1 hour, the solution was cooled at 5° C. 28% Sodium methoxide in methanol (5.52 ml) was added to the cold solution and the mixture was stirred at 0°–10° C. for 10 minutes. After removal of insoluble material by filtration, the filtrate was concentrated under reduced pressure. Acetonitrile (23.3 ml) was added to the residue and the solution was evaporated. The residue was washed with n-hexane (20 ml) five times and evaporated to give (2R,4R)-1-allyloxycarbonyl-2-cyanomethyl-4-hydroxypyrrolidine (2.99 g).

IR (Film): 3370, 2250, 1670, 1400 cm⁻¹

NMR (CDCl₃, δ): 1.70–2.40 (2H, m), 2.71 (1H, dd, J=2.8 Hz, 16.8 Hz), 3.17 (1H, dd, J=6.0 Hz, 16.8 Hz), 3.50–3.80 (2H, m), 4.15–4.30 (1H, m), 4.45–4.60 (1H, m), 4.60–4.80 (2H, m), 5.20–5.40 (2H, m), 5.80–6.10 (1H, m)

Mass: 211

Preparation 24-2)

To a solution of (2R,4R)-1-allyloxycarbonyl-2-cyanomethyl-4-hydroxypyrrolidine (2.95 g) in dichloromethane (30 ml) were added triethylamine (1.85 g) and a solution of methanesulfonyl chloride (1.76 g) in dichloromethane (2 ml) at ice-cooling. After stirring at 5°–10° C. for 1 hour, the solution was poured into an ice water. The separated organic layer was washed with water and aqueous sodium hydrogen carbonate solution, dried over magnesium sulfate and evaporated to give (2R,4R)-1-allyloxycarbonyl-2-cyanomethyl-4-methanesulfonyloxypyrrolidine (4.44 g).

IR (Film): 2250, 1690, 1400 cm⁻¹

NMR (CDCl₃, δ): 1.64 (1H, s), 2.15–2.40 (1H, m), 2.55–2.80 (2H, m), 3.06 (3H, s), 3.26 (1H, dd, J=5.8 Hz, 17.0 Hz), 3.72 (1H, dd, J=3.6 Hz, 13.0 Hz), 3.90–4.40 (2H, m), 4.60–4.70 (2H, m), 5.20–5.40 (2H, m), 5.80–6.05 (1H, m)

Mass: 289

Preparation 24-3)

To a mixture of potassium t-butoxide (2.18 g) and N,N-dimethylformamide (43 ml) was added thioacetic acid (1.48 g) at −10° C. After stirring at 0°–5° C. for 30 minutes, a solution of (2R,4R)-1-allyloxycarbonyl-2-cyanomethyl-4-methanesulfonyloxypyrrolidine (4.30 g) in N,N-dimethylformamide (4 ml) was added to the cold mixture. After stirring at 80° C. for 3 hours, the mixture was poured into a mixture of ethyl acetate and water. The separated organic layer was washed with aqueous sodium chloride solution twice, dried over magnesium sulfate and evaporated to give (2R,4S)-4-acetylthio-1-allyloxy-carbonyl-2-(cyanomethyl) pyrrolidine (4.04 g).

IR (Film): 2250, 1680, 1400 cm⁻¹

NMR (CDCl₃, δ): 1.55–1.70 (1H, m), 1.80–2.10 (1H, m), 2.36 (3H, s), 2.60–3.10 (2H, m), 3.29 (1H, dd, J=8.2 Hz, 10.6 Hz), 3.80–4.00 (1H, m), 4.00–4.20 (2H, m), 4.50–4.70 (2H, m), 5.20–5.40 (2H, m), 5.80–6.10 (1H, m)

Preparation 24-4)

To a solution of (2R,4S)-4-acetylthio-1-allyloxycarbonyl-2-(cyanomethyl) pyrrolidine (8.20 g) in tetrahydrofuran (40 ml) and methanol (40 ml) was added a 28% sodium methoxide in methanol solution (6.03 ml) at ice-cooling. After stirring at ice-cooling for 30 minutes, chlorotriphenylmethane (8.31 g) was added to the cold solution. After stirring at the same temperature for 2 hours, the solution was poured into a mixture of ethyl acetate and water. The separated organic layer was washed with aqueous sodium chloride solution twice, dried over magnesium sulfate and evaporated. The residue was subjected to a column chromatography on silica gel (eluent; n-hexane:ethyl acetate=5:1) to give (2R,4S)-1-allyloxycarbonyl-2-cyanomethyl-4-(triphenylmethylthio)pyrrolidine (11.7 g).

IR (Nujol): 2250, 1680, 1590, 1390 cm$^{-1}$

NMR (CDCl$_3$, δ): 1.50–1.80 (1H, m), 1.90–2.20 (1H, m), 2.60–3.20 (5H, m), 3.70–3.90 (1H, m), 4.40–4.60 (2H, m), 5.15–5.35 (2H, m), 5.75–6.00 (1H, m), 7.15–7.50 (15H, m)

Preparation 24-5)

To a solution of (2R,4S)-1-allyloxycarbonyl-2-cyanomethyl-4-(triphenylmethylthio) pyrrolidine (1.17 g) in dimethyl sulfoxide (3.75 ml) were added potassium carbonate (50 mg) and 30% hydrogen peroxide (313 μl). After stirring at 60° C. for 2 hours, the mixture was poured into a mixture of ethyl acetate and water. The separated organic layer was washed with aqueous sodium chloride solution twice, dried over magnesium sulfate and evaporated. The residue was subjected to column chromatography on silica gel (eluent; n-hexane:ethyl acetate=1:1) to give (2R,4S)-1-allyloxycarbonyl-2-carbamoylmethyl-4-(triphenylmethylthio)pyrrolidine (0.93 g).

IR (Nujol): 1650, 1590 cm$^{-1}$

NMR (CDCl$_3$, δ): 1.50–1.90 (1H, m), 2.20–2.50 (2H, m), 2.60–3.00 (4H, m), 3.80–4.00 (1H, m), 4.40–4.60 (2H, m), 5.15–5.35 (2H, m), 5.27 (1H, br s), 5.70–6.00 (2H, m), 7.15–7.60 (15H, m)

FAB-Mass: M$^+$=487.2

Preparation 24-6)

To a solution of (2R,4S)-1-allyloxycarbonyl-2-carbamoylmethyl-4-(triphenylmethylthio) pyrrolidine (255 mg) in ethylene glycol dimethyl ether (5 ml) was added Lawesson's reagent (106 mg). After stirring at 50° C. for 4 hours, the solution was poured into a mixture of ethyl acetate and water, and adjusted to pH 7.0 with aqueous sodium hydrogen carbonate solution. The separated organic layer was washed with aqueous sodium chloride solution, dried over magnesium sulfate and evaporated. The residue was subjected to column chromatography on silica gel (eluent; n-hexane:ethyl acetate=2:1) to give (2R,4S)-1-allyloxycarbonyl-2-thiocarbamoylmethyl-4-(triphenyl-methylthio) pyrrolidine (130 mg).

NMR (CDCl$_3$, δ): 1.70–2.00 (1H, m), 2.20–2.45 (1H, m), 2.60–3.10 (4H, m), 3.20 (1H, dd, J=3.6 Hz, 13.8 Hz), 3.75–4.00 (1H, m), 4.40–4.60 (2H, m), 5.15–5.35 (2H, m), 5.75–6.00 (1H, m), 7.15–7.60 (15H, m)

Preparation 24-7)

To a solution of (2R,4S)-1-allyloxycarbonyl-2-thiocarbamoylmethyl-4-(triphenylmethylthio) pyrrolidine (110 mg) in acetonitrile (4 ml) were added iodomethane (497 mg) and potassium carbonate (61 mg). After stirring at room temperature for 3 hours, the solution was poured into a mixture of ethyl acetate and water. The separated organic layer was washed with aqueous sodium chloride solution, dried over magnesium sulfate and evaporated. The residue was subjected to column chromatography on silica gel (eluent; n-hexane:ethyl acetate=3:2) to give (2R,4S)-1-allyloxycarbonyl-2-(2-imino-2-methylthioethyl)-4(triphenylmethylthio) pyrrolidine (72 mg).

NMR (CDCl$_3$, δ): 1.20–1.80 (2H, m), 2.00–2.40 (1H, m), 2.26 (3H, s), 2.48 (1H, dd, J=7.8 Hz, 14.0 Hz), 2.60–2.90 (2H, m), 2.90–3.30 (1H, m), 3.80–4.05 (1H, m), 4.35–4.60 (2H, m), 5.15–5.40 (2H, m), 5.70–6.00 (1H, m), 7.10–7.50 (15H, m)

Mass: 517

Preparation 24-8)

To a solution of (2R,4S)-1-allyloxycarbonyl-2-(2-imino-2-methylthioethyl)-4-(triphenylmethylthio)pyrrolidine (1.95 g) in methanol (39 ml) was added ammonium chloride (222 mg). After stirring at 50° C. for 2 hours, the solution was evaporated under reduced pressure. The residue was triturated with diisopropyl ether to give (2R,4S)-1-allyloxycarbonyl-2-amidinomethyl-4-(triphenylmethylthio)pyrrolidine hydrochloride (1.36 g).

IR (Nujol): 1670, 1580, 1410 cm$^{-1}$

NMR (DMSO-d$_6$, δ): 1.30–1.60 (1H, m), 2.10–2.30 (1H, m), 2.30–2.50 (1H, m), 2.50–3.00 (4H, m), 3.90–4.10 (1H, m), 4.30–4.50 (2H, m), 5.10–5.30 (2H, m), 5.70–6.00 (1H, m), 7.20–7.50 (15H, m), 8.69 (1H, br s), 8.99 (1H, br s)

Mass: 486 (M+1)-HCl

Preparation 24-9)

To a solution of 28% sodium methoxide in methanol solution (104 mg) in methanol (10 ml) were added (2R,4S)-1-allyloxycarbonyl-2-amidinomethyl-4-(triphenylmethylthio)pyrrolidine hydrochloride (1.0 g) and 3-dimethylaminoacrylaldehyde (190 mg). After stirring under reflux for 8 hours, the solution was poured into a mixture of ethyl acetate and water. The separated organic layer was washed with aqueous sodium chloride solution, dried over magnesium sulfate and evaporated. The residue was subjected to column chromatography on silica gel to give (2R,4S)-1-allyloxycarbonyl-2-(pyrimidin-2-ylmethyl)-4-(triphenylmethylthio) pyrrolidine (75 mg).

IR (Film): 1680, 1550, 1400 cm$^{-1}$

NMR (CDCl$_3$, δ): 1.80–2.20 (2H, m), 2.60–3.00 (3H, m), 2.98 (1H, dd, J=8.4 Hz, 14.0 Hz), 3.40–3.70 (1H, m), 4.10–4.30 (1H, m), 4.40–4.60 (2H, m), 5.05–5.30 (2H, m), 5.70–6.00 (1H, m), 7.12 (1H, t, J=5.0 Hz), 7.10–7.50 (15H, m), 8.64 (2H, d, J=5.0 Hz)

Mass: 522

Preparation 25-1)

To a solution of (2R,4R)-1-allyloxycarbonyl-4-(t-butyldimethylsilyloxy)-2-(2-methanesulfonyloxyethyl) pyrrolidine (37.6 g) and ammonium chloride (5.84 g) in dimethylformamide (185 ml) was added portionwise sodium azide (7.1 g) at ambient temperature. The mixture was stirred at 70° C. for 3 hours, and poured into a mixture of ethyl acetate and water. The organic layer was separated and the aqueous layer was extracted twice with ethyl acetate. The combined organic layer was washed twice with water and once with brine, dried over magnesium sulfate and evaporated under reduced pressure to give (2R,4R)-1-allyloxycarbonyl-2-(2-azidoethyl)-4-(t-butyl-dimethylsilyloxy) pyrrolidine (29.7 g).

Rf: 0.95 (hexane:ethyl acetate=1:1)

IR (Neat): 2080, 1680, 1400 cm$^{-1}$

NMR (CDCl$_3$, δ): 0.06 (3H, s), 0.80 (3H, s), 0.86 (9H, s), 1.50–2.30 (4H, m), 3.30–4.40 (6H, m), 4.60 (2H, m), 5.18–5.34 (2H, m), 5.85–6.01 (1H, m)

Preparation 25-2)

To a solution of (2R,4R)-1-allyloxycarbonyl-2-(2-azidoethyl)-4-(t-butyldimethylsilyloxy) pyrrolidine (29.7 g) in tetrahydrofuran was added dropwise 12N hydrochloric acid (15 ml) at ambient temperature. After stirring for 6 hours, the mixture was poured into a mixture of ethyl acetate and water. The organic layer was separated and the aqueous layer was extracted twice with ethyl acetate. The combined organic layer was washed with sat. sodium bicarbonate and brine, dried over magnesium sulfate and evaporated under reduced pressure to give (2R, 4R)-1-allyloxycarbonyl-2-(2-azidoethyl)-4-hydroxypyrrolidine (20.0 g).

Rf: 0.10 ( hexane:ethyl acetate=1:1)

Preparation 25-3)

To a solution of (2R,4R)-1-allyloxycarbonyl-2-(2-azidoethyl)-4-hydroxypyrrolidine (20.0 g) and triethylamine (15.2 ml) in dichloromethane (300 ml) was added methanesulfonyl chloride (7.8 ml) under ice-cooling. After stirring for 1 hour, water was poured into the mixture. The organic layer was separated and the aqueous layer was extracted twice with dichloromethane. The combined organic layer was washed with 1N hydrochloric acid, sat. sodium bicarbonate, water and brine, dried over magnesium sulfate and evaporated under reduced pressure to give (2R,4R)-1-allyloxycarbonyl-2-(2-azidoethyl)-4-methanesulfonyloxypyrrolidine (15.3 g).

Rf: 0.35 (hexane:ethyl acetate=1:1)

IR (Neat): 2080, 1670, 1400 cm$^{-1}$

NMR (CDCl$_3$, δ): 1.65 (1H, m), 1.94–2.07 (1H, m), 2.10–2.40 (1H, m), 2.40–2.60 (1H, m), 3.04 (3H, s), 3.38 (2H, t, J=14 Hz), 3.40–4.70 (1H, m), 3.90–4.20 (2H, m), 4.62 (2H, d, J=4.7 Hz), 5.20–5.40 (3H, m), 5.80–6.05 (1H, m)

Preparation 25-4)

To a suspension of potassium t-butoxide (6.99 g) in dimethylformamide (150 ml) was added thioacetic acid (4.45 ml) under ice-cooling. After stirring for 15 minutes, a solution of (2R,4R)-1-allyloxycarbonyl-2-(2-azidoethyl)-4-methanesulfonyloxypyrrolidine (15.3 g) in dimethylformamide (20 ml) was added to the mixture under ice-cooling. The mixture was warmed to 80° C. and stirred for 4 hours, then cooled to ambient temperature and poured into water and ethyl acetate. The organic layer was separated, and the aqueous layer was extracted twice with ethyl acetate. The combined organic layer was washed with sat. sodium bicarbonate, water (twice) and brine, dried over magnesium sulfate, and evaporated under reduced pressure to give (2R,4S)-4-acetylthio-1-allyloxycarbonyl-2-(2-azidoethyl) pyrrolidine (14.7 g).

Rf: 0.77 (hexane:ethyl acetate=1:1)

IR (Neat): 2080, 1660, 1400 cm$^{-1}$

NMR (CDCl$_3$, δ): 1.60–1.90 (2H, m), 2.10–2.40 (1H, m), 2.34 (3H, s), 2.46–2.70 (1H, m), 3.18 (1H, dd, J=7.4 Hz, 11.4 Hz), 3.36 (2H, t, J=6.8 Hz), 3.80–4.20 (3H, m), 4.59 (2H, d, J=4.9 Hz), 5.20–5.40 (2H, m), 5.80–6.10 (1H, m)

Preparation 25-5)

To a solution of (2R,4S)-4-acetylthio-1-allyloxy-carbonyl-2-(2-azidoethyl) pyrrolidine (14.7 g) in methanol (74 ml) was added dropwise 4.8N sodium methoxide in methanol (11.3 ml) under ice-cooling. After stirring for 1 hour at 0° C., triphenylmethyl chloride (14.4 g) was added to the mixture. After stirring for 5 hours at 0° C., the mixture was poured into ethyl acetate and water. The organic layer was separated and the aqueous layer was extracted twice with ethyl acetate. The combined organic layer was washed with water and brine, dried over magnesium sulfate, and evaporated under reduced pressure. The residue was column chromatographed on silica gel (hexane:ethyl acetate=10:1 to 5:1) to give (2R,4S)-1-allyloxycarbonyl-2-(2-azidoethyl)-4-(triphenylmethylthio)pyrrolidine (16.5 g).

Rf: 0.55 (hexane:ethyl acetate=4:1)

IR (Neat): 2080, 1680, 1400 cm$^{-1}$

NMR (CDCl$_3$, δ): 1.30–1.80 (2H, m), 1.90–2.25 (2H, m), 2.60–3.00 (3H, m), 3.10–3.40 (2H, m), 3.60–3.80 (1H, m), 4.40–4.60 (2H, m), 5.10–5.30 (2H, m), 5.80–6.00 (1H, m), 7.20–7.50 (15H, m)

Preparation 25-6)

To a solution of (2R,4S)-1-allyloxycarbonyl-2-(2-azidoethyl)-4-(triphenylmethylthio) pyrrolidine (10.1 g) in pyridine (30 ml) was added triphenylphosphine at ambient temperature. The mixture was stirred at the same temperature for 1 hour, and then 28% aqueous ammonia was added. After stirring at ambient temperature overnight, the mixture was evaporated under reduced pressure, and co-evaporated with toluene. The residue was column chromatographed on silica gel (chloroform:methanol=9:1) to give (2R,4S)-1-allyloxycarbonyl-2-(2-aminoethyl)-4(triphenylmethylthio)pyrrolidine (9.0 g).

Rf: 0.43 (chloroform:methanol=9:1)

IR (Neat) : 1660, 1400 cm$^{-1}$

NMR (CDCl$_3$, δ): 1.30–2.30 (5H, m), 2.50–3.00 (4H, m), 3.60–3.80 (1H, m), 4.40–4.60 (2H, m), 5.10–5.40 (2H, m), 5.75–6.00 (1H, m)

Preparation 25-7)

A solution of (2R,4S)-1-allyloxycarbonyl-2-(2aminoethyl)4-(triphenylmethylthio) pyrrolidine (5.78 g) and 1-(2,4-dinitrophenyl)pyridinium chloride (4.19 g) in n-butanol (60 ml) was stirred under reflux condition for 4 hours, and then evaporated under reduced pressure. The residue was column chromatographed on silica gel (chloroform:methanol=5:1 to 4:1) to give (2R,4S)-1-allyloxycarbonyl-2-{2-(1-pyridinio)ethyl}-4(triphenylmethylthio)pyrrolidine chloride (5.88 g).

Rf: 0.17 (chloroform:methanol=9:1)

NMR (CDCl$_3$, δ): 1.50–1.80 (1H, m), 2.20–3.00 (6H, m), 3.50–3.80 (1H, m), 4.43 (2H, d, J=5.4 Hz), 4.80–5.30 (4H, m), 5.70–6.00 (1H, m), 7.00–7.50 (15H, m), 8.07

(2H, t, J=7.0 Hz), 8.44 (1H, t, J=7.8 Hz ), 9.66 ( 2H, d, J=5.5 Hz)

Preparation 26-1)

To a solution of (2R,4R)-1-allyloxycarbonyl-4-t-butyldimethylsilyloxy-2-{2-(5-formylimidazol-1-yl)ethyl}pyrrolidine (12.65 g) in a mixture of tetrahydrofuran (60 ml) and methanol (60 ml) was portionwise added sodium borohydride (1.17 g) with stirring under ice-cooling. The mixture was stirred at the same temperature for 1 hour. The reaction mixture was adjusted to pH 8 with 6N hydrochloric acid at the same condition. The resulting precipitates were filtered off and the filtrate was evaporated in vacuo to give a residue. The residue was chromatographed on silica gel (250 g) eluting with a mixture of chloroform and methanol (9:1, V/V). The fractions containing the desired compound were collected and evaporated in vacuo to give (2R,4R)-1-allyloxycarbonyl-4-t-butyldimethylsilyloxy-2-{2-(5-hydroxymethylimidazol-1-yl)ethyl}pyrrolidine (10.23 g).

NMR (CDCl$_3$, δ): 0.05 (6H, s), 0.86 (9H, s), 1.55–2.45 (4H, m), 3.25–3.60 (2H, m), 3.90–4.10 (3H, m), 4.30–4.45 (1H, m), 4.50–4.60 (4H, m), 5.10–5.35 (2H, m), 5.80–6.05 (1H, m), 6.87 (1H, s), 7.45 (1H, s)

Preparation 26-2)

To a solution of (2R,4R)-1-allyloxycarbonyl-4-t-butyldimethylsilyloxy-2-{2-(5-hydroxymethylimidazol-1-yl)ethyl}pyrrolidine (9.22 g) in tetrahydrofuran (100 ml) was added potassium t-butoxide (3.54 g) with stirring under ice-cooling and then added dropwise methyl iodide (2.80 ml) at the same condition. The mixture was stirred at the same temperature for 1 hour. Ethyl acetate (100 ml) was added to a reaction mixture. The solution was washed successively with water and saturated aqueous sodium chloride, dried over anhydrous magnesium sulfate and evaporated in vacuo. The resulting residue was chromatographed on silica gel (200 g) eluting with a mixture of chloroform and methanol (19:1, V/V). The fractions containing the desired compound were collected and evaporated in vacuo to give a residue. To a solution of the residue (7.79 g) in methanol (100 ml) was added conc. hydrochloric acid (4.60 ml) with stirring at ambient temperature. The mixture was allowed to stand overnight. To the solution was added 28% sodium methoxide-methanol solution (10.6 ml) with stirring under ice-cooling. The resulting precipitates were filtered off and the filtrate was evaporated in vacuo to give a residue. The residue was chromatographed on silica gel (200 g) eluting with a mixture of chloroform and methanol (9:1, V/V). The fractions containing the desired compound were collected and evaporated in vacuo to give (2R,4R)-1-allyloxycarbonyl-4-hydroxy-2-{2-(5-methoxymethylimidazol-1-yl) ethyl}pyrrolidine (3.63 g).

NMR (CDCl$_3$, δ): 1.50–2.50 (4H, m), 3.29 (3H, s), 3.35–4.40 (8H, m), 4.45–4.65 (2H, m), 5.15–5.40 (2H, m), 5.80–6.05 (1H, m), 6.98 (1H, s), 7.55 (1H, broad s)

Preparation 26-3)

To a solution of (2R,4R)-1-allyloxycarbonyl-4-hydroxy-2-{2-(5-methoxymethylimidazol-1-yl)ethyl}pyrrolidine (3.63 g) in ethyl acetate (40 ml) were added successively triethylamine (2.29 ml) and methanesulfonyl chloride (1.09 ml) with stirring under ice-cooling. The mixture was stirred at the same temperature for 1 hour. To the reaction mixture was added water (20 ml). The organic layer was separated and washed with saturated aqueous sodium chloride, dried over anhydrous magnesium sulfate and evaporated in vacuo to give a residue. The residue was chromatographed on silica gel (150 g) eluting with a mixture of chloroform and methanol (19:1, V/V). The fractions containing the desired compound were collected and evaporated in vacuo to give (2R,4R)-1-allyloxycarbonyl-4-methanesulfonyloxy-2-{2(5-methoxymethylimidazol-1-yl)ethyl}pyrrolidine (3.85 g).

NMR (CDCl$_3$, δ): 1.70–2.10 (2H, m), 2.30–2.60 (2H, m), 3.03 (3H, s), 3.30 (3H, s), 3.50–3.70 (1H, m), 3.90–4.20 (4H, m), 4.40 (2H, s), 4.62 (2H, broad d, J=5.55 Hz), 5.10–5.35 (3H, m), 5.80–6.10 (1H, m), 7.01 (1H, s), 7.55 (1H, broad s)

Preparation 26-4)

(2R, 4S)-4-Acetylthio-1-allyloxycarbonyl-2-{2-(5-methoxymethylimidazol-1-yl)ethyl}pyrrolidine (2.25 g) was obtained in substantially the same manner as that of Preparation 18-3).

NMR (CDCl$_3$, δ): 1.50–1.75 (1H, m), 1.80–2.10 (1H, m), 2.34 (3H, s), 2.34–2.70 (2H, m), 3.21 (1H, dd, J=7.11 Hz, 11.4 Hz), 3.30 (3H, s), 3.80–4.20 (5H, m), 4.41 (2H, s), 4.58 (2H, d, J=5.56 Hz), 5.15–5.40 (2H, m), 5.75–6.10 (1H, m), 7.00 (1H, s), 7.54 (1H, broad s)

Preparation 27-1)

(2R,4R)-1-Allyloxycarbonyl-4-methanesulfonyloxy-2-(2-methanesulfonyloxyethyl)pyrrolidine (13.2 g) was reacted with 4-(t-butyldimethylsilyloxymethyl)imidazol (8.30 g) and potassium t-butoxide (4.39 g) in substantially the same manner as Preparation 10-3) to give (2R,4R)-1-allyloxycarbonyl-2-[2-{4-(t-butyldimethylsilyloxymethyl)-imidazol-1-yl}ethyl]-4-methanesulfonyloxypyrrolidine (23.7 g) as a brown paste.

NMR (CDCl$_3$, 200 MHz, δ): 0.10 (6H, s), 0.93 (9H, s), 1.7–2.5 (4H, m), 3.04 (3H, s), 3.4–3.6 (1H, m), 3.8–4.2 (4H, m), 4.5–4.6 (2H, m), 4.64 (2H, s), 5.1–5.3 (3H, m), 5.8–6.0 (1H, m), 6.85 (1H, s), 7.50 (1H, s)

Preparation 27-2)

To a solution of (2R,4R)-1-allyloxycarbonyl-2-[2-{4-(t-butyldimethylsilyloxymethyl)imidazol-1-yl}ethyl]-4-methanesulfonyloxypyrrolidine (23.7 g) in acetonitrile (120 ml) was added concentrated hydrochloric acid (12 ml) dropwise under cooling in an ice-bath. After stirring at the same temperature for 2 hours, the mixture was quenched by the addition of a solution of sodium methoxide in methanol (28% W/W, 27.8 g) then ethyl acetate (240 ml) was added. The precipitate was filtered off and the filtrate was concentrated in vacuo. The residue was dissolved in acetonitrile (120 ml) and dried over magnesium sulfate. The solution was filtered and the filtrate was washed with hexane (200 ml×5) then concentrated in vacuo. The residual yellow paste was chromatographed on a 140 g of silica gel eluting with a mixture of chloroform and methanol (100:0 to 99:1 to 95:5) to give (2R,4R)-1-allyloxycarbonyl-2-[2-(4-hydroxymethylimidazol-1-yl) ethyl]-4-methanesulfonyloxypyrrolidine (6.02 g) as a yellow paste.

NMR (CDCl$_3$, 200 MHz, δ): 1.8–2.6 (5H, m), 3.03 (3H, s), 3.5–3.7 (1H, m), 3.9–4.2 (4H, m), 4.5–4.7 (4H, m), 5.2–5.4 (3H, m), 5.8–6.0 (1H, m), 6.9–7.0 (1H, m), 7.4–7.6 (1H, m)

Preparation 27-3)

(2R, 4R) -1-Allyloxycarbonyl-2-[2-(4-hydroxymethyl-imidazol-1-yl) ethyl]-4-methanesulfonyloxypyrrolidine (6.02 g) was reacted with thioacetic acid (2.42 ml) and potassium t-butoxide (3.61 g) in substantially the same manner as Preparation 4-12) to give (2R,4S)-1-allyloxycarbonyl-4-acetylthio-2-[2-(4-hydroxymethylimidazol-1-yl) ethyl]pyrrolidine ( 5.46 g) as an orange paste.

NMR (CDCl$_3$, 200 MHz, δ): 1.5–2.6 (4H, m), 2.34 (3H, s), 3.2–3.3 (1H, m), 3.8–4.2 (6H, m), 4.5–4.7 (4H, m), 5.2–5.4 (2H, m), 5.8–6.0 (1H, m), 6.9–7.0 (1H, m), 7.4–7.5 (1H, m)

Preparation 28-1)

(2R,4R)-1-Allyloxycarbonyl-4-methanesulfonyloxy-2-(2-methanesulfonyloxyethyl)pyrrolidine (19.6 g) were reacted with 4-carbamoylmethylimidazole (7.25 g) and potassium t-butoxide (6.52 g) in substantially the same manner as that of Preparation 10-3) to give (2R,4R)-1-allyloxy-carbonyl-2-{2-(4-carbamoylmethylimidazol-1-yl)ethyl}-4-methanesulfonyloxypyrrolidine (2.75 g) as a yellow paste.

NMR (CDCl$_3$, 200 MHz, δ) : 1.8–2.0 (2H, m), 2.3–2.5 (2H, m), 3.04 (3H, s), 3.51 (2H, s), 3.5–3.6 (1H, m), 3.9–4.1 (4H, m), 4.61 (2H, d, J=5.5 Hz), 5.2–5.6 (4H, m), 5.8–6.0 (1H, m), 6.85 (1H, br), 7.06 (1H, br), 7.49 (1H, br)

Preparation 28-2)

(2R,4R)-1-Allyloxycarbonyl-2-{2-(4-carbamoylmethyl-imidazol-1-yl) ethyl}-4-methanesulfonyloxypyrrolidine (2.74 g) were reacted with thiobenzoic acid (1.69 ml) and potassium t-butoxide (1.54 g) in substantially the same manner as Preparation 19-2) to give (2R,4S)-1-allyloxycarbonyl-4-benzoylthio-2-[2-(4-carbamoylmethyl-imidazol-1-yl) ethyl]pyrrolidine (2.30 g) as a yellow solid.

NMR (CDCl$_3$, 200 MHz, δ): 1.7–2.2 (2H, m), 2.4–2.7 (2H, m), 3.3–3.4 (1H, m), 3.51 (2H, s), 3.9–4.3 (5H, m), 4.5–4.7 (2H, m), 5.2–5.4 (3H, m), 5.9–6.1 (1H, m), 6.9–8.1 (8H, m)

Preparation 29-1)

To a solution of (2R,4R)-1-allyloxycarbonyl-4-methanesulfonyloxy-2-{2-(methanesulfonyloxy)ethyl}pyrrolidine (38.8 g) in N,N-dimethylformamide (380 ml) were added 4-formylimidazole (13.0 g) and potassium t-butoxide (15.2 g) and the mixture was stirred at 50°–60° C. for 2 hours. The reaction mixture was poured into water (600 ml) and extracted three times with ethyl acetate (400 ml). The extract was washed with saturated aqueous sodium chloride, dried over magnesium sulfate and evaporated in vacuo. The resulting residue was chromatographed on silica gel (750 g) eluting with a mixture of chloroform and methanol (19:1, V/V). The fractions containing the desired compound were collected and evaporated in vacuo to give (2R,4R)-1-allyloxycarbonyl-4-methanesulfonyloxy-2-{2-(5-formylimidazol-1-yl)ethyl}pyrrolidine (14.2 g).

NMR (CDCl$_3$, δ): 1.80–2.60 (4H, m), 3.05 (3H, s), 3.50–3.65 (1H, m), 3.90–4.50 (4H, m), 4.55–4.70 (2H, m), 5.20–5.40 (3H, m), 5.80–6.10 (1H, m), 7.82 (2H, s), 9.87 (1H, s)

Preparation 29-2)

(2R,4R)-1-Allyloxycarbonyl-2-{2-(5-hydroxymethyl-imidazol-1-yl) ethyl}-4-methanesulfonyloxypyrrolidine (7.13 g) was obtained in substantially the same manner as that of Preparation 26-1).

NMR (CDCl$_3$, δ): 1.80–2.10 (2H, m), 2.30–2.60 (2H, m), 3.03 (3H, s), 3.45–3.65 (1H, m), 3.90–4.15 (4H, m), 4.50–4.65 (4H, m), 5.10–5.40 (3H, m), 5.80–6.10 (1H, m), 6.83 (1H, s), 7.47 (1H, broad s)

Preparation 29-3)

(2R,4R)-1-Allyloxycarbonyl-2-[2-(5-hydroxymethyl-imidazol-1-yl) ethyl]-4-methanesulfonyloxypyrrolidine (1.63 g) was reacted with thioacetic acid (0.65 ml) and potassium t-butoxide (0.978 g) in substantially the same manner as that of Preparation 14-12) to give (2R,4S)-1-allyloxycarbonyl-4-acetylthio-2-[2-(5-hydroxymethyl-imidazol-1-yl)ethyl]pyrrolidine (884 mg) as an orange paste.

NMR (CDCl$_3$, 200 MHz, δ): 1.6–2.1 (2H, m), 2.34 (3H, s), 2.4–2.6 (3H, m), 3.2–3.3 (1H, m), 3.8–4.2 (5H, m), 4.58 (2H, d, J=5.5 Hz), 4.62 (2H, s), 5.1–5.3 (2H, m), 5.8–6.0 (1H, m), 6.94 (1H, br), 7.51 (1H, br)

Preparation 30-1)

(2R,4R)-1-Allyloxycarbonyl-4-methanesulfonyloxy-2-(2methanesulfonyloxyethyl)pyrrolidine (36.1 g) was reacted with 4-cyanoimidazole (10.0 g) and potassium t-butoxide (12.0 g) in substantially the same manner as Preparation 10-3) to give (2R,4R)-1-allyloxycarbonyl-2-[2-(4-cyanoimidazol-1-yl)ethyl]-4-methanesulfonyloxypyrrolidine (14.1 g) as a yellow paste.

NMR (CDCl$_3$, 200 MHz, δ): 1.8–2.0 (2H, m), 2.2–2.6 (2H, m), 3.05 (3H, s), 3.5–3.6 (1H, m), 3.9–4.2 (4H, m), 4.6–4.7 (2H, m), 5.2–5.4 (3H, m), 5.8–6.0 (1H, m), 7.5–7.7 (2H, m)

Preparation 30-2)

(2R,4R)-1-Allyloxycarbonyl-2-[2-(4-cyanoimidazol-1-yl) ethyl]-4-methanesulfonyloxypyrrolidine (13.4 g) was reacted with thioacetic acid (5.46 ml) and potassium t-butoxide (8.17 g) in substantially the same manner as Preparation 4-12) to give (2R,4S)-1-allyloxycarbonyl-4-acetylthio-2-[2-(4-cyanoimidazol-1-yl)ethyl]pyrrolidine (12.5 g) as a yellow paste.

NMR (CDCl$_3$, 200 MHz, δ): 1.5–1.8 (1H, m), 1.9–2.1 (1H, m), 2.3–2.6 (2H, m), 2.35 (3H, s), 3.2–3.3 (1H, m), 3.8–4.3 (5H, m), 4.59 (2H, d, J=5.6 Hz), 5.2–5.4 (2H, m), 5.8–6.0 (1H, m), 7.59 (2H, br)

Preparation 31-1)

A mixture of (2R,4R)-1-allyloxycarbonyl-4-(t-butyldimethylsilyloxy)-2-(2-methanesulfonyloxyethyl)pyrrolidine (10.0 g) and 1,2,4-triazole sodium salt (2.45 g) in dimethylformamide (50 ml) was stirred at 60° C. for 3.5 hours. After cooling to room temperature, the mixture was quenched by the addition of water (100 ml) and extracted with a mixture of hexane and ethyl acetate (2:1, 50 ml×4). The combined extract was washed with water (400 ml), brine (100 ml) and dried over magnesium sulfate. Evaporation of the solvent gave (2R,4R)-1-allyloxy-carbonyl-4-(t-butyldimethylsilyloxy)-2-[2-(1,2, 4-triazol-1-yl)ethyl]pyrrolidine (8.82 g) as a light brown paste.

NMR (CDCl₃, 200 MHz, δ): 0.05 (6H, s), 0.86 (9H, s), 1.5–2.4 (4H, m), 3.3–4.6 (2H, m), 3.9–4.3 (4H, m), 4.5–4.6 (2H, m), 5.1–5.3 (4H, m), 5.8–6.0 (1H, m), 7.9–8.2 (2H, m)

Preparation 31-2)

(2R,4R)-1-Allyloxycarbonyl-4-(t-butyldimethyl-silyloxy)-2-[2-(1, 2,4-triazol-1-yl)ethyl]pyrrolidine (8.74 g) was desilylated in the same manner as Preparation 4-10) to give (2R,4R)-1-allyloxycarbonyl-4-hydroxy-2-[2-(1,2, 4-triazol-1-yl)ethyl]pyrrolidine (5.89 g) as a yellow paste.

NMR (CDCl₃, 200 MHz, δ): 1.6–1.8 (1H, m), 2.0–2.2 (2H, m), 2.3–2.5 (1H, m), 2.74 (1H, br), 3.3–3.8 (2H, m), 4.0–4.5 (4H, m), 4.58 (2H, d, J=5.5 Hz), 5.2–5.3 (2H, m), 5.8–6.0 (1H, m), 7.9–8.2 (2H, m)

Preparation 31-3)

(2R,4R)-1-Allyloxycarbonyl-4-hydroxy-2-[2-(1,2, 4-triazol-1-yl)ethyl]pyrrolidine (5.82 g) was reacted with triphenylphosphine (8.62 g), diethyl azodicarboxylate (5.17 ml) and thiobenzoic acid (4.64 ml) in tetrahydrofuran (58 ml) in the same manner as Preparation 3-6) to give (2R,4S)-1-allyloxycarbonyl-4-benzoylthio-2-[2-(1,2, 4-triazol-1-yl) ethyl]pyrrolidine (7.92 g) as a yellow paste.

NMR (CDCl₃, 200 MHz, δ): 1.6–2.7 (4H, m), 3.32 (1H, dd, J=6.8 Hz, 11.3 Hz), 4.0–4.4 (5H, m), 4.5–4.7 (4H, m), 5.2–5.4 (4H, m), 5.8–6.1 (1H, m), 7.4–8.3 (7H, m)

Preparation 32-1)

To a solution of (2R,4R)-1-allyloxycarbonyl-4-methanesulfonyloxy-2-[2-(4-cyanoimidazol-1-yl)ethyl]pyrrolidine (24.8 g) in dimethyl sulfoxide (100 ml) were added potassium carbonate (1.86 g) and 30% hydroperoxide aqueous solution (9.92 ml) at ambient temperature and the mixture was stirred at 60° C. for 5 hours. The reaction mixture was poured into saturated aqueous sodium chloride (400 ml) and extracted four times with a mixture of ethyl acetate (100 ml) and tetrahydrofuran (100 ml). The extract was dried over anhydrous magnesium sulfate and evaporated in vacuo to give a residue. The residue was chromatographed on silica gel (300 g) eluting with a mixture of chloroform and methanol (14:1, V/V). The fractions containing the desired compound were collected and evaporated in vacuo to give (2R,4R)-1-allyloxy-carbonyl-2-[2-(4-carbamoylimidazol-1-yl)ethyl]-4-methanesulfonyloxypyrrolidine (11.54 g).

NMR (CDCl₃, δ): 1.75–2.05 (2H, m), 2.25–2.55 (2H, m), 3.04 (3H, s), 3.45–3.65 (1H, m), 3.90–4.20 (4H, m), 4.61 (2H, broad d, J=5.53 Hz), 5.15–5.40 (3H, m), 5.80–6.10 (2H, m), 7.02 (1H, broad s), 7.35–7.55 (1H, m), 7.64 (1H, broad s)

APCI Mass: 387 (M⁺+1)

Preparation 32-2)

To a solution of potassium t-butoxide (5.14 g) in N,N-dimethylformamide (50 ml) was added dropwise thiobenzoic acid (5.39 ml) at −10° C. and the mixture was stirred for 30 minutes under ice-cooling. To a solution of (2R,4R)-1-allyloxycarbonyl-2-[2-(4-carbamoylimidazol-1-yl) ethyl]-4-methanesulfonyloxypyrrolidine (11.8 g) in N,N-dimethylformamide (55 ml) was added the solution obtained above and the mixture was stirred at 85°–90° C. for 2 hours. The reaction mixture was poured into ice-water (400 ml) and extracted three times with ethyl acetate (200 ml). The extract was washed with saturated aqueous sodium chloride, dried over anhydrous magnesium sulfate and evaporated in vacuo to give a residue. The residue was chromatographed on silica gel (300 g) eluting with a mixture of chloroform and methanol (19:1, V/V). The fractions containing the desired compound were collected and evaporated in vacuo to give (2R,4S)-1-allyloxy-carbonyl-4-benzoylthio-2-[2-(4-carbamoylimidazol-1-yl)ethyl]pyrrolidine (6.38 g).

NMR (CDCl₃, δ): 1.65–1.90 (1H, m), 1.90–2.20 (1H, m), 3.34 (1H, dd, J=6.23 Hz, 11.1 Hz), 3.95–4.30 (5H, m), 4.60 (2H, d, J=5.58 Hz), 5.15–5.40 (2H, m), 5.80–6.10 (2H, m), 7.04 (1H, broad s), 7.40–7.65 (5H, m), 7.85–7.95 (2H, m)

Preparation 33-1)

To a solution of 2,3-dihydroimidazo[1,2-b]pyrazole (3.14 g) in N,N-dimethylformamide (60 ml) was added potassium t-butoxide (3.23 g) with stirring under ice-cooling and the mixture was stirred for 10 minutes at the same temperature. The solution was added to a solution of (2R,4S)-1-allyloxycarbonyl-2-{2-(methanesulfonyloxy) ethyl}-4-tritylthiopyrrolidine (12.23 g) in N,N-dimethylformamide (60 ml) with stirring at ambient temperature and the mixture was stirred at 50°–60° C. for 2 hours. The reaction mixture was poured into water (200 ml) and extract three times with ethyl acetate (100 ml). The extract was washed with saturated aqueous sodium chloride, dried over anhydrous magnesium sulfate and evaporated in vacuo to give a residue. The residue was chromatographed on silica gel (400 g) eluting with a mixture of hexane and ethyl acetate (1:2, V/V). The fractions containing the desired compound were collected and evaporated in vacuo to give (2R,4S)-1-allyloxycarbonyl-2-{2-(2,3-dihydroimidazo[1,2-b]pyrazol-1-yl}ethyl-4-tritylthiopyrrolidine trifluoroacetate (11.21 g).

NMR (CDCl₃, δ): 1.30–1.70 (2H, m), 2.10–2.40 (2H, m), 3.45–3.90 (3H, m), 4.00–4.15 (2H, m), 4.35–4.70 (2H, m), 5.10–5.40 (3H, m), 5.70–6.00 (1H, m), 7.00–7.55 (17H, m)

Preparation 33-2)

To a solution of (2R,4S)-1-allyloxycarbonyl-2-{2-(2,3-dihydroimidazo[1,2-b]pyrazol-1-yl}ethyl-4-tritylthiopyrrolidine (11.2 g) in dichloromethane (40 ml) were successively added trifluoroacetic acid (40 ml) and triethylsilane (4.12 ml) with stirring under ice-cooling. The mixture was stirred at ambient temperature for 30 minutes. The reaction mixture was evaporated in vacuo to give a residue. The residue was washed three times with hexane (50 ml) and concentrated in vacuo. The resulting residue was chromatographed on silica gel (200 g) eluting with a mixture of hexane and ethyl acetate (1:2, V/V). The fractions containing the desired compound were collected and evaporated in vacuo to give (2R,4S)-1-allyloxycarbonyl-2-{2-(2,3-dihydroimidazo-[1, 2-b]pyrazol-1-yl}ethyl-4-mercaptopyrrolidine (4.82 g).

EI Mass: 322 (M⁺)

Preparation 34-1)

(2R,4R)-1-Allyloxycarbonyl-4-methanesulfonyloxy-2-[2(1,2,3-triazol-1-yl)ethyl]pyrrolidine (5.0 g) was obtained in substantially the same manner as that of Preparation 10-3).

NMR (CDCl₃, δ): 1.91 (1H, br), 2.09–2.23 (1H, m), 2.41–2.61 (2H, m), 3.07 (3H, s ), 3.52–3.59 (1H, m), 3.96–4.14 (2H, m), 4.46–4.53 (2H, m), 4.59–4.61 (2H, m), 5.19–5.35 (2H, m), 5.84–6.03 (1H, m), 7.70 (1H, s), 8.01 (1H, s)

Preparation 34-2)

(2R, 4S)-1-Allyloxycarbonyl-4-acetylthio-2-[2-(1,2,3-triazol-1-yl) ethyl]pyrrolidine (3.39 g) was obtained in substantially the same manner as that of Preparation 4-12).

NMR (CDCl$_3$, δ): 1.63 (1H, br), 2.04–2.22 (1H, m), 2.34 (3H, s), 2.51 (2H, br), 3.15–3.25 (1H, m), 3.80–3.97 (2H, m), 4.06–4.15 (1H, m), 4.44–4.51 (2H, m), 4.56–4.60 (2H, m), 5.19–5.34 (2H, m), 5.83–6.00 (1H, m), 7.70 (1H, s), 7.73 (1H, br)

Preparation 35-1)

(2R,4R)-1-Allyloxycarbonyl-4-methanesulfonyloxy-2-[2-(pyrazol-1-yl) ethyl]pyrrolidine (4.24 g) was obtained in substantially the same manner as that of Preparation 10-3).

NMR (CDCl$_3$, δ): 1.81 (1H, br), 2.01–2.15 (1H, br), 2.25–2.49 (2H, br), 3.04 (3H, s), 3.50–3.57 (1H, br), 3.92–4.22 (4H, m), 4.60 (2H, d, J=5.5 Hz), 5.14–5.35 (3H, m), 5.84–6.03 (1H, m), 6.25 (1H, t, J=1.9 Hz), 7.41–7.53 (2H, m)

Preparation 35-2)

(2R,4S)-1-Allyloxycarbonyl-4-acetylthio-2-[2-(pyrazol-1-yl) ethyl]pyrrolidine (8.45 g) was obtained in substantially the same manner as that of Preparation 14-2).

NMR (CDCl$_3$, δ): 1.51 (1H, br), 1.98–2.19 (1H, m), 2.32 (3H, s), 2.47 (3H, br), 3.07–3.22 (1H, m), 3.77–3.99 (2H, m), 4.04–4.24 (3H, m), 4.56–4.60 (2H, m), 5.18–5.34 (2H, m), 5.83–6.02 (1H, m), 6.24 (1H, t, d=2.0 Hz), 7.48 (2H, br)

Preparation 36

To a solution of (2R,4R)-1-allyloxycarbonyl-4-tert-butyldimethylsilyloxy-2-(2-methanesulfonyloxyethyl)pyrrolidine (63 g) and 4-formylimidazole (17.8 g) in N,N-dimethylformamide (300 ml) was added potassium tert-butoxide (20.8 g) by portions. Then, the mixture was stirred at 45° C. for 2 hours. Evaporation of the solvent gave a residue, which was dissolved in a mixture of ethyl acetate (1.5 l) and water (200 ml). The organic layer was separated, washed in turn with 1N hydrochloric acid (100 ml) and brine (300 ml×3), and dried over magnesium sulfate. Evaporation of the solvent gave an oil, which was chromatographed on silica gel (2 l) eluting with a mixture of hexane and ethyl acetate (1:1 to 1:2 to 0:1). The former active fractions were collected and concentrated in vacuo to give (2R,4R)-1-allyloxycarbonyl-4-tert-butyldimethylsilyloxy-2-{2-(5-formylimidazol-1-yl)ethyl}pyrrolidine (14.9 g).

NMR (CDCl$_3$, δ): 0.02 (6H, s), 0.80 (9H, s), 1.70–2.30 (4H, m), 3.30–3.60 (2H, m), 3.95–4.10 (1H, m), 4.20–4.40 (3H, m), 4.50–4.55 (2H, m), 5.10–5.30 (2H, m), 5.78–6.27 (1H, m), 7.61–7.78 (2H, m), 9.68 (1H, s)

The latter active fractions were collected and concentrated in vacuo to give (2R,4R)-1-allyloxycarbonyl-4-tert-butyldimethylsilyloxy-2-{2-(4-formylimidazol-1-yl)ethyl}pyrrolidine (22.4 g).

NMR (CDCl$_3$, δ): 0.02 (6H, s), 0.80 (9H, s), 1.50–1.70 (1H, m), 1.79–2.00 (2H, m), 2.10–2.30 (1H, m), 3.28–3.55 (2H, m), 3.90–4.10 (2H, m), 4.25–4.36 (1H, m), 4.53–4.57 (2H, m), 5.15–5.30 (2H, m), 5.79–6.00 (1H, m), 7.50–7.75 (2H, m), 9.81 (1H, m)

Preparation 37-1)

To a solution of diethyl carbamoylmethylphosphonate (12.7 g) and potassium tert-butoxide (13.9 g) in tetrahydrofuran (400 ml) were added a solution of (2R,4R)-1-allyloxycarbonyl-4-tert-butyldimethylsilyloxy-2-{2-(4-formylimidazol-1-yl)ethyl}pyrrolidine (24 g) in tetrahydrofuran (50 ml) at 45° C. After stirring for 1 hour, to the reaction mixture were added water (3 ml). Evaporation of the solvent gave a residue, which was dissolved in a mixture of ethyl acetate (500 ml) and water (50 ml). The organic layer was separated, washed in turn with water (50 ml×2) and brine (50 ml×2), and dried over magnesium sulfate. Evaporation of the solvent gave an oil, which was chromatographed on silica gel (500 ml) eluting with a mixture of dichloromethane and methanol (10:1) to give (2R,4R)-1-allyloxycarbonyl-4-tert-butyl-dimethylsilyloxy-2-[2-{4-(2-carbamoylethenyl)imidazol-1-yl}ethyl]pyrrolidine (13.87 g).

NMR (CDCl$_3$, δ) : 0.38 (6H, s), 0.85 (9H, s), 1.50–1.75 (1H, m), 1.80–2.10 (2H, m), 2.17–2.35 (1H, m), 3.33–3.50 (2H, m), 3.90–4.20 (3H, m), 4.30–4.35 (1H, m), 4.50–4.61 (2H, m), 5.18–5.34 (2H, m), 5.57 (2H, br s), 5.83–6.02 (1H, m), 6.61 (1H, d, J=15.2 Hz), 7.11 (1H, br s), 7.50 (1H, d, J=15.0 Hz), 7.51 (1H, br s)

Preparation 37-2)

(2R, 4R)-1-Allyloxycarbonyl-2-[2-{4-(2-carbamoylethenyl) imidazol-1-yl}ethyl]-4-hydroxypyrrolidine was obtained in 96.0% yield in substantially the same manner as that of Preparation 2-2).

NMR (CDCl$_3$-MeOD, δ): 1.60–2.50 (4H, m), 3.35–3.70 (2H, m), 3.90–4.20 (3H, m), 4.37 (1H, br s), 4.56–4.60 (2H, m), 5.20–5.40 (2H, m), 5.80–6.03 (1H, m), 6.57 (1H, d, J=15.4 Hz), 7.16 (1H, br s), 7.42 (1H, d, J=15.47 Hz), 7.57 (1H, br s)

Preparation 37-3)

(2R,4R)-1-Allyloxycarbonyl-2-[2-{4-(2-carbamoylethenyl) imidazol-1 -yl}ethyl]-4-methanesulfonyloxypyrrolidine was obtained in 72.4% yield in substantially the same manner as that of Preparation 2-3).

NMR (CDCl$_3$, δ): 1.86–2.05 (2H, m), 2.30–2.50 (2H, m), 3.04 (3H, s), 3.50–3.60 (1H, m), 4.04 (4H, m), 4.59–4.63 (2H, m), 5.20–5.40 (3H, m), 5.67 (2H, br s), 5.80–6.04 (1H, m), 6.63 (1H, d, J=15.2 Hz), 7.13 (1H, br s), 7.50 (1H, d, J=15.0 Hz), 7.53 (1H, br s)

Preparation 37-4)

(2R,4S)-1-Allyloxycarbonyl-4-benzoylthio-2-[2-{4-(2-carbamoylethenyl)imidazol-1-yl}ethyl]pyrrolidine was obtained in 88% yield in substantially the same manner as that of Preparation 19-2).

NMR (CDCl$_3$, δ): 1.70–2.70 (4H, m), 3.29–3.38 (1H, m), 4.00–4.26 (5H, m), 4.58–4.62 (2H, m), 5.22–5.37 (2H, m), 5.64 (2H, br s), 5.84–6.04 (1H, m), 6.63 (1H, d, J=15.2 Hz), 7.14 (1H, br s), 7.40–7.94 (7H, m)

Preparation 38-1)

(2R, 4R)-1-Allyloxycarbonyl-4-tert-butyldimethyl-silyloxy-2-[2-{5-(2-carbamoylethenyl)imidazol-1-yl}ethyl]pyrrolidine was obtained in 76.0% yield in substantially the same manner as that of Preparation 7-1).

NMR (CDCl$_3$, δ): 0.38 (6 H, s), 0.85 (9H, s), 1.55–1.70 (1H, m), 1.80–2.05 (2H, m), 2.10–2.20 (1H, m), 3.30–3.50 (2H, m), 3.95–4.10 (3H, m), 4.27–4.32 (1H, m), 4.50–4.55 (2H, m), 5.10–5.30 (2H, m), 5.75–6.00 (1H, m), 6.34 (1H, d, J=15.9 Hz), 7.31–7.54 (3H, m)

Preparation 38-2)

(2R,4R)-1-Allyloxycarbonyl-2-[2-{5-(2-carbamoylethenyl) imidazol-1-yl}ethyl]-4-hydroxypyrrolidine was obtained in 82% yield in substantially the same manner as that of Preparation 37-2).

NMR (CDCl$_3$, δ): 1.60–2.40 (4H, m), 3.05 (1H, br s), 3.40–3.70 (2H, m), 4.00–4.10 (3H, m), 4.37 (1H, br s), 4.55–4.60 (2H, m), 5.15–5.35 (2H, m), 5.80–6.02 (1H, m), 6.22 (1H, br s), 6.64 (1H, d, J=15.35 Hz), 7.15 (1H, br s), 7.35 (1H, s), 7.44 (1H, d, J=14.92 Hz), 7.50–7.64 (1H, m)

Preparation 38-3)

(2R,4R)-1-Allyloxycarbonyl-2-[2-{5-(2-carbamoylethenyl) imidazol-1-yl}ethyl]-4-methanesulfonyloxypyrrolidine was obtained in 27.5% yield in substantially the same manner as that of Preparation 37-3).

NMR (CDCl$_3$, δ): 1.80–2.04 (2H, m), 2.25–2.60 (2H, m), 3.05 (3H, s), 3.50–3.65 (1H, m), 3.90–4.20 (4H, m), 4.60–4.63 (2H, m), 5.20–5.40 (3H, m), 5.83–6.03 (1H, m), 6.37 (1H, d, J=15.88 Hz), 7.41 (1H, s), 7.48 (1H, d, J=15.80 Hz), 7.61 (1H, s)

Preparation 38-4)

(2R,4S)-1-Allyloxycarbonyl-4-benzoylthio-2-[2-{5-(2-carbamoylethenyl) imidazol-1-yl}ethyl]pyrrolidine was obtained in 90.9% yield in substantially the same manner as that of Preparation 37-4).

NMR (CDCl$_3$, δ): 1.67–1.80 (1H, m), 1.99–2.18 (1H, m), 2.35–2.80 (2H, m), 3.25–3.40 (1H, m), 4.00–4.30 (5H, m), 4.58–4.62 (2H, m), 5.20–5.35 (2H, m), 5.83–6.03 (1H, m), 6.41 (1H, d, J=15.8 Hz), 7.30–8.00 (8H, m)

Preparation 39

To a solution of diethyl 1-ethoxycarbonyl-1,4-dihydropyridine 4-phosphonate (0.75 g) in tetrahydrofuran (10 ml) were added n-butyllithium (1.66N in n-hexane solution) (1.56 ml) at −60° C. After stirring at −70° C. for 1 hour, to the mixture was added a solution of (2S,4R)-1-allyloxycarbonyl-4-t-butyldimethylsilyloxy-2-(iodomethyl)pyrrolidine (1.0 g) in tetrahydrofuran at −60° C. After stirring at 0° C. for 20 minutes, to the mixture was added n-butyllithium (3.12 ml) at −70° C. And the mixture was warmed to 0° C. slowly, quenched by water (20 ml), and extracted with ethyl acetate (50 ml×3). The combined organic layer was washed with brine, dried over magnesium sulfate and evaporated. Obtained residue was chromatographed on silica gel (70 ml) eluting with a mixture of N-hexane and ethyl acetate (1:1) to give (2R,4R)-1-allyloxycarbonyl-4-t-butyldimethylsilyloxy-2-(4-pyridylmethyl)pyrrolidine (270 mg).

NMR (CDCl$_3$, δ): 0.00 (6H, s), 0.83 (9H, s), 1.6–2.0 (2H, m), 2.7–2.9 (1H, m), 3.0–3.5 (3H, m), 4.1–4.4 (2H, m), 4.6–4.7 (2H, m), 5.1–5.4 (2H, m), 5.8–6.1 (1H, m), 7.0–7.2 (2H, m), 8.5–8.6 (2H, m)

Preparation 40

To a solution of diethyl 1-ethoxycarbonyl-1,4-dihydropyridine-4-phosphonate (24 g) in tetrahydrofuran (160 ml) were added n-butyllithium (1.66N in n-hexane solution) (50 ml) at −50° C. After stirring at −70° C. for 30 minutes, to the mixture was added a solution of (2S,4R)-1-allyloxycarbonyl-4-t-butyldimethylsilyloxy-2-formylpyrrolidine (20 g) in tetrahydrofuran (40 ml) at −50° C. After stirring at −70° C. for 30 minutes, the reaction mixture was warmed to room temperature slowly. After stirring at room temperature for 8 hours, the mixture was quenched with water (200 ml), extracted with ethyl acetate (400 ml, 200 ml×2). The combined organic layer was washed with brine, dried over magnesium sulfate and evaporated. Obtained residue was chromatographed on silica gel (880 ml), eluting with a mixture of n-hexane and ethyl acetate (1:1) to give (2R,4R)-1-allyloxy-carbonyl-4-t-butyldimethylsilyloxy-2-(4-pyridylmethyl) pyrrolidine (25.44 g).

NMR (CDCl$_3$, δ): 0.00 (6H, s), 0.83 (9H, s), 1.6–2.0 (2H, m), 2.7–2.9 (1H, m), 3.0–3.5 (3H, m), 4.1–4.4 (2H, m), 4.6–4.7 (2H, m), 5.1–5.4 (2H, m), 5.8–6.1 (1H, m), 7.0–7.2 (2H, m), 8.5–8.6 (2H, m)

Preparation 41-1)

1-{(2S,4R)-1-Benzyl-4-(t-butyldimethylsilyloxy)-pyrrolidin-2-yl}-1-(3-pyridyl) methanol was obtained in 74% yield in substantially the same manner as that of Preparation 15-1).

NMR (D$_2$O, δ): −0.07–0 (6H, m), 0.79 (4.5H, s), 0.84 (4.5H, s), 1.1–2.5 (3H, m), 2.8–3.8 (4H, m), 4.0–4.9 (2H, m), 7.2–7.4 (6H, m), 7.6–8.6 (3H, m)

Preparation 41-2)

1-{(2S,4R)-1-Allyloxycarbonyl-4-(t-butyldimethyl-silyloxy) pyrrolidin-2-yl}-1-(3-pyridyl)methanol was obtained in 53% yield in substantially the same manner as that of Preparation 15-2).

NMR (D$_2$O, δ): −0.03–0.02 (6H, m), 0.83 (9H, s), 1.5–2.1 (3H, m), 2.5–3.1 (1H, m), 3.3–3.7 (2H, m), 4.0–4.5 (2H, m), 4.6–4.8 (2H, m), 5.1–5.4 (2H, m), 5.8–6.1 (1H, m), 7.2–7.4 (1H, m), 7.6–7.8 (1H, m), 8.5–8.7 (2H, m)

Example 1-1)

A solution of (4R,5S,6S)-6-[(1R)-1-hydroxyethyl]-4-methyl-3-[(2S,4S)-2-{(E)-2-(1-methyl-3-pyridinio)vinyl}-pyrrolidin-4-yl]thio-7-oxo-1-azabicyclo[3.2.0]hept-2-ene-2-carboxylic acid iodide (1.11 g), 20% palladium hydroxide on carbon (0.9 g), 0.1M phosphoric acid buffer (pH=6.5 50 ml) and water (50 ml) was stirred for 4 hours under atmospheric pressure of hydrogen at ambient temperature. After the catalyst was filtered off, the filtrate was evaporated in vacuo. The residue was chromatographed on nonionic adsorption resin "Diaion HP-20" (40 ml) elution in turn with water (120 ml) and 5% aqueous acetone (240 ml). The fractions containing the desired compound were collected and evaporated to give a residue (30 ml). The residue was passed through ion exchange resin, Amberlist A-26 (Cl$^-$ type, trademark, made by Rohm and Haas Co., Ltd.) (10 ml) eluting with water (70 ml). The eluate was lyophilized to give (4R,5S, 6S)-6-[(1R)-1-hydroxyethyl]-4-methyl-3-[(2R,4S)-2-{2-(1-methyl-3-pyridinio)ethyl}-pyrrolidin-4-yl]thio-7-oxo-1-azabicyclo[3.2.0]hept-2-ene-2-carboxylic acid chloride (492 mg).

IR (Nujol): 1740–1735, 1570–1550 cm$^{-1}$

NMR (D$_2$O, δ): 1.24 (3H, d, J=7.19 Hz), 1.31 (3H, d, J=6.35 Hz), 1.70–1.85 (1H, m), 2.15–2.36 (2H, m), 2.76–3.06 (3H, m), 3.35–3.50 (3H, m), 3.67–3.89 (2H, m), 3.99–4.09 (1H, m), 4.22–4.29 (2H, m), 4.39 (3H, s), 8.00 (1H, dd, J=6.22 Hz, J=8.00 Hz), 8.45 (1H, d, J=8.19 Hz), 8.67 (1H, d, J=6.07 Hz), 8.76 (1H, s)

FAB Mass: 432.2 (M$^+$)

Example 1- 2)

A solution of (4R,5S,6S)-3-[(2S,4S)-2-[(Z)-2-{(1-(N,N-dimethylcarbamoylmethyl)-3-pyridinio}vinyl]pyrrolidin-4yl]thio-6-[(1R)-1-hydroxyethyl]-4-methyl-7-oxo-1-azabicyclo-[3.2.0]hept-2-ene-2-carboxylic acid chloride (490 mg) and 20% palladium hydroxide on carbon (0.5 g) in phosphoric acid buffer (pH=6.5) (30 ml) was stirred for 4 hours under atmospheric pressure of hydrogen at ambient temperature. After the catalyst was filtered off, the filtrate was evaporated in vacuo. The residue was chromatographed on nonionic adsorption resin "Diaion HP-20" (40 ml) eluting in turn with water (120 ml) and 5% aqueous acetone (240 ml). The fractions containing the desired compound were collected and evaporated in vacuo. The resulting residue (30 ml) was passed through ion exchange resin, "Amberlist A-26 (Cl$^-$ type, trademark, made by Rohm and Haas Co., Ltd.)" eluting with water (150 ml). The eluate was lyophilized to give (4R,5S,6S)-3-[(2R,4S)-2-[2-{1-(N,N-dimethylcarbamoylmethyl)-3-pyridinio}ethyl]pyrrolidin-4-yl]thio-6-[(1R)-1-hydroxyethyl]-4-methyl-7-oxo-1-azabicyclo[3.2.0]hept-2-ene-2-carboxylic acid chloride (148 mg).

IR (Nujol): 1730, 1650–1630, 1580–1540, 1140 cm$^{-1}$

NMR (D$_2$O, δ): 1.23 (3H, d, J=7.19 Hz), 1.29 (3H, d, J=6.36 Hz), 1.65–1.85 (1H, m), 2.15–2.35 (2H, m), 2.78–3.00 (1H, m), 2.98–3.05 (1H, m), 3.02 (3H, s), 3.17 (3H, s), 3.30–4.35 (8H, m), 5.72 (2H, s), 8.08 (1H, dd, J=6.12 Hz, J=8.06 Hz), 8.51–8.75 (3H, m)

FAB Mass: 503.2 (M$^+$)

Example 2-1)

To a solution of allyl (4R)-2-diazo-4-[(2R,3S)-3{(1R)-1-hydroxyethyl}-4-oxoazetidin-2-yl]-3-oxopentanoate (1.96 g) in ethyl acetate (20 ml) was added rhodium(II) octanoate (52 mg) under refluxing in a stream of nitrogen. The mixture was refluxed for 30 minutes and evaporated in vacuo to give a residue. The residue was dissolved in acetonitrile (20 ml) and cooled at 0°–5° C. under atmosphere of nitrogen. To the solution were added diphenyl phosphorochloridate (1.45 ml) and N,N-diisopropyl-N-ethylamine (1.27 ml) successively and the mixture was stirred at the same condition for 3 hours.

On the other hand, to a solution of (2R,4S)-4-acetylthio-1-allyloxycarbonyl-2-[2-(pyridin-3-yl)ethyl]pyrrolidine (3.11 g) in a mixture of acetonitrile (30 ml) was added dropwise 28% sodium methoxide-methanol solution (1.79 ml) at −20°–−10° C. and the mixture was stirred at the same temperature for 10 minutes. The reaction mixture was added to the solution described above with stirring under ice-cooling. The mixture was stirred at the same temperature for 2 hours. To the reaction mixture were added ethyl acetate (100 ml) and water (50 ml) with stirring. The organic layer was separated, washed twice with saturated aqueous sodium chloride, dried over anhydrous magnesium sulfate and evaporated in vacuo. The resulting residue was chromatographed on silica gel (150 g) eluting with a mixture of chloroform and acetone (4:1, V/V). The fractions containing the desired compound were collected and evaporated in vacuo to give allyl (4R,5S,6S)-3-[(2R,4S)-1-allyloxycarbonyl-2-{2-(pyridin-3-yl)ethyl}pyrrolidin-4-yl]thio-6-[(1R)-1-hydroxyethyl]-4-methyl-7-oxo-1-azabicyclo[3.2.0]hept-2-ene-2-carboxylate (1.84 g).

IR (Neat): 1760, 1690, 1405, 1325, 1215, 1120 cm$^{-1}$

NMR (CDCl$_3$, δ): 1.26 (3H, d, J=7.18 Hz), 1.33 (3H, d, J=6.23 Hz), 1.65–2.10 (2H, m), 2.20–2.90 (6H, m), 3.15–3.70 (4H, m), 3.85–4.45 (4H, m), 4.50–4.90 (4H, m), 5.20–5.55 (4H, m), 5.80–6.10 (2H, m), 7.15–7.35 (1H, m), 7.55 (1H, broad s), 8.44 (2H, broad s)

Example 2-2)

To a solution of allyl (4R)-2-diazo-4-[(2R,3S)-3-{(1R)-1-hydroxyethyl}-4-oxoazetidin-2-yl]-3-oxopentanoate (9.35 g) in ethyl acetate (94 ml) was added rhodium(II) octanoate (123 mg) and the solution was refluxed for 30 minutes. The solvent was evaporated and the residue was dissolved in acetonitrile (94 ml). To the solution was added successively diphenyl phosphorochloridate (7.23 ml), N,N-diisopropyl-N-ethylamine (6.35 ml) and 4-(N,N-dimethylamino)pyridine (39 mg) under ice-bath cooling and the solution was stirred for 4 hours.

On the other hand, to a solution of (2R,4S)-1-allyloxycarbonyl-4-benzoylthio-2-[3-(imidazol-1-yl) propyl]pyrrolidine (15.2 g) in methanol was added 28% sodium methoxide-methanol solution (7.92 ml) dropwise under ice-bath cooling and the solution was stirred at the same temperature for 2 hours. The reaction mixture was quenched by the addition of acetic acid (2.18 ml). Then N,N-dimethylacetamide (20 ml) was added and the mixture was concentrated in vacuo. The residue was dissolved in ethyl acetate and washed with brine (50 ml×2), then dried over magnesium sulfate. To the solution was added N,N-dimethylacetamide (20 ml) and concentrated in vacuo. The residue was dissolved in acetonitrile (94 ml). To the former solution were added successively the latter solution and diisopropylethylamine (6.62 ml) dropwise under ice-bath cooling and the solution was allowed to stand in a refrigerator for 12 hours. To the reaction mixture was added ethyl acetate (200 ml) and the solution was washed with water (200 ml×2), and brine (200 ml×2). The aqueous washings were extracted with ethyl acetate (100 ml×1) and the organic layer was washed with brine (100 ml×1). The organic layers were combined and dried over magnesium sulfate. After evaporation of the solvent, the residue was chromatographed on a 290 g of silica gel eluting with a mixture of dichloromethane and acetone (1:1, V/V) to give allyl (4R,5S,6S)-3-[(2R,4S)-1-allyloxycarbonyl-2-{3-(imidazol-1-yl)propyl}pyrrolidin-4-yl]thio-6-[(1 R)-1-hydroxyethyl]-4-methyl-7-oxo-1-azabicyclo[3.2.0]hept-2-ene-2-carboxylate (10.4 g) as a pale yellow solid.

NMR (CDCl$_3$, 200 MHz, δ): 1.25 (3H, d, J=7.2 Hz), 1.36 (3H, d, J=6.2 Hz), 1.46–2.65 (7H, m), 3.06–3.66 (4H, m), 3.80–4.33 (6H, m), 4.56–4.86 (4H, m), 5.22–5.49 (4H, m), 5.90–6.04 (2H, m), 6.91 (1H, s), 7.06 (1H, s), 7.49 (1H, s)

Example 2-3)

To a solution of allyl (4R)-2-diazo-4-[(2R,3S)-3{(1R)-1-hydroxyethyl}-4-oxoazetidin-2-yl]-3-oxopentanoate (3.76 g) in ethyl acetate (38 ml) was added rhodium(II) octanoate (50 mg) under stirring at ambient temperature in a stream of nitrogen. The mixture was refluxed for 30 minutes. The solution was cooled to ambient temperature and evaporated in vacuo to give a residue. The residue was dissolved in acetonitrile (38 ml). To the solution were added diphenyl phosphorochloridate (2.78 ml) and N,N-diisopropyl-N-ethylamine (2.45 ml) successively at 0°–5° C. under stirring and the solution was stirred at the same temperature for 3 hours.

On the other hand, to a solution of (2R,4S)-1-allyloxycarbonyl-4-acetylthio-2-[2-(imidazol-1-yl)ethyl]pyrrolidine (4.54 g) in a mixture of methanol (45 ml) and tetrahydrofuran (45 ml) was added dropwise 28% sodium methoxide-methanol solution (2.97 ml) under ice-cooling with stirring and the solution was stirred at the same temperature for 30 minutes. To the reaction mixture was added acetic acid (0.80 ml) and the solution was evaporated in vacuo. The resulting residue was dissolved in a mixture of ethyl acetate and water. The organic layer was washed with brine, dried over anhydrous magnesium sulfate and evaporated in vacuo to give a residue. The residue was dissolved in N,N-dimethylacetamide (38 ml). This solution and N,N-diisopropyl-N-ethylamine (2.67 ml) were successively added to the solution described above with stirring under ice-cooling and the solution was allowed to stand in a refrigerator for 12 hours. The solution was poured into water and extracted with a mixture of ethyl acetate and tetrahydrofuran (1:1, V/V). The organic layer was washed with brine, dried over anhydrous magnesium sulfate and evaporated in vacuo. The resulting residue was purified by silica gel chromatography eluting with a mixture of chloroform and methanol (20:1, V/V) to give allyl (4R,5S,6S)-3-[(2R,4S)-1-allyloxycarbonyl-2-{2-(imidazol-1-yl)ethyl}pyrrolidin-4-yl]thio-6-[(1R)-1-hydroxyethyl]-4-methyl-7-oxo-1-azabicyclo[3.2. 0]hept-2-ene-2-carboxylate (4.74 g).

NMR (CDCl$_3$, δ): 1.25 (3H, d, J=7.2 Hz), 1.36 (3H, d, J=6.2 Hz), 1.59 (1H, br), 1.96 (1H, br), 2.48 (3H, br), 3.21–3.30 (3H, m), 3.54–3.61 (1H, m), 4.04 (4H, br), 4.21–4.28 (2H, m), 4.58–4.88 (4H, m), 5.23–5.49 (4H, m), 5.84–6.04 (2H, m), 6.98 (1H, br), 7.07 (1H, s), 7.52 (1H, s)

Example 2-4)

Allyl (4R,5S,6S)-3-[(2R,4S)-1-allyloxycarbonyl-2-{2-(pyridin-4-yl)ethyl}pyrrolidin-4-yl]thio-6-[(1R)-1-hydroxyethyl]-4-methyl-7-oxo-1-azabicyclo[3.2. 0]hept-2-ene-2-carboxylate (1.45 g) was obtained by reacting allyl (4R)-2-diazo-4-[(2R,3S)-3-{(1R)-1-hydroxyethyl}-4-oxoazetidin-2-yl]-3-oxopentanoate (2.94 g) with rhodium(II) octanoate (39 mg) and then successively with diphenyl phosphorochloridate (2.17 ml) and (2R,4S)-1-allyloxycarbonyl-4-acetylthio-2-[2-(pyridin-4-yl)ethyl]pyrrolidine (4.35 g) in substantially the same manner as that of Example 2-1).

NMR (CDCl$_3$, δ): 1.27 (3H, d, J=7.1 Hz), 1.36 (3H, d, J=6.2 HZ), 1.65–1.98 (2H, m), 2.34–2.69 (4H, 3.20–3.39 (2H, m), 3.59–3.81 (2H, m), 3.97–4.27 (4H, m), 4.57–4.88(4H, m), 5.10–5.49 (4H, m), 5.83–6.06 (2H, m), 7.16 (2H, br) 8.48 (2H, d, J=5.8 Hz)

Example 2-5)

Allyl (4R,5S,6S)-3-[(2R,4S)-1-allyloxycarbonyl-2-{2-(pyridin-2-yl)ethyl}pyrrolidin-4-yl]thio-6-[(1R)-1-hydroxyethyl]-4-methyl-7-oxo-1-azabicyclo[3.2.0]hept-2-ene-2-carboxylate (2.53 g) was obtained by reacting allyl (4R)-2-diazo-4-[(2R,3S)-3-{(1R)-1-hydroxyethyl}-4-oxoazetidin-2-yl]-3-oxopentanoate (3.0 g) with rhodium(II) octanoate (79 mg) and then successively with diphenyl phosphorochloridate (2.21 ml) and (2R,4S)-1-allyloxy-carbonyl-4-acetylthio-2-[2-(pyridin-2-yl)ethyl]pyrrolidine (4.41 g) in substantially the same manner as that of Example 2-1).

IR (Neat): 1760, 1690, 1595, 1540 cm$^{-1}$

NMR (CDCl$_3$, δ): 1.26 (3H, d, J=7.18 Hz), 1.36 (3H, d, J=6.26 Hz), 1.60–2.90 (10H, m), 3.10–4.40 (8H, m), 4.56 (2H, d, J=5.51 Hz), 4.60–4.90 (2H, m), 5.10–5.55 (4H, m), 5.80–6.05 (2H, m), 7.05–7.30 (2H, m), 7.61 (1H, dt, J=1.83 Hz, J=7.67 Hz), 8.51 (1H, d, J=4.07 Hz)

Example 2-6)

To a solution of allyl (4R)-2-diazo-4-[(2R,3S)-3{(1R)-1-hydroxyethyl}-4-oxoazetidin-2-yl]-3-oxopentanoate (2.15 g) in ethyl acetate (22 ml) was added rhodium(II) octanoate (57 mg) under refluxing in a stream of nitrogen. The mixture was refluxed for 30 minutes and evaporated in vacuo to give a residue. The residue was dissolved in acetonitrile (22 ml) and cooled at 0°~5° C. under atmosphere of nitrogen. To the solution was added diphenyl phosphorochloridate (1.59 ml) and N,N-diisopropyl-N-ethylamine (1.40 ml) successively and the mixture was stirred at the same condition for 3 hours.

On the other hand, to a solution of (2R,4S)-4-acetylthio-1-allyloxycarbonyl-2-[2-(1-methylimidazol-2-yl)ethyl]pyrrolidine (3.19 g) in acetonitrile (32 ml) was added dropwise 28% sodium methoxide-methanol solution (1.82 ml) at −10°~0° C. and the mixture was stirred at the same temperature for 10 minutes. The reaction mixture and N,N-dimethylacetamide (10 ml) were added to the solution described above with stirring under ice-cooling. The mixture was stirred at the same temperature for 2 hours. To the reaction mixture were added ethyl acetate (100 ml) and water (50 ml) with stirring. The organic layer was separated, washed twice with saturated aqueous sodium chloride, dried over anhydrous magnesium sulfate and evaporated in vacuo. The resulting residue was chromatographed on silica gel (200 g) eluting with a mixture of chloroform and methanol (19:1, V/V). The fractions containing the desired compound were collected and evaporated in vacuo to give allyl (4R, 5S,6S)-3-[(2R,4S)-1-allyloxycarbonyl-2-[2-(1-methylimidazol-2-yl)-ethyl) pyrrolidin-4-yl]thio-6-[(1R)-1-hydroxyethyl]-4-methyl-7-oxo-1-azabicyclo [3.2.0]hept-2-ene-2-carboxylate (2.11 g).

IR (Neat): 1760, 1700, 1680, 1540 cm$^{-1}$

NMR (CDCl$_3$, δ): 1.25 (3H, d, J=7.22 Hz), 1.35 (3H, d, J=6.23 Hz), 2.10–2.80 (5H, m), 3.05–3.55 (4H, m), 3.59 (3H, s), 3.80–4.35 (4H, m), 4.45–4.90 (4H, m), 5.10–5.50 (4H, m), 5.75–6.05 (2H, m), 6.80 (1H, d, J=1.2 Hz), 6.90 (1H, d, J=1.2 Hz)

Example 3-1)

To a solution of allyl (4R,5S,6S)-3-[(2R,4S)-1-allyloxycarbonyl-2-{2-(pyridin-3-yl)ethyl}pyrrolidin-4-yl]thio-6-[(1 R)-1-hydroxyethyl]-4-methyl-7-oxo-1-azabicyclo [3.2.0]hept-2-ene-2-carboxylate (1.83 g) in acetone (10 ml) was added iodoacetamide (1.87 g) with stirring and then the mixture was allowed to stand at ambient temperature for 2 days. The reaction mixture was evaporated in vacuo and dried in vacuo for 1 hour to give allyl (4R,5S,6S)-3-[(2R, 4S)-1-allyloxycarbonyl-2-{2-(1-carbamoylmethyl-3-pyridinio)ethyl}pyrrolidin-4-yl]thio-6[(1R)-1-hydroxyethyl]-4-methyl-7-oxo-1-azabicyclo[3.2.0]hept-2-ene-2-carboxylate iodide (3.55 g). This compound was immediately used as the starting compound for the next step.

Example 3-2)

To a solution of allyl (4R,5S,6S)-3-[(2R,4S)-1-allyloxycarbonyl-2-{3-(imidazol-1-yl)propyl}pyrrolidin-4yl]thio-6-[(1R)-1-hydroxyethyl]-4-methyl-7-oxo-1-azabicyclo[3.2.0] hept-2-ene-2-carboxylate (4.00 g) in acetone (20 ml) was added methyl iodide (4.57 ml) at room temperature and the solution was allowed to stand overnight. The solvent was evaporated to give allyl (4R,5S,6S)-3-[(2R,4S)-1-allyloxycarbonyl-2-{3-(3-methyl-1-imidazolio) propyl}pyrrolidin-4-yl]thio-6-[(1R)-1-hydroxyethyl]-4-methyl-7-oxo-1-azabicyclo[3.2.0]hept-2-ene-2-carboxylate iodide (5.01 g) as a yellow solid. This compound was immediately used as the starting compound for the next step.

Example 3-3)

Allyl (4R,5S,6S)-3-[(2R,4S)-1-allyloxycarbonyl-2-{3-(3-carbamoylmethyl-1-imidazolio)propyl}pyrrolidin-4-yl]-thio-6-[(1R)-1-hydroxyethyl]-4-methyl-7-oxo-1-azabicyclo[3.2.0]hept-2-ene-2-carboxylate iodide (8.16 g) was obtained by reacting allyl (4R,5S,6S)-3-[(2R,4S)-1-allyloxycarbonyl-2-{3-(imidazol-1-yl)propyl}pyrrolidin-4-yl]thio-6-[(1R)-1-hydroxyethyl]-4-methyl-7-oxo-1-azabicyclo[3.2.0]hept-2-ene-2-carboxylate (4.86 g) with iodoacetamide (3.30 g) in acetone (24 ml) in substantially the same manner as that of Example 3-1).

Example 3-4)

To a solution of allyl (4R,5S,6S)-3-[(2R,4S)-1-allyl-oxycarbonyl-2-{2-(imidazol-1-yl)ethyl}pyrrolidin-4-yl]-thio-6-[(1R)-1-hydroxyethyl]-4-methyl-7-oxo-1-azabicyclo[3.2.0]hept-2-ene-2-carboxylate (6.94 g) in acetone (35 ml) was added methyl iodide (8.14 ml) with stirring at ambient temperature and then allowed to stand overnight at the same temperature. The reaction mixture was evaporated in vacuo to give allyl (4R,5S,6S)-3-[(2R,4S)-1-allyloxy-carbonyl-2-{2-(3-methyl-1-imidazolio)ethyl}pyrrolidin-4yl]thio-6-[(1R)-1-hydroxyethyl]-4-methyl-7-oxo-1-azabicyclo[3.2.0]hept-2-ene-2-carboxylate iodide (8.80 g).

This compound was immediately used as the starting compound for the next step.

Example 3-5)

Allyl(4R,5S,6S)-3-[(2R,4S)-1-allyloxycarbonyl-2-{2-(3-carbamoylmethyl-1-imidazolio)ethyl}pyrrolidin-4-yl]-thio-6-[(1R)-1-hydroxyethyl]-4-methyl-7-oxo-1-azabicyclo[3.2.0]hept-2-ene-2-carboxylate iodide (1.72 g) was obtained by reacting allyl (4R,5S,6S)-3-[(2R,4S)-1-allyloxycarbonyl-2-{2-(imidazol-1-yl)ethyl}pyrrolidin-4yl]thio-6-[(1R)-1-hydroxyethyl]-4-methyl-7-oxo-1-azabicyclo[3.2.0]hept-2-ene-2-carboxylate (0.84 g) with iodoacetamide (0.88 g) in acetone (4 ml) in substantially the same manner as that of Example 3-1).

Example 3-6)

Allyl (4R,5S,6S)-3-[(2R, 4S)-1-allyloxycarbonyl-2-{2-(1-carbamoylmethyl-4-pyridinio)ethyl}pyrrolidin-4-yl]thio-6-[(1R)-1-hydroxyethyl]-4-methyl-7-oxo-1-azabicyclo[3.2.0]hept-2-ene-2-carboxylate iodide (2.94 g) was obtained by reacting allyl (4R,5S,6S)-3-[(2R,4S)-1-allyloxycarbonyl-2-{2-(pyridin-4-yl)ethyl}pyrrolidin-4yl]thio-6-[(1R)-1-hydroxyethyl]-4-methyl-7-oxo-1azabicyclo[3.2.0]hept-2-ene-2-carboxylate (1.45 g) with iodoacetamide (1.49 g) in acetone (7.3 ml) in substantially the same manner as that of Example 3-1).

Example 3-7)

Allyl (4R,5S,6S)-3-[(2R,4S)-1-allyloxycarbonyl-2-[2-[1-{N-(2-hydroxyethyl)carbamoylmethyl}-3-pyridinio]ethyl]-pyrrolidin-4-yl]thio-6-[(1R)-1-hydroxyethyl]-4-methyl-7-oxo-1-azabicyclo[3.2.0]hept-2-ene-2-carboxylate iodide (4.77 g) was obtained by reacting allyl (4R,5S,6S)-3[(2R, 4S)-1-allyloxycarbonyl-2-{2-(pyridin-3-yl)ethyl}-pyrrolidin-4-yl]thio-6-[(1R)-1-hydroxyethyl]-4-methyl-7-oxo-1-azabicyclo[3.2.0]hept-2-ene-2-carboxylate (3.35 g) in acetone (16 ml) in substantially the same manner as that of Example 3-1).

This compound was immediately used as the starting compound for the next step.

Example 3-8)

Allyl(4R,5S,6S)-3-[(2R,4S)-1-allyloxycarbonyl-2-{2-(1-methyl-2-pyridinio)ethyl}pyrrolidin-4-yl]thio-6-[(1R)-1-hydroxyethyl]-4-methyl-7-oxo-1-azabicyclo[3.2.0]hept-2-ene-2-carboxylate iodide (1.54 g) was obtained by reacting allyl (4R,5S,6S)-3-[(2R,4S)-1-allyloxycarbonyl-2-{2-(pyridin-2-yl)ethyl}pyrrolidin-4-yl]thio-6-[(1R)-1-hydroxyethyl]-4-methyl-7-oxo-1-azabicyclo[3.2.0]hept-2-ene-2-carboxylate (1.54 g) with methyl iodide (1.40 ml) in substantially the same manner as that of Example 3-2).

IR (Neat): 1760, 1680, 1630, 1405 $cm^{-1}$

This compound was immediately used as the starting compound for the next step.

Example 3-9)

Allyl (4R,5S,6S)-3-[(2R,4S)-1-allyloxycarbonyl-2-{2-(1-carbamoylmethyl-2-pyridinio)ethyl}pyrrolidin-4-yl]-thio-6-[(1R)-1-hydroxyethyl]-4-methyl-7-oxo-1-azabicyclo[3.2.0]hept-2-ene-2-carboxylate iodide (1.65 g) was obtained by reacting allyl (4R,5S,6S)-3-[(2R,4S)-1-allyloxycarbonyl-2-{2-(pyridin-2-yl)ethyl}pyrrolidin-4yl]thio-6-[(1R)-1-hydroxyethyl]-4-methyl-7-oxo-1-azabicyclo[3.2.0]hept-2-ene-2-carboxylate (1.23 g) with 2-iodoacetamide (1.26 g) in acetone (6 ml) in substantially the same manner as that of Example 3-1).

This compound was immediately used as the stirring compound for the next step.

Example 3-10)

To a solution of allyl (4R,5S,6S)-3-[(2R,4S)-1-allyloxycarbonyl-2-{2-(1-methylimidazol-2-yl)ethyl}-pyrrolidin-4-yl]thio-6-[(1R)-1-hydroxyethyl]-4-methyl-7-oxo-1-azabicyclo[3.2.0]hept-2-ene-2-carboxylate (3.58 g) in acetone (17 ml) was added iodomethane (2.05 ml) with stirring at ambient temperature and then allowed to stand overnight. The reaction mixture was evaporated in vacuo and dried in vacuo for 1 hour to give allyl (4R,5S,6S)-3[(2R,4S)-1-allyloxycarbonyl-2-{2-(1,3-dimethyl-2-imidazolio)ethyl}pyrrolidin-4-yl]thio-6-[(1R)-1-hydroxyethyl]-4-methyl-7-oxo-1-azabicyclo[3.2.0]hept-2-ene-2-carboxylate iodide (3.68 g).

This compound was immediately used as the starting compound for the next step.

Example 3-11)

To a solution of allyl (4R,5S,6S)-3-[(2R,4S)-1-allyloxycarbonyl-2-{2-(1-methylimidazol-2-yl)ethyl}-pyrrolidin-4-yl]thio-6-[(1R)-1-hydroxyethyl]-4-methyl-7-oxo-1-azabicyclo[3.2.0]hept-2-ene-2-carboxylate (1.04 g) in acetone (5 ml) was added iodoacetamide (1.06 g) with stirring at ambient temperature and then allowed to stand overnight. The reaction mixture was evaporated in vacuo and dried in vacuo for 1 hour to give allyl (4R,5S,6S)-3-[(2R,4S)-1-allyloxycarbonyl-2-{2-(3-carbamoylmethyl-1-methyl-2-imidazolio) ethyl}pyrrolidin-4-yl]thio-6-[(1R)-1-hydroxyethyl]-4-methyl-7-oxo-1-azabicyclo[3.2.0]hept-2-ene-2-carboxylate iodide (1.39 g).

IR (Neat): 1750, 1700 (sh), 1680 $cm^{-1}$

This compound was immediately used as the starting compound for the next step.

Example 4-1)

To a solution of allyl (4R,5S,6S)-3-[(2R,4S)-1-allyloxycarbonyl-2-{2-(1-carbamoylmethyl-3-pyridinio)ethyl}pyrrolidin-4-yl]thio-6-[(1R)-1-hydroxyethyl]-4-methyl-7-oxo-1-azabicyclo[3.2.0]hept-2-ene-2-carboxylate iodide (3.55 g), triphenylphosphine (88 mg), acetic acid (0.77 ml) and tetrakis(triphenylphosphine)palladium(0) (117 mg) in a mixture of tetrahydrofuran (25 ml) and ethanol (25 ml) was added dropwise tributyltin hydride (3.63 ml) at ambient temperature with stirring. The mixture was stirred at the same temperature for 30 minutes. The resulting precipitates were collected by filtration, washed with tetrahydrofuran (50 ml), dried in vacuo and dissolved in water (50 ml). The solution was chromatographed on nonionic adsorption resin, Diaion HP-20 (trademark, made by Mitsubishi Chemical Industries) (100 ml) eluting in turn with water (300 ml) and 5% aqueous acetone (600 ml). The fractions containing the desired compound were collected and evaporated in vacuo. The resulting residue (50 ml) was passed through ion exchange resin, Amberlist A-26 (Cl⁻ type, trademark, made by Rohm and Haas Co., Ltd.) (10 ml) eluting with water (150 ml). The eluate was lyophilized to give (4R,5S,6S)-6-[(1R)-1-hydroxyethyl]-4-methyl-3-[(2R,4S)-2-{2-(1-carbamoylmethyl-3-pyridinio)ethyl}pyrrolidin-4-yl]-thio-7-oxo-1-azabicyclo[3.2.0]hept-2-ene-2-carboxylic acid chloride (383 mg).

IR (Nujol): 1740, 1690, 1580, 1380 cm$^{-1}$

NMR (D$_2$O, δ): 1.23 (3H, d, J=7.12 Hz), 1.26 (3H, d, J=6.31 Hz), 1.70–1.90 (1H, m), 2.10–2.50 (2H, m), 2.70–2.95 (1H, m), 2.95–4.35 (9H, m), 5.52 (2H, s), 8.09 (1H, t, J=6.34 Hz), 8.57 (1H, d, J=8.05), 8.71 (1H, d, J=6.01 Hz), 8.78 (1H, s)

FAB Mass: 475.3 (M$^+$)

Example 4-2)

To a solution of allyl (4R,5S,6S)-3-[(2R,4S)-1-allyloxycarbonyl-2-{3-(3-methyl-1-imidazoliopropyl}-pyrrolidin-4-yl]thio-6-[(1R)-1-hydroxyethyl]-4-methyl-7-oxo-1-azabicyclo[3.2.0]hept-2-ene-2-carboxylate iodide (5.10 g), triphenylphosphine (195 mg), acetic acid (1.11 ml) and tetrakis(triphenylphosphine)palladium(0) (258 mg) in a mixture of tetrahydrofuran (51 ml) and ethanol (51 ml) was added tributyltin hydride (4.80 ml) at room temperature and the mixture was stirred for 30 minutes. The precipitates were collected by filtration and washed well with tetrahydrofuran. The solid was dissolved in water (50 ml) and washed with ethyl acetate (50 ml×2). The solution was concentrated to c.a. 20 ml and chromatographed on nonionic adsorption resin, Diaion HP-20 (trademark, made by Mitsubishi Chemical Industries) (500 ml) eluting in turn with water and 6% aqueous acetonitrile. The fractions containing the desired compound were collected and evaporated in vacuo. The resulting residue (30 ml) was passed through ion exchange resin, Amberlist A-26 (Cl⁻ type, trademark, made by Rohm and Haas Co., Ltd.) (25 ml) eluting with water (75 ml). The eluate was lyophilized to give a solid. The solid was dissolved in pH standard buffer solution (pH=6.86, 20 ml). The solution was chromatographed on reversed-phase silica gel, chromatorex ODS (trademark, made by Fuji-Davison Chemical Ltd.) (200 ml) eluting with a mixture of pH standard buffer solution (pH=6.86) and acetonitrile (5:1, V/V). The fractions containing the desired compound were collected and evaporated in vacuo. The resulting residue (20 ml) was chromatographed on nonionic adsorption resin, Diaion HP-20 (200 ml) eluting in turn with water and 6% aqueous acetonitrile. The fractions containing the desired compound were collected and evaporated in vacuo. The resulting residue (50 ml) was adjusted to pH 4.5 with 1N hydrochloric acid and passed through ion exchange resin, Amberlist A-26 (Cl⁻ type) (25 ml) eluting with water (75 ml). The eluate was lyophilized to give (4R,5S,6S)-6-[(1R)-1-hydroxyethyl]-4-methyl-3-[(2R,4S)-2-{3-(3-methyl-1-imidazolio)propyl}pyrrolidin-4-yl]thio-7-oxo-1-azabicyclo[3.2.0]hept-2-ene-2-carboxylic acid chloride (2.05 g) as a white solid.

IR (Nujol): 1724, 1570 cm$^{-1}$

NMR (CDCl$_3$, 200 MHz, δ): 1.20 (3H, d, J=7.2 Hz), 1.28 (3H, d, J=6.4 Hz), 1.59–2.08 (5H, m), 2.67–2.87 (1H, m), 3.35–3.48 (3H, m), 3.59–3.77 (2H, m), 3.89 (3H, s), 3.94–4.10 (1H, m), 4.19–4.30 (4H, m), 7.45 (1H, d, J=1.7 Hz), 7.49 (1H, d, J=1.8 Hz), 8.75 (1H, s)

Example 4-3)

(4R,5S,6S)-3-[(2R,4S)-2-{3-(3-Carbamoylmethyl-1-imidazolio)propyl}pyrrolidin-4-yl]thio-6-[(1R)-1-hydroxyethyl]-4-methyl-7-oxo-1-azabicyclo[3.2.0]hept-2-ene-2-carboxylic acid chloride (1.49 g) was obtained by reacting allyl (4R,5S,6S)-3-[(2R,4S)-1-allyloxycarbonyl-2-{3-(3-carbamoylmethyl-1-imidazoliopropyl}pyrrolidin-4-yl]-thio-6-[(1R)-1-hydroxyethyl]-4-methyl-7-oxo-1-azabicyclo[3.2.0]hept-2-ene-2-carboxylate iodide (crude 8.16 g) with triphenylphosphine (234 mg), acetic acid (1.33 ml), tetrakis(triphenylphosphine)palladium(0) (309 mg) and tributyltin hydride (5.76 ml) in a mixture of tetrahydrofuran (65 ml) and ethanol (65 ml) in substantially the same manner as that of Example 4-1).

IR (Nujol): 1740, 1680, 1560 cm$^{-1}$

NMR (CDCl$_3$, 200 MHz, δ): 1.22 (3H, d, J=7.2 Hz), 1.29 (3H, d, J=6.4 Hz), 1.60–2.10 (5H, m), 2.71–2.87 (1H, m), 3.31–3.50 (3H, m), 3.61–3.78 (2H, m), 3.94–4.12 (1H, m), 4.20–4.37 (4H, m), 5.13 (2H, s), 7.53–7.55 (1H, m), 7.59 (1H, d, J=1.7 Hz), 8.92 (1H, s)

Example 4-4)

To a solution of allyl (4R,5S,6S)-3-[(2R,4S)-1-allyloxycarbonyl-2-{2-(3-methyl-1-imidazolio)ethyl}-pyrrolidin-4-yl]thio-6-[(1R)-1-hydroxyethyl]-4-methyl-7-oxo-1-azabicyclo[3.2.0]hept-2-ene-2-carboxylate iodide (8.80 g), triphenylphosphine (0.69 g), acetic acid (4.50 ml) and tetrakis(triphenylphosphine)palladium(0) (0.60 g) in a mixture of tetrahydrofuran (88 ml) and ethanol (88 ml) was added tributylthin hydride (14.1 ml) at ambient temperature with stirring and the mixture was stirred at the same temperature for 30 minutes. The resulting precipitates were collected by filtration, washed with tetrahydrofuran and dried in vacuo. The solid was dissolved in water (45 ml). The solution was adjusted to pH 6 with 1N hydrochloric acid and chromatographed on nonionic adsorption resin, Diaion HP-20 (trademark, made by Mitsubishi Chemical Industries) (440 ml) eluting in turn with water and 5% aqueous acetone. The fractions containing the desired compound were collected and concentrated in vacuo. The resulting residue was passed through ion exchange resin, Amberlist A-26 (Cl⁻ type, trademark, made by Rohm and Haas Co., Ltd.) (44 ml) eluting with water. The eluate was lyophilized to give (4R,5S,6S)-6-[(1R)-1-hydroxyethyl]-4-methyl-3-[(2R,4S)-2-{2-(3-methyl-1-imidazolio)ethyl}pyrrolidin-4-yl]thio-7- oxo-1-azabicyclo[3.2.0]hept-2-ene-2-carboxylic acid chloride (3.49 g).

IR (Nujol): 1744 cm$^{-1}$

NMR (D$_2$O, δ): 1.23 (1H, d, J=7.2 Hz), 1.30 (1H, d, J=6.4 Hz), 1.65–1.79 (1H, m), 2.41–2.52 (2H, m), 2.72–2.79 (1H, m), 3.34–3.50 (3H, m), 3.57–3.74 (2H, m), 3.91 (3H, s), 4.02 (1H, br), 4.21–4.40 (4H, m), 7.49 (1H, d, J=1.7 Hz), 7.56 (1H, d, J=1.7 Hz), 8.81 (1H, s)

Example 4-5)

(4R,5S,6S)-3-[(2R,4S)-2-{2-(3-Carbamoylmethyl-1-imidazolio)ethyl}pyrrolidin-4-yl]thio-6-[(1R)-1-hydroxyethyl]-4-methyl-7-oxo-1-azabicyclo[3.2.0]hept-2-ene-2-carboxylic acid chloride (0.23 g) was obtained by reacting allyl (4R,5S,6S)-3-[(2R,4S)-1-allyloxycarbonyl2-{2-(3-carbamoylmethyl-1-imidazolio)ethyl}pyrrolidin-4yl]thio-6-[(1R)-1-hydroxyethyl]-4-methyl-7-oxo-1-azabicyclo[3.2.0]hept-2-ene-2-carboxylate iodide (1.72 g) with triphenylphosphine (83 mg), acetic acid (0.54 ml), tetrakis(triphenylphosphine)palladium(0) (73 mg) and tributyltin hydride (1.70 ml) in a mixture of tetrahydrofuran (11 ml) and ethanol (11 ml) in substantially the same manner as that of Example 4-1).

IR (Nujol): 1865, 1745 cm$^{-1}$

NMR (D$_2$O, δ): 1.23 (3H, d, J=7.2 Hz ), 1.30 (3H, d, J=6.3 Hz), 1.69–1.83 (1H, m), 2.41–2.63 (2H, m), 2.72–2.87 (1H, m), 3.34–3.50 (3H, m), 3.65–3.83 (2H, m), 3.95–4.11 (1H, m), 4.16–4.29 (2H, m), 4.43 (2H, t, J=7.6 Hz), 5.14 (2H, s), 7.60 (2H, d, J=14.5 Hz), 8.98 (1H, s)

FAB Mass: 464 (M$^+$)

Example 4-6)

(4R,5S ,6S)-6-[(1R)-1-Hydroxyethyl]-4-methyl-3-[(2R,4S)-2-{2-(1-carbamoylmethyl-4-pyridinio)ethyl}-pyrrolidin-4-yl]thio-7-oxo-1-azabicyclo[3.2.0]hept-2-ene-2-carboxylic acid chloride (309 mg) was obtained by reacting allyl (4R,5S,6S)-3-[(2R,4S)-1-allyloxycarbonyl-2-{2-(1-carbamoylmethyl-4-pyridinio)ethyl}pyrrolidin-4-yl]-thio-6-[(1R)-1-hydroxyethyl]-4-methyl-7-oxo-1-azabicyclo-[3.2.0]hept-2-ene-2-carboxylate iodide (2.94 g) with triphenylphosphine (140 mg), acetic acid (0.92 ml), tetrakis(triphenylphosphine)palladium(0) (124 mg) and tributyltin hydride (2.88 ml) in a mixture of tetrahydrofuran (15 ml) and ethanol (15 ml) in substantially the same manner as that of Example 4-1).

IR (Nujol): 1637, 1685, 1748 cm$^{-1}$

NMR (D$_2$O, δ): 1.23 (3H, d, J=7.3 Hz), 1.31 (3H, d, J=6.0 Hz), 1.75–1.85 (1H, m), 2.24–2.38 (2H, m), 2.77–2.92 (1H, m), 3.09–3.17 (2H, m), 3.35–3.47 (2H, m), 3.67–3.91 (3H, m), 4.05–4.26 (3H, m), 5.48 (2H, s), 8.03 (2H, d, J=5.3 Hz), 8.70 (2H, d, J=5.3 Hz)

FAB Mass: 475 (M$^+$)

Example 4-7)

(4R,5S,6S)-6-[(1R)-1-Hydroxyethyl]-3-[(2R,4S)-2-[1-{N-(2-hydroxyethyl)carbamoylmethyl}-3-pyridinio]ethyl]-pyrrolidin-4-yl]thio-4-methyl-7-oxo-1-azabicyclo[3.2.0]-hept-2-ene-2-carboxylic acid chloride (1.38 g) was obtained by reacting allyl (4R,5S,6S)-3-[(2R,4S)-1-allyloxycarbonyl-2-[2-[1-{N-(2-hydroxyethyl)carbamoylmethyl}-3-pyridinio]ethyl]pyrrolidin-4-yl]thio-6-[(1R)-1-hydroxyethyl]-4-methyl-7-oxo-1-azabicyclo[3.2.0]hept-2-ene-2-carboxylate iodide (4.77 g) with triphenylphosphine (162 mg), acetic acid (1.42 ml), tetrakis(triphenylphosphine)palladium(0) (286 mg) and tri-n-butylthin hydride (6.66 ml) in a mixture of tetrahydrofuran (50 ml) and ethanol (50 ml) in substantially the same manner as that of Example 4-1).

IR (Nujol): 1750–1720, 1670–1640 cm$^{-1}$

NMR (D$_2$O, δ): 1.24 (3H, d, J=7.18 Hz), 1.32 (3H, d, J=6.35 Hz), 1.72–1.87 (1H, m), 2.19–2.40 (2H, m), 2.78–2.93 (1H, m), 3.07 (2H, t, J=8.07 Hz), 3.34–4.30 (12H, m), 5.52 (2H, s), 8.11 (1H, d, J=6.15 Hz, J=8.07 Hz), 8.60 (1H, d, J=8.23 Hz), 8.74 (1H, d, J=6.11 Hz), 8.81 (1H, s)

FAB Mass: 519.2 (M$^+$)

Example 4-8)

(4R,5S,6S)-6-[(1R)-1-Hydroxyethyl]-4-methyl-3-[(2R,4S)-2-{2-(1-methyl-2-pyridinio)ethyl}pyrrolidin-4-yl]thio-7-oxo-1-azabicyclo[3.2.0]hept-2-ene-2-carboxylic acid chloride (262 mg) was obtained by reacting allyl (4R,5S,6S)-3-[(2R,4S)-1-allyloxycarbonyl-2-{2-(1-methyl-2-pyridinio)ethyl}pyrrolidin-4-yl]thio-6-[(1R)-1-hydroxyethyl]-4-methyl-7-oxo-1-azabicyclo[3.2.0]hept-2-ene-2-carboxylate iodide (1.54 g) with triphenylphosphine (59 mg), acetic acid (0.52 ml), tetrakis(triphenylphosphine)palladium(0) (78 mg) and tri-n-butylthin hydride (2.42 ml) in a mixture of tetrahydrofuran (16 ml) and ethanol (16 ml) in substantially the same manner as that of Example 16-2).

IR (Nujol): 1740–1720, 1630–1610, 1580 cm$^{-1}$

NMR (D$_2$O, δ): 1.23 (3H, d, J=7.20 Hz), 1.30 (3H, d, J=6.35 Hz), 1.70–1.95 (1H, m), 2.25–2.55 (2H, m), 2.80–3.00 (1H, m), 3.20–4.27 (11H, m), 4.32 (1H, s), 7.90 (1H, t, J=6.48 Hz), 7.98 (1H, d, J=8.02 Hz), 8.47 (1H, t, J=7.23 Hz), 8.75 (1H, d, J=6.12 Hz)

FAB Mass: 432.1 (M$^+$)

Example 4-9)

(4R,5S,6S)-6-[(1R)-1-Hydroxyethyl]-3-[(2R,4S)-2-{2-(1-carbamoylmethyl-2-pyridinio)ethyl}pyrrolidin-4-yl]-thio-4-methyl-7-oxo-1-azabicyclo[3.2.0]hept-2-ene-2-carboxylic acid chloride (181 mg) was obtained by reacting allyl (4R,5S,6S)-3-[(2R,4S)-1-allyloxycarbonyl-2-{2-(1-carbamoylmethyl-2ethyl}pyrrolidin-4-yl]thio-6-[(1R)-1-hydroxyethyl]-4-methyl-7-oxo-1-azabicyclo[3.2. 0]-hept-2-ene-2-carboxylate iodide (1.65 g) with triphenylphosphine (60 mg), acetic acid (0.52 ml), tetrakis(triphenylphosphine)palladium(0) (79 mg) and tri-n-butylthin hydride (2.44 ml) in a mixture of tetrahydrofuran (16 ml) and ethanol (16 ml) in substantially the same manner as that of Example 4-1).

IR (Nujol): 1750–1730, 1690, 1630, 1580 cm$^{-1}$

NMR (D$_2$O, δ): 1.22 (3H, d, J=7.09 Hz), 1.29 (3H, d, J=6.32 Hz), 1.60–1.90 (1H, m), 2.20–2.60 (2H, m), 2.65–4.30 (11H, m), 5.20–5.70 (3H, m), 7.95–8.15 (2H, m), 8.34 (1H, broad d, J=8.05 Hz), 8.50–8.95 (2H, m)

FAB Mass: 475.1 (M$^+$)

Example 4-10)

To a solution of allyl (4R,5S,6S)-3-[(2R,4S)-1-allyloxycarbonyl-2-{2-(1,3-dimethyl-2-imidazolio)ethyl}-pyrrolidin-4-yl]thio-6-[(1R)-1-hydroxyethyl]-4-methyl-7-oxo-1-azabicyclo[3.2.0]hept-2-ene-2-carboxylate iodide (3.68 g), triphenylphosphine (141 mg), acetic acid (1.23 ml) and tetrakis(triphenylphosphine)palladium(0) (186 mg) in a mixture of tetrahydrofuran (40 ml) and ethanol (40 ml) was added dropwise tri-n-butylthin hydride (5.77 ml) at ambient temperature with stirring. The mixture was stirred at the same temperature for 30 minutes. The resulting precipitates were collected by filtration, washed with tetrahydrofuran (60 ml), dried in vacuo and dissolved in water (50 ml). The solution was chromatographed on nonionic adsorption resin, Diaion HP-20 (trademark, made by Mitsubishi Chemical Industries) (100 ml) eluting in turn with water (200 ml) and 5% aqueous acetone (700 ml). The fractions containing the desired compound were collected and evaporated in vacuo. The resulting residue (50 ml) was passed through ion exchange resin, Amberlist A-26 (Cl⁻ type, trademark, made by Rohm and Haas Co., Ltd.) (20 ml) eluting with water (150 ml). The eluate was lyophilized to give a solid. The solid was dissolved in pH standard buffer solution (pH=6.86, 20 ml). The solution was chromatographed on reversed-phase silica gel, chromatorex ODS (trademark, made by Fuji-Davison Chemical Ltd.) (100 ml) eluting with a mixture of pH standard buffer solution (pH=6.86) and acetonitrile (5:1, V/V). The fractions containing the desired compound were collected and evaporated in vacuo. The resulting residue (40 ml) was chromatographed on nonionic adsorption resin, Diaion HP-20 (80 ml) eluting in turn with water (200 ml) and 5% aqueous acetone (600 ml). The fractions containing the desired compound were collected and evaporated in vacuo. The resulting residue (50 ml) was passed through ion exchange resin, Amberlist A-26 (Cl⁻ type) (20 ml) eluting with water (100 ml). The eluate was lyophilized to give (4R,5S,6S)-3-[(2R,4S)-2-{2-(1,3-dimethyl-2-imidazolio)ethyl}pyrrolidin-4-yl]thio-6-[(1R)-1-hydroxyethyl]-4-methyl-7-oxo-1-azabicyclo[3.2.0]hept-2-ene-2-carboxylic acid chloride (904 mg).

IR (Nujol): 1740, 1580–1570, 1130 cm⁻¹

NMR (D$_2$O, δ): 1.24 (3H, d, J=7.17 Hz), 1.30 (3H, d, J=6.31 Hz), 1.70–1.88 (1H, m), 2.10–2.40 (2H, m), 2.79–3.55 (6H, m), 3.74 (1H, dd, J=6.75 Hz, J=12.4 Hz), 3.85 (6H, s), 3.86–4.35 (4H, m), 7.36 (2H, s)

FAB Mass: 435.2 (M⁺)

Example 4-11)

To a solution of allyl (4R,5S,6S)-3-[(2R, 4S)-1-allyloxycarbonyl-2-{2-(3-carbamoylmethyl-1-methyl-2imidazolio)ethyl}pyrrolidin-4-yl]thio-6-[(1R)-1-hydroxyethyl]-4-methyl-7-oxo-1-azabicyclo[3.2.0]hept-2-ene-2-carboxylate iodide (1.39 g), triphenylphosphine (50 mg), acetic acid (0.44 ml) and tetrakis(triphenylphosphine)palladium(0) (66 mg) in a mixture of tetrahydrofuran (14 ml) and ethanol (14 ml) was added dropwise tri-n-butylthin hydride (2.05 ml) at ambient temperature with stirring. The mixture was stirred at the same temperature for 30 minutes. The resulting precipitates were collected by filtration, washed with tetrahydrofuran (30 ml), dried in vacuo and dissolved in water (30 ml). The solution was chromatographed on nonionic adsorption resin, Diaion HP-20 (trademark, made by Mitsubishi Chemical Industries) (50 ml) eluting in turn with water (100 ml) and 5% aqueous acetone (500 ml). The fractions containing the desired compound were collected and evaporated in vacuo. The resulting residue (50 ml) was passed through ion exchange resin, Amberlist A-26 (Cl⁻ type, trade mark, made by Rohm and Haas Co., Ltd.) (10 ml) eluting with water (150 ml). The eluate was lyophilized to give (4R,5S,6S)-3-[(2R, 4S)-2-{2-(3-carbamoylmethyl-1-methyl-2-imidazolio)ethyl}-pyrrolidin-4-yl]thio-6-[(1R)-1-hydroxyethyl]-4-methyl-7-oxo-1-azabicyclo[3.2.0]hept-2-ene-2-carboxylic acid chloride (131 mg).

IR (Nujol): 1740, 1685, 1580 cm⁻¹

NMR (D$_2$O, δ): 1.23 (3H, d, J=7.21 Hz), 1.29 (3H, d, J=6.35), 1.65–1.85 (1H, m), 2.00–2.35 (2H, m), 2.75–3.50 (6H, m), 3.71 (1H, dd, J=6.58 Hz, J=12.5 Hz), 3.91 (3H, s), 4.00–4.35 (3H, m), 5.12 (2H, s), 7.43 (1H, d, J=2.1 Hz), 7.47 (1H, d, J=2.1 Hz)

FAB Mass: 478.1 (M⁺)

Example 5

To a solution of allyl (4R,5S,6S)-3-[(2R,4S)-1-allyloxycarbonyl-2-{3-(imidazol-1-yl)propyl}pyrrolidin-4yl]thio-6-[(1R)-1-hydroxyethyl]-4-methyl-7-oxo-1-azabicyclo[3.2.0]hept-2-ene-2-carboxylate (1.00 g), triphenylphosphine (48 mg), acetic acid (0.274 ml) and tetrakis(triphenylphosphine) palladium(0) (64 mg) in a mixture of tetrahydrofuran (10 ml) and ethanol (10 ml) was added tributyltin hydride (1.19 ml) at room temperature and the solution was stirred at the same temperature for 30 minutes. 50 ml of ethyl acetate was added and the precipitates were collected by filtration. The solid was washed well with ethyl acetate. The solid was dissolved in water (30 ml) and washed with ethyl acetate (20 ml×2). The aqueous solution was concentrated to c.a. 10 ml and chromatographed on nonionic adsorption resin, Diaion HP-20 (trademark, made by Mitsubishi Chemical Industries) (100 ml) eluting in turn with water and 10% aqueous acetonitrile. The fractions containing the desired compound were collected and evaporated in vacuo. The resulting residue (20 ml) was passed through ion exchange resin, Amberlist A-26 (Cl⁻ type, trademark, made by Rohm and Haas Co., Ltd.) (5 ml) eluting with water (15 ml). The eluate was lyophilized to give (4R,5S,6S)-6-[(1R)-1-hydroxyethyl]-3-[(2R, 4S)-2-{3-(imidazol-1-yl)propyl}pyrrolidin-4-yl] thio-4-methyl-7-oxo-1-azabicyclo[3.2.0]hept-2-ene-2-carboxylic acid hydrochloride (467 mg) as a light yellow solid.

IR (Nujol) : 1740, 1570 cm⁻¹

NMR (CDCl$_3$, 200 MHz, δ): 1.22 (3H, d, J=7.2 Hz), 1.30 (3H, d, J=6.4 Hz), 1.56–1.98 (5H, m), 2.68–2.84 (1H, m), 3.33–3.53 (3H, m), 3.60–3.69 (2H, m), 3.94–4.08 (1H, m), 4.15–4.29 (4H, m), 7.18 (1H, s), 7.30 (1H, s), 8.03 (1H, s)

Example 6-1)

To a solution of allyl (4R)-2-diazo-4-[(2R,3S)-3{(1R)-1-hydroxyethyl}-4-oxoacetidin-2-yl]-3-oxopentanoate (2.06 g) in ethyl acetate (20 ml) was added rhodium (II) octanoate (27 mg) under stirring at ambient temperature. The mixture was refluxed for 30 minutes. The solution was cooled to ambient temperature and evaporated in vacuo to give a residue. The residue was dissolved in acetonitrile (20 ml). To the solution were added diphenyl phosphorochloridate (1.53 ml) and N,N-diisopropyl-N-ethylamine (1.34 ml) successively at 0°–5° C. under stirring and the mixture was stirred at the same temperature for 3 hours. On the other hand, to a solution of (2S,4S)-4-acetylthio-1-allyloxycarbonyl-2-(2-oxo-4-methylpiperazin-1-yl)methylpyrrolidine (3.24 g) in a mixture of methanol (32 ml) and tetrahydrofuran (35 ml) was added dropwise 28% sodium methoxide-methanol solution (1.93 ml) under ice cooling with stirring and the mixture was stirred a the same temperature for 2=30 minutes. To a reaction mixture was stirred a the same temperature for 30 minutes. To a reaction mixture was added acetic acid (0.57 ml) and the mixture was evaporated in vacuo. The resulting residue was dissolved in a mixture of ethyl acetate and water. The organic layer was washed with brine, dried over anhydrous magnesium sulfate and evaporated in vacuo to give a residue. The residue was dissolved in N,N-dimethylacetamide (20 ml). This solution and N,N-diisopropyl-N-ethylamine (20 ml) were successively added to the solution described above with stirring under ice cooling and the mixture was allowed to stand in a refrigerator for 12 hours. The mixture was poured into water and extracted with a mixture of ethyl acetate and tetrahydrofuran (1:1 v/v). The organic layer was washed with brine, dried over anhydrous magnesium sulfate and evaporated in vacuo. The resulting residue was purified by silica gel column chromatography eluting with a mixture of chloroform and methanol (15:1 v/v) to give allyl (4R,5S,6S)-3-[(2S, 4S)-1-allyloxycarbonyl-2-(2-oxo-4-methylpiperazin-1-yl) methylpyrrolidin-4-yl]thio-6[(1R)-hydroxyethyl]-4-methyl-7-oxo-1-azabicyclo [3.2.0]-hept-2-ene-2-carboxylate (1.64 g).

NMR (CDCl$_3$, δ): 1.26 (3H, d, J=7.2 Hz), 1.35 (3H, d, J=6.2 Hz), 1.98 (3H, br), 2.33 (3H, s), 2.43–2.65 (6H, m), 3.11 (2H, s), 3.22–4.26 (11H, m), 4.59–4.82 (4H, m), 5.22–5.49 (4H, m), 5.88–6.04 (2H, m)

Example 6-2)

Allyl (4R,5S,6S)-3-[(2S, 4S)-1-allyloxycarbonyl-2-(4-allyloxycarbonyl-2-oxopiperazin-1-yl) methylpyrrolidin-4yl] thio-4-methyl-7-oxo-1-azabicyclo[3.2.0]hept-2-ene-2-carboxylate (1.99 g) was obtained by reacting ally (4R)-2-diazo-4-[(2R,3S)-3-{(1R)-1-hydroxyethyl}-4-oxoazetidin-2-yl ]-3-oxopentanoate (1.28 g) with rhodium (II) octanoate (17 mg) and then successively with diphenyl phosphorochloridate (0.95 ml) and (2S,4S)-4-acetylthio-1-allyloxycarbonyl-2-(4-allyloxycarbonyl-2-oxopiperazin-1-yl) methylpyrrolidine (2.41 g) in substantially the same manner as that of Example 6-1).

NMR (CDCl$_3$, δ): 1.22–1.36 (6H, m), 1.84–1.88 (1H, m), 2.47–2.62 (3H, m), 3.23–3.70 (9H, m), 4.10–4.27 (5H, m), 4.58–4.80 (6H, m), 5.21–5.49 (6H, m), 5.87–6.07 (3H, m)

Example 7-1)

(4R,5S,6S)-6-[(1R)-1-Hydroxyethyl]-4-methyl-3-[(2S, 4S)-2-(4-methyl-2-oxopiperazin-1-yl)methylpyrrolidin-4-yl]thio-7-oxo-1-azabicyclo[3.2.0]hept-2-ene-2-carboxylic acid hydrochloride (0.40 g) was obtained by reacting allyl (4R,5S,6S)-3-[(2S, 4S)-1-allyloxycarbonyl-2-(4-methyl-2-oxopiperazin-1-yl)methylpyrrolidin-4-yl]-thio-6-[(1R)-1-hydroxyethyl]-4-methyl-7-oxo-1-azabicyclo[3.2.0]hept-2-ene-2-carboxylate (0.80 g) with triphenylphosphine (75 mg), acetic acid (0.49 ml), tetrakis (triphenylphosphine) palladium (0) (66 mg) and tributyltin hydride (1.53 ml) in a mixture of tetrahydrofuran (16 ml) and ethanol (8 ml) in substantially the same manner as that of Example 7-1).

NMR (D$_2$O, δ): 1.22 (3H, d, J=7.2 Hz), 1.30 (3H, d, J=6.3 Hz), 1.69–1.85 (1H, m), 2.43 (3H, s), 2.54–2.96 (3H, m), 3.24–3.76 (9H, m), 3.96–4.06 (3H, m), 4.20–4.28 (2H, m)

Example 7-2)

(4R,5S,6S)-6-[(1R)-1-Hydroxyethyl]-3-[(2S, 4S)-2-(2-oxopiperazin-1-yl)methylpyrrolidin-4-yl]thio-4-methyl7-oxo-1-azabicyclo [3.2.0]hept-2-ene-2-carboxylic acid (0.54 g) was obtained by reacting allyl (4R,5S,6S)-3-[(2S,4S)-1-allyloxycarbonyl-2- (4-allyloxycarbonyl-2-oxopiperazin-1-yl)methylpyrrolidin-4-yl]thio-6-[(1R)-1-hydroxyethyl]-4-methyl-7-oxo-1-azabicyclo-[3.2.0]hept-2-ene-2-carboxylate (1.99 g) with triphenylphosphine (247 mg), acetic acid (1.62 ml), tetrakis(triphenylphosphine)palladium (0) (218 mg) and tributyltin hydride (5.08 ml) in a mixture of tetrahydrofuran (20 ml) and ethanol (20 ml) in substantially the same manner as that of Example 7-1).

IR (Nujol): 1752 cm$^{-1}$

NMR (D$_2$O, δ): 1.23 (3H, d, J=7.2 Hz), 1.30 (3H, d, J=6.4 Hz), 1.66–1.82 (1H, m), 2.66–2.81 (1H, m), 3.06–3.14 (2H, m), 3.21–3.67 (9H, m), 3.93–4.04 (3H, m), 4.20–4.32 (2H, m),

FAB Mass 425 (M$^+$)

Example 8

To a solution of allyl (4R,5S,6S)-3-[(2S,4S)-1-allyl-oxycarbonyl-2-(2-oxo-4-methylpiperazin-1-yl)methyl-pyrrolidin-4-yl]thio-6-[(1R)-1-hydroxyethyl]-4-methyl-7-oxo-1-azabicyclo[3.2.0]hept-2-ene-2-carboxylate (0.838 g) in acetone (4 ml) was added methyl iodide (0.92 ml) with stirring at ambient temperature, and the mixture was allowed to stand overnight at he same temperature. The reaction mixture was evaporated in vacuo to give allyl (4R,5S,6S)-3-[(2S,4S)-1-allyloxycarbonyl-2-(4,4-dimethyl-2-oxopiperazino) methylpyrrolidin-4-yl]thio-6-[(1R)-1-hydroxyethyl]-4-methyl-7-oxo-1-azabicyclo[3.2.0]hept-2-ene-2-carboxylate iodide (1.05 g).

This compound was immediately used as the starting compound for the next step.

Example 9

To a solution of ally (4R,5S,6S)-3-[(2S,4S)-1-allyl-oxycarbonyl-2-(4, 4-dimethyl-2-oxopiperazino)methyl-pyrrolidin-4-yl]thio-6-[(1R)-1-hydroxyethyl]-4-methyl-7-oxo-1-azabicyclo[3.2.0]hept-2-ene-2-carboxylate iodide (1.05 g), triphenylphosphine (78 mg), acetic acid (0.51 ml) and tetrakis(triphenylphosphine)palladium (0) (69 mg) in a mixture of tetrahydrofuran (10 ml) and ethanol (10 ml) was added tri-butylthin hydride (1.60 ml) at ambient temperature with stirring and the mixture was stirred at the same temperature for 30 minutes, the resulting precipitates were collected by filtration, washed with tetrahydrofuran and dried in vacuo. The solid was dissolved in water (5 ml). The solution was adjusted to pH 6 with 1N hydrochloric acid and chromatographed on nonionic adosorption resin, Diaion HP-20 (Trademark, made by Mitsubishi Chemical Industries) (50 ml) eluting in turn with water and 5% aqueous acetone. The fractions containing the desired compound were collected and concentrated in vacuo. The resulting residue was passed through ion exchange resin, Amberlist A-26 (Cl$^-$ Type, Trademark, made by Rohm and Haas Co Ltd.) (2 ml) eluting with water. The eluate was lyophilized to give (4R,5S,6S)-3-[(2S,4S)-2-(4,4-dimethyl-2-oxo-piperazino)-methylpyrrolidin-4-yl]thio-6-[(1R)-1-hydroxyethyl]-4-methyl-7-oxo-1-azabicyclo[3.2.0]hept-2-ene-2-carboxylic acid chloride (259 mg).

IR (Nujol): 1655, 1750 cm$^{-1}$

NMR (D$_2$O, δ): 1.23 (3H, d, J=7.2 Hz), 1.30 (3H, d, J=6.3 Hz), 1.72–1.87 (1H, m), 2.72–2.87 (1H, m), 3.35–3.50 (10H, m), 3.66–3.76 (2H, m), 3.89–4.38 (10H, m)

FAB Mass 453 (M$^+$)

Example 10

Allyl (4R,5S,6S)-3-[(2R,4S)-1-allyloxycarbonyl-2-(2-pyridylmethyl) pyrrolidin-4-yl]thio-6-[(1R)-1-hydroxyethyl]-4-methyl-7-oxo-1-azabicyclo[3.2.0]hept-2-ene-2-carboxylate (0.92 g) was obtained in substantially the same manner as that of Example 2 from (2R, 4S)-1-allyloxycarbonyl-4-benzoylthio-2-(2-pyridylmethyl)-pyrrolidine (5.3 g).

IR (CHCl$_3$): 3300, 1745, 1680 cm$^{-1}$

Example 11

To a solution of allyl (4R,5S,6S)-3-[(2R,4S)-1-allyloxycarbonyl-2-(2-pyridylmethyl) pyrrolidin-4-yl]thio-6-[(1R)-1-hydroxyethyl]-4-methyl-7-oxo-1-azabicyclo[3.2.0]hept-2-ene-2-carboxylate (0.92 g) in acetone (13.8 ml) was added iodomethane (1.09 ml) at room temperature. The mixture was stirred for 5 days and then evaporated under reduced pressure to give a residue containing allyl (4R,5S,6S)-3-[(2R, 4S)-1-allyloxycarbonyl-2-{(1-methyl-2-pyridinio)methyl}pyrrolidin-4-yl]thio-6-[(1R)-1-hydroxyethyl]-4-methyl-7-oxo-1-azabicyclo[3.2.0]hept-2-ene-2-carboxylate iodide. The residue was treated in substantially the same manner as that of the latter part of Example 3-1) to give (4R,5S,6S)-3-[(2R,4S)-2-(1-methyl-2-pyridinio) methylpyrrodidin-4-yl]thio-6-[(1R)-1-hydroxyethyl]-4-methyl-7-oxo-1-azabicyclo[3.2.0]hept-2-ene-2-carboxylic acid chloride (126 mg).

IR (Nujol): 3600–3000, 1725, 1570, 1445 cm$^{-1}$

NMR (CDCl$_3$, δ): 1.23 (3H, d, J=7.2 Hz), 1.30 (3H, d, J=6.4 Hz ), 1.35–1.60 (0.5H, m), 2.05–2.20 (1H, m), 2.55–2.85 (0.5H, m), 2.90–3.10 (1H, m), 3.20–3.50 (6H, m), 3.60–4.05 (2H, m), 4.20–4.30 (2H, m), 4.33 (3H, s), 7.90 (1H, dd, J=5.9 and 7.9 Hz), 8.02 (1H, d, J=7.5 Hz), 8.47 (1H, dd, J=7.5 and 7.9 Hz), 8.75 (1H, d, J=5.9 Hz)

FAB Mass : 418.2 (M-Cl)$^+$

Example 12

Allyl (4R,5S,6S)-3-[(2R,4S)-1-allyloxycarbonyl-2-(3-pyridylmethyl) pyrrolidin-4-yl]thio-6-[(1R) -1-hydroxyethyl]-4-methyl-7-oxo-1-azabicyclo [3.2.0]hept-2-ene-2-carboxylate was obtained in substantially the same manner as that of Example 10

IR (CHCl$_3$, δ): 3300, 1750, 1680 (cm$^{-1}$)

NMR (CDCl$_3$, δ): 1.21 (3H, d, J=6.4 Hz), 1.35 (3H, d, J=6.2 Hz), 1.6–1.8 (1H, m), 2.1–2.6 (2H, m), 2.8–3.0 (1H, m), 3.1–3.5 (4H, m), 3.9–4.3 (3H, m), 4.6–5.0 (5H, m), 5.2–5.6 (4H, m), 5.8–6.1 (2H, m), 7.2–7.4 (1H, m), 7.4–7.6 (1H, m), 8.4–8.6 (1H, m)

Example 13

(4R,5S,6S)-3-[(2R,4S)-2-(1-Methyl-3-pyridiniomethyl)pyrrolidin-4-yl]thio-6-[(1R)-1-hydroxyethyl]-4-methyl-7-oxo-1-azabicyclo[3.2.0]hept-2-ene-2-carboxylic acid chloride was obtained in substantially the same manner as that of Example 11.

IR (Nujol): 1740 cm$^{-1}$ $^1$H—NMR (D$_2$O, δ): 1.21 (3H, d, J=7.2 Hz), 1.29 (3H, d,J=6.4 Hz), 1.5–1.7 (1H, m), 2.5–2.7 (1H, m), 3.2–3.6 (5H, m), 3.7–4.0 (2H, m), 4.1–4.3 (2H, m), 4.39 (3H, s), 8.02 (1H, dd, J=8.0 and 6.0 Hz), 8.49 (1H, d, J=8.0 Hz), 8.72 (1H, d, J=6.0 Hz), 8.80 (1H, s)

Example 14-1)

Allyl (4R,5S,6S)-3-[(2R,4S)-1-allyloxycarbonyl-2-(4-pyridylmethyl) pyrrolidin-4-yl]thio-6-[(1R)-1-hydroxyethy-1] -4-methyl-7-oxo-1-azabicyclo[3.2.0]hept-2-ene-2-carboxylate was obtained in 25% yield in substantially the same manner as that of Example 10.

IR (CH$_2$Cl$_2$): 3350, 1750, 1680 cm$^{-1}$

NMR (CDCl$_3$, δ): 1.23 (3H, d, J=7.4 Hz), 1.35 (3H, d, J=6.2 Hz), 1.6–1.8 (1H, m), 2.2–2.5 (1H, m), 2.6–3.0 (2H, m), 3.1–3.5 (4H, m), 3.8–4.3 (4H, m), 4.5–4.9 (4H, m), 5.1–5.5 (4H, m), 5.8–6.1 (2H, m), 7.0–7.3 (2H, m), 8.4–8.5 (2H, m)

Example 14-2)

Allyl (4R,5S,6S)-3-[(2R,4S)-1-allyloxycarbonyl-2-(1-methyl-4-pyridiniomethyl) pyrrolidin-4-yl]thio-6-[(1R)-1-hydroxyethyl]-4-methyl-7-oxo-1-azabicyclo[3.2.0]hept-2-ene-2-carboxylate iodide was obtained quantitatively in substantially the same manner as that of Example 11.

IR (CHCl$_3$): 3300, 1740, 1680 cm$^{-1}$

NMR (CDCl$_3$, δ): 1.25 (3H, d, J=7.0 Hz), 1.31 (3H, d, J=6.2 Hz), 1.6–1.8 (1H, m), 2.5–2.7 (1H, m), 3.1–3.8 (6H, m), 3.9–4.4 (4H, m), 4.58 (3H, s), 4.5–4.9 (4H, m), 5.2–5.6 (4H, m), 5.8–6.1 (2H, m), 7.93 (2H, d, J=6.5 Hz), 9.11 (2H, d, J=5.9 Hz)

Example 14-3)

(4R,5S,6S)-3-[(2R,4S)-2-(1-Methyl-4-pyridiniomethyl)-pyrrolidin-4-yl]thio-6-[(1R)-1-hydroxyethyl]-4-methyl-7-oxo-1-azabicyclo[3.2.0]hept-2-ene-2-carboxylic acid chloride was obtained in 21% yield in substantially the same manner as that of Example 13.

IR (Nujol): 1740 cm$^{-1}$

NMR (D$_2$O, δ): 1.21 (3H, d, J=7.1 Hz), 1.30 (3H, d, J=6.3 Hz), 1.4–1.6 (1H, m), 2.5–2.7 (1H, m), 3.0–4.0 (8H, m), 4.1–4.3 (2H, m), 4.34 (3H, s), 7.96 (2H, d, J=6.0 Hz), 8.68 (2H, d, J=6.6 Hz)

Mass (FAB+1); 418 (M+1—HCl)

Example 15-1)

Allyl (4R,5S,6S)-3-[(2R,4S)-1-allyloxycarbonyl-2-(1-methylimidazol-2-ylmethyl) pyrrolidin-4-yl]thio-6-[(1R)-1-hydroxyethyl]-4-methyl-7-oxo-1-azabicyclo[3.2.0]-hept-2-ene-2-carboxylate was obtained in 58.4% yield by the similar procedure as Example 10.

NMR (CDCl$_3$, δ): 1.24 (3H, d, J=7.2 Hz), 1.35 (3H, d, J=6.2 Hz), 1.82–2.54 (2H, m), 2.54–2.78 (1H, m), 2.78–3.04 (1H, m), 3.19–3.62 (5H, m), 3.62 (3H, s), 3.83–4.50 (4H, m), 4.59–4.87 (4H, m), 5.21–5.49 (4H, m), 5.80–6.04 (1H, m), 6.80 (1H, d, J=1.2 Hz), 6.93 (1H, d, J=1.2 Hz)

FAB-Mass (m/z): 531.3 (M$^+$)

Example 15-2)

To a solution of allyl (4R,5S,6S)-3-[(2R,4S)-1-allyloxycarbonyl-2-(1-methylimidazol-2-ylmethyl)-pyrrolidin-4-yl]thio-6-[(1R)-1-hydroxyethyl ]-4-methyl-7-oxo-1-azabicyclo [3.2.0]hept-2-ene-2-carboxylate (1.25 g) in acetone (12 ml) was added methyl iodide (1.47 ml ) at room temperature. The mixture was stirred for 35 hours at the same temperature. The reaction mixture was evaporated in vacuo to give allyl (4R,5S,6S)-3-[(2R,4S)-1-allyloxycarbonyl-2-(1, 3-dimethyl-2-imidazoliomethyl)-pyrrolidin-4-yl]thio-6-[(1R)-1-hydroxyethyl]-4-methyl-7-oxo-1-azabicyclo[3.2.0] hept-2-ene-2-carboxylate iodide (1.49 g) as an amorphous solid.

NMR (CDCl$_3$, δ): 1.29 (3H, d, J=7.4 Hz), 1.33 (3H, d, J=6.2 Hz), 1.97–2.13 (1H, m), 2.15–2.57 (1H, m), 2.81–3.50 (1H, m), 3.22–3.53 (2H, m), 3.62–3.81 (2H, m), 3.82–4.09 (2H, m), 3.97 (6H, s), 4.10–4.28 (2H, m), 4.28–4.60 (4H, m), 4.60–4.87 (2H, m), 5.20–5.50 (4H, m), 5.71–6.06 (2H, m), 7.37 (2H, br s)

FAB-Mass: 545.3 (MH$^+$-MeI)

Example 15-3)

To a solution of allyl (4R,5S,6S)-3-[(2R,4S)-1-allyloxycarbonyl-2-(1, 3-dimethyl-2-imidazoliomethyl)-pyrrolidin-4-yl]thio-6-[(1R)-1-hydroxyethyl]-4-methyl-7-oxo-1-azabicyclo[3.2.0]hept-2-ene-2-carboxylate iodide (1.44 g) in tetrahydrofuran-ethanol (1:2, 27 ml) were added triphenylphosphine (142 mg) and morpholine (522 μl), and then tetrakis(triphenylphosphine)palladium(0) (125 mg) at room temperature. The mixture was stirred for 50 minutes. To the reaction mixture was added THF (27 ml), and the precipitate was collected by filtration. The precipitate was poured into a mixture of ethyl acetate (EtOAc) and water (H$_2$O), and adjusted to pH 6.2 with 1N-hydrochloric acid (HCl). The separated aqueous layer was washed with EtOAc, and traces of organic solvent in the aqueous layer was removed by evaporation in vacuo. The resulting solution was passed through an ion exchange resin, Amberlist A-26 (Cl$^-$ type, Trademark, made by Rohm and Haas Co., Ltd.) (8 ml) eluting with water. The eluate was chromatographed on nonionic adsorption resin, Diaion HP-20 (Trademark, made by Mitsubishi Chemical Industries) (240 ml) eluting in turn with water and 2~5% aqueous acetonitrile. The fractions containing the desired compound were collected and concentrated in vacuo, and then lyophilized to give (4R,5S,6S)-3-[(2R,4S)-2-(1,3-dimethyl-2-imidazoliomethyl) pyrrolidin-4-yl]thio-6-[(1R)-1-hydroxyethyl]-4-methyl-7-oxo-1-azabicyclo[3.2.0]hept-2-ene-2-carboxylic acid chloride (323 mg).

IR (Nujol): 3600–3000, 1720, 1570, 1440 cm$^{-1}$

NMR (D$_2$O, δ): 1.22 (3H, d, J=7.1 Hz), 1.30 (3H, d, J=6.3 Hz), 1.30–1.54 (1H, m), 2.49–2.70 (1H, m), 2.94–3.12 (1H, m), 3.12–3.60 (6H, m), 3.70–3.94 (1H, m), 3.86 (6H, s), 4.12–4.37 (2H, m), 7.37 (2H, s)

FAB-Mass (m/z): 421.3 (M-Cl$^-$)

Example 16-1)

Allyl (4R,5S,6S)-3-[(2R,4S)-1-allyloxycarbonyl-2-(1-methylpyrazol-4-ylmethyl) pyrrolidin-4-yl]thio-6-[(1R)-1-hydroxyethyl]-4-methyl-7-oxo-1-azabicyclo [3.2.0]hept-2-ene-2-carboxylate (12.8 g) was obtained by the similar procedure as that of Example 10.

IR (CHCl$_3$): 3350, 1750, 1670, 1395, 1315 cm$^{-1}$

NMR (CDCl$_3$, δ): 1.23 (3H, d, J=7.2 Hz), 1.36 (3H, d, J=6.2 Hz), 1.55–1.82 (2H, m), 2.30–2.50 (1H, m), 2.72–3.30 (5H, m), 3.40–3.60 (1H, m), 3.87 (3H, s), 3.88–4.32 (4H, m), 4.54–4.90 (4H, m), 5.20–5.52 (4H, m), 5.87–6.07 (2H, m), 7.16 (1H, s), 7.29 (1H, s)

APCI-Mass (m/z) : 531 (MH$^+$)

Example 16-2)

To a solution of allyl (4R,5S,6S)-3-[(2R,4S)-1-allyloxycarbonyl-2-(1-methylpyrazol-4-ylmethyl) pyrrolidin-4-yl]thio-6-[(1R)-1-hydroxyethyl]-4-methyl-7-oxo-1azabicyclo [3.2.0]hept-2-ene-2-carboxylate (8.9 g) in dichloromethane (180 ml) was added methyl triflate (2.09 ml) at 0° C. The mixture was stirred for 10 minutes at the same temperature and then for additional 2.5 hours at room temperature. Dichloromethane was evaporated under reduced pressure. The residue was dissolved in tetrahydrofuranethanol (1:2, 140 ml). To the solution were added triphenylphosphine (1.76 g), and morpholine (3.67 ml), and then tetrakis(triphenylphosphine)palladium(0) (1.55 g) at room temperature. After one hour the reaction mixture was poured into a mixture of ethyl acetate (500 ml) and water (300 ml). The aqueous layer was separated and washed with dichloromethane (×2). The aqueous solution was adjusted to pH 6 with 1N-hydrochloric acid and chromatographed on nonionic adsorption resin, "Diaion HP-20" (1 l) eluting in turn with water and 5% aqueous acetone. The fractions containing the desired compound were collected and concentrated in vacuo. The resulting residue was passed through ion exchange resin, "Amberlist A-26" (100 ml) eluting with water. The eluate was lyophilized to give (4R,5S,6S)-3-[(2R, 4S)-2-(1,2-dimethyl-4-pyrazoliomethyl) pyrrolidin-4-yl]thio-6-[(1R) -1-hydroxyethyl]-4-methyl-7-oxo-1-azabicyclo [3.2.0]hept-2-ene-2-carboxylic acid chloride (5.0 g).

NMR (D$_2$O, δ): 1.22 (3H, d, J=7.2 Hz), 1.29 (3H, d, J=6.4 Hz), 1.70–1.88 (1H, m), 2.67–2.84 (1H, m), 3.05–3.20 (2H, m), 3.28–3.83 (4H, m), 3.85–4.15 (2H, m), 4.10 (6H, s), 4.18–4.32 (2H, m), 8.19 (2H, s)

APCI-Mass (m/z): 421 (M-Cl$^-$)

Example 17-1)

Allyl (4R)-2-diazo-4-[(2R,3S)-3-}(1R)-1-hydroxyethyl}-4-oxoazetidin-2-yl]-3-oxopentanoate (4.96 g) and (2R,4S)-4-acetylthio-1-allyloxycarbonyl-2-[2-(2-hydroxymethylimidazol-1-yl) ethyl]pyrrolidine (5.93 g) were reacted in substantially the same manner as that of Example 2-3) to give allyl (4R,5S,6S)-3-[(2R,4S)-1-allyloxycarbonyl-2-{2-(2-hydroxymethylimidazol-1-yl)-ethyl}pyrrolidin-4-yl]thio-6-[(1R)-1-hydroxyethyl]-4-methyl-7-oxo-1-azabicyclo [3.2.0]hept-2-ene-2-carboxylate (5.06 g) as a light yellow solid.

IR (CHCl$_3$): 1766, 1685 cm$^{-1}$

NMR (CDCl$_3$, 200 MHz, δ): 1.25 (3H, d, J=7.2 Hz), 1.36 (3H, d, J=6.2 Hz), 1.5–2.7 (4H, m), 3.1–4.3 (12H, m), 4.6–4.9 (6H, m), 5.2–5.5 (4H, m), 5.9–6.0 (2H, m), 6.9–7.1 (2H, m)

Example 17-2)

To a solution of allyl (4R,5S,6S)-3-[(2R,4S)-1-allyloxycarbonyl-2-{2-(2-hydroxymethylimidazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (3.02 g) in acetone (15 ml) was added methyl iodide (3.36 ml) at room temperature and the solution was allowed to stand for 6 hours. The solvent was evaporated to give allyl (4R,5S,6S)-3-[(2R,4S)-1-allyloxycarbonyl-2-{2-(2-hydroxymethyl-3-methyl-1-imidazolio)ethyl}-pyrrolidin-4-yl]thio-6-[(1R)-1-hydroxyethyl]-4-methyl-7-oxo-1-azabicyclo [3.2.0]hept-2-ene-2-carboxylate iodide (3.75 g) as a yellow solid. This compound was immediately used as the starting compound for the next step.

Example 17-3)

(4R,5S,6S)-3-[(2R,4S)-2-{2-(2-Hydroxymethyl-3-methyl-1-imidazolio) ethyl}pyrrolidin-4-yl]thio-6-[(1R)-1-hydroxyethyl]-4-methyl-7-oxo-1-azabicyclo[3.2.0]hept-2-ene-2-carboxylic acid chloride (91 mg) was obtained in substantially the same manner as that of Example 4-4).

IR (Nujol): 1755, 1585 cm$^{-1}$

NMR (CDCl$_3$, 200 MHz, δ): 1.22 (3H, d, J=7.2 Hz), 1.29 (3H, d, J=6.3 Hz), 1.7–1.9 (1H, m), 2.4–2.6 (2H, m), 2.7–2.9 (1H, m), 3.3–4.5 (10H, m), 3.92 (3H, s), 4.94 (2H, d, J=13.3 Hz), 7.5–7.6 (2H, m)

Example 18-1)

To a solution of allyl (4R)-2-diazo-4-[(2R,3S)-3-{(1R)-1-hydroxyethyl}-4-oxoazetidin-2-yl]-3-oxopentanoate (7.44 g) in ethyl acetate (74 ml) was added rhodium(II) octanoate under stirring at room temperature in a stream of nitrogen. The solution was refluxed for 30 minutes and then cooled to room temperature. After evaporation of the solvent, the residue was dissolved in acetonitrile (74 ml). To the solution were added successively diphenyl phosphorochloridate (5.75 ml), N,N-diisopropyl-N-ethylamine (5.04 ml) and dimethylaminopyridine (31 mg) at 0°–5° C. under stirring, and the solution was stirred at the same temperature for 30 minutes (solution A). On the other hand, to a solution of (2R,4S)-1-allyloxycarbonyl-4-benzoylthio-2-[2-(2-carbamoylimidazol-1-yl) ethyl]pyrrolidine (10.8 g) in acetonitrile (74 ml) was added 28% sodium methoxide methanol solution (4.86 g) under ice-salt bath with stirring. After stirring for 1 hour, N,N-dimethylacetamide (37 ml) was added to the solution, and then the solution was poured into the solution A described above. The solution was allowed to stand in a refrigerator for 12 hours. The solution was diluted with ethyl acetate (150 ml) and washed successively with 10% sodium chloride solution in water (80 ml×1), brine (80 ml×9), water (80 ml×2), and brine (80 ml×2), and then dried over magnesium sulfate. The solvent was evaporated and the residue was chromatographed on a silica gel (210 g) eluting with a mixture of chloroform and methanol (95:5, V/V) to give allyl (4R,5S,6S)-3-[(2R,4S)-1-allyloxycarbonyl-2-{2-(2-carbamoylmethylimidazol-1-yl)-ethyl}pyrrolidin-4-yl]thio-6-[(1R)-1-hydroxyethyl]-4-methyl-7-oxo-1-azabicyclo[3.2.0]hept-2-ene-2-carboxylate (6.16 g) as a yellow solid.

NMR (CDCl$_3$, 200 MHz, δ): 1.25 (3H, d, J=7.2 Hz), 1.36 (3H, d, J=6.2 Hz), 1.6–2.7 (4H, m), 3.2–4.9 (15H, m), 5.2–5.5 (5H, m), 5.8–6.0 (2H, m), 7.0–7.3 (3H, m)

Example 18-2)

To a solution of allyl (4R,5S,6S)-3-[(2R,4S)-1-allyloxycarbonyl-2-{2-(2-carbamoylmethylimidazol-1-yl)-ethyl}pyrrolidin-4-yl]thio-6-[(1R)-1-hydroxyethyl]-4-methyl-7-oxo-1-azabicyclo[3.2.0]hept-2-ene-2-carboxylate (5.31 g) in dichloromethane (80 ml) was added methyl trifluoromethanesulfonate (triflate) (3.14 ml) at room temperature and the solution was stirred at the same temperature for 20 minutes. The solvent was evaporated to give allyl (4R,5S,6S)-3-[(2R,4S)-1-allyloxycarbonyl-2-{2-(2-carbamoyl-3-methyl-1-imidazolio)ethyl}pyrrolidin-4-yl]thio-6-[(1R)-1-hydroxyethyl]-4-methyl-7-oxo-1-azabicyclo[3.2.0]hept-2-ene-2-carboxylate trifluoromethanesulfonate (7.96 g) as a yellow solid. This compound was immediately used as the starting compound for the next step.

Example 18-3)

(4R,5S,6S)-3-[(2R,4S)-2-{2-(2-Carbamoyl-3-methyl-1-imidazolio)ethyl}pyrrolidin-4-yl]thio-6-[(1R)-1-hydroxyethyl]-4-methyl-7-oxo-1-azabicyclo [3.2.0]hept-2-ene-2-carboxylic acid chloride (290 mg) was obtained in substantially the same manner as that of Example 4-4).

IR (Nujol): 1750, 1695 cm$^{-1}$

NMR (CDCl$_3$, 200 MHz, d): 1.23 (3H, d, J=7.3 Hz), 1.30 (3H, d, J=6.3 Hz), 1.6–1.8 (1H, m), 2.4–2.6 (2H, m), 2.7–3.1 (1H, m), 3.3–3.8 (6H, m), 4.02 (3H, s), 4.2–4.5 (4H, m), 7.62 (1H, d, J=2.0 Hz), 7.71 (1H, d, J=2.0 Hz)

Example 19-1)

Allyl (4R,5S,6S)-3-[(2R,4S)-1-allyloxycarbonyl-2-(1-methyl-1,2,4-triazol-5-ylmethyl)pyrrolidin-4-yl]thio-6-[(1R)-1-hydroxyethyl]-4-methyl-7-oxo-1-azabicyclo[3.2.0]-hept-2-ene-2-carboxylate (1.77 g) was obtained by the same procedure as Example 16-1).

NMR (CDCl$_3$, δ): 1.25 (3H, d, J=7.25 Hz), 1.36 (3H, d, J=6.25 Hz), 1.80–2.20 (1H, m), 2.50–2.70 (1H, m), 3.05 (1H, dd, J=9.5 Hz, 14.9 Hz), 3.20–4.45 (total 12H, complex m), 4.55–4.90 (4H, m), 5.17–5.50 (4H, m), 5.80–6.06 (2H, m), 7.80 (1H, s)

APCI-Mass (m/z): 532 (MH$^+$)

Example 19-2)

(4R,5S,6S)-3-[(2R,4S)-2-{1,4-Dimethyl-5-(1,2,4-triazolio)methyl}pyrrolidin-4-yl]thio-6-[(1R)-1hydroxyethyl]-4-methyl-7-oxo-1-azabicyclo[3.2.0]hept-2-ene-2-carboxylic acid chloride (510.7 mg) was obtained by the same procedure as Example 16-2).

IR (Nujol): 1725 (broad) cm$^{-1}$

NMR (D$_2$O, δ): 1.22 (3H, d, J=7.2 Hz), 1.29 (3H, d, J=6.4 Hz), 1.58 (1H, m), 2.64–2.79 (1H, m), 3.18–4.00 (total 8H, complex m), 3.96 (3H, s), 4.13 (3H, s), 4.18–4.35 (2H, m), 8.79 (1H, s)

FAB-Mass (m/z): 422.3 (M$^+$—Cl)

Example 20-1)

Allyl (4R,5S,6S)-3-[(2R,4S)-1-allyloxycarbonyl-2-(1-methylpyrazol-5-ylmethyl) pyrrolidin-4-yl]thio-6-[(1R)-1-hydroxyethyl]-4-methyl-7-oxo-1-azabicyclo[3.2.0]hept-2-ene-2-carboxylate (6.5 g) was obtained in the same procedure as Example 16-1).

IR (CHCl$_3$): 3350, 1750, 1680, 1400, 1320 cm$^{-1}$

NMR (CDCl$_3$, δ): 1.25 (3H, d, J=7.2 Hz), 1.36 (3H, d, J=6.2 Hz), 1.65–1.86 (1H, m), 2.32–2.55 (1H, m), 2.75–2.97 (1H, m), 3.10–3.70 (5H, m), 3.76–4.33 (7H, m), 4.54–4.90 (4H, m), 5.18–5.52 (4H, m), 5.82–6.10 (2H, m), 6.05 (1H, d, J=1.8 Hz), 7.40 (1H, d, J=1.8 Hz)

APCI-Mass (m/z): 531 (MH$^+$)

Example 20-2)

To a solution of allyl (4R,5S,6S)-3-[(2R,4S)-1-allyloxycarbonyl-2-(1-methylpyrazol-5-ylmethyl)pyrrolidin-4-yl]thio-6-[(1R)-1-hydroxyethyl]-4-methyl-7-oxo-1-azabicyclo [3.2.0]hept-2-ene-2-carboxylate (6.0 g) in dichloromethane (120 ml) was added methyl triflate (1.54 ml) at room temperature. The mixture was stirred for 2 hours, then dichloromethane was evaporated under reduced pressure. The residue was dissolved in tetrahydrofuran-ethanol (1:2, 90 ml). To the solution was added triphenylphosphine (1.19 g), morpholine (2.48 ml), then tetrakis(triphenylphosphine) palladium(0) (660 mg) at room temperature. After one hour to the reaction mixture was added tetrahydrofuran (100 ml), and precipitate was collected by filtration. The precipitate was dissolved in water (200 ml) and washed with dichloromethane (×2). The aqueous solution was adjusted to pH 6 with 1N-hydrochloric acid and chromatographed on nonionic adsorption resin, Diaion HP-20 (Trademark, made by Mitsubishi Chemical Industries) (600 ml) eluting in turn with water and 5% aqueous acetone. The fractions containing the desired compound were collected and concentrated in vacuo. The resulting residue was passed through ion exchange resin, amberlist A-26 (Cl⁻ type, Trademark, made by Rohm and Haas Co., Ltd.) (60 ml) eluting with water. The elution was lyophilized to give (4R,5S,6S)-3-[(2R,4S)-2-(1, 2-dimethyl-5-pyrazolio-methyl) pyrrolidin-4-yl]thio-6-[(1R)-1-hydroxyethyl]-4-methyl-7-oxo-1-azabicyclo[3.2.0] hept-2-ene-2-carboxylic acid chloride (2.7 g).

IR (Nujol): 3300, 1760, 1605 cm⁻¹

NMR ($D_2O$, δ): 1.21 (3H, d, J=7.2 Hz), 1.28 (3H, d, J=6.4 Hz), 1.78–1.93 (1H, m), 2.78–2.94 (1H, m), 3.30–3.55 (5H, m), 3.73 (1H, dd, J=12.5 Hz, 6.6 Hz), 4.02 (3H, s), 4.10 (3H, s), 4.00–4.30 (4H, m), 6.76 (1H, d, J=3.0 Hz), 8.16 (1H, d, J=3.0 Hz)

FAB-Mass (m/z): 421 (M-Cl⁻)

Example 21- 1)

Allyl (4R,5S,6S)-3-[(2R,4S)-1-allyloxycarbonyl-2-(1-methylimidazol-5-ylmethyl) pyrrolidin-4-yl]thio-6-[(1 R)-1-hydroxyethyl]-4-methyl-7-oxo-1-azabicyclo[3.2.0] hept-2-ene-2-carboxylate (2.20 g) was obtained by the similar procedure as Example 16-1).

NMR ($CDCl_3$, δ): 1.24 (3H, d, J=7.2 Hz), 1.36 (3H, d, J=6.2 Hz), 1.73–2.62 (3H, m), 2.72–2.98 (1H, m), 3.11–3.51 (3H, m), 3.52–3.84 (2H, m), 3.65 (3H, s), 3.88–4.41 (4H, m), 4.57–4.93 (4H, m), 5.22–5.55 (4H, m), 5.82–6.10 (2H, m), 6.82 (1H, s), 7.41 (1H, s)

APCI-Mass (m/z): 531 ( MH⁺)

Example 21-2)

To a solution of allyl(4R,5S,6S)-3-[(2R,4S)-1-allyloxycarbonyl-2-(1-methylimidazol-5-ylmethyl)-pyrrolidin-4-yl] thio-6-[(1R)-1-hydroxyethyl]-4-methyl-7-oxo-1-azabicyclo [3.2.0]hept-2-ene-2-carboxylate (350 mg) in tetrahydrofuran-ethanol (1:1, 5.2 ml) were added triphenylphosphine (34.6 mg), morpholine (127 µl), then tetrakis(triphenylphosphine)palladium(0) (30.5 mg) at room temperature. The mixture was stirred for 60 minutes. To the reaction mixture was added ethyl acetate (10 ml), and the precipitate was collected by filtration. The precipitate was poured into a mixture of ethyl acetate (EtOAc) and water ($H_2O$), and the pH was adjusted to 6.0 with 1N-HCl. The separated aqueous layer was washed with EtOAc, and traces of organic solvent in the aqueous layer were removed by evaporation in vacuo. The resulting solution was chromatographed on nonionic adsorption resin, Diaion HP-20 (Trademark, made by Mitsubishi Chemical Industries) (40 ml) eluting in turn with water and 3–10% aqueous acetonitrile. The fractions containing the desired compound were collected and concentrated in vacuo. The resulting solution was adjusted to pH 4.0 with 1N-HCl, and lyophilized to give (4R,5S,6S)-3-[(2R,4S)-2-(1-methylimidazol-5-ylmethyl) pyrrolidin-4-yl]thio-6-[(1R )-1-hydroxyethyl ]-4-methyl-7-oxo-1-azabicyclo[3.2.0]hept-2-ene-2-carboxylic acid hydrochloride (61.1 mg).

NMR ($D_2O$, δ): 1.22 (3H, d, J=7.2 Hz), 1.29 (3H, d, J=6.4 Hz), 1.72–1.98 (1H, m), 2.73–2.97 (1H, m), 3.22–3.55 (5H, m), 3.75 (1H, dd, J=6.8 Hz, 12.5 Hz), 3.86 (3H, s), 3.96–4.35 (4H, m), 7.44 (1H, s), 8.70 (1H, s)

Example 21-3)

Allyl (4R,5S,6S)-3-[(2R,4S)-1-allyloxycarbonyl-2-(1, 3-dimethyl-5-imidazoliomethyl)pyrrolidin-4-yl]thio-6-[(1R)-1-hydroxyethyl]-4-methyl-7-oxo-1-azabicyclo[3.2.0]- hept-2-ene-2-carboxylate iodide (2.10 g) was obtained by the similar procedure as Example 15-2).

IR (Nujol): 3500–3100, 1740, 1670, 1280 cm⁻¹

NMR ($CDCl_3$, δ): 1.28 (3H, d, J=6.9 Hz), 1.36 (3H, d, J=6.2 Hz), 1.62–1.93 (2H, m), 2.59–3.09 (2H, m), 3.22–3.57 (4H, m), 4.68–5.40 (11H, m), 4.51–5.9 (4H, m), 5.09–5.53 (4H, m), 5.82–6.08 (2H, m), 7.24 (1H, s), 9.63 (1H, br s)

FAB-Mass (m/z): 545.4 (M-I⁻)

Example 21-4)

(4R,5S,6S)-3-[(2R, 4S)-2-(1,3-Dimethyl-5-imidazoliomethyl) pyrrolidin-4-yl]thio-6-[(1R)-1-hydroxyethyl]-4-methyl-7-oxo-1-azabicyclo [3.2.0]hept-2-ene-2-carboxylic acid chloride (532 mg) was obtained by the similar procedure as Example 15-3).

IR (Nujol): 3400–3100, 1750–1710, 1580–1530 cm⁻¹

NMR ($D_2O$, δ): 1.22 (3H, d, J=7.2 Hz), 1.29 (3H, d, J=6.4 Hz), 1.73–1.94 (1H, m), 2.71–2.97 (1H, m), 3.22–3.56 (5H, m), 3.72 (1H, dd, J=6.6 Hz, 12.4 Hz), 3.83 (3H, s), 3.86 (3H, s), 4.00–4.33 (4H, m), 7.43 (1H, s), 8.69 (1H, s)

FAB-Mass (m/z): 421.3 (M-Cl⁻)

Example 22-1)

Under nitrogen atmosphere a solution of allyl (4R)-2-diazo-4-[(2R,3S)-3-[(1R)-1-hydroxyethyl]-4-oxoazetidin-2-yl ]-3-oxopentanoate (4.59 g) in ethyl acetate (46 ml) was refluxed and rhodium(II) octanoate dimer (61 mg) was added thereto little by little. After the reaction mixture was refluxed for 30 minutes, it was cooled, evaporated, and then distilled off with acetonitrile (40 ml). The residue was dissolved into acetonitrile (46 ml). Under nitrogen atmosphere were added firstly diphenyl chlorophosphate (4.60 g), secondly N,N-diisopropyl-N-ethylamine (2.41 g), and lastly 4-(N,N-dimethylamino)pyridine (190 mg) thereto at 0° C. The reaction mixture was stirred for an hour at the same temperature [solution (A)]. Otherwise, under nitrogen atmosphere to a solution of (2R,4S)-4-acetylthio-1-allyloxycarbonyl-2-(pyrimidin-5-ylmethyl)pyrrolidine (6.0 g) in acetonitrile (60 ml) was dropped slowly 28% sodium methoxide-methanol solution (3.59 ml) at 4°–6° C. and the reaction mixture was stirred for an hour at the same temperature, and then was added acetic acid (1.12 g) thereto. After the reaction mixture was poured into ethyl acetate (350 ml) and water (300 ml), the organic layer was separated, washed with water (300 ml) and brine (300 ml), and dried over magnesium sulfate and then evaporated under reduced pressure. N,N-Dimethylacetamide (30 ml) was added to the residue and the solution was distilled off with acetonitrile (50 ml) under reduced pressure. After the solution was cooled to 10° C., it was added to solution (A), and then N,N-diisopropyl-N-ethylamine (2.80 g) was added thereto. After the reaction mixture was stirred for 12 hours at 7° C., it was poured into ethyl acetate (600 ml) and then the solution was poured into ice-water (250 ml). The organic layer was separated, washed with water (300 ml) six times and brine (300 ml) two times and then dried over magnesium sulfate and evaporated. The residue was subjected to column chromatography on silica gel (85 g) (solvent; dichloromethane:acetone=8:1 to 4:1 to 1:2) to give allyl (4R,5S, 6S)-3-[(2R,4S)-1-allyloxycarbonyl-2-(pyrimidin-5-ylmethyl) pyrrolidin-4-yl]thio-6-[(1R)-1-hydroxyethyl]-4-methyl-7-oxo-1-azabicyclo[3.2.0]hept-2-ene-2-carboxylate (4.3 g).

IR (Nujol): 3500–3200, 1750, 1700, 1680, 1540, 1400, 1320, 1190 cm$^{-1}$

NMR (CDCl$_3$, δ) : 1.25 (3H, d, J=7.2 Hz), 1.36 (3H, d, J=6.3 Hz), 1.55–1.80 (1H, m), 2.30–2.50 (1H, m), 2.83–2.95 (1H, m), 3.22–3.35 (4H, m), 3.53–3.68 (1H, m), 3.90–4.31 (4H, m), 4.60–4.89 (4H, m), 5.23–5.49 (4H, m), 5.88–6.07 (2H, m), 8.60 (2H, s), 9.12 (1H, s)

FAB-Mass:=M$^+$–1=529.3

Example 22-2)

To a solution of allyl (4R,5S,6S)-3-[(2R,4S)-1-allyloxycarbonyl-2-(pyrimidin-5-ylmethyl) pyrrolidin-4-yl]-thio-6-[(1R)-1-hydroxyethyl]-4-methyl-7-oxo-1-azabicyclo[3.2.0]hept-2-ene-2-carboxylate (170 mg) in ethanol (1.4 ml) and tetrahydrofuran (0.7 ml) were added at first triphenylphosphine (27 mg), secondly morpholine (55 mg), and lastly tetrakis(triphenylphosphine)palladium (24 mg) at room temperature under nitrogen atmosphere. After the reaction mixture was stirred at the same temperature for an hour, tetrahydrofuran (3 ml), ethyl acetate (10 ml), and water (15 ml) were added. The aqueous layer was separated and washed with ethyl acetate (15 ml) three times. The aqueous layer was evaporated under reduced pressure to eliminate organic solvent, and after it was adjusted to pH 5.9 with 1N-hydrochloric acid, it was subjected to column chromatography on Diaion HP-20 (14 ml). The column was washed with water (80 ml), and the object compound was eluted with 5% aqueous acetone (70 ml). The active fractions were collected, evaporated under reduced pressure, and lyophilized to give (4R,5S,6S)-3-[(2R,4S)-2-(pyrimidin-5-ylmethyl) pyrrolidin-4-yl]thio-6-[(1R)-1-hydroxyethyl]-4-methyl-7-oxo-1-azabicyclo[3.2.0]hept-2-ene-2-carboxylic acid (70 mg).

IR (Nujol): 3350–3200, 1730, 1555 cm$^{-1}$

NMR (D$_2$O, δ): 1.21 (3H, d, J=7.2 Hz), 1.29 (3H, d, J=6.3 Hz), 1.75–1.90 (1H, m), 2.69–2.84 (1H, m), 3.26–3.30 (2H, m), 3.32–3.49 (3H, m), 3.65–3.75 (1H, m), 3.95–4.10 (2H, m), 4.19–4.28 (2H, m), 8.80 (2H, s), 9.09 (1H, s)

FAB-Mass: M$^+$+1=405.5

Example 22-3)

To a solution of allyl (4R,5S,6S)-3-[(2R,4S)-1-allyloxycarbonyl-2-(pyrimidin-5-ylmethyl) pyrrolidin-4-yl]-thio-6-[(1R)-1-hydroxyethyl]-4-methyl-7-oxo-1-azabicyclo[3.2.0]hept-2-ene-2-carboxylate (4.3 g) in acetone (43 ml) was added iodomethane (17.3 g) at room temperature. After the reaction mixture was stirred at room temperature for a day, iodomethane (15.0 g) was added thereto at the same temperature. After the reaction mixture was stirred one more day, it was evaporated under reduced pressure to give allyl (4R,5S,6S)-3-[(2R,4S)-1-allyloxycarbonyl-2-(1-methyl-5-pyrimidiniomethyl) pyrrolidin-4-yl]thio-6-[(1R)-1-hydroxyethyl]-4-methyl-7-oxo-1-azabicyclo[3.2.0]hept-2-ene-2-carboxylate iodide (5.8 g) as a foamy powder.

IR (Nujol): 3250, 1740, 1690, 1670 cm$^{-1}$

NMR (CDCl$_3$+DMSO-d$_6$, δ): 1:24 (3H, d, J=7.4 Hz), 1.31 (3H, d, J=6.1 Hz), 1.89–1.96 (1H, m), 2.85–2.92 (1H, m), 3.22–3.48 (5H, m), 3.60–3.80 (1H, m), 3.90–4.28 (3H, m), 4.40–4.87 (8H, m), 5.25–5.50 (4H, m), 5.83–6.05 (2H, m), 9.05 (1H, s), 9.53 (1H, s), 10.05 (1H, s)

FAB-Mass: M$^+$–I$^-$=543.4

Example 22-4)

Allyl(4R,5S,6S)-3-[(2R,4S)-1-allyloxycarbonyl-2-(1-methyl-5-pyrimidiniomethyl) pyrrolidin-4-yl]thio-6-[(1R)-1-hydroxyethyl]-4-methyl-7-oxo-1-azabicyclo[3.2.0]hept-2-ene-2-carboxylate iodide (1.2 g) was dissolved in dichloromethane (5 ml) and methanol (5 ml) and then the solution was subjected to column chromatography on Amberlist (10 ml) (Trademark, made by Rohm & Haas Co.). The column was washed with mixed solvent of dichloromethane (20 ml) and methanol (20 ml), and the collected fractions were evaporated under reduced pressure to give allyl (4R,5S,6S)-3-[(2R,4S)-1-allyloxycarbonyl-2-(1-methyl-5-pyrimidiniomethyl)pyrrolidin-4-yl]thio-6-[(1R)-1-hydroxyethyl]-4-methyl-7-oxo-1-azabicyclo [3.2.0]-hept-2-ene-2-carboxylate chloride (1.03 g) as a foamy powder.

IR (Nujol) : 3200, 1740, 1660 cm$^{-1}$

NMR (CDCl$_3$+DMSO-d$_6$, δ): 1.22 (3H, d, J=7.2 Hz), 1.30 (3H, d , J=6.2 Hz), 1.90–2.02 (1H, m), 2.85–2.95 (1H, m), 3.21–3.72 (6H, m), 3.85–4.35 (3H, m), 4.40–4.92 (8H, m), 5.24–5.53 (4H, m), 5.81–6.10 (2H, m), 9.00 (1H, s), 9.66 (1H, s), 10.46 (1H, s)

FAB-Mass: M$^+$–Cl$^-$=543.4

Example 22-5)

To a solution of allyl (4R,5S,6S)-3-[(2R,4S)-1-allyloxycarbonyl-2-(1-methyl-5-pyrimidiniomethyl)-pyrrolidin-4-yl]thio-6-[(1R)-1-hydroxyethyl]-4-methyl-7-oxo-1-azabicyclo[3.2.0]hept-2-ene-2-carboxylate chloride (510 mg) in ethanol (5 ml) and tetrahydrofuran (5 ml) were added firstly triphenylphosphine (69.3 mg), secondly acetic acid (0.20 ml), thirdly tributyltin hydride (1.03 g), and lastly tetrakis(triphenylphosphine)palladium (40.7 mg) in tetrahydrofuran (2 ml) at room temperature. After the reaction mixture was stirred at the same temperature for an hour, tetrahydrofuran (10 ml) was added thereto and resulting precipitate was collected by filtration, washed with tetrahydrofuran (20 ml). The precipitate was dissolved in water (30 ml) at pH 6.5. It was washed with ethyl acetate (40 ml) three times, and the aqueous layer was evaporated under reduced pressure to eliminate organic solvent. The aqueous solution was adjusted to pH 5.9 with 1N-hydrochloric acid, and then it was subjected to column chromatography on Diaion HP-20 (Trademark, made by Mitsubishi Kasei Co.) (40 ml). The column was washed with water (200 ml), and the object compound was eluted with 3% aqueous acetone (240 ml). The active fractions were collected, concentrated to 60 ml and lyophylized to give (4R,5S,6S)-3-[(2R,4S)-2-{(1,6-dihydro-1-methylpyrimidin-5-yl) methyl}pyrrolidin-4-yl] thio-6-[(1R)-1-hydroxyethyl]-4-methyl-7-oxo-1-azabicyclo [3.2.0]hept-2-ene-2-carboxylic acid hydrochloride (70 mg).

IR (Nujol): 1740, 1720, 1660, 1580 cm$^{-1}$

NMR (D$_2$O, δ): 1.23 (3H, d, J=7.2 Hz), 1.30 (3H, d, J=6.4 Hz), 1.65–1.81 (1H, m), 2.45–2.62 (2H, m), 2.65–2.87 (1H, m), 3.16 (3H, s), 3.23–3.50 (3H, m), 3.65–3.75 (1H, m), 3.80–4.10 (2H, m), 4.18–4.29 (4H, m), 6.25 (1H, s), 7.89 (1H, s)

FAB-Mass: M$^+$–HCl=421.3

Example 23-1)

To a solution of allyl (4R)-2-diazo-4-[(2R,3S)-3-{(1R)-1-hydroxyethyl}-4-oxoazetidin-2-yl]-3-oxopentanoate (849 mg) in ethyl acetate (8.5 ml) was added rhodium(II) octanoate dimer (11 mg) under nitrogen atmosphere. After stirring under reflux for 15 minutes, the solution was evaporated and distilled off with acetonitrile twice. To a solution of the residue in acetonitrile (5.9 ml) were added diphenyl chlorophosphate (812 mg), N,N-diisopropyl-N-ethylamine (390 mg) and 4-dimethylaminopyridine (3.5 mg) at 0° C. under nitrogen atmosphere. The solution was stirred at 0° C. for 1 hour [Solution I]. Otherwise, to a solution of (2R,4S)-1-allyloxycarbonyl-2-(pyrimidin-2-ylmethyl)-4-(triphenylmethylthio) pyrrolidine (1.5 g) in dichloromethane (5.25 ml) were added trifluoroacetic acid (5.25 ml) and triethylsilane (502 mg) at 0° C. under nitrogen atmosphere. After stirring at room temperature for 45 minutes, the solution was evaporated. The residue was poured into a mixture of ethyl acetate and water. The separated organic layer was washed with aqueous sodium hydrogen carbonate twice, dried over magnesium sulfate, evaporated and distilled off with acetonitrile. The residue was dissolved with N,N-dimethylacetamide (5 ml) [Solution II]. To the cold solution [Solution I] were added the solution [Solution II] and N,N-diisopropyl-N-ethylamine (558 mg) at 0° C. under nitrogen atmosphere. After stirring at 5° C. overnight, the mixture was poured into a mixture of ethyl acetate and water. The separated organic layer was washed with water and aqueous sodium chloride solution, dried over magnesium sulfate and evaporated. The residue was subjected to column chromatography on silica gel (eluent; ethyl acetate:methanol=100:0 to 20:1) to give allyl (4R,5S,6S)-3-[(2R,4S)-1-allyloxycarhonyl-2-(pyrimidin-2-ylmethyl) pyrrolidin-4-yl]thio-6-[(1R)-1-hydroxyethyl]-4-methyl-7-oxo-1-azabicyclo [3.2.0]hept-2-ene-2-carhoxylate (640 mg).

IR (Nujol): 3350, 1740, 1680, 1620, 1540 cm$^{-1}$

NMR (CDCl$_3$, δ): 1.24 (3H, d, J=7.2 Hz), 1.35 (3H, d, J=6.4 Hz), 1.80–2.10 (1H, m), 2.40–2.70 (1H, m), 3.05–3.45 (4H, m), 3.50–3.80 (2H, m), 3.90–4.30 (3H, m), 4.40–4.90 (5H, m), 5.10–5.55 (4H, m), 5.80–6.10 (2H, m), 7.16 (1H, t, J=5.0 Hz), 8.66 (2H, d, J=5.0 Hz)

Mass: 529

Example 23-2)

To a solution of allyl (4R,5S,6S)-3-[(2R,4S)-1-allyloxycarbonyl-2-(pyrimidin-2-ylmethyl)pyrrolidin-4-yl]-thio-6-[(1R)-1-hydroxyethyl]-4-methyl-7-oxo-1-azabicyclo[3.2.0] hept-2-ene-2-carboxylate (1.3 g) in tetrahydrofuran (16.9 ml) and ethanol (6.5 ml) were added triphenylphosphine (129 mg), acetic acid (886 mg) and tetrakis(triphenylphosphine)palladium (142 mg) at 30° C. under nitrogen atmosphere. After stirring at 30° C. for 5 minutes, the solution was cooled to room temperature. Tributyltin hydride (2.86 g) was added to the solution. After stirring at room temperature for 30 minutes, ethyl acetate (40 ml) was added to the mixture. The resulting precipitate was collected by filtration, dissolved into a mixture of ethyl acetate and water and adjusted to pH 7.0 with aqueous sodium hydrogen carbonate. After being washed with ethyl acetate, the aqueous layer was subjected to column chromatography on "Diaion HP-20" [eluent; 4% aqueous acetone]. The eluate was evaporated under reduced pressure and freeze dried to give (4R,5S,6S)-3-[(2R,4S)-2-(pyrimidin-2-ylmethyl) pyrrolidin-4-yl]thio-6-[(1R)-1-hydroxyethyl]-4-methyl-7-oxo-1-azabicyclo [3.2.0]hept-2-ene-2-carboxylic acid (710 mg).

IR (Nujol): 3350, 1740, 1700, 1560 cm$^{-1}$

NMR (D$_2$O, δ): 1.22 (3H, d, J=7.2 Hz), 1.30 (3H, d, J=6.4 Hz), 1.75–2.00 (1H, m), 2.70–2.95 (1H, m), 3.30–3.65 (5H, m), 3.65–3.85 (1H, m), 3.95–4.15 (1H, m), 4.15–4.35 (3H, m), 7.49 (1H, t, J=5.0 Hz ), 8.79 (2H, d, J=5.0 Hz)

FAB-Mass: M$^+$=405.3

Example 24-1)

To a solution of allyl (4R)-2-diazo-4-[(2R,3S)-3-{(1R)-1-hydroxyethyl}-4-oxoazetidin-2-yl]-3-oxopentanoate (1.55 g) in ethyl acetate (25 ml) was added Rhodium octanoate (17 mg) at 80° C. under nitrogen atmosphere. After stirring for 1 hour, the mixture was cooled to ambient temperature and evaporated under reduced pressure. To the residue in acetonitrile (25 ml) were added dropwise diphenyl chlorophosphate (1.2 ml), then diisopropyl ethylamine (1.4 ml) and dimethylaminopyridine under ice-cooling. After stirring for 2 hours at 0° C., a solution of (2R,4S)-1-allyloxycarbonyl-2-{2-(1-pyridinio)ethyl}-4-mercaptopyrrolidine trifluoroacetate in dimethylacetamide and acetonitrile, which had been prepared by the method described below, and then diisopropylethylamine (3.66 ml) were added dropwise to the mixture at the same temperature. After stirring for 16 hours, the reaction mixture was evaporated under reduced pressure. The residue was column chromatographed on silica gel (100 ml silica gel, chloroform:methanol=4:1 to 1:1) to give allyl (4R,5S,6S)-3-[(2R,4S)-1-allyloxycarbonyl-2-{2-(1-pyridinio)ethyl}pyrrolidin-4-yl]-thio-6-[(1R)-1-hydroxyethyl]-4-methyl-7-oxo-1-azabicyclo [3.2.0]hept-2-ene-2-carboxylate trifluoroacetate.

Preparation of mercapto compound:

To a solution of (2R,4S)-1-allyloxycarbonyl-2-{2-(1-pyridinio) ethyl}-4-(triphenylmethylthio)pyrrolidine chloride (2.5 g) in dichloromethane (8.8 ml) was added dropwise triethylsilane (840 μl), and trifluoromethanesulfonic acid (8.75 ml) under ice-cooling. After stirring for 1 hour at ambient temperature, the mixture was evaporated under reduced pressure. The residue was washed with hexane, and evaporated after addition of dimethylacetamide and acetonitrile (10 ml). The residue dissolved in acetonitrile (10 ml) was the required mercapto compound solution.

IR (CHCl$_3$): 3100–3600, 1740, 1640 cm$^{-1}$

Example 24-2)

(4R,5S,6S)-3-[(2R,4S)-2-{2-(1-Pyridinio) ethyl}-pyrrolidin-4-yl]thio-6-[(1R)-1-hydroxyethyl]-4-methyl-7-oxo-1-azabicyclo [3.2.0]hept-2-ene-2-carboxylic acid chloride was obtained from allyl (4R,5S,6S)-3-[(2R,4S)-1-allyloxycarbonyl-2-{2-(1-pyridinio)ethyl}pyrrolidin-4-yl]-thio-6-[(1R)-1-hydroxyethyl]-4-methyl-7-oxo-1-azabicyclo[3.2.0]hept-2-ene-2-carboxylate trifluoromethanesulfonate in substantially the same procedure as that of Example 4-4).

IR (Nujol): 3300–3600, 1720 cm$^{-1}$

NMR (D$_2$O, δ): 1.23 (3H, d, J=7.2 Hz), 1.30 (3H, d, J=6.4 Hz), 1.70–1.90 (1H, m), 2.50–3.00 (3H, m), 3.30–3.55 (3H, m), 3.60–3.95 (3H, m), 3.95–4.15 (1H, m), 4.10–4.30 (2H, m), 8.13 (2H, t, J=7.3 Hz), 8.61 (1H, t, J=7.8 Hz), 8.93 (2H, d, J=5.5 Hz)

Example 25-1)

Allyl (4R)-2-diazo-4-[(2R,3S)-3-{(1R)-1-hydroxyethyl}-4-oxoazetidin-2-yl]-3-oxopentanoate (709 mg) and (2R,4S)-4-acetylthio-1-allyloxycarbonyl-2-[2-(5-hydroxymethylimidazol-1-yl) ethyl]pyrrolidine (849 mg) were reacted in substantially the same manner as that of Example 2-3) to give allyl (4R,5S,6S)-3-[(2R,4S)-1-allyloxycarbonyl-2-{2-(5-hydroxymethylimidazol-1-yl)ethyl}pyrrolidin-4-yl]thio-6-[(1R)-1-hydroxyethyl]-4-methyl-7-oxo-1-azabicyclo [3.2.0]hept-2-ene-2-carboxylate (802 mg) as a yellow solid.

NMR (CDCl$_3$, δ): 1.24 (3H, d, J=7.1 Hz), 1.33 (3H, d, J=6.2 Hz), 1.6–2.6 (4H, m), 3.1–4.3 (12H, m), 4.6–4.9

(6H, m), 5.2–5.5 (4H, m), 5.9–6.0 (2H, m), 6.9–7.5 (2H, m)

Example 25-2)

To a solution of allyl (4R,5S,6S)-3-[(2R,4S)-1-allyloxycarbonyl-2-{2-(5-hydroxymethylimidazol-1-yl)ethyl}pyrrolidin-4-yl]thio-6-[(1R)-1-hydroxyethyl]-4-methyl-7-oxo-1-azabicyclo [3.2.0]hept-2-ene-2-carboxylate (790 mg) in acetone (4.0 ml) was added methyl iodide (0.88 ml) at room temperature and the solution was allowed to stand for 12 hours. The solvent was evaporated to give allyl (4R,5S,6S)-3-[(2R,4S)-1-allyloxycarbonyl-2-{2-(5-hydroxymethyl-3-methyl-1-imidazolio)ethyl}pyrrolidin-4-yl]thio-6-[(1R)-1-hydroxyethyl]-4-methyl-7-oxo-1-azabicyclo [3.2.0]hept-2-ene-2-carboxylate iodide (991 mg) as a yellow solid. This compound was immediately used as the starting compound for the next step.

Example 25-3)

(4R,5S,6S)-3-[(2R,4S)-2-{2-(5-Hydroxymethyl-3-methyl-1-imidazolio) ethyl}pyrrolidin-4-yl]thio-6-[(1R)-1-hydroxyethyl]-4-methyl-7-oxo-1-azabicyclo[3.2.0]hept-2-ene-2-carboxylic acid chloride (148 mg) was obtained in substantially the same manner as Example 4-4).

IR (Nujol): 1753, 1585 cm$^{-1}$

NMR (CDCl$_3$, 200 MHz, δ): 1.22 (3H, d, J=7.2 Hz), 1.29 (3H, d, J=6.4 Hz), 1.7–1.9 (1H, m), 2.4–2.6 (2H, m), 2.8–2.9 (1H, m), 3.3–3.5 (3H, m), 3.6–3.8 (2H, m), 3.83 (3H, s), 4.0–4.1 (1H, m), 4.2–4.4 (2H, m), 4.73 (2H, s), 7.48 (1H, s), 8.85 (1H, s)

Example 26-1)

Allyl (4R)-2-diazo-4-[(2R,3S)-3-{(1R)-1-hydroxyethyl}-4-oxoazetidin-2-yl]-3-oxopentanoate (4.55 g) and (2R,4S)-4-acetylthio-1-allyloxycarbonyl-2-[2-(4-hydroxymethylimidazol-1-yl)ethyl]pyrrolidine (5.46 g) were reacted in substantially the same manner as Example 2–3) to give allyl (4R,5S,6S)-3-[(2R,4S)-1-allyloxycarbonyl-2-{2-(4-hydroxymethylimidazol-1-yl)ethyl}pyrrolidin-4-yl]-thio-6-[(1R)-1-hydroxyethyl]-4-methyl-7-oxo-1-azabicyclo[3.2.0] hept-2-ene-2-carboxylate (5.83 g) as a yellow solid.

IR (CHCl$_3$): 1763, 1685 cm$^{-1}$

NMR (CDCl$_3$, 200 MHz, δ): 1.18 (3H, d, J=6.5 Hz), 1.34 (3H, d, J=6.5 Hz), 1.6–2.6 (4H, m), 3.1–4.3 (12H, m), 4.4–4.9 (6H, m), 5.1–5.5 (4H, m), 5.8–6.0 (2H, m), 6.9–7.1 (2H, m)

Example 26-2)

To a solution of allyl (4R,5S,6S)-3-[(2R, 4S)-1-allyloxycarbonyl-2-{2-(4-hydroxymethylimidazol-1-yl)ethyl}pyrrolidin-4-yl]thio-6-[(1R)-1-hydroxyethyl]-4-methyl-7-oxo-1-azabicyclo[3.2 0]hept-2-ene-2-carboxylate (2.50 g) in acetone (12.5 ml) was added methyl iodide (2.78 ml) at room temperature and the solution was allowed to stand for 12 hours. The solvent was evaporated to give allyl (4R,5S,6S)-3-[(2R,4S)-1-allyloxycarbonyl-2-{2-(4-hydroxymethyl-3-methyl-1-imidazolio)ethyl}pyrrolidin-4yl] thio-6-[(1R)-1-hydroxyethyl]-4-methyl-7-oxo-1-azabicyclo [3.2.0]hept-2-ene-2-carboxylate iodide (2.95 g) as a yellow solid. This compound was immediately used as the starting compound for the next step.

Example 26-3)

(4R,5S,6S)-3-[(2R, 4S)-2-{2-(4-Hydroxymethyl-3-methyl-1-imidazolio )ethyl}pyrrolidin-4-yl]thio-6-[(1R)-1-hydroxyethyl]-4-methyl-7-oxo-1-azabicyclo[3.2.0]hept-2-ene-2-carboxylic acid chloride (255 mg) was obtained in substantially the same manner as Example 4-4).

IR (Nujol): 1750, 1580 cm$^{-1}$

NMR (CDCl$_3$, 200 MHz, δ): 1.22 (3H, d, J=7.2 Hz), 1.30 (3H, d, J=6.4 Hz), 1.7–1.9 (1H, m), 2.4–2.6 (2H, m), 2.7–2.9 (1H, m), 3.3–3.5 (3H, m), 3.6–3.8 (2H, m), 3.89 (3H, s), 4.0–4.1 (1H, m), 4.2–4.4 (4H, m), 4.73 (2H, d, J=2.4 Hz), 7.5–7.6 (1H, m), 8.84 (1H, s)

Example 26-4)

(4R,5S,6S)-3-[(2R,4S)-2-{2-(4-Hydroxymethylimidazol-1-yl) ethyl}pyrrolidin-4-yl ]thio-6-[(1R)-1-hydroxyethyl]-4-methyl-7-oxo-1-azabicyclo[3.2.0]hept-2-ene-2-carboxylic acid hydrochloride (1.08 g) was obtained in substantially the same manner as Example 5.

NMR (CDCl$_3$, 200 MHz, δ): 1.21 (3H, d, J=7.2 Hz), 1.29 (3H, d, J=6.4 Hz), 1.7–1.9 (1H, m), 2.4–2.6 (2H, m), 2.7–2.9 (1H, m), 3.3–3.5 (3H, m), 3.6–3.8 (3H, m), 4.0–4.1 (1H, m), 4.2–4.5 (5H, m), 7.45 (1H, s), 8.5–8.7 (1H, m)

Example 27-1)

Allyl (4R)-2-diazo-4-[(2R,3S)-3-{(1R)-1-hydroxyethyl}-4-oxoazetidin-2-yl]-3-oxopentanoate (1.81 g) and (2R,4S)-4-acetylthio-1-allyloxycarbonyl-2-[2-(5-methoxymethylimidazol-1-yl) ethyl]pyrrolidine (2.25 g) were reacted in substantially the same manner as Example 2-3) to give allyl (4R,5S,6S)-3-[(2R,4S)-1-allyloxycarbonyl-2-{2-(5-methoxymethylimidazol-1-yl)ethyl}pyrrolidin-4-yl]-thio-6-[(1R)-1-hydroxyethyl]-4-methyl-7-oxo-1-azabicyclo[3.2.0] hept-2-ene-2-carboxylate (1.81 g) as a yellow solid.

NMR (CDCl$_3$, 200 MHz, δ): 1.25 (3H, d, J=7.2 Hz), 1.36 (3H, d, J=6.2 Hz), 1.5–2.7 (4H, m), 3.2–4.3 (11H, m), 3.30 (3H, s), 4.42 (2H, s), 4.6–4.9 (6H, m), 5.2–5.5 (4H, m), 5.9–6.1 (1H, m), 7.00 (1H, s), 7.56 (1H, br)

Example 27-2)

To a solution of allyl (4R,5S,6S)-3-[(2R,4S)-1-allyloxycarbonyl-2-{2-(5-methoxymethylimidazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (1.79 g) in acetone (9.0 ml) was added methyl iodide (1.9 ml) at room temperature and the solution was allowed to stand for 3.5 hours. The solvent was evaporated to give allyl (4R,5S,6S)-3-[(2R,4S)-1-allyloxycarbonyl-2-{2-(5-methoxymethyl-3-methyl-1-imidazolio)ethyl}pyrrolidin-4-yl] thio-6-[(1R)-1-hydroxyethyl]-4-methyl-7-oxo-1-azabicyclo [3.2.0]hept-2-ene-2-carboxylate iodide (2.24 g) as a yellow solid. This compound was immediately used as the starting compound for the next step.

Example 27-3)

(4R,5S,6S)-3-[(2R,4S)-2-{2-(5-Methoxymethyl-3-methyl-1-imidazolio) ethyl}pyrrolidin-4-yl]thio-6-[(1R)-1-hydroxyethyl]-4-methyl-7-oxo-1-azabicyclo[3.2.0]hept-2-ene-2-carboxylic acid chloride (600 mg) was obtained in substantially the same manner as Example 4-4).

IR (Nujol): 1753, 1585 cm$^{-1}$

NMR (CDCl₃, 200 MHz, δ) : 1.23 (3H, d, J=7.2 Hz), 1.30 (3H, d, J=6.4 Hz), 1.7–1.9 (1H, m), 2.4–2.6 (2H, m), 2.7–2.9 (1H, m), 3.3–3.5 (3H, m), 3.42 (3H, s), 3.6–3.9 (2H, m), 3.90 (3H, s), 4.0–4.1 (1H, m), 4.2–4.4 (4H, m), 4.63 (2H, s), 7.58 (1H, s), 8.90 (1H, s)

Example 28-1)

Allyl (4R)-2-diazo-4-[(2R,3S)-3-{(1R)-1-hydroxyethyl}-4-oxoazetidin-2-yl]-3-oxopentanoate (1.51 g) and (2R,4S)-1-allyloxycarbonyl-4-benzoylthio-2-[2-(4-carbamoylmethylimidazol-1-yl) ethyl]pyrrolidine (2.27 g) were reacted in substantially the same manner as Example 18-1) to give allyl (4R,5S,6S)-3-[(2R,4S)-1-allyloxy-carbonyl-2-{2-(4-carbamoylmethylimidazol-1-yl)ethyl}-pyrrolidin-4-yl]thio-6-[(1R)-1-hydroxyethyl]-4-methyl-7-oxo-1-azabicyclo[3.2.0]hept-2-ene-2-carboxylate (1.11 g) as a yellow solid.

IR (CHCl₃): 1763, 1682 cm⁻¹

NMR (CDCl₃, 200 MHz, d): 1.24 (3H, d, J=7.2 Hz), 1.36 (3H, d, J=6.3 Hz), 1.6–2.6 (4H, m), 3.2–4.3 (13H, m), 4.6–4.9 (4H, m), 5.2–5.5 (5H, m), 5.9–6.0 (2H, m), 6.8–7.5 (3H, m)

Example 28-2)

To a solution of allyl (4R,5S,6S)-3-[(2R,4S)-1-allyloxycarbonyl-2-{2-(4-carbamoylmethylimidazol-1-yl)ethyl}pyrrolidin-4-yl]thio-6-[(1R)-1-hydroxyethyl]-4-methyl-7-oxo-1-azabicyclo [3.2.0]hept-2-ene-2-carboxylate (1.08 g) in acetone (5.4 ml) was added methyl iodide (1.15 ml) at room temperature and the solution was allowed to stand for 5.5 hours. The solvent was evaporated to give allyl (4R,5S,6S)-3-[(2R,4S)-1-allyloxycarbonyl-2-{2-(4-carbamoylmethyl-3-methyl-1-imidazolio)ethyl}pyrrolidin-4yl]thio-6-[(1R)-1-hydroxyethyl]-4-methyl-7-oxo-1-azabicyclo [3.2.0]hept-2-ene-2-carboxylate iodide (1.31 g) as a yellow solid. This compound was immediately used as the starting compound for the next step.

Example 28-3)

(4R,5S,6S)-3-[(2R,4S)-2-{2-(4-Carbamoylmethyl-3-methyl-1-imidazolio)ethyl}pyrrolidin-4-yl]thio-6-[(1R)-1-hydroxyethyl]-4-methyl-7-oxo-1-azabicyclo [3.2.0]hept-2ene-2-carboxylic acid chloride (138 mg) was obtained in substantially the same manner as Example 4-4).

IR (Nujol) 1750, 1675, 1575 cm⁻¹

NMR (CDCl₃, 200 MHz, δ): 1.22 (3H, d, J=7.2 Hz), 1.29 (3H, d, J=6.3 Hz), 1.7–1.9 (1H, m), 2.4–2.6 (2H, m), 2.7–2.9 (1H, m), 3.3–3.5 (4H, m), 3.6–3.9 (6H, m), 4.0–4.1 (1H, m), 4.2–4.4 (4H, m), 7.53 (1H, s), 8.84 (1H, s)

Example 29-1)

Allyl (4R)-2-diazo-4-[(2R,3S)-3-{(1R)-1-hydroxyethyl}-4-oxoazetidin-2-yl]-3-oxopentanoate (10.3 g) and (2R,4S)-1-allyloxycarbonyl-4-acetylthio-2-[2-(4-cyanoimidazol-1-yl)ethyl]pyrrolidine (12.2 g) were reacted in substantially the same manner as that of Example 2-3) to give allyl (4R,5S,6S)-3-[(2R,4S)-1-allyloxycarbonyl-2-{2-(4-cyanoimidazol-1-yl)ethyl}pyrrolidin-4-yl]thio-6-(1R)-1-hydroxyethyl]-4-methyl-7-oxo-1-azabicyclo[3.2.0]-hept-2-ene-2-carboxylate (9.69 g) as a yellow solid.

NMR (CDCl₃, 200 MHz, δ): 1.26 (3H, d, J=7.2 Hz), 1.36 (3H, d, J=6.3 Hz), 1.5–2.7 (5H, m), 3.2–3.4 (3H, m), 3.6–3.7 (1H, m), 3.8–4.3 (6H, m), 4.6–4.9 (4H, m), 5.2–5.5 (4H, m), 5.8–6.0 (2H, m), 7.62 (2H, br)

Example 29-2)

(4R,5S,6S)-3-[(2R,4S)-2-{2-(4-Cyanoimidazol-1-yl) ethyl}pyrrolidin-4-yl]thio-6-[(1R)-1-hydroxyethyl]-4-methyl-7-oxo-1-azabicyclo [3.2.0]hept-2-ene-2-carboxylic acid hydrochloride (701 mg) was obtained in substantially the same manner as Example 5.

IR (Nujol): 1745 cm⁻¹

NMR (CDCl₃, 200 MHz, δ): 1.21 (3H, d, J=7.2 Hz), 1.29 (3H, d, J=6.4 Hz), 1.6–1.8 (1H, m), 2.3–2.5 (2H, m), 2.6–2.8 (1H, m), 3.3–3.5 (3H, m), 3.6–3.7 (2H, m), 4.0–4.1 (1H, m), 4.2–4.3 (4H, m), 7.88 (1H, d, J=1.2Hz), 7.97 (1H, d, J=1.2 Hz)

Example 29-3)

To a solution of allyl (4R,5S,6S)-3-[(2R,4S)-1-allyloxycarbonyl-2-{2-(4-cyanoimidazol-1-yl)ethyl}-pyrrolidin-4-yl]thio-6-[(1R)-1-hydroxyethyl]-4-methyl-7-oxo-1-azabicyclo[3.2.0]hept-2-ene-2-carboxylate (7.56 g) in dichloromethane (110 ml) was added methyl trifluoromethanesulfonate (3.1 ml) at room temperature and the solution was stirred at the same temperature for 30 minutes. The solvent was evaporated to give allyl (4R,5S,6S)-3-[(2R,4S)-1-allyloxycarbonyl-2-{2-(4-cyano-3-methyl-1-imidazolio)ethyl}pyrrolidin-4-yl]thio-6-[(1R)-1-hydroxyethyl]-4-methyl-7-oxo-1-azabicyclo[3.2.0]hept-2-ene-2-carboxylate trifluoromethanesulfonate (10.4 g) as a yellow paste. This compound was immediately used as the starting compound for the next step.

Example 29-4)

(4R,5S,6S)-3-[(2R,4S)-2-{2-(4-Cyano-3-methyl-1-imidazolio) ethyl}pyrrolidin-4-yl]thio-6-[(1R)-1-hydroxyethyl]-4-methyl-7-oxo-1-azabicyclo[3.2.0]hept-2-ene-2-carboxylic acid chloride (1.83 g) was obtained in substantially the same manner as Example 4-4).

IR (Nujol): 1750, 1580 cm⁻¹

NMR (CDCl₃, 200 MHz, δ): 1.23 (3H, d, J=7.2 Hz), 1.30 (3H, d, J=6.4 Hz), 1.7–1.9 (1H, m), 2.4–2.6 (2H, m), 2.8–2.9 (1H, m), 3.3–3.5 (3H, m), 3.6–3.9 (2H, m), 4.0–4.1 (1H, m), 4.06 (3H, s), 4.2–4.3 (2H, m), 4.4–4.5 (2H, m), 8.46 (1H, s)

Example 30

(4R,5S,6S)-3-[(2R, 4S)-2-{2-(2-Carbamoylimidazol-1-yl ethyl}pyrrolidin-4-yl]thio-6-[(1R)-1-hydroxyethyl]-4-methyl-7-oxo-1-azabicyclo[3.2.0]hept-2-ene-2-carboxylic acid hydrochloride (285 mg) was obtained in substantially the same manner as Example 5.

IR (Nujol): 1750, 1670, 1580 cm⁻¹

NMR (CDCl₃, 200 MHz, δ): 1.21 (3H, d, J=7.2 Hz), 1.30 (3H, d, J=6.4 Hz), 1.6–1.8 (1H, m), 2.3–2.5 (2H, m), 2.6–2.8 (1H, m), 3.3–3.5 (3H, m), 3.6–3.7 (3H, m), 3.9–4.1 (1H, m), 4.2–4.3 (3H, m), 7.14 (1H, s) , 7.39 (1H, d, J=1.1 Hz)

Example 31

(4R,5S,6S)-3-[(2R,4S)-2-{2-(2-Hydroxymethylimidazol-1-yl) ethyl}pyrrolidin-4-yl]thio-6-[(1R)-1-hydroxyethyl]-4-methyl-7-oxo-1-azabicyclo [3.2.0]hept-2-ene-2-carboxylic acid hydrochloride (472 mg) was obtained in substantially the same manner as Example 5.

IR (Nujol): 1750, 1580 cm⁻¹

NMR (CDCl$_3$, 200 MHz, δ): 1.22 (3H, d, J=7.3 Hz), 1.29 (3H, d, J=6.4 Hz), 1.7–1.9 (1H, m), 2.3–2.6 (2H, m), 2.7–2.9 (1H, m), 3.3–4.1 (6H, m), 4.2–4.3 (4H, m), 4.92 (2H, s), 7.39 (1H, d, J=2.0 Hz), 7.49 (1H, d, J=2.0 Hz)

Example 32

(4R,5S,6S)-3-[(2R,4S)-2-{2-(Imidazol-1-yl) ethyl}-pyrrolidin-4-yl]thio-6-[(1R)-1-hydroxyethyl]-4-methyl-7-oxo-1-azabicyclo[3.2.0]hept-2-ene-2-carboxylic acid hydrochloride (674 mg) was obtained in substantially the same manner as Example 5.

IR (Nujol): 1745, 1570 cm$^{-1}$

NMR (CDCl$_3$, 200 MHz, δ): 1.22 (3H, d, J=7.2 Hz), 1.29 (3H, d, J=6.4 Hz), 1.7–1.8 (1H, m), 2.4–2.6 (2H, m), 2.7–2.9 (1H, m), 3.3–3.5 (3H, m), 3.6–3.8 (2H, m), 4.0–4.1 (1H, m), 4.2–4.4 (4H, m), 7.5–7.6 (2H, m), 8.77 (1H, s)

Example 33-1)

To a solution of allyl (4R,5S,6S)-3-[(2R,4S)-1-allyloxycarbonyl-2-{2-(imidazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (7.00 g) in dimethylformamide (35 ml) was added 3-allyloxycarbonylamino-1-iodopropane (4.26 g) and the solution was warmed to 50° C. After stirring at the same temperature for 8 hours, the solution was cooled to room temperature. The solvent was evaporated and the residue was washed with diisopropyl ether (175 ml×5) to give allyl (4R,5S,6S)-3-[(2R,4S)-1-allyloxycarbonyl-2-[2-[3-{3-(allyloxycarbonylamino)propyl}-1-imidazolio]ethyl]-pyrrolidin-4-yl]thio-6-[(1R)-1-hydroxyethyl]-4-methyl-7-oxo-1-azabicyclo[3.2.0]hept-2-ene-2-carboxylate iodide (10.4 g) as a light brown paste. This compound was immediately used as the starting compound for the next step.

Example 33-2)

(4R,5S,6S)-3-[(2R,4S)-2-[2-{3-(3-Aminopropyl)-1-imidazolio}ethyl]pyrrolidin-4-yl]thio-6-[(1R)-1-hydroxyethyl]-4-methyl-7-oxo-1-azabicyclo[3.2.0]hept-2-ene-2carboxylic acid chloride (499 mg) was obtained in substantially the same manner as Example 4-4).

IR (Nujol): 1750, 1565 cm$^{-1}$

NMR (CDCl$_3$, 200 MHz, δ) : 1.23 (3H, d, J=7.2 Hz), 1.30 (3H, d, J=6.3 Hz), 1.7–1.9 (1H, m), 2.2–2.9 (5H, m), 3.0–3.1 (2H, m), 3.3–3.5 (3H, m), 3.6–3.9 (2H, m), 4.0–4.1 (1H, m), 4.2–4.5 (6H, m), 7.61 (2H, s), 8.97 (1H, s)

Example 34-1)

Allyl (4R)-2-diazo-4-[(2R,3S)-3-{(1R)-1-hydroxyethyl}-4-oxoazetidin-2 -yl]-3-oxopentanoate (6.02 g) and (2R,4S)-1-allyloxycarbonyl-4-benzoylthio-2-[2-(1,2,4-triazol-1-yl) ethyl]pyrrolidine (7.89 g) were reacted in substantially the same manner as Example 18-1) to give allyl (4R,5S,6S)-3-[(2R,4S)-1-allyloxycarbonyl-2-{2-(1,2,4-triazol-1-yl)ethyl}pyrrolidin-4-yl]thio-6-[(1R)-1-hydroxyethyl]-4-methyl-7-oxo-1-azabicyclo[3.2.0]hept-2-2-carboxylate (4.76 g) as a light yellow solid.

NMR (CDCl$_3$, 200 MHz, δ): 1.26 (3H, d, J=7.2 Hz), 1.36 (3H, d, J=6.3 Hz), 1.5–2.7 (5H, m), 3.2–4.4 (10H, m), 4.6–4.9 (4H, m), 5.2–5.5 (4H, m), 5.9–6.0 (1H, m), 7.9–8.3 (2H, m)

Example 34-2)

(4R,5S,6S)-3-[(2R,4S)-2-{2-(1,2,4-Triazol-1-yl)ethyl}pyrrolidin-4-yl]thio-6-[(1R)-1-hydroxyethyl]-4-methyl-7-oxo-1-azabicyclo[3.2.0 ]hept-2-ene-2-carboxylic acid hydrochloride (841 mg) was obtained in substantially the same manner as Example 5.

IR (Nujol): 1749, 1580 cm$^{-1}$

NMR (CDCl$_3$, 200 MHz, δ): 1.22 (3H, d, J=7.2 Hz), 1.30 (3H, d, J=6.4 Hz), 1.6–1.8 (1H, m), 2.3–2.8 (3H, m), 3.3–3.5 (3H, m), 3.6–3.7 (2H, m), 3.9–4.1 (1H, m), 4.2–4.3 (2H, m), 4.4–4.5 (2H, m), 8.10 (1H, s), 8.50 (1H, s)

Example 34-3)

To a solution of allyl (4R,5S,6S)-3-[(2R,4S)-1-allyloxycarbonyl-2-{2-(1,2,4-triazol-1-yl)ethyl}-pyrrolidin-4-yl]thio-6-[(1R)-1-hydroxyethyl]-4-methyl-7-oxo-1-azabicyclo[3.2.0]hept-2-ene-2-carboxylate (1.58 g) in acetone (7.9 ml) was added methyl iodide (1.85 ml) at room temperature and the solution was allowed to stand for 8 days. The solvent was evaporated to give allyl (4R,5S,6S)-3-[(2R,4S)-1-allyloxycarbonyl-2-[2-{4-methyl-1-(1,2,4-triazolio)}ethyl]pyrrolidin-4-yl]thio-6-[(1R)-1hydroxyethyl]-4-methyl-7-oxo-1-azabicyclo[3.2.0]hept-2-ene-2-carboxylate iodide (2.00 g) as a yellow solid, This compound was immediately used as the starting compound for the next step.

Example 34-4)

(4R,5S,6S)-3-[(2R,4S)-2-[2-{4-Methyl-1-(1,2,4)triazolio)}ethyl]pyrrolidin-4-yl]thio-6-[(1R)-1-hydroxyethyl]-4-methyl-7-oxo-1-azabicyclo[3.2.0]hept-2-ene-2-carboxylic acid chloride (520 mg) was obtained in substantially the same manner as Example 4-4).

IR (Nujol) : 1745, 1580 cm$^{-1}$

NMR (CDCl$_3$, 200 MHz, δ): 1.22 (3H d, J=7.2 Hz), 1.30 (3H, d, J=6.4 Hz), 1.7–1.9 (1H, m), 2.5–2.7 (2H, m), 2.8–2.9 (1H, m), 3.3–3.5 (3H, m), 3.6–3.9 (2H, m), 4.00 (3H, s), 4.0–4.1 (1H, m), 4.2–4.3 (2H, m), 4.6–4.7 (2H, m), 8.86 (2H, s)

Example 35-1)

Allyl (4R,5S,6S)-3-[(2R,4S)-1-allyloxycarbonyl-2-{2(4-carbamoylimidazol-1-yl)ethyl}pyrrolidin-4-yl]thio-6-[(1R)-1-hydroxyethyl]-4-methyl-7-oxo-1-azabicyclo[3.2.0]-hept-2-ene-2-carboxylate (2.23 g) was obtained in substantially the same manner as that of Example 18-1).

IR (Neat): 1740, 1640, 1580, 1390, 1310 cm$^{-1}$

NMR (CDCl$_3$, δ): 1.24 (3H, d, J=7.21 Hz), 1.34 (3H, d, J=6.24 Hz), 1.50–1.75 (1H, m), 1.90–2.10 (1H, m), 2.30–2.70 (2H, m), 3.15–3.40 (3H, m), 3.45–3.70 (1H, m), 3.85–4.45 (6H, m), 4.50–4.90 (4H, m), 5.20–5.70 (4H, m), 5.80–6.10 (2H, m), 7.00 (1H, broad s), 7.40–7.65 (2H, m)

Example 35-2)

To a solution of allyl (4R,5S,6S)-3-[(2R,4S)-1-allyloxycarbonyl-2-{2-(4-carbamoylimidazol-1-yl)ethyl}-pyrrolidin-4-yl]thio-6-[(1R)-1-hydroxyethyl]-4-methyl-7-oxo-1-azabicyclo[3.2.0]hept-2-ene-2-carboxylate (2.07 g) in dichloromethane (20 ml) was added methyl trifluoromethanesulfonate (1.16 ml) at 0° C. and the solution was stirred for 30 minutes. To the mixture was added a suspension of ion exchange resin, Amberlist A-26 (Cl$^-$ type, Trademark, made by Rohm and Haas Co., Ltd.) (10 ml) in dichloromethane (10 ml) and the whole was stirred for 5 minutes. The resin was removed by filtration and washed with a mixture of dichloromethane and methanol (4/1, 50 ml). The filtrate was concentrated in vacuo to give allyl (4R,5S,6S)-3-[(2R,4S)-1-allyloxycarbonyl-2-{2-(4-carbamoyl-3-methyl-1-imidazolio)ethyl}pyrrolidin-4yl]thio-6-[(1R)-1-hydroxyethyl]-4-methyl-7-oxo-1azabicyclo[3.2.0] hept-2-ene-2-carboxylate chloride (2.75 g) as a pale yellow solid. This compound was immediately used as the starting compound for the next step.

Example 35-3)

(4R,5S,6S)-3-[(2R,4S)-2-{2-(4-Carbamoyl-3-methyl-1-imidazolio)ethyl}pyrrolidin-4-yl]thio-6-[(1R)-1-hydroxyethyl]-4-methyl-7-oxo-1-azabicyclo[3.2.0]hept-2-ene-2-carboxylic acid chloride (421 mg) was obtained in substantially the same manner as Example 4-4).

NMR (CDCl$_3$, 200 MHz, $\delta$): 1.22 (3H, d, J=7.7 Hz), 1.29 (3H, d, J=6.2 Hz), 1.7–1.9 (1H, m), 2.4–2.6 (2H, m), 2.7–2.9 (1H, m), 3.3–3.8 (6H, m), 4.04 (3H, s), 4.2–4.5 (4H, m), 8.15 (1H, s), 9.01 (1H, s)

Example 36-1)

To a solution of allyl (4R)-2-diazo-4-[(2R,3S)-3-{(1 R)-1-hydroxyethyl}-4-oxoazetidin-2-yl]-3-oxopentanoate (2.72 g) in ethyl acetate (30 ml) was added rhodium(II) octanoate (36 mg) under refluxing in a stream of nitrogen. The mixture was refluxed for 30 minutes and then evaporated in vacuo to give a residue. The residue was dissolved in acetonitrile (30 ml) and cooled at 0°–5° C. under atmosphere of nitrogen. To the solution were successively added diphenyl phosphorochloridate (2.01 ml) and N,N-diisopropyl-N-ethylamine (1.76 ml) and the mixture was stirred at the same temperature overnight. To this solution were successively added N,N-dimethylacetamide (15 ml), a solution of (2R,4S)-1-allyloxycarbonyl-2-{2-(2,3-dihydroimidazo[1,2-b]pyrazol-1-yl}ethyl-4-mercaptopyrrolidine trifluoroacetate (4.82 g) in acetonitrile (30 ml) and N,N-diisopropyl-N-ethylamine (1.93 ml) under ice-cooling. The mixture was stirred at the same temperature for 3 hours. To the reaction mixture were added ethyl acetate (100 ml) and water (50 ml) with stirring and the organic layer was separated. The organic layer was washed with saturated aqueous sodium chloride, dried over anhydrous magnesium sulfate and evaporated in vacuo. The resulting residue was chromatographed on silica gel (200 g) eluting with a mixture of dichloromethane and acetone (1:2, V/V). The fractions containing the desired compound were collected and evaporated in vacuo to give allyl (4R,5S,6S)-3-[(2R,4S)-1-allyloxycarbonyl-2-{2-(2,3dihydroimidazo[1,2-b]pyrazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (2.41 g).

IR (Neat): 1740, 1680, 1610, 1390 cm$^{-1}$

NMR (CDCl$_3$, $\delta$): 1.26 (3H, d, J=7.15 Hz), 1.35 (3H, d, J=6.20 Hz), 1.65–2.05 (4H, m), 3.20–3.65 (3H, m), 3.65–4.35 (9H, m), 4.55–4.90 (4H, m), 5.20–5.60 (5H, m), 5.80–6.10 (2H, m), 7.34 (1H, broad s)

Example 36-2)

To a solution of allyl (4R,5S,6S)-3-[(2R,4S)-1-allyloxycarbonyl-2-{2-(2,3-dihydroimidazo[1,2-b]pyrazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (2.41 g) in acetone (10 ml) with stirring at ambient temperature and the mixture was allowed to stand overnight. The reaction mixture was evaporated in vacuo to give allyl (4R,5S,6S)-3-[(2R,4S)-1-allyloxycarbonyl-2-{2-(5-methyl-2,3-dihydro-1-imidazo[1,2-b]pyrazolio) ethyl}-pyrrolidin-4-yl]thio-6-[(1R)-1-hydroxyethyl]-4-methyl-7-oxo-1-azabicyclo[3.2.0]hept-2-ene-2-carboxylate iodide (2.52 g). This compound was immediately used as the starting compound for the next step.

Example 36-3)

(4R,5S,6S)-6-[(1R)-1-Hydroxyethyl]-4-methyl-3-[(2R,4S)-2-{2-(5-methyl-2,3-dihydro-1-imidazo[1,2-b] pyrazolio)ethyl}pyrrolidin-4-yl]thio-7-oxo-1-azabicyclo-[3.2.0]hept-2-ene-2-carboxylic acid chloride (722 mg) was obtained in substantially the same manner as that of Example 4-4).

IR (Nujol): 1730, 1580–1570 cm$^{-1}$

NMR (D$_2$O, $\delta$): 1.22 (3H, d, J=7.18 Hz), 1.30 (3H, d, J=6.34 Hz), 1.60–1.80 (1H, m), 2.00–2.35 (2H, m), 2.65–2.85 (1H, m), 3.25–3.80 (7H, m), 3.81 (3H, s), 3.90–4.45 (7H, m), 5.88 (1H, d, J=3.1 Hz), 7.81 (1H, d, J=3.1 Hz)

FAB Mass: 462.2 (M$^+$)

Example 37-1)

Allyl (4R,5S,6S)-3-[(2R, 4S)-1-allyloxycarbonyl-2-{2-(1,2,3-triazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (3.35 g) was obtained in substantially the same manner as that of Example 2-3).

NMR (CDCl$_3$, $\delta$): 1.26 (3H, d, J=7.2 Hz), 1.31 (3H, d, J=6.3 Hz), 1.64 (1H, br), 2.08–2.22 (1H, m), 2.58 (2H, br), 3.23–3.36 (3H, m), 3.55–3.70 (1H, m), 3.87–4.28 (5H, m), 4.49–4.82 (6H, m), 5.22–5.49 (4H, m), 5.87–5.99 (2H, m), 7.72 (2H, br)

Example 37-2)

(4R,5S,6S)-6-[(1R)-1-Hydroxyethyl]-4-methyl-3-[(2R,4S)-2-{2-(1,2,3-triazol-1-yl)ethyl}pyrrolidin-4-yl]-thio-7-oxo-1-azabicyclo [3.2.0]hept-2-ene-2-carboxylic acid hydrochloride (317 mg) was obtained in substantially the same manner as that of Example 5.

IR (Nujol): 1740 cm$^{-1}$

NMR (D$_2$O, $\delta$): 1.20 (3H, d, J=7.2 Hz), 1.29 (3H, d, J=6.4 Hz), 1.54–1.70 (1H, m), 2.39–2.72 (3H, m), 3.27–3.48 (3H, m), 3.56–3.72 (2H, m), 3.90–4.03 (1H, m), 4.19–4.27 (2H, m), 4.66 (2H, t, J=6.6 Hz), 7.81 (2H, s)

FAB Mass: 408 (M$^+$)

Example 37-3)

To a solution of allyl (4R,5S,6S)-3-[(2R,4S)-1-allyloxycarbonyl-2-{2-(1,2,3-triazol-1-yl)ethyl}-pyrrolidin-4-yl] thio-6-[(1R)-1-hydroxyethyl]-4-methyl-7-oxo-1-azabicyclo [3.2.0]hept-2-ene-2-carboxylate (3.55 g) in dichloromethane (71 ml) was added methyl trifluoromethanesulfonate (1.14 ml) with stirring under ice-cooling. The mixture was stirred for 20 minutes at ambient temperature. The mixture was evaporated in vacuo to give a product (4.65 g) of allyl (4R,5S,6S)-3(2R,4S)-1-allyloxycarbonyl-2-[2-{3-methyl-1-(1,2,3-triazolio)}ethyl]pyrrolidin-4-yl]thio-6-[(1R)-1-hydroxyethyl]-4-methy1-7-oxo-1-azabicyclo[3.2.0]hept-2-ene-2-carbonate trifluoromethanesulfonate which may contain allyl (4R,5S,6S)-3-[(2R,4S)-1-allyloxycarbonyl-2-[2-{2-methyl-1-(1,2,3-triazolio)}ethyl]pyrrolidin-4-yl]-thio-6-[(1R)-1-hydroxyethyl]-4-methyl-7-oxo-1-azabicyclo[3.2.0]hept-2-ene-2-carbonate trifluoromethanesulfonate. This compound was immediately used as the starting compound for the next step.

Example 37-4)

A product of (4R,5S,6S)-6-[(1R)-1-hydroxyethyl]-4-methyl-3-[(2R,4S)-2-[2-{3-methyl-1-(1,2,3-triazolio)}ethyl]pyrrolidin-4-yl]thio-7-oxo-1-azabicyclo[3.2.0]hept-2-ene-2-carboxylic acid chloride which may contain (4R,5S,6S)-6-[(1R)-1-hydroxyethyl]-4-methyl-3-[(2R,4S)-2-[2-{2-methyl-1-(1,2,3-triazolio)}ethyl]pyrrolidin-4-yl]-thio-7-oxo-1-azabicyclo[3.2.0]hept-2-ene-2-carboxylate chloride (0.88 g) was obtained from the product of allyl (4R,5S,6S)-3-[(2R,4S)-1-allyloxycarbonyl-2-[2-{3-methyl-1-(1,2,3-triazolio)}ethyl]pyrrolidin-4-yl]thio-6-[(1R)-1-hydroxyethyl]-4-methyl-7-oxo-1-azabicyclo[3.2.0]hept-2-ene-2-carbonate trifluoromethanesulfonate which may contain allyl (4R,5S,6S)-3-[(2R,4S)-1-allyloxycarbonyl-2-[2-{2-methyl-1-(1,2,3-triazolio)}ethyl]pyrrolidin-4-yl]-thio-6-[(1R)-1-hydroxyethyl]-4-methyl-7-oxo-1-azabicyclo[3.2.0]hept-2-ene-2-carbonate trifluoromethanesulfonate (4.65 g) obtained in Example 37-3) in substantially the same manner as that of Example 4-4).

IR (Nujol): 1752 cm$^{-1}$

NMR (D$_2$O, δ): 1.23 (3H, d, J=7.2 Hz), 1.30 (3H, d, J=6.4 Hz), 1.73–1.87 (1H, m), 2.55–2.71 (2H, m), 2.74–2.91 (1H, m), 3.33–3.50 (4H, m), 3.66–3.89 (3H, m), 3.99–4.08 (1H, m), 4.21–4.28 (2H, m), 4.36 (3H, s), 8.55 (1H, d, J=1.3 Hz), 8.63 (1H, d, J=1.4 Hz )

FAB Mass: 422 (M$^+$)

Example 38-1)

Allyl (4R,5S,6S)-3-[(2R,4S)-1-allyloxycarbonyl-2-{2-(pyrazol-1-yl) ethyl}pyrrolidin-4-yl]thio-6-[(1R)-1-hydroxyethyl-4-methyl-7-oxo-1-azabicyclo[3.2.0]hept-2-ene-2-carbonate (10.4 g) was obtained in substantially the same manner as that of Example 2-3).

NMR (CDCl$_3$, δ): 1.24 (3H, d, J=7.2 Hz), 1.35 (3H, d, J=6.2 Hz), 1.54 (1H, br), 1.96–2.50 (5H, m), 3.22–3.31 (3H, m), 3.53 (1H, m), 3.91–4.27 (6H, m), 4.56–4.81 (4H, m), 5.20–5.48 (4H, m), 5.87–6.26 (2H, m), 6.25 (1H, t, d=2.1 Hz), 7.48 (2H, m)

Example 38-2)

(4R,5S,6S)-6-[(1R)-1-Hydroxyethyl]-4-methyl-3-[(2R,4S)-2-{2-(pyrazol-1-yl)ethyl}pyrrolidin-4-yl]thio-7-oxo-1-azabicyclo[3.2.0]hept-2-ene-2-carboxylic acid hydrochloride (1.65 g) was obtained in substantially the same manner as that of Example 5.

(Nujol): 1747 cm$^{-1}$

NMR (D$_2$O, δ): 1.19 (3H, d, J=7.1 Hz), 1.29 (3H, d, J=6.2 Hz), 1.52–1.68 (1H, m), 2.28–2.68 (3H, m), 3.33–3.47 (3H, m), 3.56–3.69 (2H, m), 3.92–3.98 (1H, m), 4.20–4.36 (4H, m), 6.40 (1H, d, J=1.7 Hz), 7.61 (1H, m), 7.71 (1H, m)

FAB Mass: 407 (M$^+$)

Example 38-3)

To a solution of allyl (4R,5S,6S)-3-[(2R,4S)-1-allyloxycarbonyl-2-{2-(pyrazol-1-yl)ethyl}pyrrolidin-4-yl]thio-6-[(1R)-1-hydroxyethyl]-4-methyl-7-oxo-1-azabicyclo[3.2.0]hept-2-ene-2-carboxylate (10.49 g) in dichloromethane (150 ml) was added methyl fluorosulfonate (2.33 ml) with stirring under ice-cooling. The mixture was stirred for 1.5 hours at the same temperature. The mixture was evaporated in vacuo to give allyl (4R,5S,6S)-3-[(2R,4S)-1-allyloxycarbonyl-2-{2-(2-methyl-1-pyrazolio)ethyl}pyrrolidin-4-yl]thio-6-[(1R)-1-hydroxyethyl]-4-methyl-7-oxo-1-azabicyclo[3.2.0]hept-2-ene-2-carboxylate fluorosulfonate (12.75 g). This compound was immediately used as the starting compound for the next step.

Example 38-4)

To a solution of allyl (4R,5S,6S)-3-[(2R,4S)-1-allyloxycarbonyl-2-{2-(2-methyl-1-pyrazolio)ethyl}-pyrrolidin-4-yl]thio-6-[(1R)-1-hydroxyethyl]-4-methyl-7-oxo-1-azabicyclo[3.2.0]hept-2-ene-2-carboxylate fluorosulfonate (12.75 g), triphenylphosphine (1.04 g), acetic acid (6.79 ml) and tetrakis(triphenylphosphine)palladium(0) (0.91 g) in a mixture of tetrahydrofuran (100 ml) and ethanol (100 ml) was added tributyltin hydride (21.3 ml) at ambient temperature with stirring, and the mixture was stirred at the same temperature for 30 minutes. To the mixture were added water (150 ml) and ethyl acetate (300 ml). After separation, the aqueous layer was concentrated. The residue was adjusted to pH 6 with saturated aqueous sodium hydrogen carbonate and chromatographed on nonionic adsorption resin, Diaion HP-20 (Trademark, made by Mitsubishi Chemical Industries) (1 l) eluting in turn with water and 5% aqueous acetone. The fractions containing the desired compound were collected and concentrated in vacuo. The resulting residue was adjusted to pH 4 with 1N hydrochloric acid and passed through in exchange resin, Amberlist A-26 (Cl$^-$ type, Trademark, made by Rohm and Haas Co., Ltd.) (60 ml) eluting with water. The eluate was lyophilized to give (4R,5S,6S)-6-[(1R)-1-hydroxyethyl]-4-methyl-3-[(2R,4S)-2-{2-(2-methyl-1-pyrazolio)ethyl}-pyrrolidin-4-yl]thio-7-oxo-1-azabicyclo[3.2.0]hept-2-ene-2-carboxylic acid chloride (2.34 g).

IR (Nujol): 1740 cm$^{-1}$

NMR (D$_2$O, δ): 1.22 (3H, d, J=7.2 Hz), 1.29 (3H, d, J=6.4 Hz), 2.42–2.65 (2H, m), 2.76–2.91 (1H, m), 3.33–3.49 (3H, m), 3.67–4.90 (1H, m), 4.17 (3H, s), 4.22–4.28 (2H, m), 4.62 (2H, t, J=8.0 Hz), 6.80 (1H, t, J=3.0 Hz), 8.22 (1H, d, J=2.8 Hz), 8.29 (1H, d, J=2.3 Hz)

FAB Mass: 421 (M$^+$)

Example 39-1)

Allyl (4R,5S,6S)-3-[(2R,4S)-1-allyloxycarbonyl-2-{2-(4-(2-carbamoylethenyl)imidazol-1-yl)ethyl}pyrrolidin-yl]thio-6-{(1R)-1-hydroxyethyl}-4-methyl-7-oxo-1-azabicyclo[3.2.0]hept-2-ene-2-carboxylate was obtained in 68.7% yield in substantially the same manner as that of Example 18-1).

IR (Neat): 1755, 1665, 1580 cm$^{-1}$

NMR ( CDCl$_3$, δ): 1.22 (3H, d, J=7.34 Hz), 1.35 (3H, d, J=6.23 Hz ), 1.40–1.65 (1H, m), 1.80–2.10 (1H, m), 2.30–2.60 (2H, m), 3.20–3.35 (3H, m), 3.50–3.70 (1H, m), 3.80–4.15 (1H, m), 4.20–4.30 (2H, m), 4.50–4.80 (4H, m), 5.22–5.50 (4H, m), 5.80–6.03 (2H, m), 6.61 (1H, d, J=15.0 Hz), 7.14 (1H, br s), 7.51 (1H, d, J=14.9 Hz), 7.54 (1H, br s)

Example 39-2)

A mixture of allyl (4R,5S,6S)-3-[(2R,4S)-1-allyloxycarbonyl-2-{2-(4-(2-carbamoylethenyl)imidazol-1-yl)ethyl}pyrrolidin-4-yl]thio-6-{(1R)-1-hydroxyethyl}-4-methyl-7-oxo-1-azabicyclo[3.2.0]hept-2-ene-2-carboxylate (3.6 g) and methyl iodide (3.74 ml) in N,N-dimethylformamide (20 ml) was stirred for 2 days at room temperature. The solvent was removed under reduced pressure to give a residue, which was dissolved in a mixture of tetrahydrofuran (45 ml) and ethanol (45 ml). To the solution were added in turn triphenylphosphine (472 mg), acetic acid (893 ml), tri-n-butyltin hydride (3.9 ml) and tetrakis(triphenylphosphine)palladium (500 mg) under nitrogen atmosphere at room temperature. After 20 minutes, the reaction mixture was poured into a mixture of phosphate pH standard equimolal solution (pH 6.86, 100 ml) and dichloromethane (300 ml). The aqueous layer was separated and concentrated in vacuo to give a residual solution, which was chromatographed on nonionic adsorption resin, Diaion HP-20 (Trademark, made by Mitsubishi Chemical Industries) (350 ml) eluting in turn with water, 2% aqueous acetonitrile and 4% aqueous acetonitrile. The active fractions were collected and passed through ion exchange resin, Amberlist A-26 (Cl$^-$ type, Trademark, Rohm and Haas Co., Ltd.) (10 ml) eluting with water. The resulting solution was lyophilized to give a crude compound, which was chromatographed on Aluminum AC-12 eluting with water. The fractions containing the desired compound were collected and lyophilized to give (4R,5S,6S)-3-[(2R,4S)-2-{2-(4-(2-carbamoylethenyl)-3-methyl-1-imidazolio)ethyl}pyrrolidin-4-yl]thio-6-{(1R)-1-hydroxyethyl}-4-methyl-7-oxo-1-azabicyclo[3.2.0]hept-2-ene-2-carboxylic acid chloride (1.08 g).

IR (Nujol): 1735 cm$^{-1}$

NMR (D$_2$O, δ): 1.23 (3H, d, J=7.2 Hz), 1.30 (3H, d, J=6.38 Hz), 1.70–1.85 (1H, m), 2.40–2.60 (2H, m), 2.70–2.90 (1H, m), 3.30–3.84 (5H, m), 3.95 (3H, s), 4.00–4.10 (1H, m), 4.20–4.50 (4H, m), 6.76 (1H, d, J=15.95 Hz), 7.41 (1H, d, J=16.25 Hz), 8.00 (1H, s), 8.92 (1H, s)

Example 40-1)

Allyl (4R,5S,6S)-3-[(2R,4S)-1-allyloxycarbonyl-2-{2-(5-(2-carbamoylethenyl)imidazol-1-yl)ethyl}pyrrolidin-4-yl]thio-6-{(1R)-1-hydroxyethyl)-4-methyl-7-oxo-1-azabicyclo[3.2.0]hept-2-ene-2-carboxylate was obtained in 64.5% yield in substantially the same manner as that of Example 39-1).

NMR (CDCl$_3$, δ): 1.22 (3H, d, J=7.12 Hz), 1.31 (3H, d, J=6.14 Hz), 1.50–1.70 (1H, m), 1.90–2.10 (1H, m), 2.30–2.60 (2H, m), 3.20–3.35 (3H, m), 3.50–3.70 (1H, m), 3.80–4.30 (6H, m), 4.50–4.90 (4H, m), 5.20–5.50 (4H, m), 5.80–6.05 (2H, m), 6.44 (1H, d, J=15.74 Hz), 6.90–7.50 (3H, m)

Example 40-2)

(4R,5S,6S)-3-[(2R,4S)-2-{2-(5-(2-Carbamoylethenyl)-3-methyl-1-imidazolio)ethyl}pyrrolidin-4-yl]thio-6-{(1R)-1-hydroxyethyl}-4-methyl-7-oxo-1-azabicyclo[3.2.0]hept-2-ene-2-carboxylic acid chloride was obtained in 13.7% yield in substantially the same manner as that of Example 39-2).

IR (Nujol): 1735, 1665, 1575 cm$^{-1}$

NMR (D$_2$O, δ): 1.22 (3H, d, J=7.16 Hz), 1.29 (3H, d, J=6.34 Hz), 1.70–1.85 (1H, m), 2.35–2.60 (2H, m), 2.70–2.90 (1H, m), 3.30–4.20 (6H, m), 3.93 (3H, s), 4.20–4.30 (2H, m), 4.40–4.50 (2H, m), 6.77 (1H, d, J=15.77 Hz), 7.40 (1H, d, J=15.80), 7.91 (1H, s), 8.92 (1H, s)

Example 41-1)

Allyl (4R,5S,6S)-3-[(2R,4S)-1-allyloxycarbonyl-2-(1-methyl-3-pyridiniomethyl)pyrrolidin-4-yl]thio-6-[(1R)-1-hydroxyethyl]-4-methyl-7-oxo-1-azabicyclo[3.2.0]hept-2-ene-2-carboxylate iodide (4.67 g) was obtained in substantially the same manner as that of Example 3-2).

IR (Nujol): 1750, 1680 cm$^{-1}$

NMR (D$_2$O, δ): 1.24 (3H, d, J=5.4 Hz), 1.34 (3H, d, J=6.2 Hz), 1.4–2.0 (2H, m), 2.17 (3H, s), 3.1–4.8 (14H, m), 5.1–5.5 (4H m), 5.7–6.1 (2H, m), 7.8–8.4 (2H, m), 8.8–9.3 (2H, m)

Example 41-2)

(4R,5S,6S)-3-[(2R,4S)-2-(1-Methyl-3-pyridiniomethyl)-pyrrolidin-4-yl]thio-6-[(1R)-1-hydroxyethyl]-4-methyl-7-oxo-1-azabicyclo[3.2.0]hept-2-ene-2-carboxylic acid chloride was obtained in substantially the same manner as that of Example 4-2).

IR (Nujol): 1740 cm$^{-1}$

NMR (D$_2$O, δ): 1.21 (3H, d, J=7.2 Hz), 1.29 (3H, d, J=6.4 Hz), 1.5–1.7 (1H, m), 2.5–2.7 (1H, m), 3.2–3.6 (5H, m), 3.7–4.0 (2H, m), 4.1–4.3 (2H, m), 4.39 (3H, s), 8.02 (1H, dd, J=8.0 Hz, 6.0 Hz), 8.49 (1H, d, J=8.0 Hz), 8.72 (1H, d, J=6.0 Hz), 8.80 (1H, s)

We claim:

1. A compound of the formula:

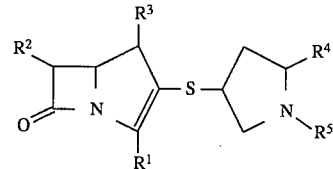

in which R$^1$ is carboxy,
R$^2$ is 1-hydroxyethyl,
R$^3$ is methyl,
R$^4$ is pyridin-2-(or 3- or 4-)yl (C$_1$–C$_2$)alkyl, imidazol-5-ylmethyl, imidazol-2-yl(C$_1$–C$_3$) alkyl, pyrazol-4-(or 5-) ylmethyl, 1,2,4-triazol-5-yl (C$_1$–C$_2$)alkyl, pyrimidin-2-(or 5-)ylmethyl, or (1,6-dihydropyrimidin-5-yl)methyl,
each of which is unsubstituted or substituted by at least one substituent selected from the group consisting of methyl, ethyl, propyl, carbamoylmethyl, N,N-dimethylcarbamoylmethyl, N-(2-hydroxyethyl)carbamoylmethyl, allyloxycarbonyl, carbamoyl, hydroxymethyl, 2-hydroxyethyl, methoxymethyl, cyano, 3-aminopropyl, 3-(allyloxycarbonylamino)propyl and 2-carbamoylethenyl, and
R$^5$ is hydrogen, or a pharmaceutically acceptable salt thereof.

2. The compound of claim 1, wherein
R$^4$ is pyridin-2-(or 3- or 4-)yl(C$_1$–C$_2$)alkyl or pyridin-2-(or 3- or 4-)yl(C$_1$–C$_2$)alkyl substituted by at least one substituent selected from the group consisting of methyl, carbamoylmethyl, N,N-dimethylcarbamoylmethyl and N-(2-hydroxyethyl) carbamoylmethyl.

3. The compound of claim 2, which is (4R,5S,6S)-6-[(1R)-1-hydroxyethyl]-4-methyl-3-[(2R,4S)-2-{2-(1-methyl-3-pyridinio)ethyl}pyrrolidin-4-yl]thio-7-oxo-1-azabicyclo[3.2.0]hept-2-ene-2-carboxylic acid chloride, (4R,5S,6S)-3-[(2R,4S)-2-[2-{1-(N,N-dimethylcarbamoylmethyl)-3-pyridinio}ethyl]pyrrolidin-4-yl]thio-6-[(1R)-1-hydroxyethyl]-4-methyl-7-oxo-1-azabicyclo-[3.2.0]hept-2-ene-2-carboxylic acid chloride, (4R,5S,6S)-6-[(1R)-1-hydroxyethyl]-4-methyl-3-[(2R,4S)-2-{2-(1-carbamoylmethyl-3-pyridinio)ethyl}-pyrrolidin-4-yl]thio-7-oxo-1-azabicyclo[3.2.0]hept-2-ene-2-carboxylic acid chloride, (4R,5S,6S)-6-[(1R)-1-hydroxyethyl]-4-methyl-3-[(2R,4S)-2-{2-(1-carbamoylmethyl-4-pyridinio)ethyl}-pyrrolidin-4-yl]thio-7-oxo-1-azabicyclo[3.2.0]hept-2-ene-2-carboxylic acid chloride, (4R,5S,6S)-6-[(1R)-1-hydroxyethyl]-3-[(2R,4S)-2-[2-[1-{N-(2-hydroxyethyl) carbamoylmethyl}-3-pyridinio]ethyl]pyrrolidin-4-yl]thio-4-methyl-7-oxo-1-azabicyclo[3.2.0]hept-2-ene-2-carboxylic acid chloride, (4R,5S,6S)-6-[(1R)-1-hydroxyethyl]-4-methyl-3-[(2R,4S)-2-{2-(1-methyl-2-pyridinio)ethyl}pyrrolidin-4-yl]thio-7-oxo-1-azabicyclo[3.2.0]hept-2-ene-2-carboxylic acid chloride, (4R,5S,6S)-6-[(1R)-1-hydroxyethyl]-3-[2R,4S)-2-{2-(1-carbamoylmethyl-2-pyridinio)ethyl}pyrrolidin-4-yl]thio-4-methyl-7-oxo-1-azabicyclo[3.2.0]hept-2-ene-2-carboxylic acid chloride, (4R,5S,6S)-3-[(2R,4S)-2-(1-methyl-2-pyridinio)methylpyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-3-[(2R,4S)-2-(1-methyl-3-pyridiniomethyl)-pyrrolidin-4-yl]thio-6-[(1R)-1-hydroxyethyl]-4-methyl-7-oxo-1-azabicyclo[3.2.0]hept-2-ene-2-carboxylic acid chloride, (4R,5S,6S)-6-[(1R)-1-hydroxyethyl]-3-[(2R,4S)-2-(1-methyl-4-pyridiniomethyl)pyrrolidin-4-yl]thio-4-methyl-7-oxo-1-azabicyclo[3.2.0]hept-2-ene-2-carboxylic acid chloride, (4R,5S,6S)-3-[(2R,4S)-2-(1-methyl-2-pyridinio)methylpyrrolidin-4-yl]thio-6-[(1R)-1-hydroxyethyl]-4-methyl-7-oxo-1-azabicyclo[3.2.0]hept-2-ene-2-carboxylic acid chloride, or (4R,5S,6S)-3-[(2R,4S)-2-{2-(1-pyridinio)ethyl}pyrrolidin-4-yl]thio-6-[(1R)-1-hydroxyethyl]-4-methyl-7-oxo-1-azabicyclo[3.2.0]hept-2-ene-2-carboxylic acid chloride.

4. The compound of claim 1, wherein $R^4$ is imidazol-5-ylmethyl or imidazol-5-ylmethyl substituted by methyl.

5. The compound of claim 1, wherein $R^4$ is imidazol-2-yl($C_1$–$C_3$)alkyl or imidazol-2-yl($C_1$–$C_3$)alkyl substituted by at least one substituent selected from the group consisting of methyl and carbamoylmethyl.

6. The compound of claim 1, wherein $R^4$ is 1,2,4-triazol-5-yl($C_1$–$C_2$)alkyl or 1,2,4-triazol-5-yl($C_1$–$C_2$)alkyl substituted by methyl.

7. The compound of claim 1, wherein $R^4$ is pyrimidin-2-(or 5-)ylmethyl or pyrimidin-2-(or 5)ylmethyl substituted by methyl.

8. The compound of claim 1, wherein $R^4$ is (1,6-dihydropyrimidin-5-yl)methyl or (1,6-dihydropyrimidin-5-yl)methyl substituted by methyl.

9. The compound of claim 1, wherein $R^4$ is pyrazol-4-(or 5-)ylmethyl or pyrazol-4-(or 5-)ylmethyl substituted by at least one substituent selected from the group consisting of methyl, ethyl, propyl, carbamoylmethyl, N,N-dimethylcarbamoylmethyl, N-(2-hydroxyethyl)carbamoylmethyl, allyloxycarbonyl, carbamoyl, hydroxymethyl, 2-hydroxyethyl, methoxymethyl, cyano, 3-aminopropyl, 3-(allyloxycarbonylamino)propyl and 2-carbamoylethenyl.

10. The compound of claim 9, wherein $R^4$ is pyrazol-4-(or 5-)ylmethyl or pyrazol-4-(or 5-)ylmethyl substituted by methyl.

11. The compound of claim 10, which is (4R,5S,6S)-3-[(2R,4S)-2-(1,2-dimethyl-4-pyrazoliomethyl)pyrrolidin-4-yl]thio-6-[(1R)-1-hydroxyethyl]-4-methyl-7-oxo-1-azabicyclo[3.2.0]-hept-2-ene-2-carboxylic acid chloride, or (4R,5S,6S)-3-[(2R,4S)-2-(1,2-dimethyl-5-pyrazoliomethyl)pyrrolidin-4-yl]thio-6-[(1R)-1-hydroxyethyl]-methyl-7-oxo-1-azabicyclo[3.2.0]-hept-2-ene-2-carboxylic acid chloride.

* * * * *